(12) United States Patent
Chen et al.

(10) Patent No.: US 8,886,283 B1
(45) Date of Patent: Nov. 11, 2014

(54) 3D AND 4D MAGNETIC SUSCEPTIBILITY TOMOGRAPHY BASED ON COMPLEX MR IMAGES

(75) Inventors: Zikuan Chen, Albuquerque, NM (US); Vince D. Calhoun, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 13/526,210

(22) Filed: Jun. 18, 2012

Related U.S. Application Data

(60) Provisional application No. 61/499,459, filed on Jun. 21, 2011.

(51) Int. Cl.
*A61B 5/055* (2006.01)

(52) U.S. Cl.
USPC .......................... 600/410; 382/128

(58) Field of Classification Search
None
See application file for complete search history.

(56) References Cited

U.S. PATENT DOCUMENTS

| | | | |
|---|---|---|---|
| 4,896,113 A * | 1/1990 | Pelc | 324/309 |
| 5,073,858 A | 12/1991 | Mills | |
| 5,233,992 A | 8/1993 | Holt | |
| 5,560,360 A | 10/1996 | Filler | |
| 6,076,004 A | 6/2000 | Kanayama | |
| 6,208,884 B1 | 3/2001 | Kumar | |
| 6,477,398 B1 | 11/2002 | Mills | |
| 6,603,989 B1 | 8/2003 | Yablonskiy | |
| 6,658,280 B1 | 12/2003 | Haacke | |
| 7,154,269 B1 | 12/2006 | Haacke | |
| 7,298,143 B2 | 11/2007 | Jaermann | |
| 7,382,129 B2 | 6/2008 | Mills | |
| 7,545,966 B2 * | 6/2009 | Lewin et al. | 382/128 |
| 7,642,512 B2 | 1/2010 | Watarai | |
| 7,782,051 B2 | 8/2010 | Haacke | |
| 7,800,367 B2 | 9/2010 | Bhardwaj | |
| 8,054,075 B2 | 11/2011 | Stuber | |
| 8,422,756 B2 * | 4/2013 | Haacke et al. | 382/131 |
| 2003/0212322 A1 | 11/2003 | Haacke | |
| 2006/0106300 A1 | 5/2006 | Seppenwoolde | |
| 2010/0002926 A1 | 1/2010 | Dahnke | |
| 2010/0142785 A1 | 6/2010 | Dahnke | |

OTHER PUBLICATIONS

Chen, Z. and V. Calhoun, Computed inverse resonance imaging for magnetic susceptibility map reconstruction. Journal of computer assisted tomography, 2012. 36(2): p. 265-74.

(Continued)

*Primary Examiner* — Long V. Le
*Assistant Examiner* — Kevin Pontius
(74) *Attorney, Agent, or Firm* — Valauskas Corder LLC

(57) ABSTRACT

Magnetic susceptibility is the physical property for T2*-weighted magnetic resonance imaging (T2*MRI). The invention relates to methods for reconstructing an internal distribution (3D map) of magnetic susceptibility values, $\chi$ (x,y,z), of an object, from 3D T2*MRI phase images, by using Computed Inverse Magnetic Resonance Imaging (CIMRI) tomography. The CIMRI technique solves the inverse problem of the 3D convolution by executing a 3D Total Variation (TV) regularized iterative convolution scheme, using a split Bregman iteration algorithm. The reconstruction of $\chi$ (x,y,z) can be designed for low-pass, band-pass, and high-pass features by using a convolution kernel that is modified from the standard dipole kernel. Multiple reconstructions can be implemented in parallel, and averaging the reconstructions can suppress noise. 4D dynamic magnetic susceptibility tomography can be implemented by reconstructing a 3D susceptibility volume from a 3D phase volume by performing 3D CIMRI magnetic susceptibility tomography at each snapshot time.

27 Claims, 42 Drawing Sheets

(56) References Cited

OTHER PUBLICATIONS

Chen, Z. and V. Calhoun, Volumetric BOLD fMRI simulation: from neurovascular coupling to multivoxel imaging. BMC medical imaging, 2012. 12(1): p. 1-8.
Chen, Z. and V.D. Calhoun, Two pitfalls of BOLD fMRI magnitude-based neuroimage analysis: non-negativity and edge effect. Journal of neuroscience methods, 2011. 199(2): p. 363-9.
Chen, Z., A. Caprihan, and V.D. Calhoun. BOLD susceptibility map reconstruction from fMRI by 3D total variation regularization. In International society for magnetic resonance in medicine 2011. Montreal, Canada: ISMRM.
Chen, Z. and V. Calhoun, A computational multiresolution BOLD fMRI model. IEEE Trans. BioMed. Eng, 2011. 58(10): p. 2995-9.
Chen, Z. and V. Calhoun. Volumetric computational model for neurovascular coupling and BOLD fMRI. In Human Brain Mapping. 2011. Quebec, CA: OHBM.
Chavhan, G.B., et al., Principles, techniques, and applications of T2*-based MR imaging and its special applications. Radiographics : a review publication of the Radiological Society of North America, Inc, 2009. 29(5): p. 1433-49.
Walsh, A.J. and A.H. Wilman, Susceptibility phase imaging with comparison to R2 mapping of iron-rich deep grey matter. Neuroimage, 2011. 57(2): p. 452-61.
Howseman, A.M. and R.W. Bowtell, Functional magnetic resonance imaging: imaging techniques and contrast mechanisms. Philos Trans R Soc Lond B Biol Sci, 1999. 354(1387): p. 1179-94.
Norris, D.G., Principles of magnetic resonance assessment of brain function. Journal of magnetic resonance imaging : JMRI, 2006. 23(6): p. 794-807.
Ogawa, S., et al., Functional brain mapping by blood oxygenation level-dependent contrast magnetic resonance imaging. A comparison of signal characteristics with a biophysical model. Biophys J, 1993. 64(3): p. 803-12.
Boxerman, J.L., et al., MR contrast due to intravascular magnetic susceptibility perturbations. Magn Reson Med, 1995. 34(4): p. 555-66.
Haacke, E.M., et al., Susceptibility mapping as a means to visualize veins and quantify oxygen saturation. Journal of magnetic resonance imaging : JMRI, 2010. 32(3): p. 663-76.
Li, W., B. Wu, and C. Liu, Quantitative susceptibility mapping of human brain reflects spatial variation in tissue composition. Neuroimage, 2011. 55(4): p. 1645-56.
Schweser, F., et al., Quantitative imaging of intrinsic magnetic tissue properties using MRI signal phase: an approach to in vivo brain iron metabolism? Neuroimage, 2011. 54(4): p. 2789-807.
Shmueli, K., et al., Magnetic susceptibility mapping of brain tissue in vivo using MRI phase data. Magnetic resonance in medicine : official journal of the Society of Magnetic Resonance in Medicine / Society of Magnetic Resonance in Medicine, 2009. 62(6): p. 1510-22.
Wharton, S., A. Schafer, and R. Bowtell, Susceptibility mapping in the human brain using threshold-based k-space division. Magn Reson Med, 2010. 63(5): p. 1292-304.
de Rochefort, L., et al., Quantitative susceptibility map reconstruction from MR phase data using bayesian regularization: validation and application to brain imaging. Magn Reson Med, 2010. 63(1): p. 194-206.
Kressler, B., et al., Nonlinear regularization for per voxel estimation of magnetic susceptibility distributions from MRI field maps. IEEE Trans Med Imaging, 2010. 29(2): p. 273-81.
Li, L., Magnetic susceptibility quantification for arbitrarily shaped objects in inhomogeneous fields. Magn Reson Med, 2001. 46(5): p. 907-16.
Li, L. and J.S. Leigh, Quantifying arbitrary magnetic susceptibility distributions with MR. Magn Reson Med, 2004. 51(5): p. 1077-82.
Sepulveda, N.G., I.M. Thomas, and J.P. Wikswo, Magnetic Susceptibility Tomography For Three-dimensional Imaging of Diamagnetic and Paramagnetic Objects. IEEE Trans. Magnetics, 1994. 30(6): p. 5062-7.

Liu, T., et al., Calculation of susceptibility through multiple orientation sampling (COSMOS): a method for conditioning the inverse problem from measured magnetic field map to susceptibility source image in MRI. Magn Reson Med, 2009. 61(1): p. 196-204.
Yao, B., et al., Susceptibility contrast in high field MRI of human brain as a function of tissue iron content. Neuroimage, 2009. 44(4): p. 1259-66.
Spees, W.M., et al., Water proton MR properties of human blood at 1.5 Tesla: magnetic susceptibility, $T(1)$, $T(2)$, $T^*(2)$, and non-Lorentzian signal behavior. Magn Reson Med, 2001. 45(4): p. 533-42.
Cai, J.F., S. Osher, and Z. Shen, split Bregman Methods and Frame Based Image Restoration, in UCLA CAM Report2009.
Combettes, P.L. and J.C. Pesquet, Image restoration subject to a total variation constraint. IEEE transactions on image processing : a publication of the IEEE Signal Processing Society, 2004. 13(9): p. 1213-22.
Goldstein, T. and S. Osher, The Slit Bregman Method for L1 Regularized Problems,. UCLA CAM Report, 2008.
Osher, S., et al., An iterative regularization method for total variation-based image restoration. Multiscale Model. Simul., 2005. 4(2): p. 460-89.
Hoist, B., et al., T2' imaging indicates decreased tissue metabolism in frontal white matter of MS patients. Multiple sclerosis, 2009. 15(6): p. 701-7.
Menon, "Postacquisition Suppression of Large-Vessel BOLD Signals in High-Resolution fMRI", Magnetic Resonance in Medicine 47:1-9 (2002), Canada.
Abe, "Magnetic Resonance Imaging of Iron in Parkinson's Disease", Current Medical Imaging Reviews, 2005, 1, 43-48, Bentham Science Publishers Ltd.
Peyre, "Chambolle's algorithm for the resolution of compressed sensing with TV regularization", http://www.ceremade.dauphine.fr/~peyre/cs-tv/, 2008.
de Rochefort, "Quantitative MR Susceptibility Mapping Using Piece-Wise constant regularized inversion of the magnetic field", Magnetic Resonance in Medicine 60:1003-1009 (2008), Canada.
de Rochefort, "Quantitative MR Susceptibility Map Reconstruction from MR Phase Data Using Bayesian Regularization: Validation and Application to Brain Imaging", Magnetic Resonance in Medicine 63:194-206 (2010), Canada.
Guerquin-Kern, "A Fast Wavelet-Based Reconstruction Method for Magnetic Resonance Imaging", IEEE Transactions on Medical Imaging, vol. 30, No. 9, Sep. 2011.
Haller, "Pitfalls in fMRI", Eur Radiol (2009) 19: 2689-27-6, Published online Jun. 6, 2009, European Society of Radiology.
Holst, "T2' imaging indicates decreased tissue metabolism in frontal white matter of MS patients", Multiple Sclerosis 2009 15:701-707; DOI: 10.1177/1352458509103713.; http://msj.sagepub.com.
Liu, "Morphology Enabled Dipole Inversion (MEDI) from a Single-Angle Acquisition: Comparison with COSMOS in Human Brain Imaging", Magnetic Resonance in Medicine 66:777-783 (2011), Canada. Published online Apr. 4, 2011 in Wiley Online Library (wileyonlinelibrary.com).
Liu, "A novel background field removal method for MRI using projection onto dipole fields (PDF)", NMR in Biomedicine, (wileyonlinelibrary.com) DOI:10.1002/nbm.1670, Published online in Wiley Online Library: Mar. 8, 2011.
Ropele, "MRI Assessment of Iron Deposition in Multiple Sclerosis", Journal of Magnetic Resonance Imaging 34:13-21 (2011), DOI 10.1002/jmri.22590, Received Nov. 15, 2010; Accepted Mar. 7, 2011.
Schweser, "Differentiation between diamagnetic and paramagnetic cerebral lesions based on magnetic susceptibility mapping", Med. Phys. 37 ,, 10 . . . , Oct. 2010; 2010 Am. Assoc. Phys. Med. 5165-5178; Medical Physics, vol. 37, No. 10, Oct. 2010. published Sep. 7, 2010; DOI: 10.1118/1.3481505.
Yan, "Gradient Distortion Correction for Low Frequency Current Density Imaging", Proceedings of the 28th IEEE EMBS Annual

(56) References Cited

OTHER PUBLICATIONS

International Conference New York City, USA, Aug. 30-Sep. 3, 2006; pp. 260-263; 1-4244-0033-3/06/IEEE. WeD02.1.
Vogel, "Fast, Robust Total Variation-Based Reconstruction of Noisy, Blurred Images", IEEE Transactions on Image Processing, vol. 7, No. 6, Jun. 1998, pp. 813-824. Publisher Item Identifier S 1057-7149(98)04002-0.
Wu, "Whole Brain Susceptibility Mapping Using Compressed Sensing", Magnetic Resonance in Medicine 000:000-000 (2011), pp. 1-11, Canada; Received Oct. 5, 2010; revised Apr. 14, 2011; accepted Apr. 19, 2011. DOI 10.1002/mrm.23000; Published online in Wiley Online Library (wileyonlinelibrary.com).
Chen, Z., Z. Chen, and V.D. Calhoun. Voxel magnetic field disturbance from remote vasculature in BOLD fMRI. In SPIE Medical Imaging. 79613x. Orlando, FL: SPIE, 2011.

* cited by examiner (a) Susceptibility Map (b) MR Magnitude (a) Fieldmap (b) MR phase (a) Pulses (b) GE and SE Signals (b) Average

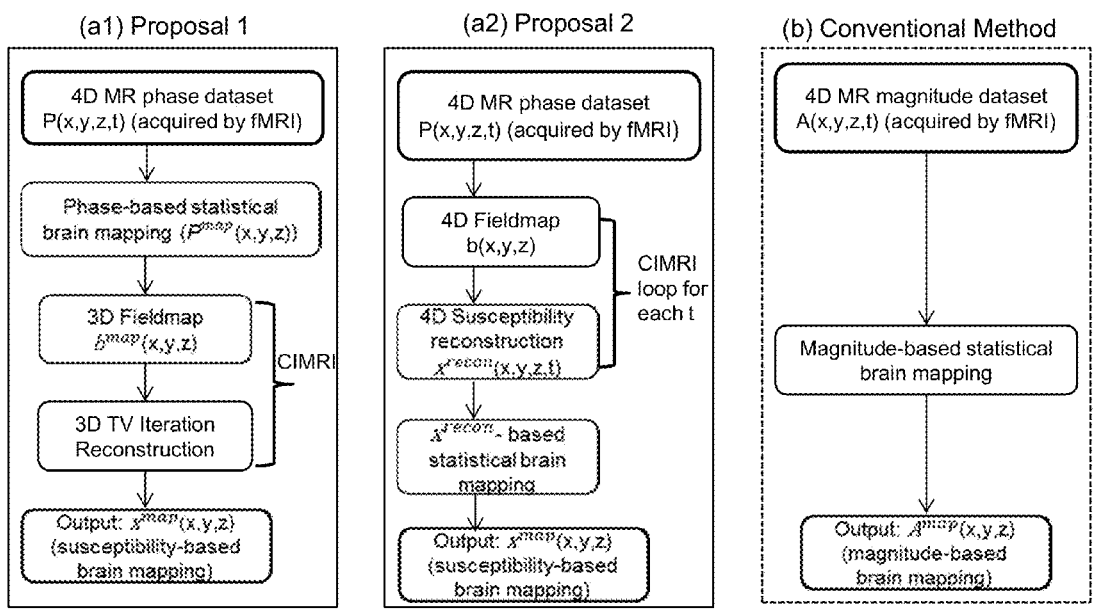
FIG. 27A  FIG. 27B  FIG. 27C Prior Art

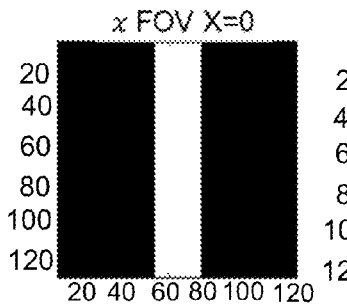
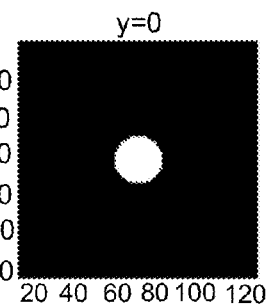
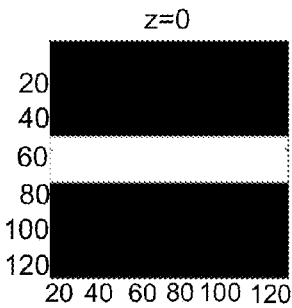
FIG. 38A  FIG. 38B  FIG. 38C
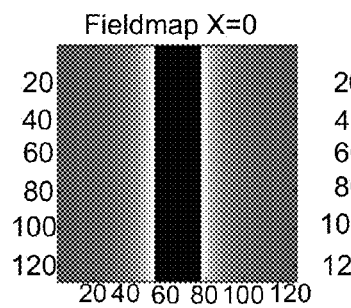
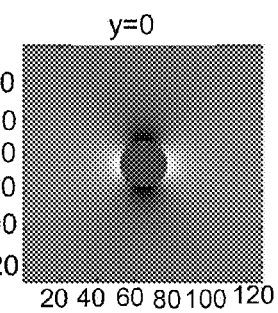
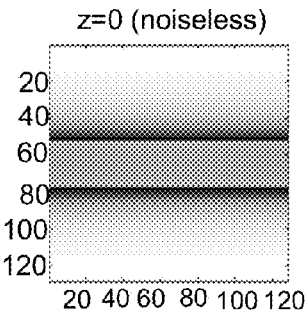
FIG. 38D  FIG. 38E  FIG. 38F
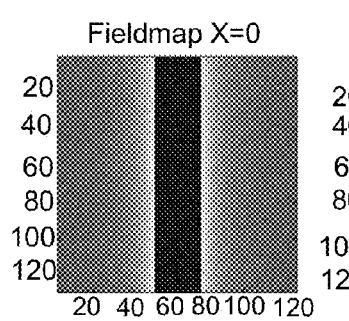
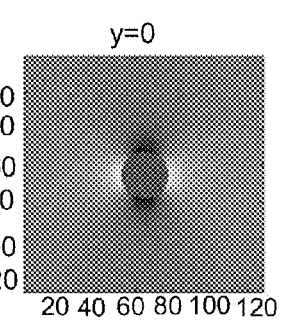
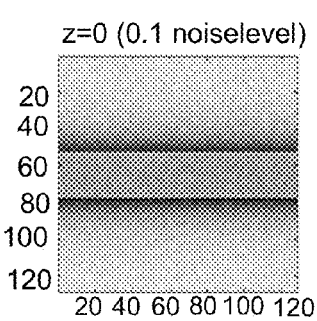
FIG. 38G  FIG. 38H  FIG. 38I

3D AND 4D MAGNETIC SUSCEPTIBILITY TOMOGRAPHY BASED ON COMPLEX MR IMAGES

FEDERALLY SPONSORED RESEARCH

The United States Government has rights in this invention pursuant to Department of Energy Contract No. DE-FG02-08ER64581 with the Mind Research Network; and pursuant to the National Institutes of Health Contract Nos. R01 EB005846 and R01 EB006841 with the University of New Mexico, Electrical and Computer Engineering Department.

CROSS-REFERENCE TO RELATED APPLICATIONS

This application claims the benefit of U.S. Provisional Patent Application Ser. No. 61/499,459, filed Jun. 21, 2011, which is incorporated herein by reference.

BACKGROUND OF THE INVENTION

1. Technical Field

The technical field of the invention is magnetic resonance imaging (MRI) in general, and more specifically: methods and algorithms for generating internal magnetic susceptibility distributions from complex-valued MR images (i.e., MR images containing complex numbers with magnitude and phase parts).

2. Introduction

In magnetic susceptibility tomography, the internal distribution of magnetic susceptibility of an object is determined by applying various configurations of magnetic fields and measuring how the object perturbs them. Measurement of the perturbed magnetic fields can be done using superconducting quantum interference devices (SQUID) called susceptometers or biosusceptometers. However, the present invention is directed to innovative computational techniques and software algorithms that analyze the data generated by magnetic resonance imaging (MRI) scanning machines (MRI scanners). In particular, the present invention primarily uses T2*-weighted images that are generated by MRI scanners using gradient-echo (GE) imaging sequences (also referred to as "T2*MRI").

T2*MRI refers to the detection of transverse magnetization dephasing signal that is caused by a combination of spin-spin relaxation (T2 effect) and magnetic field inhomogeneity (T2' effect) [1, 2]. As a noninvasive 3D imaging modality, the T2*MRI technology has been accepted for both structural iron deposit measurement in tissues and organs [3-9] and for brain functional neuroimaging [1, 10-13]. For general tissue structural imaging, the susceptibility source (dented by $\chi$) is mainly attributed to the nonheme iron deposit therein; and for brain functional imaging, the total $\chi$ source consists of a neuron-induced heme iron perturbation (superimposed on the static structural susceptibility background), as described by the blood oxygenation level dependent (BOLD) physiological model [12, 14, 15].

In electromagnetism, it is understood that, when an entity of inhomogeneous susceptibility distribution is introduced into a main magnetic field, it will be magnetized through the material and magnetic field interaction mechanism [16]) and disturbs the field distribution by superimposing an inhomogeneous fieldmap on the main field. With the T2*MRI technology, that is a frequency spatial encoding and decoding scheme for multivoxel image acquisition through the applications of field gradients, we obtain a complex-valued MR image (consisting of a pair of magnitude and phase images), of which the MR magnitude is conventionally considered as an MR image of the $\chi$ source.

Magnetic susceptibility is the physical property controlling (driving) the T2*-weighted magnetic resonance imaging modality (T2*MRI). For medical imaging, T2*MRI is used to detect the magnetic susceptibility expression of a tissue or an organ state for quantitative iron measurement. It has been found that the output image of T2*MRI is not an exact representation of the susceptibility source (due to local average and nonlinearity associated with T2*MRI), thus not directly useful for iron measurement.

Based on MRI physics, we clarify that neither the MR magnitude image, not the MR phase image, is an exact tomographic reproduction of the susceptibility source or the fieldmap [17-19]. In particular, the MR magnitude image is a nonlinear transformation of the $\chi$ source, which may suffer from non-negativity and edge-effect pitfalls [19]; whereas the MR phase image is linearly related to the fieldmap in small angle regime(a linear phase approximation condition)[17, 19]. Due to the 3D convolution transformation during susceptibility magnetization [19, 20], it is not surprising to notice that the fieldmap (or phase image) appears morphologically different from the $\chi$ source: textural, noisy, and blurry. Therefore, in this invention, we strive to reconstruct the intact $\chi$ source from MR phase image.

The T2*MRI technology imposes a series of spatial transformations to the susceptibility source. Toward representing the entity in its intact $\chi$ distribution (by removing the transformations exerted by T2*MRI detection), the $\chi$ tomography is of paramount significance [19, 21-26].

The mainstay of existent publications on magnetic susceptibility mapping can be classified into three main kinds of solvers [17]. The first kind of solver is based on matrix inverse (for the exploitation of the well-established Tikhonov regularization techniques), which however is confronted with large matrix problem (dimensionality curse) because the 3D convolution imaging formula should be converted to 2D matrix-vector-multiplication format as required by matrix algebra [17, 27-31]. Limited to very small volume reconstruction, the report in [31] only deals with 4×4×4 multivoxel image, which is too small to be meaningful. In comparison, our susceptibility tomography technique in this report can easily accommodate a very large volume such as 512×512×512.

The second kind of solver is based on the 3D inverse filtering in 3D Fourier space [22, 25, 26, 32, 33]. This strategy suffers from stripe artifact and image energy shift problem. To deal with the pole singularity (infinites) on the 3D inverse filter, a truncation regularization is always used; hence called "filter truncation". In presence of noise, the filter truncation solver will produce stripe or clutter artifacts. Furthermore, the energy of the filtered image will not be conserved due to the truncation on the inverse filter.

The third kind of solver is a 3D TV-regularized deconvolution method, which is used by preferred embodiments of the present invention to reconstruct a 3D $\chi$ source distribution from a 3D MR phase image[17, 19], as will be described later.

ACRONYMS AND NOTATIONS

3D: three dimension: (x,y,z)
4D: four dimension: (x,y,z,t)
MR: Magnetic Resonance
MRI: Magnetic Resonance Imaging
T2*MRI: T2*-weighted MRI
CIMRI: Computed Inverse MRI ƒMRI: functional MRI
FID: Free Induction Decay.
$B_0$: main magnetic field
TE, $T_E$: Echo Time for both spin echo and gradient echo signals
FOV: Field Of View
NAB: NeuroActive Blob
T1 relaxation: Longitudinal magnetization recovery process due to spin-lattice interaction.
T2 relaxation (T2 effect): Transverse magnetization dephasing process due to random spin-spin interaction. (non-refocusable).
T2' relaxation (T2' relaxation): Transverse magnetization dephasing process due to static field inhomogeneity. (refocusable).
T2* relaxation: Total transverse magnetization dephasing process, consisting of T2 effect, T2' effect, and diffusion effect. (partially refocusable).
T2' image: A complex image that is calculated by a complex division of a pair of T2* gradient-echo and spin-echo complex images.
T2' phase image: the phase part of T2'-effect complex image
T2' fieldmap: the fieldmap calculated from a T2'-effect phase image
SE: Spin Echo
GE: Gradient Echo.
EPI: Echo Planar Imaging
EVI: Echo Volume Imaging
BOLD: Blood Oxygenation Level Dependent
TV: Total Variation
DC: Direct Current (electrical engineering term)
FT: Fourier Transformation
IFT: Inverse Fourier Transformation
HP: HighPass
LP: Lowpass
BP: BandPass
BT: BandStop
trunc: truncation
struc: structural
conv: convolution
recon: reconstruction
$r=(x,y,z)$: 3D coordinates in space domain
$k=(k_x,k_y,k_z)$: 3D coordinates in Fourier domain (k-space)
$k_{max}=\max\{|k|\}$: the maximum modulus of k.
$\chi$ tomography: a technique to reproduce an internal magnetic $\chi$ distribution from external measurement data.
$\chi$ reconstruction: reconstructing a magnetic $\chi$ distribution from a MR phase image.
$\chi_0(r)$: $\chi$ reconstruction with magnetic dipole model ($\chi_0(k)$ in Fourier domain).
$\chi(r)$: $\chi$ source, or processed $\chi$, or $\chi$ reconstruction with modified kernel ($\chi(k)$ in Fourier domain).
$\Delta\chi(r)$: susceptibility perturbation in reference to the baseline.
$b(r)$: 3D fieldmap ($b(k)=FT[b(r)]$ in Fourier domain)
$h_0(r)$: point magnetic dipole field (standard 3D convolution kernel).
$H_0(k)=FT[h_0(r)]$: standard $\chi$ reconstruction filter.
$f(k)$: filter for post-recon $\chi$ filtering (as used by $\chi(k)=\chi_0(k)\cdot f(k)$) in Fourier domain).
$H(k)$: modified deconvolution filter ($H(k)=H_0(k)/f(k)=FT[h(r)]$ in Fourier domain
$h(r)$: modified deconvolution kernel (as formed by $h(r)=h_0(r)*FT[1/f(k)]$)
$\epsilon(r)$ Gaussian additive noise ($\epsilon(k)$ in Fourier domain).
$\|\chi\|_{TV}$: TV norm of $\chi$.
$|C|$: taking absolute value of C (complex modulo operation)
$\angle C$: taking phase angle of a complex number C (complex argument operation)
$\lambda$: TV regularization parameter.
$\gamma_1, \gamma_2$: auxiliary parameters of TV iteration
$\Omega(x, y, z)$: voxel at (x, y, z).
$|\Omega(x, y, z)|$: voxel size ($=d_0 \times d_0 \times d_0$) (MR image resolution)
$c, c_0, c_1, c_2$: constants.
$\epsilon_0$: a threshold for filter truncation ($0<\epsilon_0<<1$).

BRIEF SUMMARY OF THE INVENTION

The $\chi$ reconstruction methods of the present invention are based on our CIMRI model [17]. In this invention, we reconstruct the intact magnetic susceptibility source distribution by a computed inverse magnetic resonance imaging scheme (CIMRI) and use it for static tissue iron measurement and dynamic heme-iron perturbation depiction. In the sense of 3D tomographic susceptibility source reproduction from external T2*MRI observations, the CIMRI is used to implement magnetic susceptibility tomography.

The CIMRI-based 3D susceptibility tomography is implemented by two steps: Step 1: calculating the fieldmap from the MR phase image; Step 2: calculating the susceptibility distribution from the fieldmap (obtained at step 1) by a total-variation-regularized deconvolution method with an implementation of split Bregman iteration. For static brain structural imaging, CIMRI implements 3D magnetic susceptibility tomography; and for dynamic brain functional imaging, CIMRI implements 4D magnetic susceptibility tomography by reconstructing a susceptibility volume from a MR phase volume at each snapshot time.

Our CIMRI method for 3D susceptibility tomography is optimally performed on a volumetric MR image acquired with isotropic voxels and zero oblique angle (with axial slices perpendicular to $B_0$). The reconstructed $\chi$ source can be post-processed by lowpass, highpass, bandpass, and bandstop filtering to extract specific susceptibility features. We show that the post-reconstruction filtering ("post-recon filtering" can be equivalently achieved during TV iteration with a modified filter, termed as "TV-iteration filtering". With a MR phase volume, the "post-recon filtering" and the "TV-iteration filtering" can be implemented in parallel. The two results are averaged to reduce the noise. Since the TV iteration is insensitive to the regularization parameter values, we developed a noise reduction strategy by rendering parallel TV iteration reconstructions (using different parameter values) and then averaging the multiple reconstructions. The reconstructed 3D magnetic susceptibility map is interpreted as a snapshot capture of internal iron distribution.

For a BOLD ƒMRI study on a dynamic physiological process, which produces a 4D MR image dataset; from which we can implement 4D magnetic susceptibility tomography: reconstructing a 4D $\chi$ dataset by applying CIMRI to each snapshot volume. To make use of external stimulus paradigm (always available for BOLD ƒMRI study), we developed a criterion of susceptibility timecourse synchrony for the 4D susceptibility tomography: the reconstructed susceptibility timecourse at an active region should be synchronous with the stimulus timecourse. Upon the reconstruction of a dynamic 4D $\chi$ dataset, we developed a $\chi$-based BOLD activation depiction or neuroimaging, which is implemented with a conventional brain mapping and neuroimaging technique only by replacing the 4D MR magnitude dataset with our reconstructed 4D magnetic susceptibility dataset.

Concerning the fact that the static field inhomogeneity effect (T2' effect) can be refocused or canceled by spin-echo imaging, we invented a unique T2'-effect imaging scheme (shortly T2' imaging) to obtain a T2' complex image. With a T2' complex image, we calculate the T2' phase image and the T2' fieldmap. Supposing the random T2 and diffusion effects are largely repeatable at successive scans under the same circumstance, the $\chi$ reconstruction from a T2' fieldmap improves the $\chi$ tomography fidelity due to the removal of repeatable random T2 and diffusion effects.

In summary, we have developed a CIMRI model for 3D susceptibility tomography, with an implementation of 3D deconvolution by a 3D split Bregman TV-regularized iteration method. We further enhanced the 3D $\chi$ reconstruction by: 1) filtering the reconstructed susceptibility pattern by modifying the TV iteration convolution kernel; 2) performing parallel reconstruction and multi-reconstruction average for noise reduction; and 3) using T2' phase image to improve $\chi$ reconstruction fidelity. We clarify that the MR magnitude image is not a tomographic representation of the $\chi$ source; and that the magnetic susceptibility tomography can be implemented by CIMRI. Accordingly, the 3D magnetic susceptibility tomography can be used for tissue iron measurement. By repeating CIMRI for 3D $\chi$ tomography for each snapshot volume, we can implement 4D $\chi$ tomography for 4D BOLD $f$MRI study, in which using the 4D $\chi$-dataset provides a more direct and truthful brain functional mapping (or neuroimaging) than using the conventional 4D MR magnitude dataset.

BRIEF DESCRIPTION OF THE DRAWINGS

The accompanying drawings, which are incorporated in and form part of the specification, illustrate various examples of the present invention and, together with the detailed description, serve to explain the principles of the invention.

FIG. 16. Illustrations of strip feature extraction by designing the filters for horizontal stripe extraction (at top row.

DEFINITIONS

Figure 1:
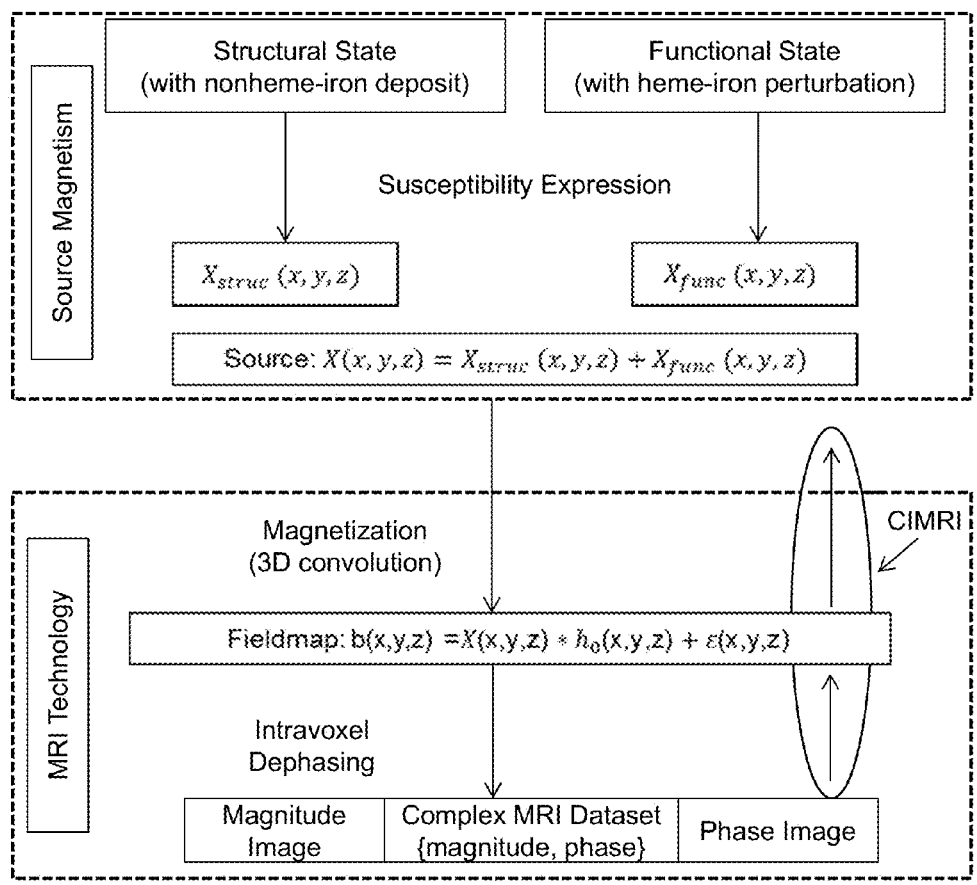
FIG. 1. The T2*MRI and CIMRI model. The T2*MRI model is decomposed into two modules: "Source Magnetism" (in the upper dotted box) and "MRI technology" (in the lower dotted box). The downward arrows indicate the forward procedure and the upward arrows indicate the backward procedure. The CIMRI model consists of two steps as diagramed in the circle.
Figure 2A:
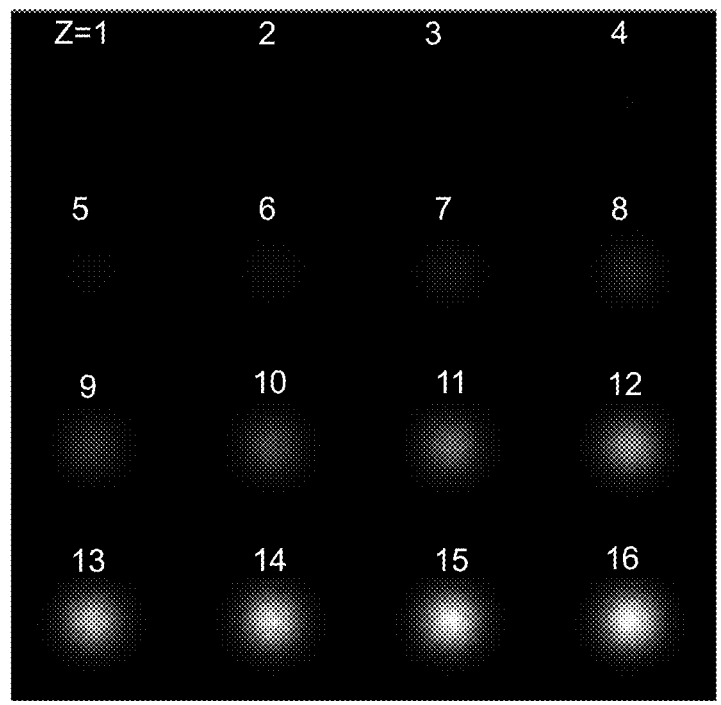
FIG. 2. (a) A predefined 3D $\chi$ distribution (16 z-slices of Gaussian blob), and (b) the magnitude image of the T2*MRI simulation.
Figure 2B:
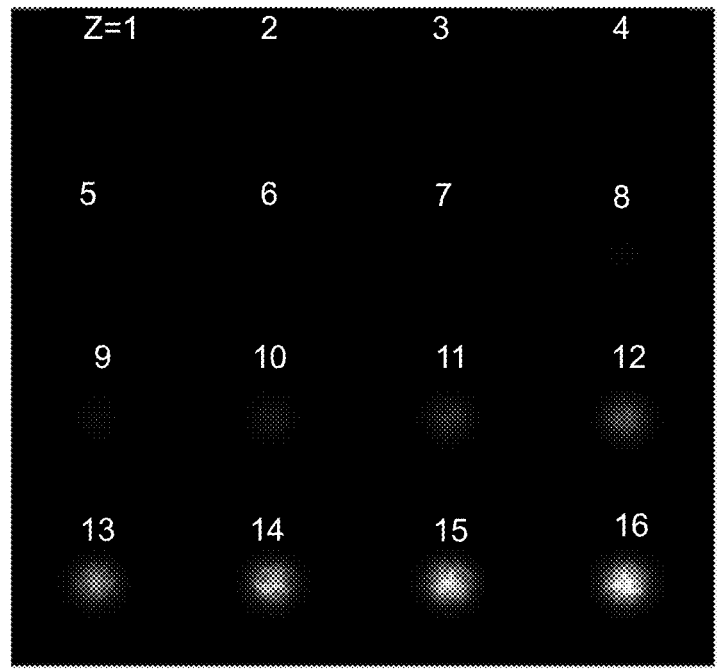
Figure 3A:
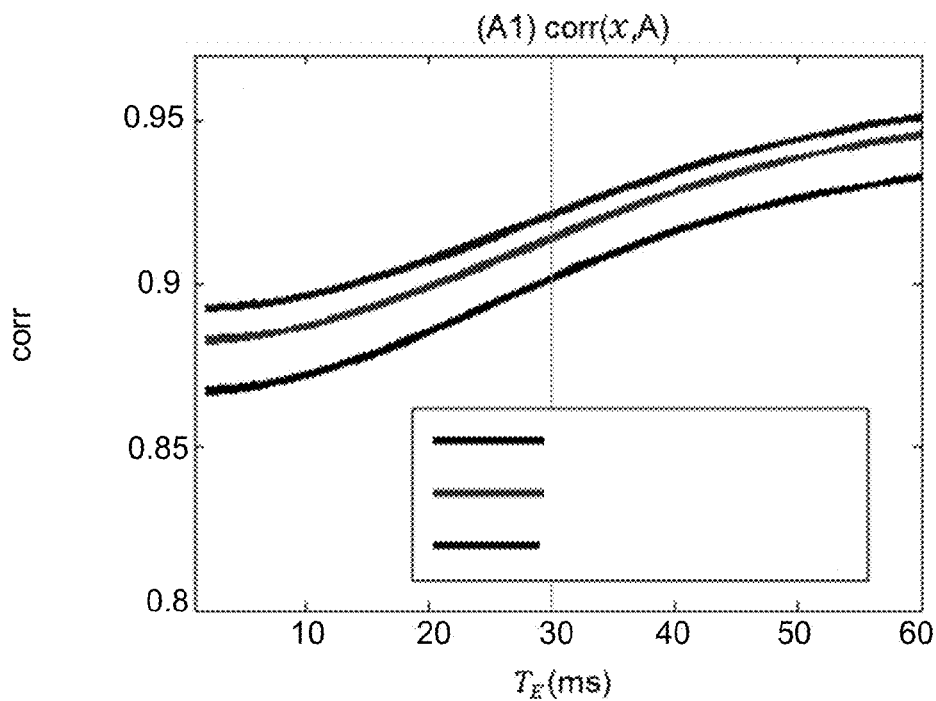
FIG. 3. The spatial correlations between the T2*MRI magnitude (denoted by A) and the predefined $\chi$ distribution for two intravoxel vasculatures (2-um-radius in (a1) (FIG. 3A) and 4-um-radius in (a2)) (FIG. 3B) and for three voxel sizes (see legend).
Figure 3B:
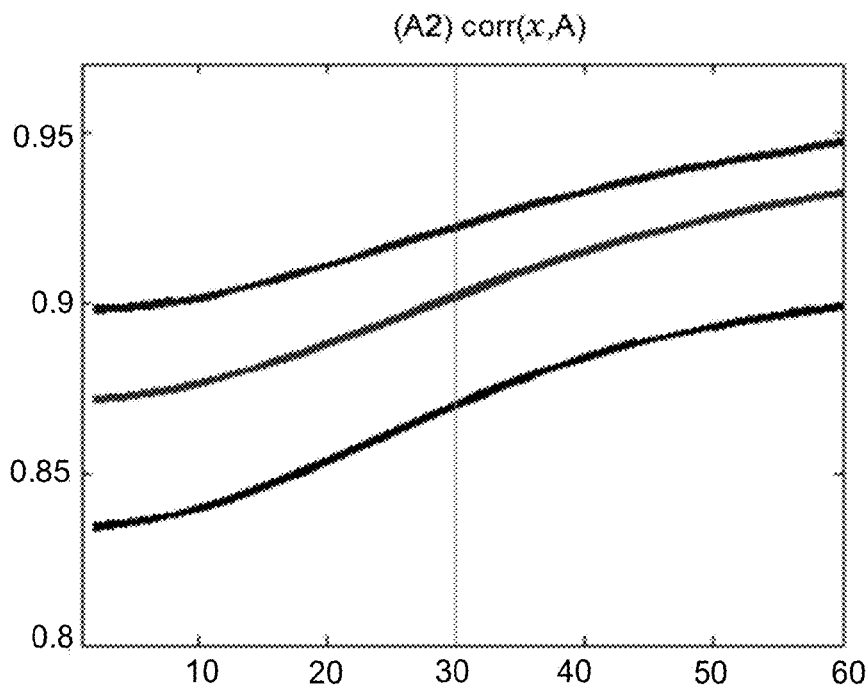

CIMRI: Computed Inverse Magnetic Resonance Imaging. It is a computational model for reconstructing the magnetic susceptibility source of T2*MRI by reversing the forward MRI procedure by computations. It comprises two computation steps: fieldmap calculation from MR phase image and susceptibility calculation from the calculated fieldmap. The CIMRI provides a means for magnetic susceptibility tomography.

Magnetic susceptibility tomography. Reconstruction of internal magnetic susceptibility distribution of an entity through the use of external MR measurement. The magnetic susceptibility tomography can be implemented by a computed inverse magnetic resonance imaging (CIMRI) model.

3D convolution magnetization. When a foreign nonferrous material is introduced into a magnetic field, it is subject to a magnetization process (due to the material and field interaction), which can be described by a magnetic dipole model in the linear magnetization regime. We describe the nonferrous material magnetization in a field by a 3D convolution model (with the convolution kernel of point magnetic dipole field) and reconstruct the material magnetic susceptibility through the framework of 3D deconvolution image restoration.

Small angle regime. This term refers to a spin precession angle that is very small, such that $\exp(-i\phi) \sim 1-i\phi$, with $\phi=\gamma \cdot b \cdot T_E$ (Larmor law), where: $\gamma$ denotes gyromagnetic ratio, b the magnetic field disturbance (the main field $B_0$ is excluded in the rotating frame representation), and $T_E$ the precession time (or relaxation time, or echo time in a gradient echo sequence). In small angle regime, the fieldmap and MR phase image are different only by a $T_E$-dependent scale factor. The condition of small angle regime can be reached by MR scanning with a small $T_E$ in a low field.

TV iteration: Total Variation iteration (or TV regularization). It is an iteration procedure for finding the optimal solution that simultaneously minimizes the TV norm and data fidelity. In this invention, we generalized the TV iteration for conventional 2D image restoration to accommodate our 3D deconvolution $\chi$ reconstruction (the core technology of CIMRI). We invented a 3D split Bregman iteration algorithm as an effective and efficient implementation of TV-regularized deconvolution problem.

Post-recon processing or Post-recon filtering. This is a postpocessing step exerted on a reconstructed susceptibility distribution. After the $\chi$ reconstruction by CIMRI, we process the reconstructed $\chi$ by imposing a spatial filtering, so as to produce specific desirable features. Typical post-recon processing strategies include: low-pass, highpass, bandpass, bandstop filtering.

Standard TV iteration and standard $\chi$ reconstruction. If the TV iteration uses the kernel of point magnetic dipole field (denoted by $h_0(r)$) (corresponding a standard filter $H_0(k)=FT[h_0(r)]$ in Fourier domain), we refer to the TV iteration as a "standard TV iteration", and the iteration output as the "standard $\chi$ reconstruction".

TV-iteration convolution. This term refers to a TV iteration process that uses a modified convolution kernel (based on $h_0(r)$). During a TV iteration process, each iteration is carried out by a 3D convolution with the same convolution kernel h(r) (a modification of $h_0(r)$) and TV regularized minimization. Based on linear filtering theory, we show that a spatial filtering exerted on a 3D reconstructed $\chi$ (as described by post-recon filtering) can be equivalently achieved during TV iteration using a modified kernel.

TV-iteration filtering. In practice, the 3D TV-iteration convolution can be efficiently implemented by performing the 3D iteration convolution part using 3D iteration filtering in the Fourier domain. Let h(r) represents the TV-iteration convolution kernel, the TV-iteration filter H(k) is calculated by H(k)=FT[h(r)], where FT stands for Fourier transform.

Reciprocal filter. The filter $1/f(k)$ is called the reciprocal of the filter $f(k)$. Reciprocal filter is also called an inverse filter.

TV-iteration kernel design. This term refers to the design of TV iteration convolution kernel h(r). We design a TV iteration convolution kernel from a filter that is used for post-recon filtering. The convolution kernel design is formed by $h(r)=h_0(r)*IFT[1/f(k)]$, where $h_0(r)$ represents the magnetic dipole kernel, $f(k)$ the filter designed for post-recon filtering, and IFT the inverse Fourier transform.

TV-iteration filter design. In the Fourier domain, the TV-iteration kernel design by $h(r)=h_0(r)*IFT[1/f(k)]$ can be expressed by $H(k)=H_0(k)/f(k)$, which is called "TV-iteration filter design"; where $H_0(k)=FT[h_0(r)]$ represents the magnetic dipole filter, and $f(k)$ the filter designed for post-recon filtering.

Comeback noise or residual noise. This term refers to the random and sparse noise that is brought back during TV iteration. The pattern and distribution of the comeback noise varies during TV iteration process and with the TV iteration setting. Two TV iterations with different parameter settings do not bring back the same noise pattern. The comeback noise is also called residual noise. Usually, the comeback noise randomly and sparsely emerges in uniform regions.

Parallel TV iteration. This term refers to performing multiple TV iterations on the same fieldmap dataset with different iteration parameter settings, which are carried out in a manner of parallel computations. In this invention, we use parallel TV iteration for the purpose of average noise reduction via parallel computations.

Multi-recon average: multi-reconstruction average. The output of parallel TV iteration comprises a multitude of $\chi$ reconstructions, which have different residual noise (or comeback noise). We average the multiple $\chi$ reconstructions to make a so-called "multi-recon average". The multi-recon average can reduce random sparse comeback noise (at the cost of performing multiple TV reconstructions).

$\chi$ tomography. Based on the conclusion that the magnetic susceptibility property (denoted by $\chi$) represents the underlying source of T2*MRI, and that the MR magnitude image is a distortedly transformed image of $\chi$ (due to local average and nonlinearity of MRI detection). We developed methods for performing magnetic susceptibility tomography ($\chi$ tomography), and we implement it by doing T2*MRI and CIMRI, that is (conceptually), $\chi$ tomography=T2*MRI+CIMRI. In this specification, the term "$\chi$ tomography" refers to $\chi$ tomographic reconstruction from T2*MRI data by CIMRI, and it is used interchangeably with the term "$\chi$ reconstruction".

Structural $\chi$ tomography (3D $\chi$ tomography). The structural $\chi$ tomography provides a $\chi$ distribution that is interpreted as iron deposit measurement for biological tissue and organs. A $\chi$ distribution can be obtained by CIMRI from a complex MR image. In contrast to functional $\chi$ tomography, the content of structural reconstructed $\chi$ is mainly the static nonheme iron deposit in tissue or organ (the microbleeding is considered as static in relative to small $T_E$).

Functional $\chi$ tomography (4D $\chi$ tomography). This term refers to as reconstructing the dynamic $\chi$ perturbations (imposed on a background) from a 4D complex MR dataset (acquired by BOLD fMRI) by implementing snapshot $\chi$ reconstruction by CIMRI. In contrast to structural $\chi$ tomography, the content of reconstructed $\chi$ at a snapshot time consists of both static nonheme iron deposit (background or baseline) and dynamic heme iron perturbation (due to brain functional activity). In contrast to the conventional magnitude-based brain mapping and neuroimaging, we invented the concept of χ-based functional imaging, which replaces the MR image dataset with the reconstructed χ dataset. The χ-based functional imaging improves the neuroimage depiction, because the reconstructed χ distribution is a more direct and truthful representative of the neuroactivity than the MR magnitude image.

Timecourse synchrony. This term refers to a synchronous response to an external stimulus paradigm. At the brain activation region, the MR signal is formed due to the neuroactive response to the external stimulation. Therefore, the signal timecourses are highly correlated with the stimulus timecourse (usually with a time lag of 2 to 4 seconds). With the magnitude timecourse synchrony, we can find the brain active site on the temporal correlation map (the conventional neuroimage depiction technique). Since the underlying source of BOLD fMRI signals is the susceptibility perturbation, it is understandable that the internal susceptibility perturbation should be synchronous to the external stimulation (with a time lag due to homodynamic response latency). Therefore, we developed a susceptibility synchrony criterion for reconstructing a meaningful 4D susceptibility dataset. That is, the susceptibility timecourse from the reconstructed 4D susceptibility dataset at the neuroactive regions assumes a high correlation with the external stimulation (with a time lag), where the neuroactive site can be determined by finding the maxima at the 3D magnitude temporal correlation map.

T2* gradient-echo imaging (also T2* imaging). This term refers to acquiring a gradient-echo image, which consists of all the transverse dephasing contributions, including the inhomogeneous fieldmap T2' effect, spin-spin interaction T2 effect, and the proton diffusion effect. The conventional EPI pulse sequence is an implementation of T2* imaging.

T2* spin-echo imaging (e.g. T2 imaging). This term refers to acquiring a spin-echo image that only captures the T2 and diffusion random effects, with the static inhomogeneity dephasing canceled by 180° pulse refocusing. T2* spin-echo imaging is always called "T2 imaging". We describe T2 image by a different name of "T2* spin-echo imaging" and use it to make a pair of T2* gradient-echo and spin-echo images.

T2'-effect imaging (T2'MRI). We invented this scheme to obtain a complex image that consists of only static (non-random) inhomogeneous field effect (the T2' effect). The T2'-effect imaging algorithm produces a complex image by a complex division of a T2* GE complex image divided by a T2* SE complex image. The output of T2'-effect imaging, denoted by T2'MRI, is not a map of T2' parameter, so our T2'-effect image scheme is different from the T2' imaging scheme. That is, T2'MRI is different from the conventional T2' imaging in that: T2'MRI deals with the MR images per se, not involving the calculation of T2' decay parameters for T2' imaging.

T2'-effect phase image (or T2' phase image). The T2'-effect phase image is calculated from T2'-effect complex image, which is in turn calculated from a pair comprising: a T2* GE complex image and a T2* SE complex image, by a complex division.

T2'-effect fieldmap (or T2' phase image). The T2'-effect fieldmap is proportional to the T2'-effect phase image by a constant factor. The T2'-effect fieldmap consists only of the static inhomogeneous fieldmap with the random T2 effect removed by the T2'-effect image scheme. Therefore, the T2'-effect fieldmap can be used for improving the χ reconstruction fidelity.

MR Image. The word "image" (e.g., "a MR phase image") is broadly defined as meaning "a 3D volumetric array (x,y,z) of voxel signal values, whose voxel values are measured at a single $T_E$ value" (i.e., multivoxels). Also, the words: "map", "distribution", "volume", "data", "3D image", "3D map", "3D distribution", "3D volume", "volumetric map", "3D image dataset", and "3D data", are equivalent to, and interchangeable with, the word "image", as it is defined above. The term "4D dataset" refers to a timeseries of MR images with 3D space and 1D time, as denoted by (x,y,z,t). The output of T2*MRI is a 3D MR image, and the output of a BOLD fMRI study is a 4D dataset that consists of a timeseries of volumetric (3D MR) images captured by T2*MRI at each snapshot in time.

MR Signal. Traditionally, a MR signal refers to the free induction decay (FID) behavior of proton spin precessions with respect to relaxation time. In the context of MRI, a MR signal refers to the FID of a specific voxel with respect to the echo time $T_E$. A MR image is a multivoxel array whose voxel values assume the voxel signals at a single value of $T_E$. Both the MR voxel signal and MR multivoxel image are complex-valued in nature. In this invention, we do not need to perform MR signal observation. Instead, we involve MR multivoxel image capture by T2*MRI with a single echo time $T_E$ (or a few of $T_E$'s).

DETAILED DESCRIPTION OF THE INVENTION

It is widely accepted that the MRI technology is an excellent noninvasive imaging modality for biological soft tissue and physiological state imaging. Currently, only the magnitude image of a MR complex image is used to represent a physiological state or a brain interior, whereas the phase image remains largely unused. In this section, we show that the MR magnitude image is not an exact representation of the underlying susceptibility source, and that the MR phase appears textural, noisy, spatially blurred. Our invention makes use of MR phase image for the χ source reconstruction. Relevant theory, models, algorithms are provided. The algorithm implementations are demonstrated with numerical simulations. Details about the parameter settings, and implementations of two numerical simulation examples are provided in Appendix A. A phantom experiment, and a real human brain imaging experiment, are presented later in separate sections.

In some preferred embodiments of the present invention, the multivoxel values that populate a 3D volumetric array (x,y,z) of multiple voxel signal values (i.e., an "image") are measured at a single TE, using a complex EPI or EVI pulse sequence, after a RF pulse has been applied.

Overall, we describe a new model of computed inverse magnetic resonance imaging (CIMRI) [17] to reconstruct a 3D susceptibility distribution (denoted by x) based on a MR phase volume image acquired by T2*MRI technology (applied to tissue/organ imaging of human subjects or animals). Essentially, the CIMRI model is to reverse the forward T2*MRI procedure by two computational steps: first calculating a fieldmap from a MR phase volume and then calculating a χ map from the computed fieldmap. In the sense of intact (free from the transformations exerted by T2*MRI) magnetic susceptibility source reconstruction, CIMRI implements magnetic susceptibility tomography (x tomography). The 3D χ reconstruction algorithm involves a 3D ill-posed deconvolution, for which we developed a 3D total variation (TV) regularized iteration solver with an efficient implementation of split Bregman iteration [17, 21]. For dynamic BOLD fMRI study, the output is a 4D complex MR dataset; from which we can reconstruct a 4D χ dataset by reconstructing each 3D snapshot volume with CIMRI (4D χ tomography).

The χ tomography by CIMRI offers a quantitative interpretation of iron deposit in a tissue/organ physiological state, structural or functional, static or dynamic, patient (physiopathology) or healthy, human or animal. Specifically, a reconstructed χ volume for a static tissue/organ state is interpreted as iron deposit therein, and a reconstructed snapshot χ volume in a dynamic BOLD process is interpreted as a composite of static brain structural iron deposit (baseline) and dynamic brain function heme-iron distribution (BOLD activity). It is known that the susceptibility distribution is the underlying source of T2*MRI, and it can represent a physiological state more directly than the MR magnitude image in the sense of its timing closeness and intactness (prior to T2*MRI scanning and being free from imaging transformations) [19]. Therefore, in this invention, we replace the MR image dataset with the reconstructed χ source dataset for more direct and truthful structural and functional brain image depictions.

Some innovative features of our methods of χ tomography using CIMRI include the following aspects:

1. We describe the fieldmap establishment from a 3D χ source via magnetization in a main field by a 3D convolution model, which offers two advantages: explanation of the morphological mismatch between the χ source and the fieldmap (corresponding to phase image), and implementation of 3D χ tomographic reconstruction in the framework of 3D-deconvolution image restoration.
2. We solve the ill-posed 3D deconvolution problem associated with the 3D χ source tomography by a novel and unique 3D split-Bregman TV-regularized iteration method; for which we also developed a self-calibration scheme that selects the regularization parameter values (usually a range of values) by making use of the MR magnitude image to as an initial estimate of χ reconstruction.
3. We developed an improved TV-iteration filtering scheme by using a modified TV iteration filter that can achieve the similar results of spatial post-reconstruction filtering.
4. We discovered that the TV iteration is almost invariant to a wide range of TV regularization parameter values, and it is almost invariant to DC term reset. However, the TV iteration may bring back sparse noise in the uniform regions. We developed a noise reduction strategy by performing parallel TV iteration reconstructions (for the same fieldmap dataset but using different iteration parameter values), followed by a multi-reconstruction average.
5. We generate a 4D χ dataset from a 4D complex MR dataset (acquired by BOLD ƒMRI) by reconstructing each snapshot susceptibility volume from a MR phase volume in the 4D complex MR dataset by CIMRI. In order to make use of the external stimulus paradigm, we developed a criterion of susceptibility timecourse synchrony: the reconstructed susceptibility timecourse at the brain active site should maximally correlate with the timecourse of external stimulation.
6. We developed a unique T2'-effect imaging scheme to remove the random T2 and diffusion effects by acquiring a pair of T2* gradient-echo and spin-echo complex images and processing them by an element-wise complex division. By calculating the T2' phase image from a T2' complex image and using it for χ reconstruction, we can improve the χ reconstruction fidelity. Our T2'-effect imaging scheme does not involve exponential decay assumption, or the calculation for T2, T2* and T2' parameters.
7. For applications, we developed a brain structural χ tomography scheme for nonheme-iron deposit measurement in tissue and organs, and a brain functional χ tomography scheme for heme-iron perturbation measurement for brain mapping and neuroimaging.

Our CIMRI methods are based on the 3D volumetric MR image that may be acquired by stacking slices (as acquired by EPI for example) or preferably by volume imaging (as acquired by EVI for example). Our reconstruction algorithm is based on 3D volume image, not based on a 2D slice image or on a few number of individual voxels. Our methods do not involve the calculation of susceptibility gradient vector map.

Our CIMRI methods do not use a by-side phantom for MRI data acquisition, and our iterative susceptibility reconstruction algorithm is based on a 3D total-variation-regularized split Bregman iteration on the MR phase volume data per se, not involving by-side phantom data. In our methods, the MR phase image is acquired by the conventional T2*MRI procedure (through the use of a standard 2D EPI sequence or a 3D EVI sequence), which is not involving a particular requirement for anisotropic diffusion imaging.

Basic Concepts of T1, T2, T2', and T2* Signal

According to MRI physics [1, 2], T1 signal represents the longitudinal magnetization recovery after a stimulus of radio frequency (RF) pulse; T2 signal represents the transverse magnetization dephasing due to random spin-spin interaction (even if in a homogenous field), and T2* signal represents the total transverse magnetization dephasing in an inhomogeneous field, consisting of both the T2 random effect and the inhomogeneous field effect (T2' effect). Assuming an exponential model for signal intensity decay, the T1, T2 and T2* signals are expressed by:

$$M_z(t) = M_z(t=0)(1-\exp(-t/T_1))$$

$$M_\perp(t) = M_\perp(t=0)\exp(-t/T_2) \text{ (in homogeneous field)}$$

$$M_\perp(t) = M_\perp(t=0)\exp(-t/T_2^*) \text{ (in inhomogeneous field)} \quad (1)$$

with $1/T_2^* = 1/T_2 + 1/T_2'$

It is noted that among the total T2* signal, the T2-effect contribution is due to random spin-spin interaction which is determined by the media of spin protons, and the T2' effect is due to dephasing in an inhomogeneous field, which represents what we are pursuing in this report. The T2* signal is detected by gradient echo (GE) imaging, which is essentially a free induction decay signal (FID) reflecting the tissue media property. We should point out that, in this report, we do not need to calculate the T2, T2' and T2* parameters by the exponential formulas in Eq. (1); we only deal with complex-valued images per se as resulted from T2 and T2* effects; we obtain a T2' complex image by a complex division of T2* image and T2 image. Concerning the fact that, a T2 signal (due to random spin-spin interaction) is non-refocusable by 180° pulse, and that the T2'signal (dephasing due to inhomogeneous field) is refocusable, and that the T2* signal consists of both T2 and T2' effects, we developed a T2' imaging scheme (by a complex division) that can provide a complex image due to static inhomogeneous field that excludes the unwanted random T2 effect (as well be reported later).

The T2*MRI and CIMRI models

Since we are concerned with an inhomogeneous χ reconstruction from its magnetized inhomogeneous fieldmap, we only address the T2*MRI, which is a non-invasive imaging modality for the measurement of inhomogeneous fieldmap in a main field $B_0$. It is known that the biomagnetism of a biological entity is mainly attributed to iron content. Overall, we describe the forward $\chi$ imaging (T2*MRI) in FIG. 1 by two modules. One is the "Source Magnetism" module (in the upper dotted box), and the other is the "MRI technology" module (in the lower dotted box). As diagramed in FIG. 1 for MRI-based brain imaging, the $\chi$ expression for a snapshot brain state consists of static structural and dynamic functional contribution, as denoted by $\chi(x,y,z)=\chi struc(x,y,z)+\chi func(x,y,z)$.

A T2*MRI procedure acquires a complex MR image for the $\chi$ source. We will show that the $\chi$ source distribution can be reconstructed from the MR phase image by reversing the MRI procedure, as designated by CIMRI (computed inverse MRI) in FIG. 1. For dynamic brain imaging, the $\chi$ expression for a brain functional process is a time-dependent 4D $\chi$ dataset, $\chi(x,y,z,t)$, which produces a complex-valued 4D MR image dataset by repeating the T2*MRI for each snapshot capture (as described by BOLD fMRI). We will show that we can reconstruct the 4D $\chi$ expression for a dynamic brain functional process by snapshot $\chi$ reconstruction, thus implementing 4D $\chi$ tomography.

FIG. 1 shows the T2*MRI and CIMRI models. The T2*MRI model is decomposed into two modules: "Source Magnetism" (in the upper dotted box) and "MRI technology" (in the lower dotted box). The downward arrows indicate the forward procedure and the upward arrows indicate the backward procedure. The CIMRI model consists of two steps, as diagramed in the circle.

As diagramed in FIG. 1, the forward MRI procedure undergoes two steps. The first step is the fieldmap establishment by susceptibility magnetization in a main field $B_0$, which can be expressed by a 3D convolution transformation [20]:

$$b(x, y, z) = B_0 \chi(x, y, z) * h_0(x, y, z) + \varepsilon(x, y, z) \quad (2)$$

$$\text{with } h_0(x, y, z) = \frac{1}{4\pi} \frac{3z^2 - |x^2 + y^2 + z^2|^{3/2}}{|x^2 + y^2 + z^2|^{5/2}}$$

(magnetic dipole kernal)

where $B_0$ denotes the main field, $\varepsilon(x,y,z)$ the noise, $h_0(x,y,z)$ (or $h_0(r)$) the 3D convolution kernel, which is the magnetic response of a point magnetic dipole at the origin (as described by point magnetic dipole model). In Fourier domain, the 3D convolution is represented by a 3D filtering, that is:

$$FT\{b(x, y, z)\} = H_0(k_x, k_y, k_z) \cdot FT\{\chi(x, y, z)\} \cdot B_0 \quad (3)$$

$$\text{with } H_0(k_x, k_y, k_z) \equiv FT\{h_0(x, y, z)\} = \frac{1}{3} - \frac{k_z^2}{k_x^2 + k_y^2 + k_z^2}$$

(magnetic dipole filter)

where FT denoted Fourier transform, and $H_0(k_x,k_y,k_z)$ the 3D filter (also denoted by $H_0(k)$, called standard filter) corresponding to the convolution kernel $h_0(x,y,z)$ in Eq. (2). It is noted that the DC term $H_0(0,0,0)$ is undefined due to a term of 0/0 (at $k_x=0$, $k_y=0$, $k_z=0$), which allows to reset it (as will be shown later).

The second forward step in FIG. 1 produces a complex-valued image by an intravoxel dephasing summation. For static intravoxel dephasing (ignoring diffusion effect), the multivoxel image is formed by:

$$C(x, y, z; T_E) = \frac{1}{|\Omega|} \iiint_{(x',y',z')\in\Omega(x,y,z)} e^{i\gamma b(x',y',z')T_E} dx'dy'dz' \quad (4)$$

where $\gamma$ denotes the proton gyromagnetic ratio, $T_E$ denotes the echo time (interpreted as an exposure time of T2*MRI), and $\chi(x,y,z)$ denotes the voxel at $(x,y,z)$, and $|\Omega|$ the voxel size.

From the complex-valued output $C(x,y,z)$ acquired by a forward T2*MRI procedure, we can extract its magnitude loss $A(x,y,z)$ and phase accrual $P(x,y,z)$ by $$\begin{cases} A(x, y, z; T_E) = \left|\frac{C(x, y, z; T_E = 0)}{C(x, y, z; T_E)}\right|, & \text{(magnitude loss)} \\ P(x, y, z; T_E) = \angle\left[\frac{C(x, y, z; T_E)}{C(x, y, z; T_E = 0)}\right], & \text{(phase accrual)} \end{cases} \quad (5)$$

The magnitude image $A(x,y,z)$ represents the 3D map of signal loss (decay), and the phase image $P(x,y,z)$ the phase angle accumulation during $T_E$ (decay signals in reference to non-decay signals at $T_E=0$).

Assuming that the voxel signal intensity follows an exponential decay, we can calculate the T2* parameter by:

$$C(T_E)=C(T_E=0)\exp(-T_E/T2^*) \text{(exponential decay model)}$$

$$A(T_E)=1-\exp(-T_E/T2^*) \text{(expoenetial magnitude loss)} \quad (6)$$

with which other researchers have used for T2*-based susceptibility mapping [3, 5, 6, 34-38]. It is noted that, in this report, we do not involve the exponential assumptions in Eq. (6) at all, and we only deal with the 3D T2*-effect images in Eq. (5). Therefore, we claim that our method is dealing with the T2 and T2* images per se, which is different from the T2 and T2*(or R2 and R2*) MR imaging techniques that involve the exponential models and decay rate calculation (requiring multi-time image acquisition through the use of a multi-echo sequence).

It is noted that the fieldmap establishment from susceptibility source by a 3D convolution in Eq. (2) is a linear and spatially spread transformation. Obviously, the complex modulo and complex argument operations in Eq. (5) are nonlinear. However, the susceptibility source reconstruction from fieldmap is a linear deconvolution problem. In small angle regime (a linear phase approximation condition), the fieldmap is linearly related to the MR phase image[19, 39], which simplifies the fieldmap calculation in the first inverse step of CIMRI. Nevertheless, the deconvolution of CIMRI is an ill-posed inverse problem that is a non-trivial task.

BOLD fMRI Model

For structural T2*MRI, the source of susceptibility distribution is attributed to the nonheme iron store, denoted by $\chi_{struc}(x,y,z)$. For dynamic BOLD fMRI, the total susceptibility distribution includes additional functional heme-iron contribution, as expressed by $$\chi_{total}(x,y,z,t)=\chi_{struc}(x,y,z)+\chi_{func}(x,y,z,t) \quad (7)$$

where the time-dependent susceptibility $\chi_{func}(x,y,z,t)$ is due to the neurovascular-coupled BOLD process. We express the susceptibility dynamics associated with a BOLD activity by [18, 40]

$$\chi_{func}(x,y,z,t) = \chi_{blood} \cdot V(x,y,z) \cdot NAB(x,y,z,t)$$

$$\chi_{blood} = Hct \cdot \chi_{RBC} + (1-Hct) \cdot \chi_{plasma}$$

$$\chi_{RBC} = \chi_{oxy} + (\chi_{deoxy} - \chi_{oxy}) \cdot (1-Y) \quad (8)$$

where Y denotes oxygenation level, $H_{ct}$ the blood hematocrit, $V(x,y,z)$ the vasculature-filled region, $NAB(x,y,z,t)$ the neuroactive blob which is modulated by the external stimulation, $\chi_{plasma}$ the magnetic susceptibility of blood plasma, $\chi_{oxy}$ the magnetic susceptibility of oxyhemoglobin, and $\chi_{deoxy}$ the magnetic susceptibility of deoxyhemoglobin with $\chi_{deoxy} - \chi_{oxy} = 0.27 \times 4\pi \times 10^{-6}$ (SI unit). For a BOLD process, we represent a BOLD state in terms of susceptibility perturbation in reference to a baseline state, denoted by $\Delta\chi(x,y,z,t)$, as expressed by $$\Delta\chi(x,y,z,t) \equiv (\chi_{deoxy} - \chi_{oxy})(1-Y) \cdot Hct \cdot V(x,y,z) \cdot NAB(x,y,z,t) \quad (9)$$

The susceptibility perturbation due to a functional activity is the underlying source of BOLD ƒMRI. Therefore, we can consider the BOLD ƒMRI as an application of T2*MRI technology to dynamic functional imaging by repeating the T2*MRI procedure for a timeseries of snapshot captures. It is noted that the 4D dataset represents a timeseries of 3D snapshot volumes.

Mismatch Between MR Magnitude Image and χ Source

We have found that there are two pitfalls inherent to the MR-magnitude-based image analysis [19], one is the magnitude's non-negativity nature which confounds the negative susceptibility values and positive susceptibility values; the other is an edge effect associated with the voxel signal formation, which manifests a central dip at a local relative plateau on a fieldmap. As a consequence of non-locality and nonlinearity associated with T2*ƒMRI, we conclude that the MR magnitude is not an exact representation of the susceptibility source. Fortunately, we have also found [17] that the MR phase image can be used for χ tomographic reconstruction by CIMRI.

In what follows, our description is based on a numerical simulation of T2*MRI. For dynamic functional imaging, the T2*MRI simulation can be considered as a snapshot capture of dynamic BOLD ƒMRI.

Considering a T2*MRI procedure as a 3D imaging process, we can numerically assess the T2*MRI model by numerical simulation [39, 41, 42]: predefining a susceptibility source, carrying out the forward T2*MRI procedure and producing a complex-valued MR image, and then comparing the output image with the predefined input source. In this way, we can quantitatively show that neither the MR magnitude image nor the MR phase image can exactly reproduce the susceptibility source. In other words, based on numerical simulations we will conclude that the MR image is not a tomographic reproduction of the susceptibility source.

Given a predefined input source (χ) and the calculated output (complex image), we can quantitatively compare the MR magnitude with χ by a spatial correlation as defined by $$\text{corr}(A, \chi; T_E) = \frac{\text{cov}\{A(:,:,T_E), \chi(:)\}}{\text{std}\{A(:,:,T_E)\}\text{std}\{\chi(:)\}} \quad (10)$$

where $A(:;T_E)$ represents the lexicographically ordered 1D array of the 3D array $A(x,y,z;T_E)$, $\chi(:)$ the 1D lexicographic array of $\chi(x,y,z)$, coy the covariance, std the standard deviation. In Eq. (10), $T_E$ is retained as an explicit parameter to remind the $T_E$-dependence of MR magnitude image. This correlation for matching two patterns is invariant to grayscale normalization (peak=1 is not required), and it produces a value for matching goodness in a range from 0 (completely different) to 1 (perfect matching with a difference of constant factor).

The predefined χ source and the calculated magnitude image are shown in FIG. 2. The quantitative measures of pattern matches for $T_E$ in a range of [0, 60] ms, two vessels sizes (intravoxel structures), and three spatial resolutions are shown in FIG. 3. FIG. 2 shows (a) a predefined 3D χ distribution (16 z-slices of Gaussian blob), and (b) the magnitude image of the T2*MRI simulation. FIG. 3 shows the spatial correlations between the T2*MRI magnitude (denoted by A) and the predefined χ distribution for two intravoxel vasculatures (2-um-radius in (a1) and 4-um-radius in (a2)) and for three voxel sizes (see legend).

The simulation results show that: 1) the pattern match between MR magnitude image and χ source gives rise to a correlation about 0.90, which is affected by voxel size (image resolution), vessel size, and echo time; and 2) a long $T_E$ is preferred to reduce the mismatch.

The simulation was done for a Gaussian-shaped χ distribution (predefined ground truth). In practice, a χ source may assume negative susceptibility value (due to negative diamagnetism of water and blood's diagmagnetic oxyhemoglobin). Therefore, we conclude the T2*MRI magnitude image is not an exact representation of the susceptibility source.

As mentioned above, we may explain the mismatch between the magnitude image and the susceptibility source from the following aspects: 1) The MR magnitude image suffers from two pitfalls: non-negativity and edge effect; 2) the process from susceptibility source to MR image acquisition is nonlinear (the summation of complex spin precession phasors is somewhat nonlinear [39], and the complex modulo operation is a severely nonlinear operation).

Morphometric Difference Between Fieldmap (or MR Phase) and χ Source

Figure 4A:
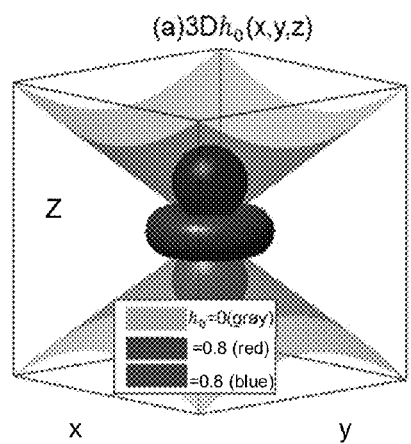
FIG. 4 (a) Visualization of the 3D convolution kernel $h_0(x,y,z)$ with three isosurfaces at isovalues of $\{0, 0.8, -0.8\}$; (b) a 2D quadruple pattern at a longitudinal plane at $h_0(x,0,z)$; (c) a digital texture detector associated with (b); and (d) a standard 2D digital edge detector. The 3D $h_0(x,y,z)$ is interpreted as a 3D texture template, which can enhance edges and boundaries.
Figure 4B:
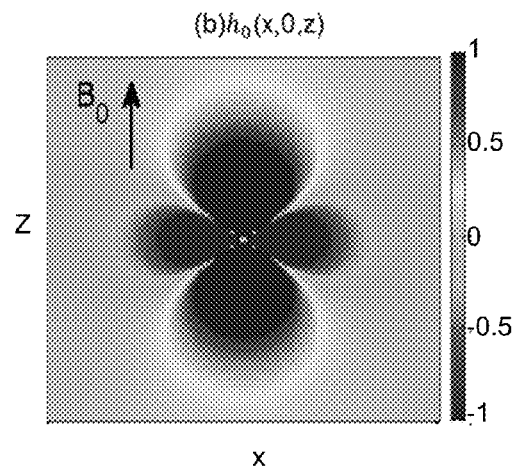
Figure 4C:
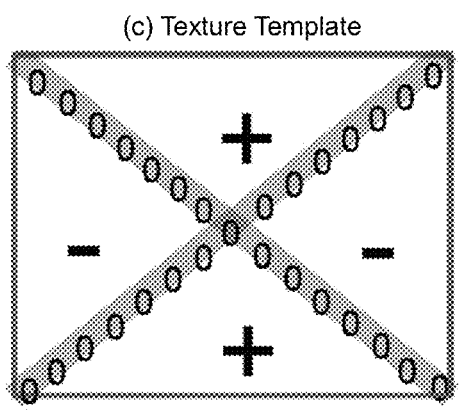
Figure 4D:
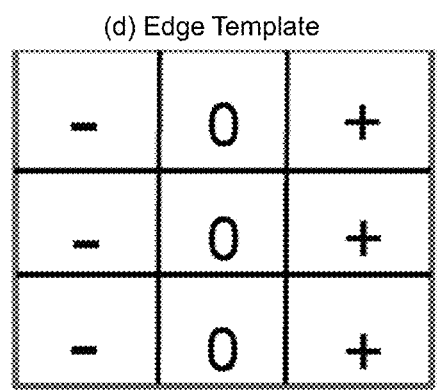
Figure 5A:
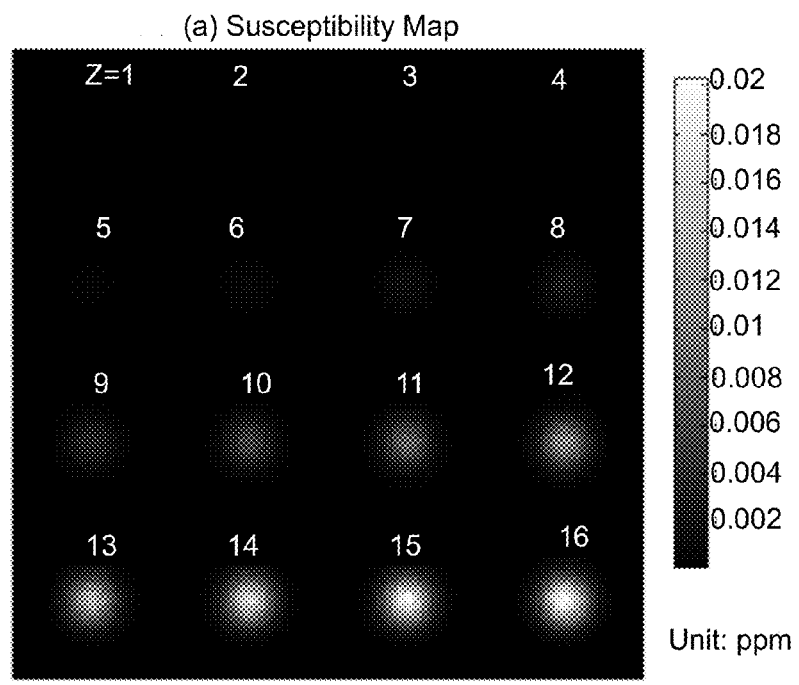
FIG. 5. Demonstration of the morphormetric difference between a Gaussian-shaped $\chi$ distribution in (a) and its fieldmap in (b). The 3D volume is represented by 32×32×32 matrix, only z=1:16 slices are displayed (z=16 at the central z-slice). It is noted the conspicuous morphormetric discrepancy between the fieldmap and the susceptibility map is due to a 3D convolution transformation.
Figure 5B:
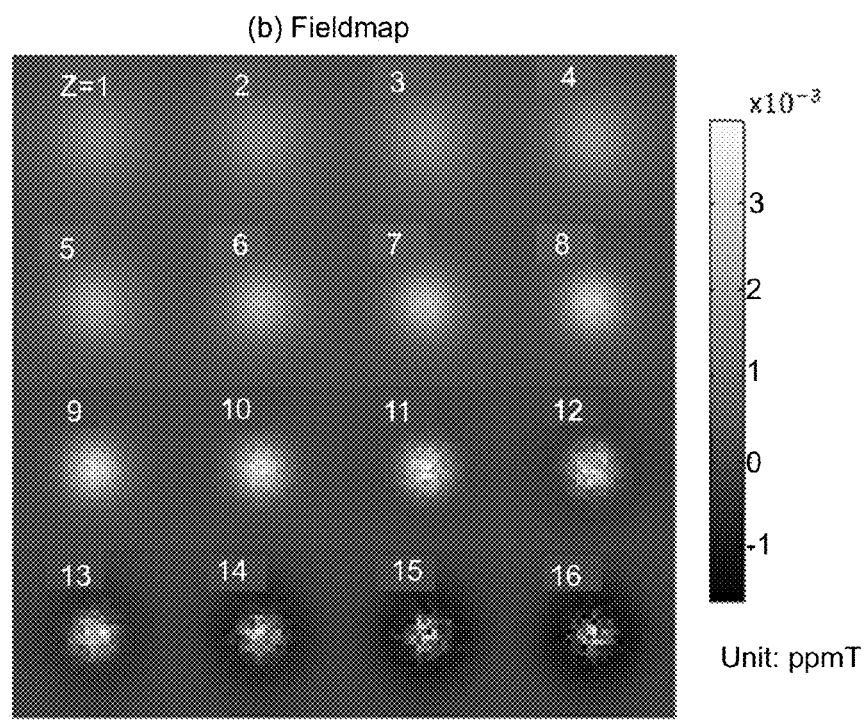

Considering Eq. (2) as a 3D imaging system, we can describe its 3D imaging transform through the characteristics of its 3D convolution kernel $h_0(r)$. It can be shown that $$\begin{cases} \iiint_{(x,y,z)} h_0(x,y,z)dx\,dy\,dz = H_0(0,0,0) & \text{(filter DC < 1)} \\ \iiint_{(x,y,z)} |h_0(x,y,z)|dx\,dy\,dz \gg H_0(0,0,0) & \text{(bipolar-valued kernel)} \end{cases} \quad (11)$$

where $H_0(k_x,k_y,k_z)$ is the Fourier transform of $h_0(x,y,z)$ (defined in Eq. (3)). Usually the DC term of the standard 3D filter $H_0(k_x, k_y, k_z)$ assumes $H_0(0,0,0)=1/3$ (when 0/0=0 is used in Eq. (11)). From the viewpoint of image processing [43], a convolution kernel $h_0(x,y,z)$ that possesses the properties in Eq. (11) serves as a 3D texture enhancer ($H_0(0,0,0)=0$ for texture detector). In FIGS. 4(a) and (b), we visualize the 3D kernel by 3D isosurfaces in (a) and a 2D slice in (b). The textural enhancement interpretation is illustrated in FIG. 4(c), where the template of bipolar-valued quadruple lobes can produce a large value in the fieldmap of a quadruple-patterned susceptibility distribution while greatly suppressing a local plateau. A texture enhancer can serve as an edge enhancer as well, as illustrated with a standard edge detector in FIG. 4(d), but is not optimal for edge detection. That is, the 3D convolution with a bipolar-valued kernel plays a 3D spatial derivative to some extent. FIG. 4 shows: (a) visualization of the 3D convolution kernel $h_0(x,y,z)$ with three isosurfaces at isovalues of $\{0, 0.8, -0.8\}$; (b) a 2D quadruple pattern at a longitudinal plane at $h_0(x,0,z)$; (c) a digital texture detector associated with (b); and (d) a standard 2D digital edge detector. The 3D $h_0(x,y,z)$ is interpreted as a 3D texture template which can enhance edges and boundaries.

Some characteristics of the 3D kernel $h_0(x,y,z)$ are summarized as follows [17, 19]:

1) It is of 3D spread distribution (not a point delta function), which explains the non-local property of the fieldmap and MRI phase image.
2) It is a 3D bipolar-valued kernel (not a unimode distribution like a Gaussian shape) and it manifests a 3D texture enhancer as understandable from Eq. (11) and FIGS. 4(*b*) and (*c*). Therefore, it is not surprising that the phase image appears noisy. It is noted that the fieldmap of a uniform $\chi$ distribution will be reduced by a factor of ⅓ (=$H_0(0,0,0)$) during the convolutional magnetization.
3) It bears a 3D zerosurface for $h_0(r)=0$ (see FIGS. 4(*a*) and (*c*)), which means the deconvolution is an ill-posed inverse problem.
4) It is anisotropic, which explains the orientation dependence in fieldmap and MRI image.
5) It is of radial symmetry about the origin and revolution symmetry about z-axis (see FIG. 4(*a*)).

The 3D convolution kernel in FIG. 4 is an unusual integral kernel because of its bipolar-valued multilobes, anisotropic spreading, and 3D zerosurface embedment. Usually, a convolution kernel for image blurring assumes a nonnegative distribution, like a Gaussian-shaped point spread function and a boxcar-shaped motion blurring function. In this report, we describe the fieldmap establishment by a 3D convolution model with a kernel of bipolar-valued multilobes, thereby we can solve the inverse problem (deconvolution) in the framework of image deconvolution restoration. To our knowledge, we are the first time to address the 3D $\chi$ reconstruction problem by extending the 2D image deconvolution restoration technique (TV regularized iteration, as will be presented later) and dealing with the unusual 3D convolution kernels.

Due to the 3D convolution of the $\chi$ source with the 3D unusual kernel in FIG. 4, we explain the morphometric difference between the $\chi$ source and the fieldmap, as demonstrated in FIG. 5. FIG. 5 shows a demonstration of the morphometric difference between a Gaussian-shaped $\chi$ distribution in (a) and its fieldmap in (b). The 3D volume is represented by 32×32×32 matrix, only z=1:16 slices are displayed (z=16 at the central z-slice). It is noted the conspicuous morphometric discrepancy between the fieldmap and the susceptibility map is due to a 3D convolution transformation.

Susceptibility Map Reconstruction from MR Phase Image

Figure 6:
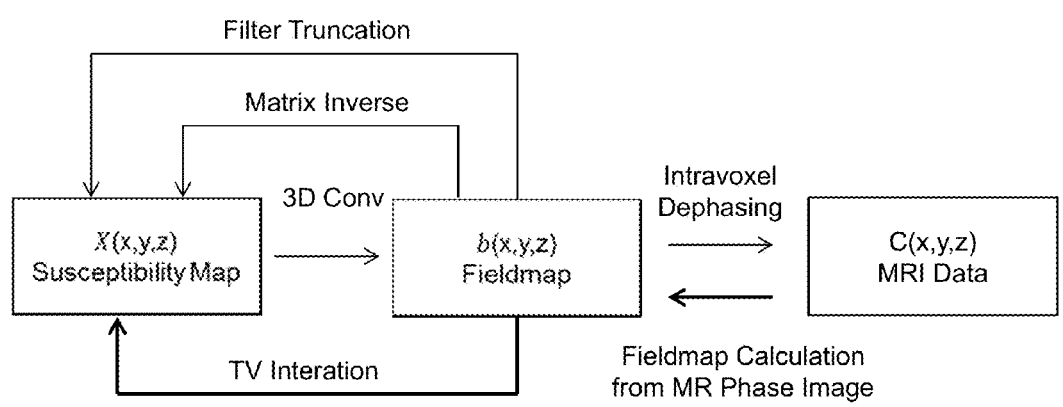
FIG. 6. The CIMRI model (diagramed with solid arrows). It consists of two inverse mappings: fieldmap calculation from MR phase image and $\chi$ reconstruction from the fieldmap. There are three solvers for $\chi$ reconstruction from fieldmap: filter truncation, matrix inverse, and TV iteration (our proposal). The forward MRI is diagrammed with rightward arrows.
Figure 7A:
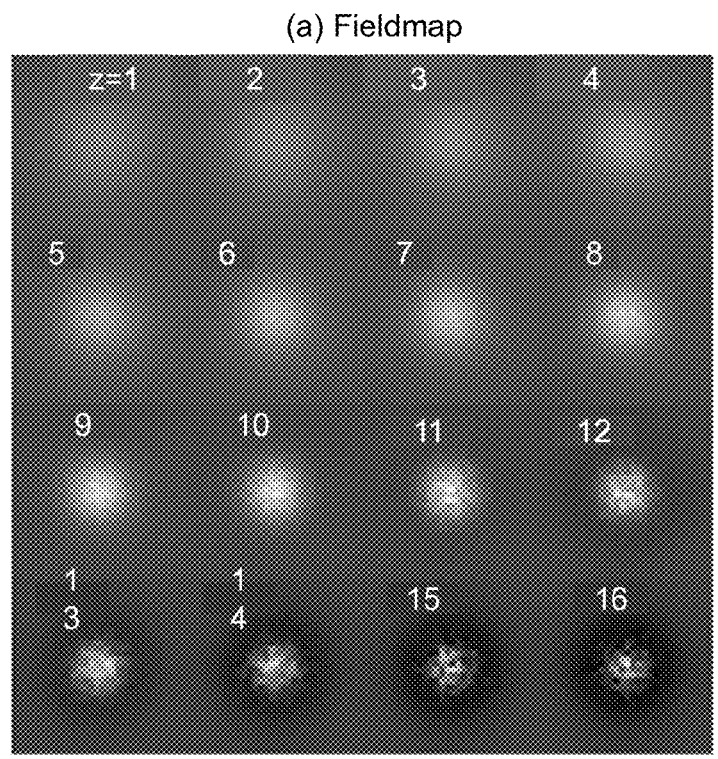
FIG. 7. (a) Precomputed fieldmap (resulting from a predefined neuroactive blob), and (b) the phase image of T2*MRI simulation. It is noted that the MR phase image can faithfully represent the fieldmap.
Figure 7B:
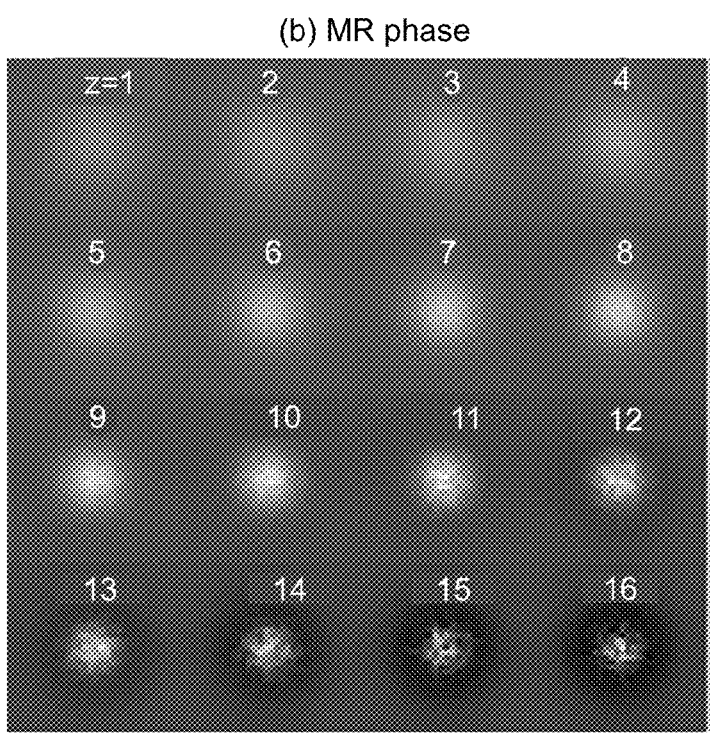
Figure 8A:
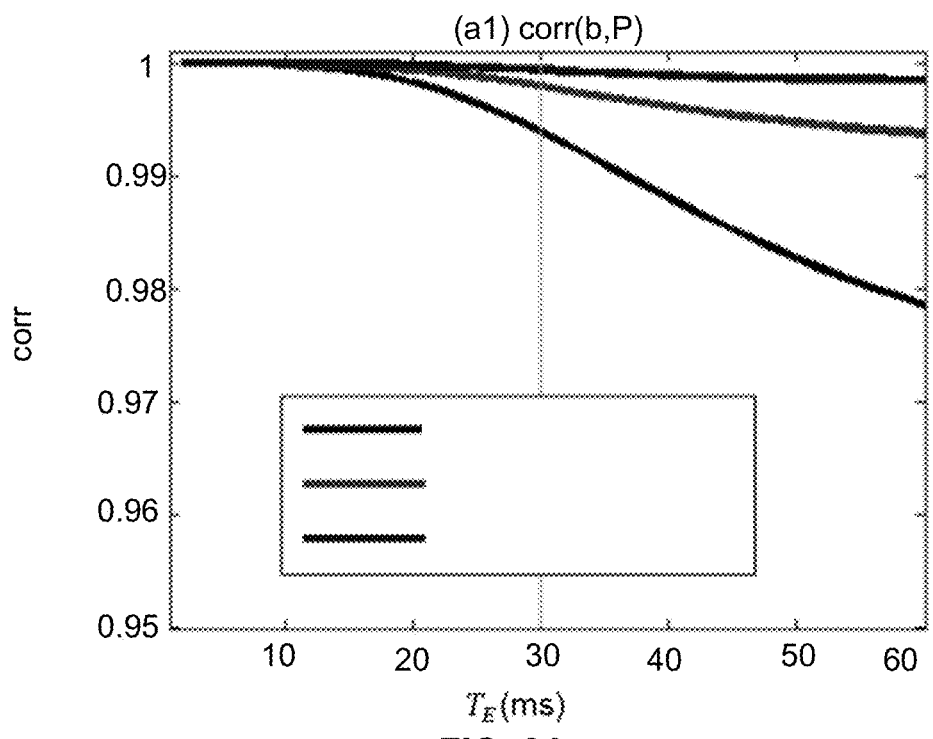
FIG. 8. The spatial correlations between the MR phase image and the precomputed fieldmap (see FIG. 7) for two intravoxel vasculatures (2-um-radius in (a1) (FIG. 8A) and 4-um-radius in (a2)) (FIG. 8B) and for three voxel sizes (see legend).
Figure 8B:
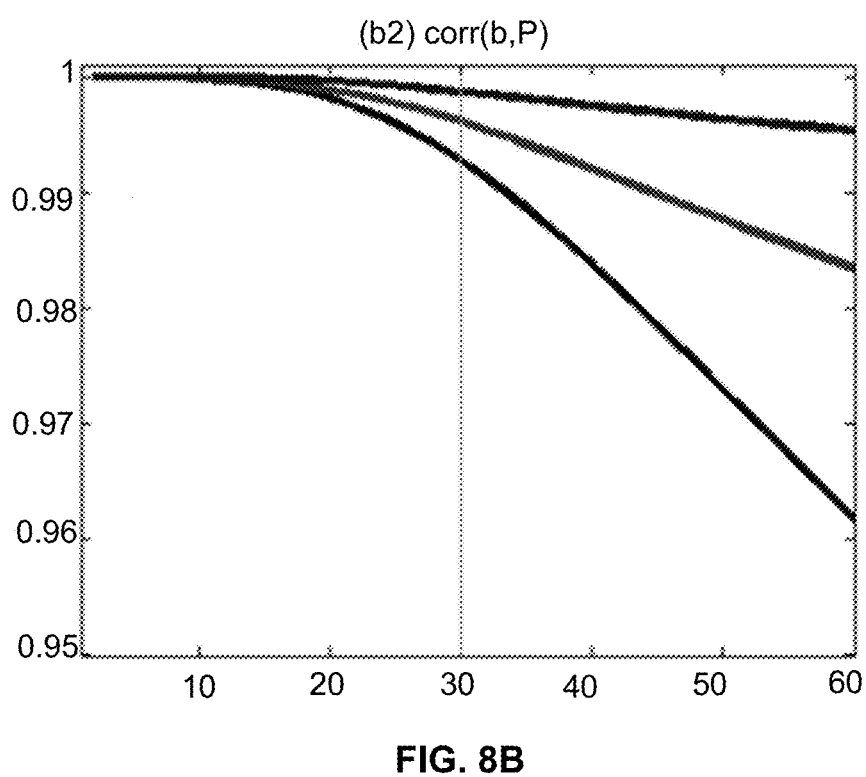

In FIG. 1, we decompose a T2*MRI procedure into two modules and diagram the forward procedure by downward arrows and the inverse procedure by upward arrows. In particular, we describe the two-step inverse mappings (from MR phase image to the susceptibility source) by CIMRI (indicated in a circle). For more clarity, we re-diagram the CIRMI model in FIG. 6. FIG. 6 shows the CIMRI model (diagrammed with solid arrows). It consists of two inverse mappings: fieldmap calculation from MR phase image and $\chi$ reconstruction from the fieldmap. There are three solvers for $\chi$ reconstruction from fieldmap: filter truncation, matrix inverse, and TV iteration (our proposal). The forward MRI is diagrammed with rightward arrows. As diagramed in FIG. 6, we decompose the forward MRI procedure into two steps:

Step 1. Fieldmap establishment $b(x,y,z)$ by magnetization of the susceptibility distribution $x(x,y,z)$ in a main field $B_0$, as expressed by Eq. (2).

Step 2. Complex-valued image generation $C(x,y,z)$ by intravoxel dephasing, as expressed by (Eq. (4)).

From the complex image, we obtain the magnitude image and phase image by Eq. (5). We reconstruct the $\chi$ source by a CIMRI model in FIG. 6. Reversing the forward MRI procedure, the CIMRI consists of two inverse mappings: (i) fieldmap calculation from MR phase image, (ii) $\chi$ calculation from fieldmap. The two inverse mapping steps are addressed below with a numerical simulation.

Inverse Step 1: From MR Phase Image to Fieldmap

By numerical simulation, we find that the MR phase image can, in fact, be considered as a faithful reproduction of fieldmap in small angle regime [19, 39] (which is reachable by using a small $T_E$ (<30 ms)). For quantitative match assessment, we can compare the MR phase image with the precomputed fieldmap (an intermediate stage of MRI procedure) by $$\text{corr}(P, b; T_E) = \frac{\text{cov}\{P(:,:,T_E), b(:)\}}{\text{std}\{P(:,:,T_E)\}\text{std}\{b(:)\}} \quad (12)$$

The simulation results are shown in FIG. 7 for image visualization and in FIG. 8 for quantitative correlation measures. FIG. 7 shows (a) precomputed fieldmap (resulting from a predefined neuroactive blob), and (b) the phase image of T2*MRI simulation. It is noted that the MR phase image can faithfully represent the fieldmap. FIG. 8 shows the spatial correlations between the MR phase image and the precomputed fieldmap (see FIG. 7) for two intravoxel vasculatures (2-um-radius in (a1) and 4-um-radius in (a2)) and for three voxel sizes (see legend).

Under the condition of small angle regime, we can simplify the fieldmap calculation from MR phase image [19, 39] by $$b(x,y,z;T_E) = c \cdot P(x,y,z;T_E) \text{ with } c=\text{const(in small angle regime)} \quad (13)$$

We point out that a MR scanning with long $T_E$ and in a high main field may violate the small angle regime, where the linear approximation is invalid, and the phase angle in the complex image may get wrapped (with a foldback of $2\pi$). In such scenarios, a phase unwrapping procedure is necessary for phase image calculation.

The simulation results in FIGS. 7 and 8 show that: 1) The phase image is almost an identical reproduction of the fieldmap in small angle regime (a small $T_E$ is required); 2) a long $T_E$ will increase the mismatch, thus not desirable (Note: this requirement is in conflict with the magnitude matching in FIG. 3 where a long $T_E$ is desirable). It is noted that it is irrational to compare the MR phase image with the $\chi$ source, because they are different by a 3D convolution in Eq. (2); so we need to proceed with inverse Step 2.

Inverse Step 2: From Fieldmap to Susceptibility Source

Based on our literature review above, we can classify the types of solvers for the inverse problems of "from fieldmap to susceptibility source" into three categories:

Solver Type 1: 3D filter truncation. This method suffers stripe effect and image energy shift.

Solver Type 2: Matrix inverse. This method is limited by a dimensionality curse, that is, it cannot accommodate a large 3D matrix. (a small 3D matrix, say 16×16×16, cannot offer meaningful image features in a large FOV).

Solver Type 3. 3D TV iteration (our preferred method). This method can produce an excellent image restoration without the sufferings as confronted in previous two methods. The theory, algorithm, and implementation are addressed below.

The three different 3D deconvolution solvers are diagrammed in FIG. 6.

Based on numerical simulation and phantom experiment [17, 18], we conclude that the split Bregman TV iteration algorithm outperforms the others solvers in the following aspects: 1) It preserves edges; 2) It denoises the data such that there is no need to render image smoothing a priori (Note that the TV iteration method was originally developed for 2D image denoising and that smoothing is prone to suppress image features); 3) It can accommodate large 3D phase maps per se without a convolutional matrix conversion; and 4) It is an iteration algorithm that can produce a stable optimal restoration by avoiding the divide-by-zero problem, and in particular, the split Bregman iteration guarantees fast convergence.

The 3D deconvolution associated with the CIMRI involves a point magnetic dipole kernel, which is in nature of 3D distribution. Therefore, CIMRI is optimal for volumetric susceptibility reconstruction from a MR phase volume. In practical implementation, the MR phase volume can be obtained by stacking 2D slices acquired by an EPI sequence. Usually, the slice-stacked volume is anisotropic (in-plane resolution is different from the across-plane resolution). An isotropic volumetric SM reconstruction can be achieved by acquiring an isotropic MR phase volume with isotropic voxels at a zero oblique angle and with no inter-slice gap. For dynamic brain BOLD ƒMRI study, the inter-slice time lag effect can be eliminated by using an echo volume imaging (EVI) sequence.

TV-Regularized 3D Deconvolution Algorithm

In recent years, the total variation (TV) iteration has been proven to be a very successful image restoration technique. However, the TV iteration methods have only been applied to 2D image restoration (including grayscale image and color vector image) under a regular blurring kernel (a centralized nonnegative distribution). In this subsection, according to the present invention, we generalize the TV-regularized iteration algorithm to accommodate our 3D deconvolution problem, which is characteristic of an unusual 3D convolution kernel of bipolar-valued quadruple lobes.

Mathematically, the TV norm for 3D x(r) is defined as $$\|\chi\|_{TV} \equiv sup\left\{\int_\Omega \chi(r)\nabla \cdot g(r)dr, \|g\|_\infty < 1\right\} \quad (14)$$

where g denotes a vector functional variable that is bounded by |g|≤1. Strictly speaking, $\|\chi\|_{TV}$ is a semi-norm for that $\|\chi\|_{TV}=0$ is allowed for $\chi\neq 0$. For a smooth 3D function $\chi(r)$, the TV norm is also given by $$\|\chi\|_{TV} \equiv \int_\Omega |\nabla \chi(r)|dr = \quad (15)$$
$$\int_\Omega \sqrt{|\nabla_x(r)|^2 + |\nabla_y(r)|^2 + |\nabla_z(r)|^2}\, dr$$

Assuming a Gaussian noise model for $\epsilon(r)$, we can solve the inverse problem in Eq. by a TV-regularized unrestraint minimization problem [44-47], as expressed by $$\hat{\chi}(r) = \min_{\chi \in BV} \|\chi(r)\|_{TV} + \frac{\lambda}{2}\|B_0 h_0(r) * \chi(r) - b(r)\|_2^2 \quad (16)$$

where BV is a bounded variation function space, and λ is the Lagrange multiplier or the regularization parameter. The TV regularization methodology lies in its searching over all possible distributions (χ∈BV) to find an optimal distribution χ̂ such that it minimizes the TV norm and the data fidelity error simultaneously.

The algorithm implementation of Eq. (16) is nontrivial. Recently researches show that the TV iteration can be effectively implemented by a split Bregman algorithm [21, 44, 48, 49]. The basic idea of the split Bregman algorithm is to transform a constrained optimization problem into a series of unconstrained subproblems; then to solve each subproblem by a Bregman-distance-based iteration. The Bregman distance (or Bregman divergence [50]) is defined for an objective function J(u) as $$D_J(u,v)=J(u)-J(v)-<\partial J(v),u-v> \quad (17)$$

where the bracket <,> represent inner product, ∂J(v) is an element of the subgradient of function J at v. Intuitively, the Bregman distance in Eq. (17) can be thought of as the difference between the value of function J at point u and the value of the first-order Taylor expansion of J around point v evaluated at point u. It has been approved that the use of Bregman distance in Eq. (17) can ensure fast convergence.

Let $J(\chi)=\|\chi\|_{TV}$ and set the initial $\chi_0=0$, then the Bregman iteration produces a series $\{\chi_k, k=1,2,\ldots\}$ by $$\chi_{k+1} = \arg\min_{\chi \in BV}\left\{D_{\|\chi\|_{TV}}(\chi, \chi_k) + \frac{\lambda}{2}\|B_0 h_0 * \chi - b\|_2^2\right\} \quad (18)$$
$$D_{\|\chi\|_{TV}}(\chi, \chi_k) = \|\chi\|_{TV} - \|\chi_k\|_{TV} - \langle \partial \|\chi_k\|_{TV}, \chi - \chi_k \rangle$$

It has been shown that the Bregman iteration can also be equivalently achieved by introducing an auxiliary variable v and carrying out the following iteration (with $v_0=0$ for initial setting)

$$\chi_{k+1} = \underset{\chi \in BV}{\operatorname{argmin}}\left\{\|\chi\|_{TV} + \frac{\lambda}{2}\|B_0 h_0 * \chi - b - v_k\|_2^2\right\} \quad (19)$$
$$v_{k+1} = v_k + (b - B_0 h_0 * \chi_{k+1})$$

In the result, the Bregman iteration produces a series of $\{(\chi_k, v_k), k=1,2,\ldots\}$. It is noted that $v_k$ is updated by adding back noise, which is called "comeback noise" or "residual noise". The iteration is stopped when a criterion is satisfied. The "comeback noise" is sparse, which may vary from iteration to iteration.

For solving our 3D deconvolution problem, we need to extend the Bregman iterations in Eq. (18) or (19) to accommodate a 3D minimization problem. We adopt the split Bregman iteration algorithm to handle the inverse problem by splitting it into three subproblems with respect to interim variables {'d', 'v', 'χ'}, where 'd' and 'v' are auxiliary variables, and the 'χ' is the variable for our solution. For TV-regularized 2D image restoration, we refer readers to previous work [44, 46, 49-52] for mathematical details. For 3D susceptibility volume reconstruction from a 3D fieldmap by solving the 3D deconvolution problem in Eq. (2), we invented a 3D TV-regularized split Bregman TV iteration algorithm [17] according to:

$$\chi^{recon} = \min_{d,v,\chi} \|d(r)\|_{TV} + \frac{\lambda}{2}\|B_0 v - b\|_2^2 + \qquad (20)$$

$$\frac{\gamma_1}{2}\|d - \nabla_\chi - a_1\|_2^2 + \frac{\gamma_2}{2}\|v - h * \chi - a_2\|_2^2$$

with $d = \nabla_\chi$ and $v = h * \chi$ where the parameters {'$\gamma_1$', '$\gamma_2$', '$a_1$', '$a_2$'} are introduced for algorithm implementation and fast convergence. It is noted that the 3D convolution in Eq. (20), such as h*$\chi$, can be implemented by 3D filtering in Fourier domain. However, the filter H(k) is not truncated at all, which is different from the inverse filtering solver with a truncated filter ("filter trunc" solver).

In iteration implementation, the 3-subproblems are solved one at a time (with respect to one of {'d', 'v', '$\chi$'} while keeping the other two fixed). The following input is required: 3D fieldmap b(x,y,z), 3D convolution kernel h(x,y,z) (corresponding to 3D filter by h(x,y,z)=IFT[H($k_x,k_y,k_z$)]), regularization parameter $\lambda$ (adjustable), and convergence control tolerance of error (preset), and maximum iteration number allowed (preset). In summary, the split Bregman TV iteration algorithm for the minimization problem in Eq. (20) can be summarized by the following algorithm [17, 53]:

Initialize $\chi=v=a_2=0$, $d=b_1=0$
Do
   Minimization of $\chi$-subproblem with (d,v) fixed;
   Minimization of d-subproblem with ($\chi$,v) fixed;
   Minimization of v-subproblem with ($\chi$,d) fixed;
   Update $a_1:=a_1+\nabla_\chi-d$
   Update $a_2:=a_2+h*\chi-v$
While "not converged"

T2'-Effect Imaging Scheme

It is known that gradient-echo (GE) imaging is used to capture the spin precession dephasing signals by a radiofrequency tipping pulse (a 90° tipping angle or less), and that spin-echo (SE) imaging can refocus static transverse dephasing through the use of an additional 180° pulse. Since the non-refocusable random effect appears in both the GE and SE signals, we are inspired to remove the dynamic random part (albeit incomplete) and extract the refocusable static inhomogeneous effect (also described as T2' effect). The principle of our T2'-effect magnetic resonance imaging (T2'MRI), is illustrated in FIG. 9, with two echoes of different $T_E$'s. FIG. 9 shows an illustration of T2'-effect signals with two echo times. (a) A pulse sequence of a 90° tipping pulse and two 180° refocusing pulses (one with $T_{E1}$ and other with $T_{E2}$); (b) T2* SE signal (echoes in black) and T2* GE signal (echoes in red). The T2* SE signals are generated by a pair of 90° and 180° pulses. The T2* GE signals are generated by only a 90° pulse and a reversal readout gradient (not drawn).

Let $b_{T2*}(x,y,z)$ denote the fieldmap responsible for T2* image formation. Then the complex-valued image acquired by GE imaging with echo time $T_E$ can be expressed by $$C_{GE}(x, y, z; T_E) = \qquad (21)$$

$$\iiint_{(x',y',z')\in\Omega(x,y,z)} \exp\left[-i\gamma \int_0^{T_E} b_{T_2^*}(x'(t), y'(t), z'(t))dt\right] dx'dy'dz'$$

Correspondingly, the complex-valued image acquired by SE imaging is given by $$C_{SE}(x, y, z, T_E) = \qquad (22)$$

$$\iiint_{(x',y',z')\in\Omega(x,y,z)} \exp\left[-i\gamma \int_0^{T_E/2} b_{T_2^*}(x'(t), y'(t), z'(t))dt\right]$$

$$\exp\left[i\gamma \int_{T_E/2}^{T_E} b_{T_2^*}(x'(t), y'(t), z'(t))dt\right] dx'dy'dz'$$

We can decompose the proton-experienced T2* fieldmap ($b_{T2*}$) into non-random static inhomogeneity part ($b_{T2'}$), random spin-spin interaction part ($b_{T2}$), and random diffusion perturbation part ($b_{diffu}$), that is $$b_{T_2^*}(x(t),y(t),z(t)) = b_{T_2'}(x,y,z) + b_{T_2}(x(t),y(t),z(t)) + b_{diffu}(x(t),y(t),z(t)) \qquad (23)$$

It is known that the static dephasing is refocusable by a 180° pulse, and that the dynamic dephasing associated with the random spin-spin interaction and diffusion motion are non-refocusable. We can describe these facts by $$b_{T2'}(x,y,z) = b_{T2'}(x(t),y(t),z(t)) = b_{T2'}(x(t+T_E/2), y(t+T_E/2), z(t+T_E/2)) \text{(refocusable)}$$

$$b_{T_2}(x(t),y(t),z(t)) \ne b_{T_2}(x(t+T_E/2),y(t+T_E/2),z(t+T_E/2))$$
(non-refocusable)

$$b_{diffu}(x(t),y(t),z(t)) \ne b_{diffu}(x(t+T_E/2),y(t+T_E/2),z(t+T_E/2))$$
(non-refocusable) (24)

Then, the complex SE image is expressed by $$C_{SE}(x, y, z; T_E) = \qquad (25)$$

$$\iiint_{(x',y',z')\in\Omega(x,y,z)} \exp\Big\{-i\gamma \int_0^{T_E/2} [b_{T_2'}(x',y',z') + b_{T_2}(x'(t),$$

$$y'(t), z'(t)) + b_{diffu}(x'(t), y'(t), z'(t))]dt +$$

$$i\gamma \int_{T_E/2}^{T_E} [b_{T_2'}(x', y', z') + b_{T_2}(x'(t), y'(t), z'(t)) +$$

$$b_{diffu}(x'(t), y'(t), z'(t))]dt\Big\} dx'dy'dz' =$$

$$\iiint_{(x,y,z)\in\Omega(x_i,y_i,z_i)} \exp\Big\{-i\gamma \int_0^{T_E/2} [b_{T_2}(x'(t), y'(t), z'(t)) -$$

$$b_{T_2}(x'(t+T_E/2), y'(t+T_E/2), z'(t+T_E/2)) +$$

$$b_{diffu}(x'(t), y'(t), z'(t)) - b_{diffu}(x'(t+T_E/2),$$

$$y'(t+T_E/2), z'(t+T_E/2))]dt\Big\} dx'dy'dz'$$

Obviously, for a special deal case in absence of dynamic T2 random effects and diffusion effects, the T2* SE refocusing gives rise to $$C_{SE}(x, y, z; T_E) = \iiint_{(x',y',z')\in\Omega(x,y,z)} \exp\Big[-i\gamma \int_0^{T_E/2} b_{T_2'}(x', y', z')dt + \qquad (26)$$

$$i\gamma \int_{T_E/2}^{T_E} b_{T_2'}(x', y', z')dt\Big] dx'dy'dz' =$$

$$\iiint_{(x',y',z')\in\Omega(x,y,z)} dx'dy'dz' = |\Omega(x, y, z)| \text{ (perfect refocusing)}$$

Since the T2* GE signal consists of both the T2 effect (random spin-spin interaction and spin diffusion) and T2' effect (static inhomogeneous field) and the T2* SE signal only consists of non-refocusable random T2 effect (that is, the T2* SE signal is the T2-effect signal), it is possible the separate the T2'-effect signal from T2* GE signal by signal decomposition. Concerning the fact that we are dealing with complex-valued MR images, we use complex division to calculate the T2'-effect complex image, as given by $$C_{T_2'}(x,y,z;T_E) = C_{GE}(x,y,z;T_E)/C_{SE}d(x,y,z,T_E) \quad (27)$$

which is called T2'-effect imaging scheme.

Assuming exponential models for the T2* and T2 magnitude decays, we obtain the T2' magnitude decay that also reveals an exponential decay behavior, that is $$|C_{GE}(x, y, z; T_E)| = |C_{GE}(x, y, z; T_E = 0)|\exp(-T_E/T_2^*) \quad (28)$$

$$|C_{SE}(x, y, z; T_E)| = |C_{SE}(x, y, z; T_E = 0)|\exp(-T_E/T_2)$$

$$|C_{T_2'}(x, y, z; T_E)| =$$

$$\frac{|C_{GE}(x, y, z; T_E)|}{|C_{SE}(x, y, z; T_E)|} = \exp(-T_E/T_2^* + T_E/T_2) = \exp(-T_E/T_2')$$

$$1/T_2' = 1/T_2^* - 1/T_2$$

Figure 9A:
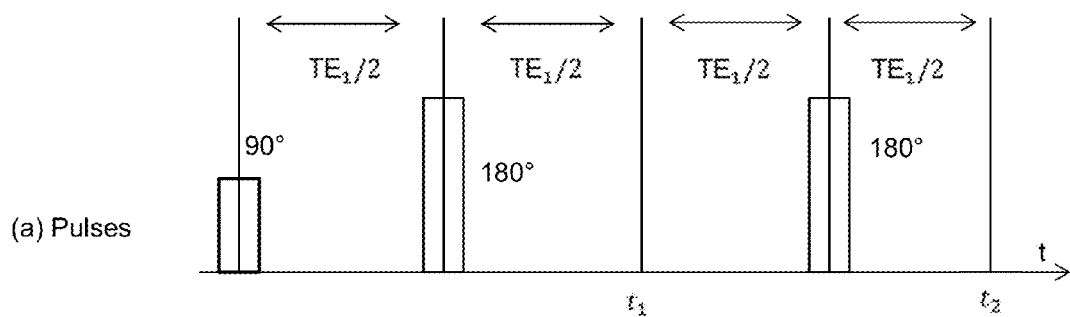
FIG. 9. Illustration of T2'-effect signals with two echo times. (a) A pulse sequence of a 90° tipping pulse and two 180° refocusing pulses (one with $T_{E1}$ and other with $T_{E2}$); (b) T2* SE signal (echoes in black) and T2* GE signal (echoes in red). The T2* SE signals are generated by a pair of 90° and 180° pulses. The T2* GE signals are generated by only a 90° pulse and a reversal readout gradient (not drawn).
Figure 9B:
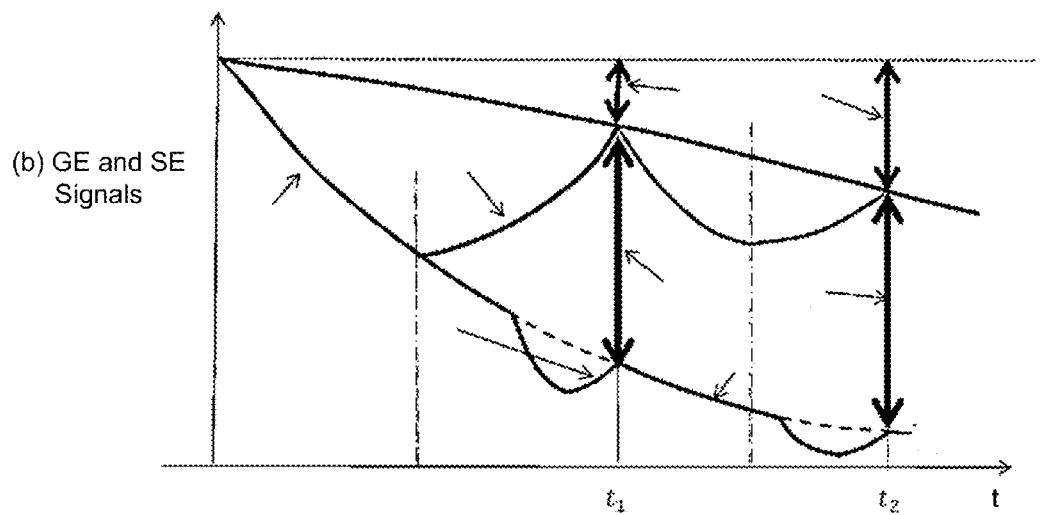

Therefore the magnitude behavior in Eq. (28) is compatible with the exponential signal intensity decay model [2]. It is seen in Eq. (28) that the maps of T2, T2* and T2' can be calculated by exponentially fitting each voxel intensity decay. The connotations of T2, T2* and T2' values for voxel signal intensity decays are illustrated in FIG. 9(b).

In this specification, we do not need to use the exponential magnitude decay models at all; instead, we are interested in the phase part of T2'-effect complex image. From the T2'-effect phase image, we can calculate the static inhomogeneous fieldmap that excludes the T2 effect, which are given by $$\angle C_{T_2'}(x, y, z; T_E) = \angle C_{GE}(x, y, z; T_E) - \angle C_{SE}(x, y, z; T_E) \quad (T_2'\text{-effect phase image}) \quad (29)$$

$$b_{T_2'}(x, y, z) = \frac{\angle C_{T_2'}(x, y, z, T_E)}{\gamma T_E} \quad (T_2'\text{-effect fieldmap})$$

It is expected that the T2' complex image will greatly remove the T2 effect and diffusion effect (albeit incomplete due to imperfect repeatability of random effect in two different times), thereby improving the $\chi$ reconstruction fidelity. In principle, our T2'-effect imaging scheme in Eq. (27) can be extended to two echo times ($T_{E1}$ and $T_{E2}$), as illustrated in FIG. 9. Because our T2'-effect imaging scheme by Eq. (27) is a complex image manipulation and it does not involves the calculations of the T2, T2* and T2' parameters, we claim that our T2'-effect imaging scheme is quite different from the T2' imaging technique as reported in [53]. More generally, the T2'MRI scheme can be extended to multi-echo imaging (with more than two echo times).

We should point out that, on one hand, the T2'MRI method cannot completely remove the random T2 and diffusion effects because of the imperfect repeatability of sheer randomness in two successive scans; on the other hand, the signals resulting from random T2 and diffusion effects are largely repeatable for different tissue types. Therefore, the T2'MRI method can remove the tissue-type-dependent T2 and diffusion effects.

3D $\chi$ Reconstructions with Specific Desirable Features

In digital image processing, the spatial structure of an image can be characterized by its spatial frequency in Fourier domain and can be modified by spatial filtering with a spatial frequency filter. After the reconstruction of a 3D $\chi$ distribution (through a TV iteration with the standard kernel $h_0(r)$), we can post-process the 3D $\chi$ source for enhancing or suppressing specific features by 3D spatial filtering with a designed filter. The typical filtering schemes include lowpass (LP), highpass (HP), bandstop (BT), and bandpass (BP). We call the post-processing of a reconstructed $\chi$ map a "post-recon filtering" approach. We will show that it is possible to accomplish the post-reconstruction filtering equivalently during the TV iteration using a designed filter, for which we call a "TV-iteration filtering" approach. In principle, both "TV-iteration filtering" approach and the "post-recon filtering" approach can produce the same results because the TV iteration algorithm is a linear procedure which allows a linear spatial filtering to be inserted in the iteration process or to be exerted after the iteration reconstruction.

Based on numerical simulation, we find that two approaches may produce similar results but are different in noise pattern due to the randomness of sparse comeback noise associated with a TV iteration. Accordingly, we developed new methods to render parallel TV iterations: one is "post-recon filtering" and the other is "TV-iteration filtering" as diagramed in FIG. 10. Since the two schemes produce the same results, we can perform an average to produce a noise-reduced result, as diagrammed in FIG. 10.

Figure 10:
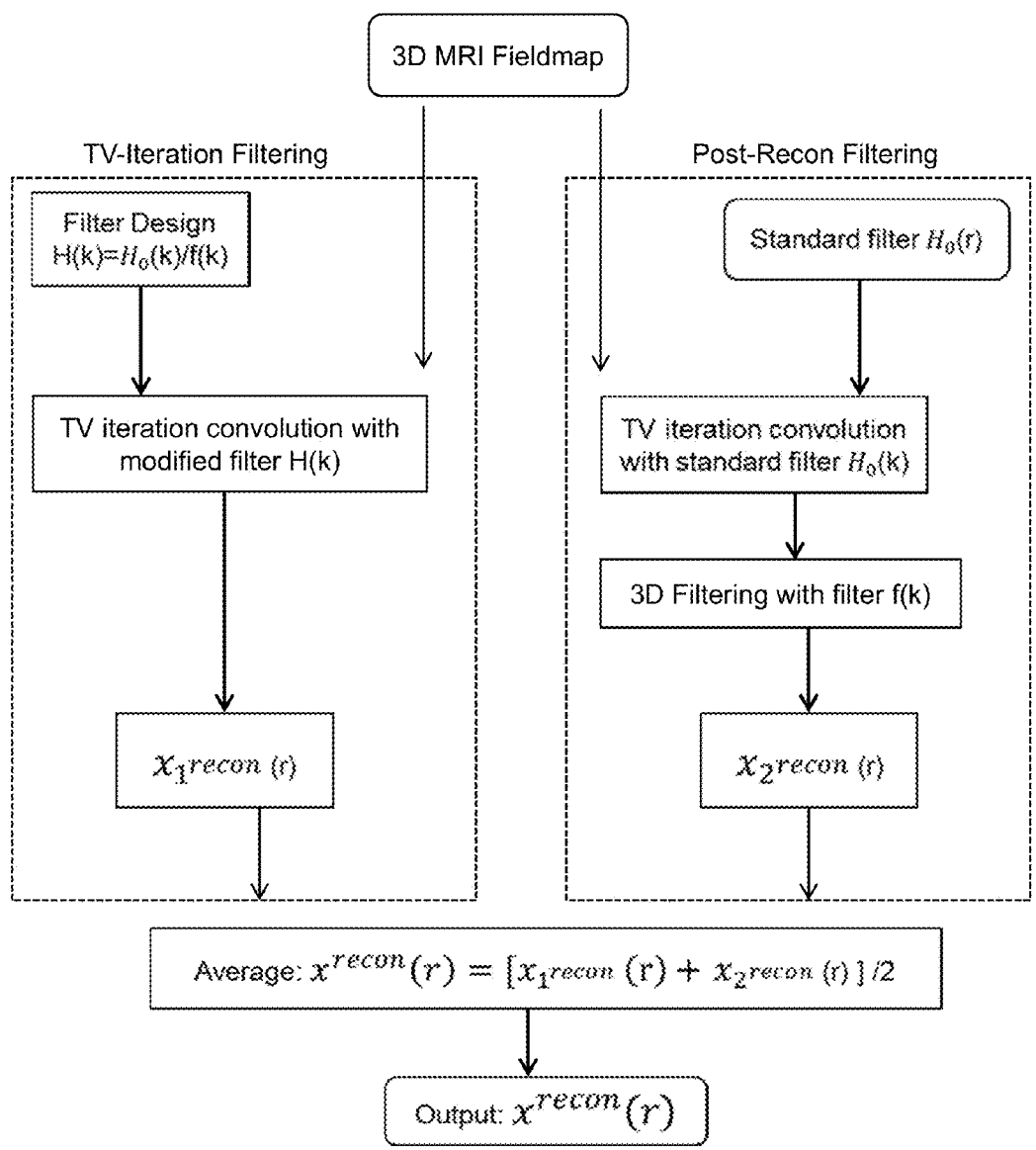
FIG. 10. Feature-specified $\chi$ reconstruction by "post-recon filtering" and "TV-iteration filtering" approaches. The "post-recon filtering" approach is carried out by first reconstructing a $\chi$ source with standard TV iteration and then exerting a spatial filtering with a feature-specified filter $f(k)$, as diagramed in the right-hand dotted box. The "TV-iteration filtering" approach is carried out by reconstructing a $\chi$ source with a modified filter $H(k)=H_0(k)/f(k)$, as diagramed in the left-hand dotted box. Two approaches are carried out in parallel, and the two resultant $\chi$ sources are averaged to produce a noise-reduced $\chi$ source.
Figure 11:
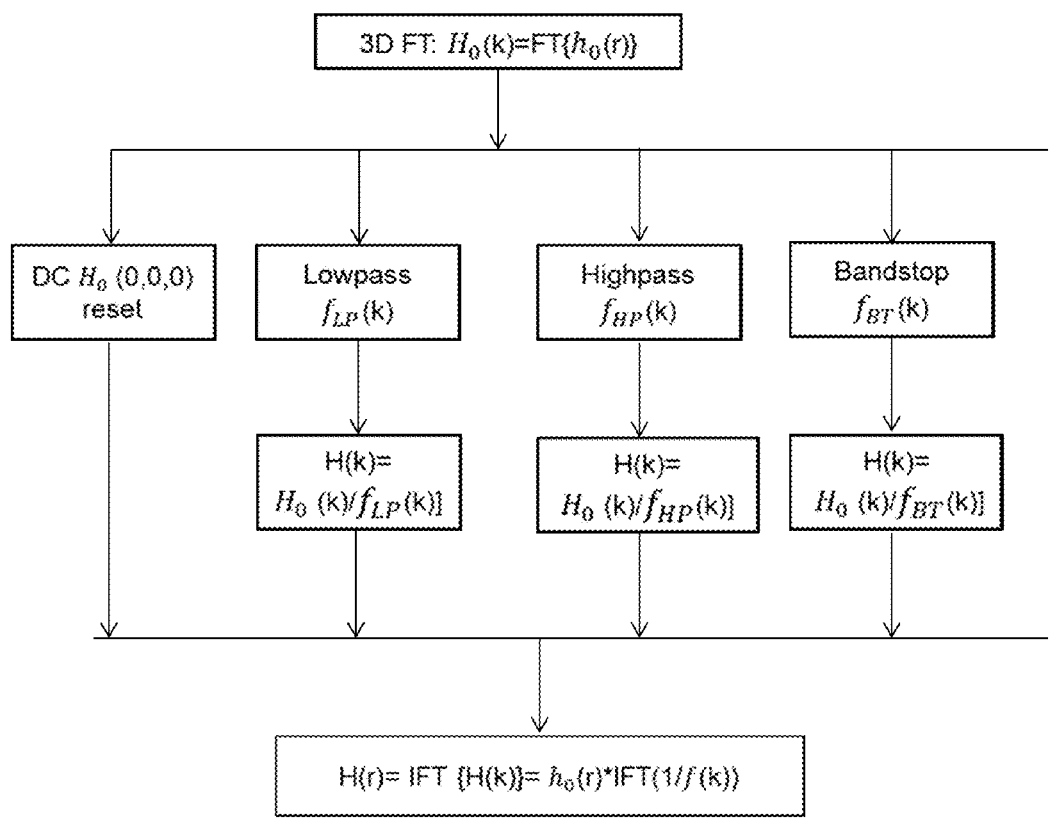
FIG. 11. 3D convolution filter design. A modified kernel can be obtained by DC term reset, lowpass, highpass, and bandstop filtering. (The bandpass filtering is not shown).
Figure 12A:
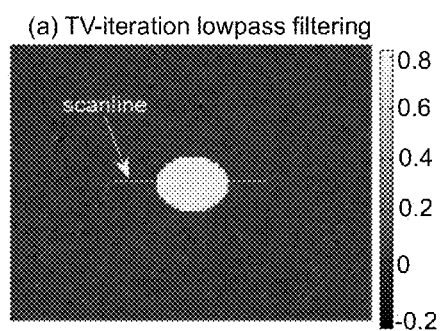
FIG. 12. Demonstration of the equivalence of "TV-iteration filtering" and "post-recon filtering" and the noise reduction by average. (a) $\chi$ reconstruction by "TV-iteration filtering" with a TV iteration filter $H(k)=H_0(k)/f_{LP}(k)$ with $f_{LP}(k)=[0.6+0.4 \cos(\pi k/k_{max})]$; (b) The "post-recon filtering" with a lowpass filter $f_{LP}(k)=[0.6+0.4 \cos(\pi k/k_{max})]$; (c) the average of (a) and (b); and (d) the profiles of scanline.
Figure 12B:
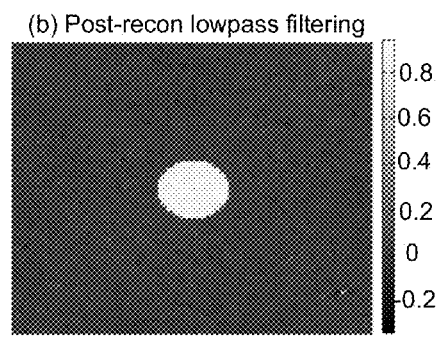
Figure 12C:
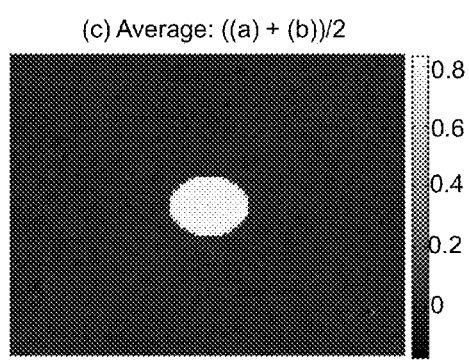
Figure 12D:
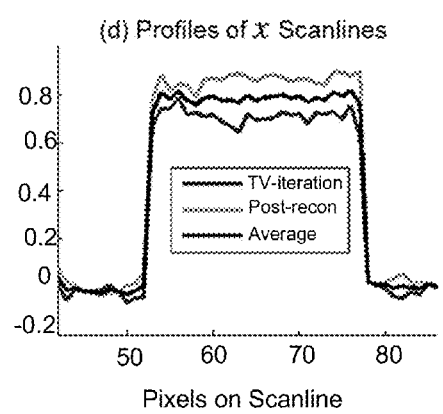

FIG. 10 shows feature-specified $\chi$ reconstruction by "post-recon filtering" and "TV-iteration filtering" approaches. The "post-recon filtering" approach is carried out by first reconstructing a $\chi$ source with standard TV iteration and then exerting a spatial filtering with a feature-specified filter $f(k)$, as diagramed in the right-hand dotted box. The "TV-iteration filtering" approach is carried out by reconstructing a $\chi$ source with a modified filter $H(k)=H_0(k)/f(k)$, as diagramed in the left-hand dotted box. Two approaches are carried out in parallel, and the two resultant $\chi$ sources are averaged to produce a noise-reduced $\chi$ source. The "filter design" part in the "TV-iteration filtering" approach (in the left-hand dotted box in FIG. 10) is drawn in FIG. 11. As one output in FIG. 11, we also convert the designed filter in Fourier domain into a convolution kernel in space domain by inverse Fourier transform (IFT). FIG. 11 shows a scheme for 3D convolution filter design. A modified kernel can be obtained by DC term reset, lowpass, highpass, and bandstop filtering. (The bandpass filtering is not shown).

In FIG. 12, we provide numerical simulations for two susceptibility filtering schemes in FIG. 10. It demonstrates that a lowpass filtering on a reconstructed susceptibility map can be equivalently achieved by "TV iteration filtering" and "post-recon filtering". Let $f_{LP}(k)=[0.6+0.4 \cos(\pi k/k_{max})]$ represent the lowpass filter used for "post-recon filtering", then the same result can be achieved by "TV-iteration filtering" with a TV-iteration filter $H(k)=H_0(k)/f_{LP}(k)$, where $H_0(k)$ represents the standard magnetic dipole filter. It is noted that the post-recon filter $f_{LP}(k)$ is used in the TV-iteration filter in a reciprocal way. It is seen in FIG. 12 that the two filtering schemes produce the same results except for a difference in noise. Therefore, we can reduce the noise by average, as shown in FIGS. 12(c) and (d). FIG. 12 shows the demonstration of the equivalence of "TV-iteration filtering" and "post-recon filtering" and the noise reduction by average: (a) $\chi$ reconstruction by "TV-iteration filtering" with a TV iteration filter $H(k)=H_0(k)/f_{LP}(k)$ with $f_{LP}(k)=[0.6+0.4 \cos(\pi k/k_{max})]$; (b) The "post-recon filtering" with a lowpass filter $f_{LP}=[0.6+0.4 \cos(\pi k/k_{max})]$; (c) the average of (a) and (b); and (d) the profiles of scanline.

Effect of DC Term Reset

Figure 13:
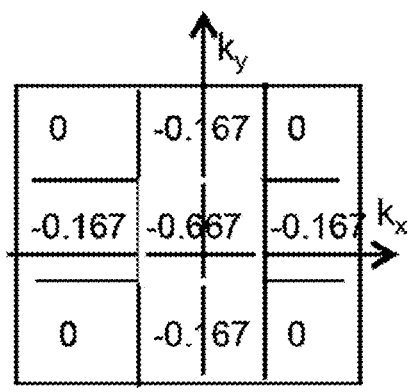
FIG. 13. The neighborhood of DC term of the standard filter $H_0(k)$. The DC term assumes ⅓ (by convention of 0/0=0), which is continuous at the $(k_x, k_y)$ plane, but not continuous along the $k_z$-axis due to $\{-0.667, ⅓, -0.667\}$ for voxels at $(k_x, k_y, k_z) = \{(0,0,-1),(0,0,0),(0,0,1)\}$.
Figure 13:
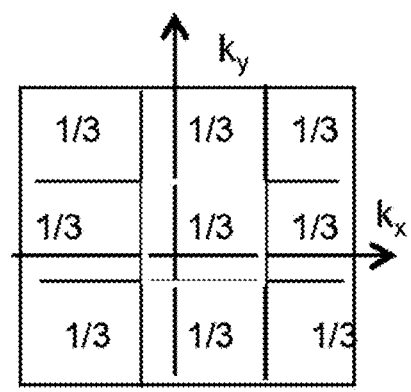
Figure 13:
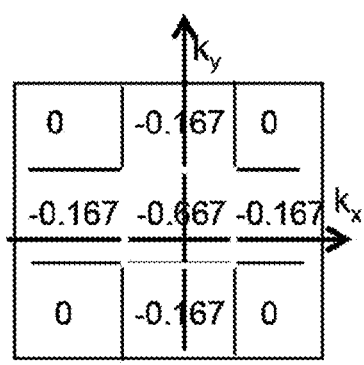
Figure 14A:
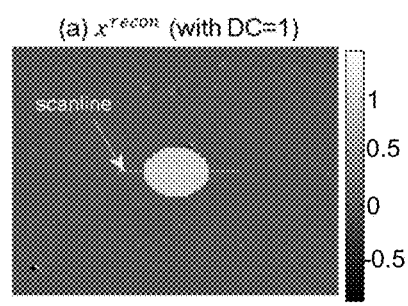
FIG. 14 Effect of DC term reset $(H(0,0,0)=\{1,⅓,-1\})$ on $\chi$ reconstruction. Cross-sections for reconstructed cylinders with (a) DC=1, (b) DC=⅓, and (c) DC=-1. The profiles of the scanline (only provided in (a)) is shown in (d). It is seen that the DC value of $H_o(k)$ has little influence on TV-regularized $\chi$ reconstruction (as described "scale invariance").
Figure 14B:
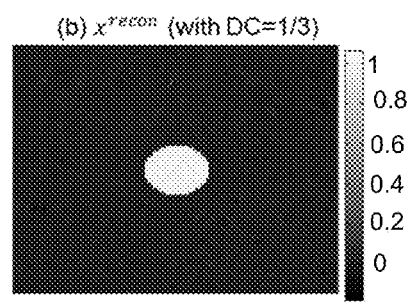
Figure 14C:
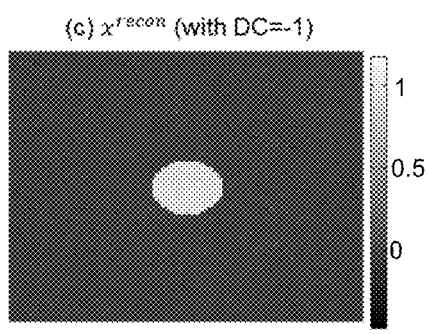
Figure 14D:
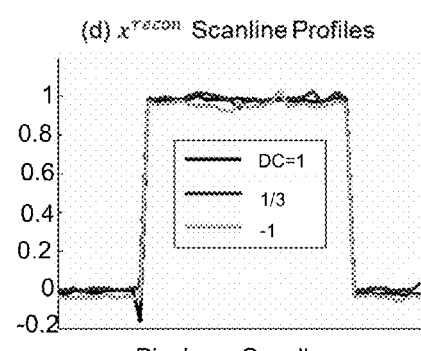

As shown in Eq. (3), the 3D filter $H_0$ bears an undefined DC term at $(k_x,k_y,k_z)=(0,0,0)$. With the convention of 0/0=0, the neighborhood values around the 3D filter DC term are shown in FIG. 13. It is seen that, the setting of $H_0(0,0,0)=\frac{1}{3}$ is continuous at the $k_x k_y$-plane (in FIG. 13(b)), but not continuous along the $k_z$-axis $(H_0(0,0,k_z)=\{-0.667, \frac{1}{3}, -0.667\}$ for voxels at $(k_x,k_y,k_z)=\{(0,0,-1),(0,0,0),(0,0,1)\}$. We can reset the DC term value to provide a modified kernel for TV iteration as one approach of iteration convolution kernel design in FIG. 11. FIG. 13 shows the neighborhood of DC term of the standard filter $H_0(k)$. The DC term assumes $\frac{1}{3}$ (by convention of 0/0=0), which is continuous at the $(k_x,k_y)$ plane, but not continuous along the $k_z$-axis due to $\{-0.667, \frac{1}{3}, -0.667\}$ for voxels at $(k_x,k_y,k_z)=\{(0,0,-1),(0,0,0),(0,0,1)\}$.

From Eq. (11), it can be shown that $$\iiint_{(x,y,z)} c \cdot h_0(x,y,z) dx dy dz = c \cdot H_0(0,0,0), \quad (30)$$

$c$ is a constant

This indicates that if the DC term $H_0(0,0,0)$ is modified by a multiplicative constant, c, it is equivalent to multiplying the kernel by the same constant. In other words, the TV-iteration reconstruction with a modified filter of a scaled DC term will produce similar result that is different mainly by a scale of c, which we call "scale invariance" (a built-in functionality of TV-regularized iteration). Due to the comeback noise effect associated with the TV iteration, two TV iterations with different DC terms will produce similar results that are different by noise patterns (randomness and sparseness). Therefore, we can make use of this "scale invariance" phenomenon for noise reduction purpose (as will be addressed later). Numerical simulations of TV-iterated $\chi$ reconstruction with a modified $H_0$ that are different in $H_0(0,0,0)$ value are demonstrated in FIG. 14.

Although there is an uncertainty (due to 0/0) associated with the DC term of the filter $H_0(k)$, our simulation shows that: 1) $H_0(0,0,0)=0$ is not allowed; 2) The TV iteration reconstruction is insensitive to the DC term values and signs (as can be seen FIG. 14). We suggest to reset the filter DC term value in a range of $0.1<|H_0(0,0,0)|<1$ to provide a modified kernel to TV iteration. The $\chi$ reconstructions from different DC values can be carried out in parallel, and then averaged over the multiple reconstructions, which suppresses the noise. FIG. 14 shows the effect of DC term reset $(H(0,0,0)=\{1, \frac{1}{3},-1\})$ on $\chi$ reconstruction. Cross-sections for reconstructed cylinders with (a) DC=1, (b) DC=$\frac{1}{3}$, and (c) DC=−1. The profiles of the scanline (only provided in (a)) is shown in (d). It is seen that the DC value of $H_0(k)$ has little influence on TV-regularized $\chi$ reconstruction (as described "scale invariance"). To some extent, the DC reset plays a seed of randomness in parallel TV iteration reconstructions.

Reciprocal Filter

We have shown that the susceptibility source map can be reconstructed by a TV-regularized split Bregman iteration algorithm (see, e.g., Eq. (20)). However, the solution can be changed by using a new convolution kernel, h(r), that is a modification of the standard dipole kernel $h_0(r)$. Suppose the use of the standard point magnetic dipole kernel $h_0(r)$, or its modified version h(r), produces a solution $\chi_0^{recon}$ (or $\chi^{recon}$, respectively), that is $$\begin{cases} \chi_0^{recon} = \min_{d,v,\chi} \|d(r)\|_{TV} + \frac{\lambda}{2}\|B_0 v - b\|_2^2 + \\ \frac{\gamma_1}{2}\|d - \nabla \chi - a_1\|_2^2 + \frac{\gamma_2}{2}\|v - h_0 * \chi - a_2\|_2^2 \\ \chi^{recon} = \min_{d,v,\chi} \|d(r)\|_{TV} + \frac{\lambda}{2}\|B_0 v - b\|_2^2 + \\ \frac{\gamma_1}{2}\|d - \nabla \chi - a_1\|_2^2 + \frac{\gamma_2}{2}\|v - h * \chi - a_2\|_2^2 \end{cases} \quad (31)$$

If $\chi^{recon}$ is more desirable than $\chi_0^{recon}$, then we can obtain $\chi^{recon}$ from $\chi_0^{recon}$ by performing a 3D spatial filtering with a filter $f(k)$ (or by a 3D convolution with a kernel $f(r)$), that is $\chi^{recon}(k)=\chi_0^{recon}(k) \cdot f(k)$ (3D filtering)

or $\chi^{recon}(r)=\chi_0^{recon}(r)*f(r)$ (3D convolution) (32)

We call Eq. (32) a "post-recon filtering" because $\chi^{recon}$ is obtained by filtering the susceptibility source $\chi_0^{recon}$ (that was reconstructed by using the standard kernel $h_0(r)$). Alternatively, as seen in Eq. (31), $\chi^{recon}$ can also be directly reconstructed from the fieldmap by using a modified filter H(k) (corresponding to a modified kernel h(r)). It can be shown that, the filter (or kernel) modification is given by $$H(k) = \frac{H_0(k)}{f(k)} \quad \text{(modified filter)} \quad (33)$$

or $h(r) = IFT[H(k)] = h_0(r) * IFT[1/f(k)]$ (modified kernel)

where IFT denotes Inverse Fourier Transform. When the modified filter H(k) obtained in Eq. (33) is used in the 3D susceptibility reconstruction by the TV iteration in Eq. (31), we say that the 3D susceptibility is reconstructed by a "TV-iteration filtering". We will show that the TV-regularized iteration convolution scheme using a new kernel h(r) (corresponding to TV-iteration filtering using a new filter H(k)) (in Eq. (33)) to reconstruct a susceptibility source $\chi^{recon}$ by Eq. (31), such that is has the same features as resulting from post-recon filtering using a filter $f(k)$ in Eq. (32).

As a result, we can achieve a feature-specific susceptibility reconstruction by at least two different ways: 1) post-recon filtering using a filter $f(k)$ in Eq. (32), or 2) TV-iteration filtering using a new filter H(k) in Eq. (33). It is noted in Eq. (33) that the filter used in the post-recon $\chi$ filtering is reciprocal to that used in the filter modification for TV-iteration filtering.

Convolution Kernel Design

Figure 15:
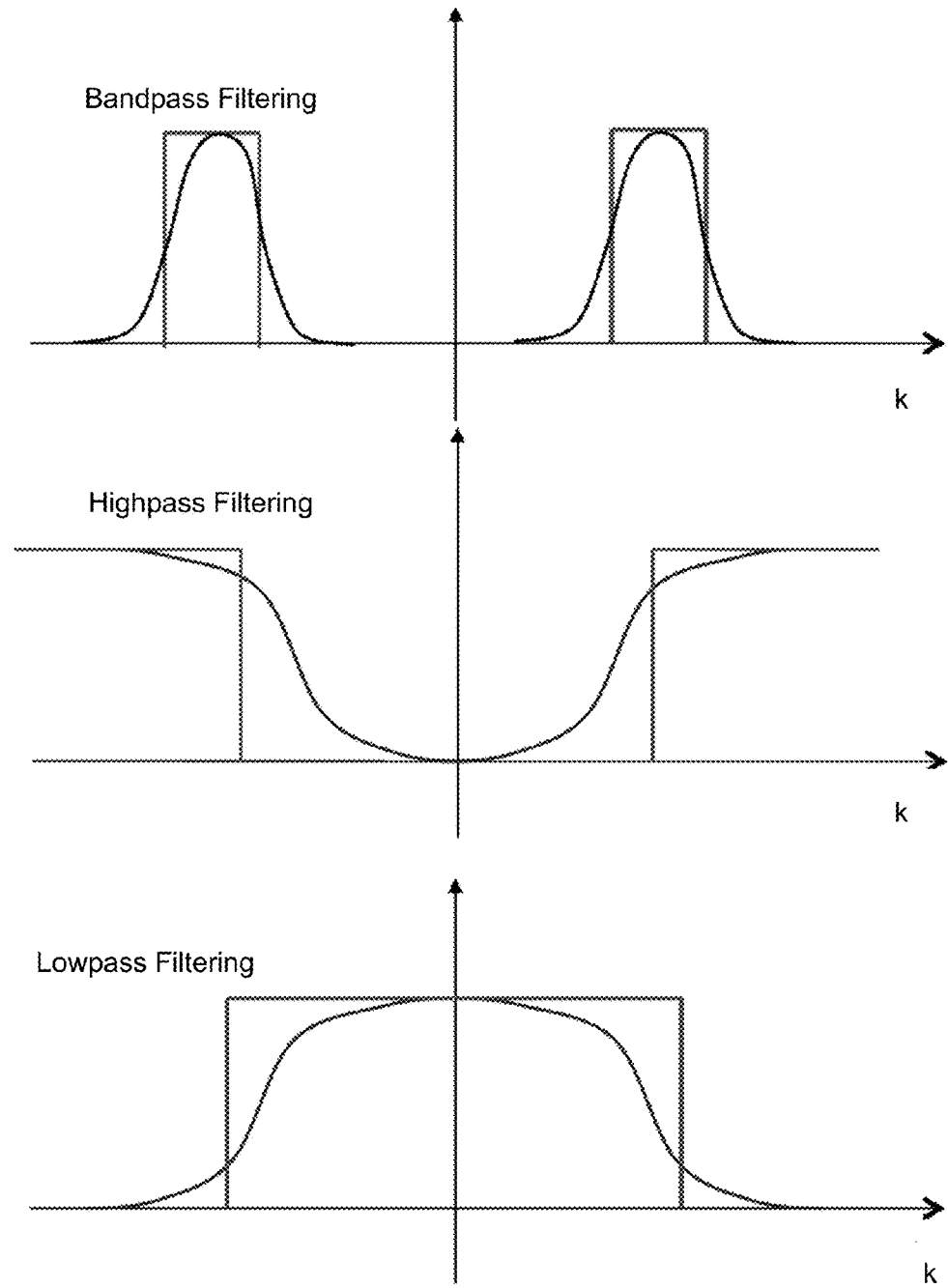
FIG. 15. Diagram for bandpass, highpass, and lowpass filtering which is applied to a direction along $k_x$-, $k_y$-, $k_z$-axis, and radial direction k, separately and jointly. The red plots have sharp cutoffs and the black plots are smooth which can suppress Gibbs effect.
Figure 16A:
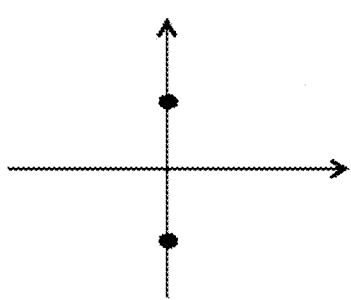
FIG. 16A), vertical stripe extraction (at middle row.
Figure 16A:
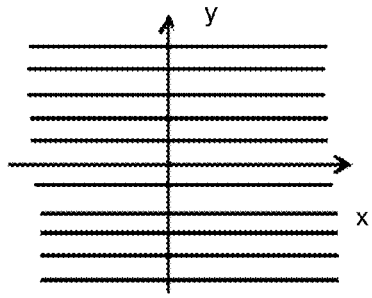
Figure 16B:
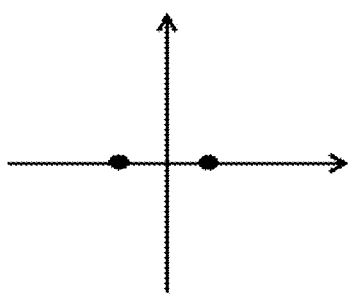
FIG. 16B), and the extraction for vertical, horizontal, diagonal, and anti-diagonal stripes (at bottom row.
Figure 16B:
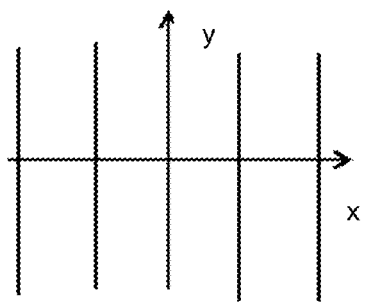
Figure 16C:
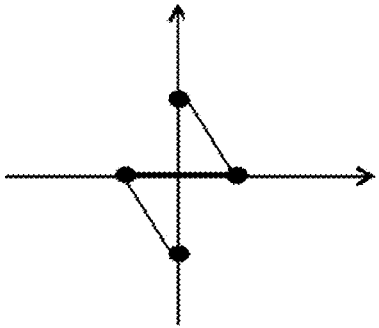
FIG. 16C). The spatial superimposition of numerous random stripes makes a clutter noise in the reconstruction.
Figure 16C:
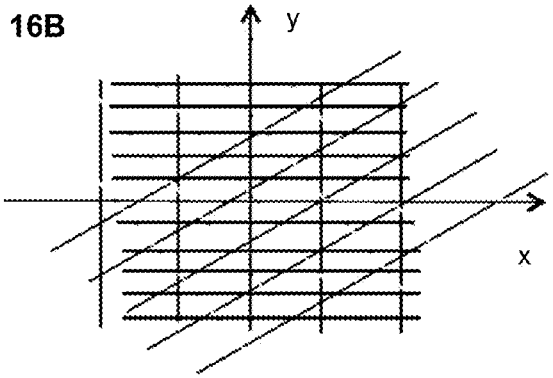
Figure 17A:
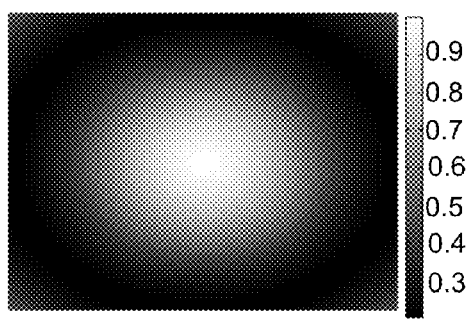
FIG. 17. Demonstration of lowpass (FIG. 17A) and highpass filters (FIG. 17C). It is noted the lowpass filter can be reshaped by a square operation (for example, constricted by Eq. with α=2) (FIG. 17B).
FIG. 17D shows the 1D profiles of lowpass, hiqhpass, and lowpass squared filters.
Figure 17B:
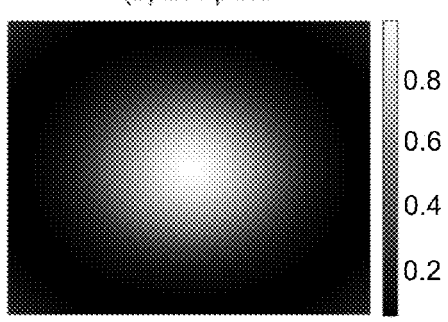
Figure 17C:
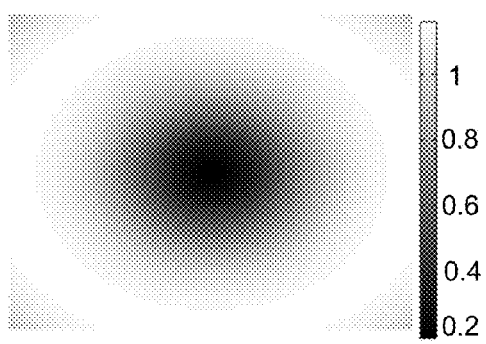
Figure 17D:
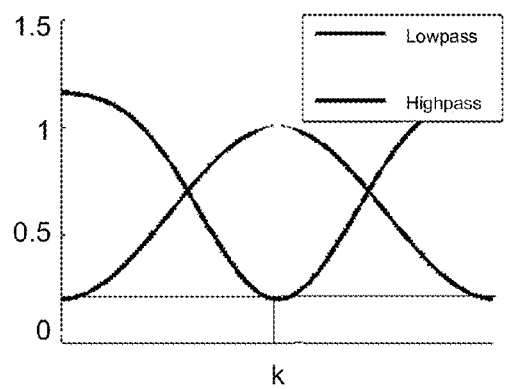
Figure 18A:
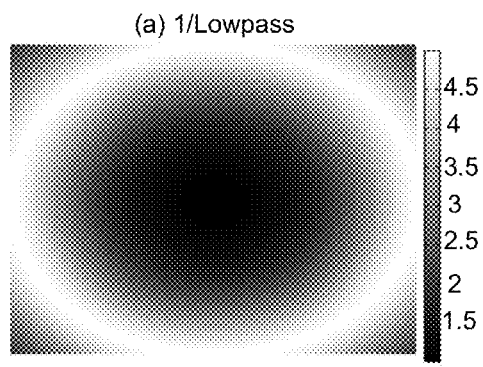
FIG. 18. The reciprocals of the filters in FIG. 17A-D are shown in FIG. 18A-D, respectively.
Figure 18B:
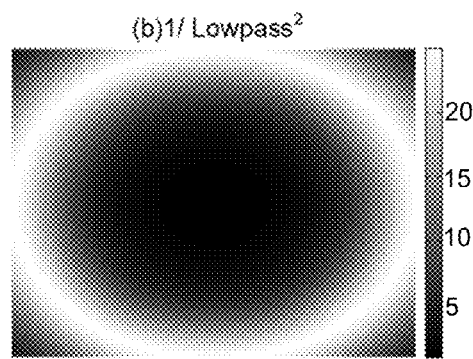
Figure 18C:
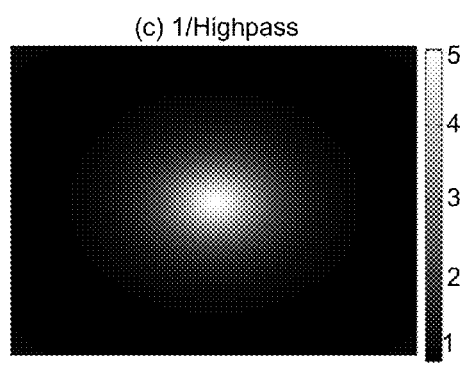
Figure 18D:
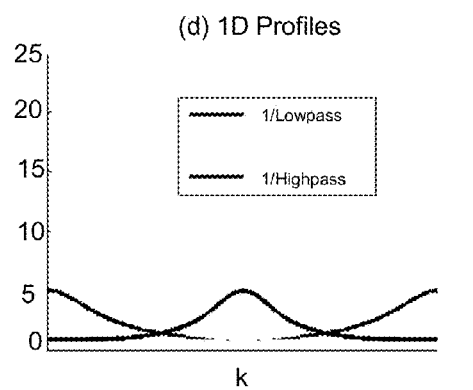
Figure 19A:
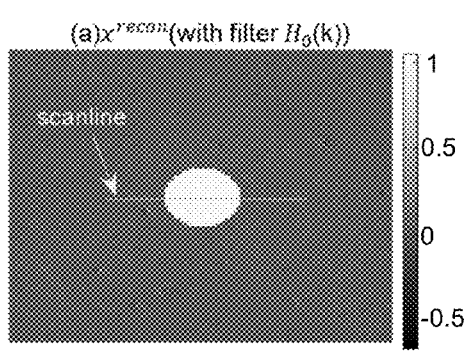
FIG. 19 Demonstration of $\chi$ reconstructions with (a) standard filter $H(k)=H_0(k)$, (b) lowpass filter $H(k)=H_0(k)//f_{LP}(k)$ with $f_{LP}(k)=[0.6+0.4 \cos(\pi k/k_{max})]^2$, (c) highpass filter $H(k)=H_0(k)/f_{HP}(k)$ with $f_{HP}(k)=1-[0.6+0.4 \cos(\pi k/k_{max})]^2+0.2$. The profiles of the scanline (indicated in (a)) are shown in (d).
Figure 19B:
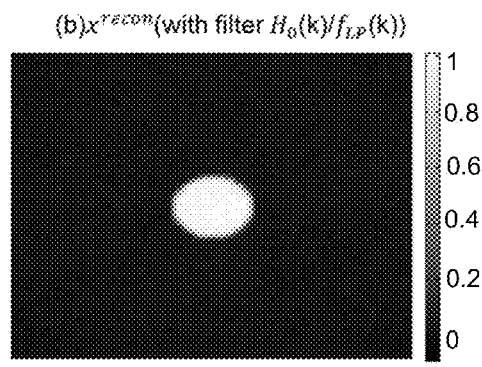
Figure 19C:
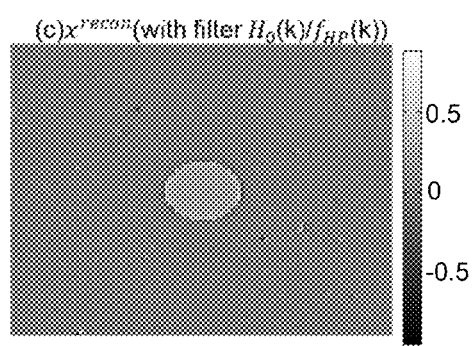
Figure 19D:
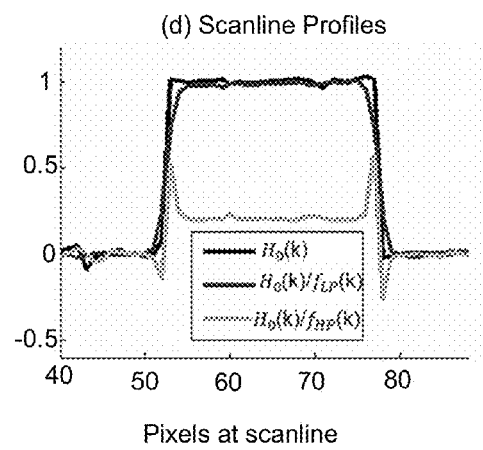

Some typical 1D filters are shown in FIG. 15. We can use the 1D filters to modify the filter $H_0(k_x,k_y,k_z)$ along $k_x$-, $k_y$-, and $k_z$-axis; or along diagonal lines of 3D Fourier domain. FIG. 15 shows diagram for bandpass, highpass, and lowpass filtering, which is applied to a direction along $k_x$-, $k_y$-, $k_g$-axis, and radial direction k, separately and jointly. The red plots have sharp cutoffs and the black plots are smooth, which can suppress Gibbs effect.

It is known that two points in Fourier domain correspond to a collection of parallel lines in the space domain. In FIG. 16, we show that the stripe features can be exacted (or enhanced) by the designed kernels. In the presence of noise, some points on the zerosurface may escape the truncation regularization. Any two points will produce a collection of parallel lines, with the interline distance determined by the two-point distance in Fourier domain, the strength by the two-point values. In this way, we can explain the streak artifacts associated with the "filter truncation" solver. FIG. 16 shows illustrations of stripe feature extraction by designing the filters for horizontal stripe extraction (at top row), vertical stripe extraction (at middle row), and the extraction for vertical, horizontal, diagonal, and anti-diagonal stripes (at bottom row). The superimposition of numerous random stripes manifests as a clutter noise in the $\chi$ reconstructions.

In implementation of the filter design for "post-recon filtering" (in Eq. (32)), we can make a basic lowpass filter using a cosine function $$f_{LP}(k) = c_1 c_2 \times \cos(\pi k/k_{max}) \; s.t. \; \min\{f_{LP}(k)\} > 0$$

$$f_{LP}(k) = 0.6 + 0.4 \times \cos(\pi k/k_{max}) \; (\text{case: } c_1 = 0.6 \text{ and } c_2 0.4) \quad (34)$$

with $k_{max} = \max\{|k|\}$

The condition for a lowpass filter is $\min\{f_{LP}(k)\} > 0$, as required by the non-singularity of $1/f_{LP}(k)$. In Eq. (34), we provide a special case of $c_1 = 0.6$ and $c_2 = 0.4$, which produces $\min\{f_{LP}(k)\} = 0.2$.

Based on a lowpass filter $f_{LP}(k)$, we can make a highpass filter by $$f_{HP}(k) = \max(f_{LP}) - f_{LP}(k) + c_0 \; s.t. \; \min\{f_{HP}(k)\} > 0$$

$$f_{HP}(k) = \max(f_{LP}) - f_{LP}(k) + 0.2 (\text{case: } c_0 = 0.2) \quad (35)$$

As required by $1/f_{HP}(k)$, we impose the highpass filter a condition of $\min\{f_{LP}(k)\} > 0$. In Eq. (35), we also provide a special case of $c_0 = 0.2$ such that $\min\{f_{LP}(k)\} = 0.2$.

Considering $f_{LP}(k)$ and $f_{HP}(k)$ obtained by Eqs. (34) and (35) are basic lowpass and highpass filters, we can also reshape them by applying a power law, that is $$f_{LP}(k;\alpha) = [f_{LP}(k)]^\alpha, \alpha = \{½, 1, 2, 3 \ldots\}$$

$$f_{Hp}(k;\alpha) = [f_{HP}(k)]^\alpha, \alpha = \{½, 1, 2, 3 \ldots\} \quad (36)$$

It is noted that the filter shape can be dilated with $0 \le \alpha \le 1$ and shrunk with $\alpha > 1$. In this way, we can design different lowpass and highpass filters by selecting proper values for the parameters of $\{c_0, c_1, c_2, \alpha\}$.

In FIG. 17, we demonstrate (with a 2D slice display) a lowpass filter $f_{LP}(k)$ in (a), a squared lowpass filter $f_{LP}(k;2)$ in (b), and a highpass filter $f_{HP}(k)$ in (c), as well as 1D profiles. FIG. 17 shows demonstration of lowpass and highpass filters. It is noted the lowpass filter can be reshaped by a square operation (for example, constricted by Eq. (36) with $\alpha = 2$).

Given a post-recon filter, we can calculate the corresponding TV-iteration filter by using Eq. (33). In implementation of the filter design for "TV-iteration filtering", we can calculate the reciprocal filters $1/f_{LP}(k;\alpha)$ and $1/f_{HP}(k;\alpha)$, where the infinite should be carefully avoided through a small offset $c_{0>0}$ in Eq. (35). The reciprocals of the filters in FIG. 17 are displayed in FIG. 18.

In FIG. 19, we demonstrate the TV-iterated $\chi$ reconstructions with the standard filter ($H_0(k)$), a lowpass filter ($H_0(k)/f_{LP}(k)$), and a highpass filter (($H_0(k)/f_{HP}(k)$). It is seen that the lowpass-filtering reconstruction smoothes the image, and highpass reconstruction enhances the edges. FIG. 19 shows demonstration of $\chi$ reconstructions with (a) standard filter $H(k) = H_0(k)$, (b) lowpass filter $H(k) = H_0(k)/f_{LP}(k)$ with $t_{LP}(k) = [0.6 + 0.4 \cos(\pi k/k_{max})]^2$, (c) highpass filter $H(k) = H_0(k)/f_{HP}(k)$ with $f_{HP}(k) = 1 - [0.6 + 0.4 \cos(\pi k/k_{max})]^2 + 0.2$. The profiles of the scanline (indicated in (a)) are shown in FIG. 19(d).

We also designed the bandstop (BT) and bandpass (BP) filters:

$$f_{BP}(k) = 1 - \exp\left(-\frac{|k|^2}{2\pi\sigma_1 k_{max}^2}\right) + \exp\left(-\frac{|k|^2}{2\pi\sigma_2 k_{max}^2}\right), \quad \sigma_1 > \sigma_2 \quad (bandpass) \quad (37)$$

$$f_{BT}(k) = \exp\left(-\frac{|k|^2}{2\pi\sigma_1 k_{max}^2}\right) - \exp\left(-\frac{|k|^2}{2\pi\sigma_2 k_{max}^2}\right), \quad \sigma_1 > \sigma_2 \quad (bandstop)$$

where $\sigma$ denotes the standard deviation of Gaussian distribution, which controls the shape of filter. Based on our numerical simulations, we find that the bandstop and bandpass filtering is useful for high spatial resolution $\chi$ reconstruction.

From our experience, the "post-recon filtering" by a filter $f(k)$ in Eq. (32), and the "TV-iteration filtering" by a filter $H(k)$ in Eq. (33) can achieve similar results, with a difference in residual noise. Therefore, we can safely use an average of the two to obtain a noise-reduced $\chi$ source, while maintaining the desirable $f(k)$ filtering features.

Estimation of TV Iteration Parameter ($\lambda$) by Self-Calibration Scheme

The TV-regularized deconvolution algorithm in Eq. (16) involves a regularization parameter $\lambda$, whose value should be preset for a TV iteration. For numerical simulation and phantom study, we can determine the proper values for $\lambda$ by comparing the iteration output with the predefined input (known). For phantom experiment, we can also compare the TV iteration output with the known phantom pattern, which is called system calibration in medical imaging. In practice, however, a phantom may be unavailable, or the magnetic susceptibility property of the phantom may deviate far differently from that of the imaging target. In such cases, especially for brain imaging where the brain interior susceptibility distribution remains unknown, we need find a way to estimate the TV iteration parameter value to ensure that the output of the TV iteration is a meaningful $\chi$ reconstruction.

Figure 20:
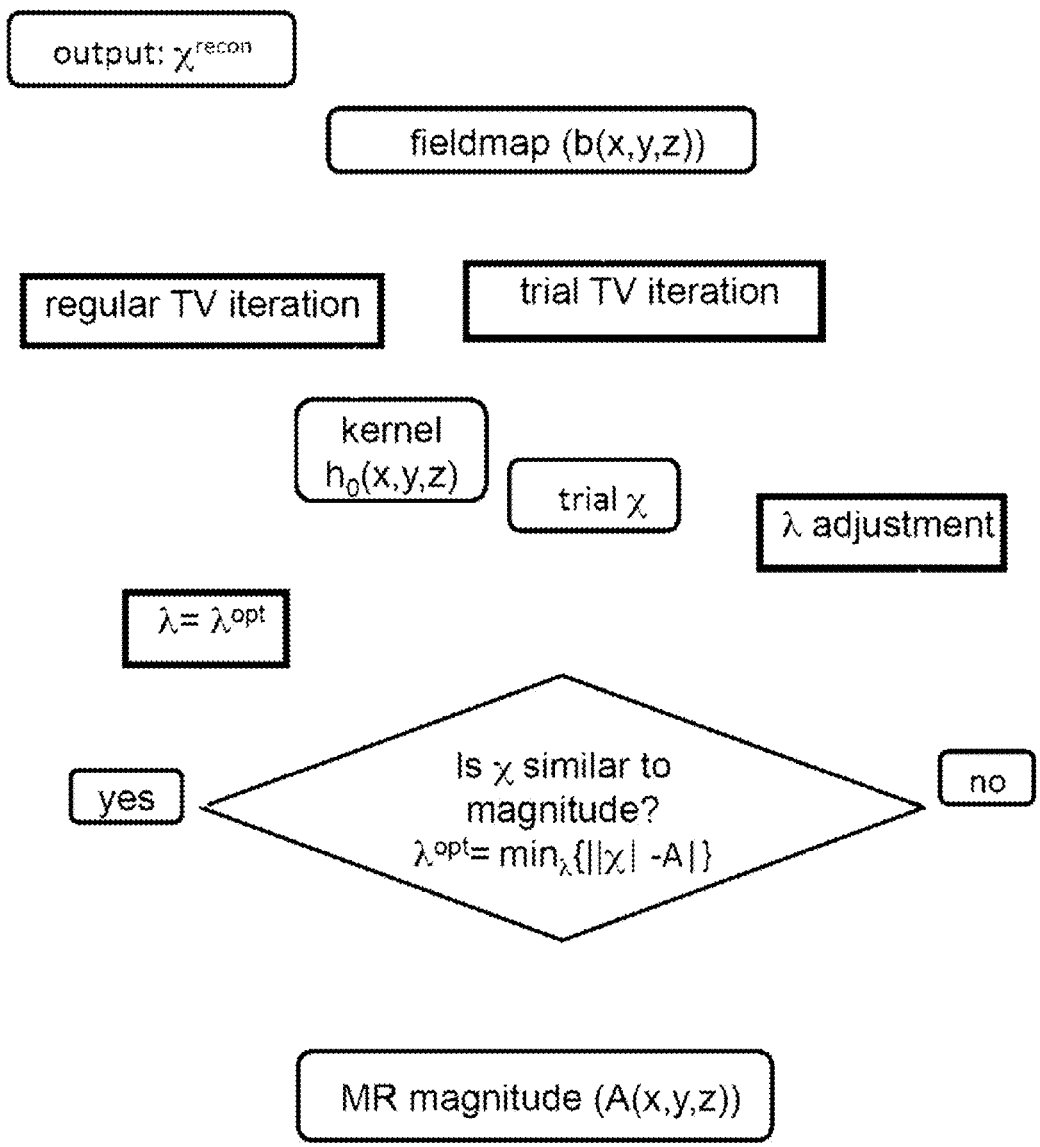
FIG. 20. A MR magnitude-based self-calibration scheme for estimating the TV regularization parameter value. The MR magnitude image is used as a reference to compare with the trial TV iteration outcome, thereby determining the initial guess of proper TV iteration parameter values for $\chi$ reconstruction. It is noted that the magnitude is compared with the absolute value of susceptibility.

Our research [17] has shown that the brain interior $\chi$ reconstruction is closely dependent upon the regularization parameter $\lambda$ selection; a very small $\lambda$ may result in oversmoothing effect, while a very large $\lambda$ may result in textural noise enhancement. It is noted that, although the MR magnitude image is not an exact representation of the unknown susceptibility source, it is a good estimate [17, 19]. Therefore, we can make use of the MR magnitude image as a guide for the TV iteration during the trial-and-error stage. Specifically, we can estimate the regularization parameter value by comparing the iteration output with the MR magnitude image of an unknown bio-physiological entity under MR scanning. In this way, we calibrate the $\chi$ tomographic imaging system based on the MR magnitude image of the $\chi$ source itself, without using a phantom, we can implement a self-calibration scheme for TV-regularized χ reconstruction. As a result, we developed a self-calibrated TV iteration parameter estimation scheme, which is shown in FIG. 20. FIG. 20 shows a magnitude-based self-calibration scheme for the TV regularization parameter value estimation. The MR magnitude image is used as a reference to compare with the trial TV iteration outcome, thereby determining the proper TV iteration parameter values for χ reconstruction. It is noted that the magnitude is compared with the absolute value of the susceptibility value (which can be positive or negative valued).

The "λ adjustment" box in FIG. 20 is for estimating an appropriate value, or a range, for the regularization parameter λ, by using the MR magnitude image as a guide or an initial estimate of χ source. Specifically, by comparing (usually by visual comparison) a reconstructed susceptibility source with the MR magnitude image during the trial iteration, we can estimate proper values for the TV regularization parameter. It is understandable that the MR magnitude image is not identical to the reconstructed susceptibility source (due to the magnitude's normegativity and T2*MRI nonlinearity). It is noted that we take into account the magnitude's non-negativity by comparing the magnitude image with the absolute value of reconstructed susceptibility. Although the magnitude image is somewhat different from the susceptibility source, it is good enough to estimate the TV regularization parameter λ, because λ may assume a wide range of values. Given an appropriate estimate of TV regularization parameter, the TV iteration convergence can reduce the iteration error, and produce a more direct and truthful result. In conclusion, for a single T2*MRI complex image, we can reconstruct its magnetic susceptibility distribution from the phase image by implementing a CIMRI tomographic procedure with a TV regularized iteration algorithm, in which we can make use of the MR magnitude image for calibrating (choosing) the TV regularization parameter, λ, without requiring use of an auxiliary phantom calibration.

Noise Reduction Scheme by Parallel TV Iterations and Average

Figure 21:
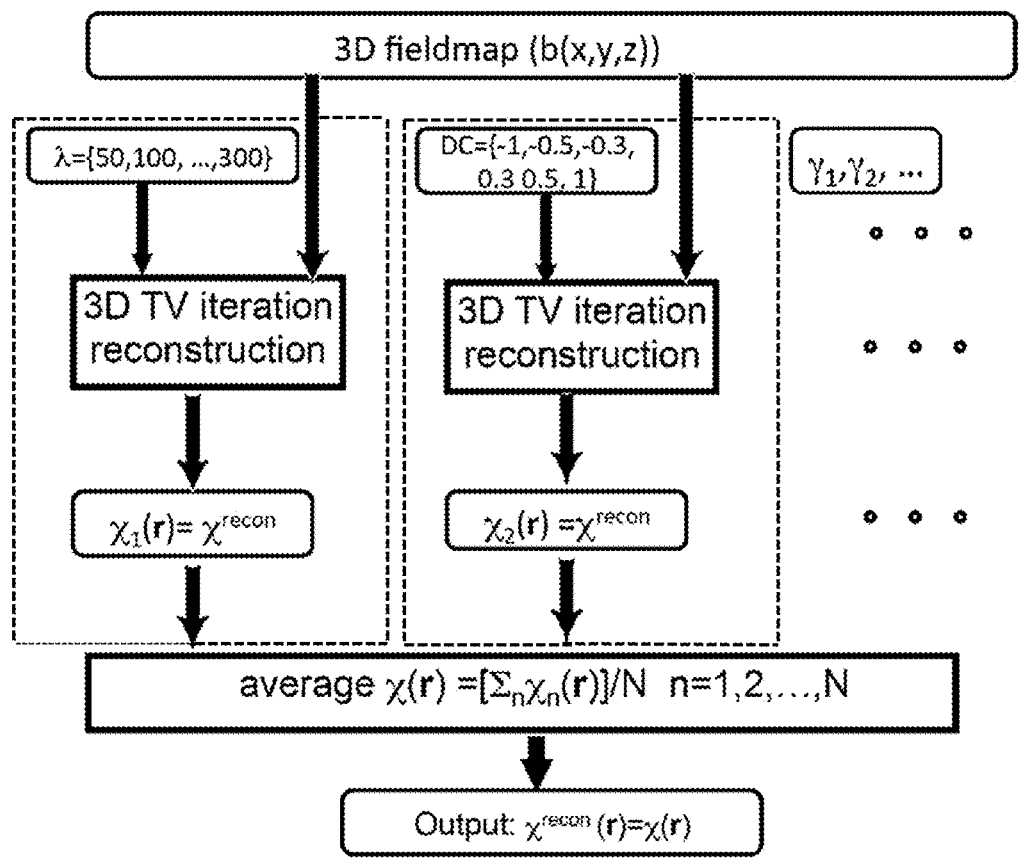
FIG. 21. Noise reduction strategy by parallel TV iteration (using different parameter values) and multiple reconstruction average.
Figures 22A, 22B, 22C:
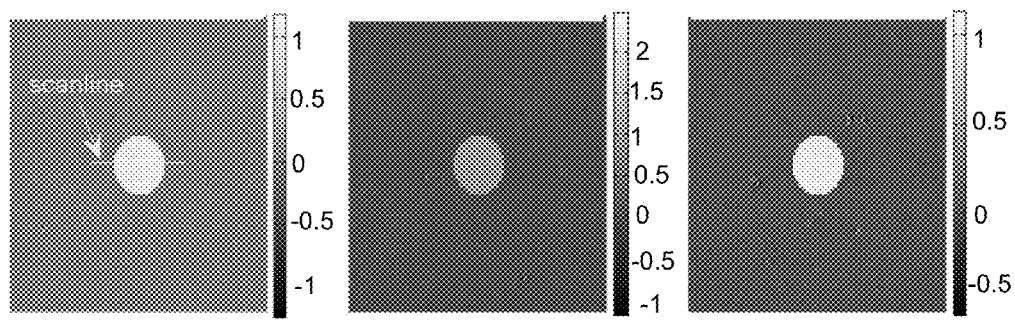
FIG. 22. Demonstration of noise reduction by multi-recon average. In each iteration, the $\chi$ reconstruction suffers sparse "residual noise" (or comeback noise associated with Bregman iteration), as indicated in dotted circles. The average of multiple reconstructions ((a1) through (a5) with different $\chi$ values) FIG. 22A-E, respectively can effectively reduce the sparse noise as shown in (b) (FIG. 22F).
Figures 22D, 22E, 22F:
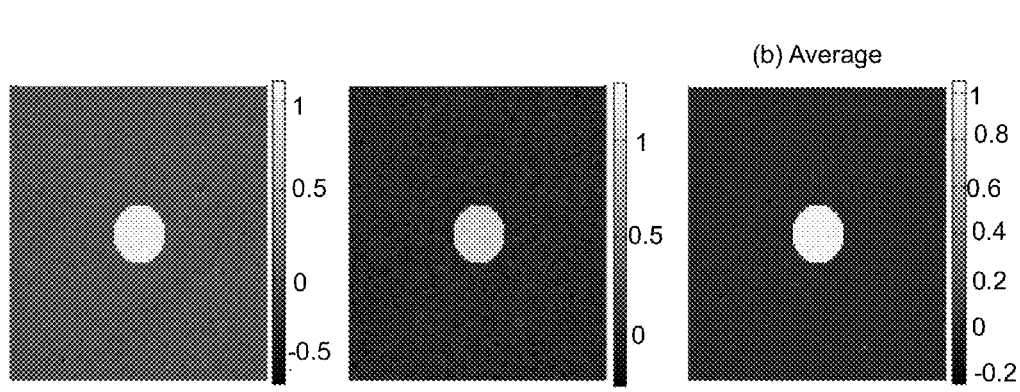

As reported above, the TV iteration may bring back sparse noise in χ reconstruction (see Eq. (19)). The comeback noise is different from the structure noise pattern in the fieldmap (phase image), that is, two iteration processes that are different by parameter settings may produce similar results that are different by residual noise pattern. Therefore, we developed a noise reduction strategy for χ reconstruction by multiple TV iterations, followed by a multi-reconstruction average. Since different TV iterations can be carried out in parallel computation, we call it "parallel TV iterations". By incorporating the DC term resetting approach, we implemented a parallel TV iteration scheme, as illustrated in FIG. 21. FIG. 21 shows a noise reduction strategy by parallel TV iteration (using different parameter values) and multiple reconstruction average. In summary, the purpose of performing multiple χ reconstructions by parallel TV iterations is for noise reduction by averaging.

In implementation, the TV regularization parameter λ may assume a large range of values, typically from 20 to 1000, which is problem-specific. Therefore, a variety of λ values can be used for TV iterations to produce a multiple of χ reconstructions that are similar and different in residual noise. By averaging over the multiple λ-variation χ reconstructions, we obtain a noise-reduced χ source. The λ-varied χ reconstructions can be used together with the scale-invariant χ reconstructions (through resetting of DC term values). The variations of auxiliary parameters $\gamma_1$ and $\gamma_2$ can also be used for multiple χ reconstructions (Typically, the values of $\gamma_1=\frac{1}{3}$ and $\gamma_2=\frac{1}{8}$ are preset). In general, any and all of the variations of parameters {regularization λ, DC term $H_0(0,0,0)$, auxiliary parameter $\gamma_1$ and $\gamma_2$} can be used for multiple χ reconstructions. The multiple reconstructions are carried out in parallel (at the cost of doing multiple computations). Then, the multi-reconstruction average is performed to produce a noise-reduced χ source.

Figure 23:
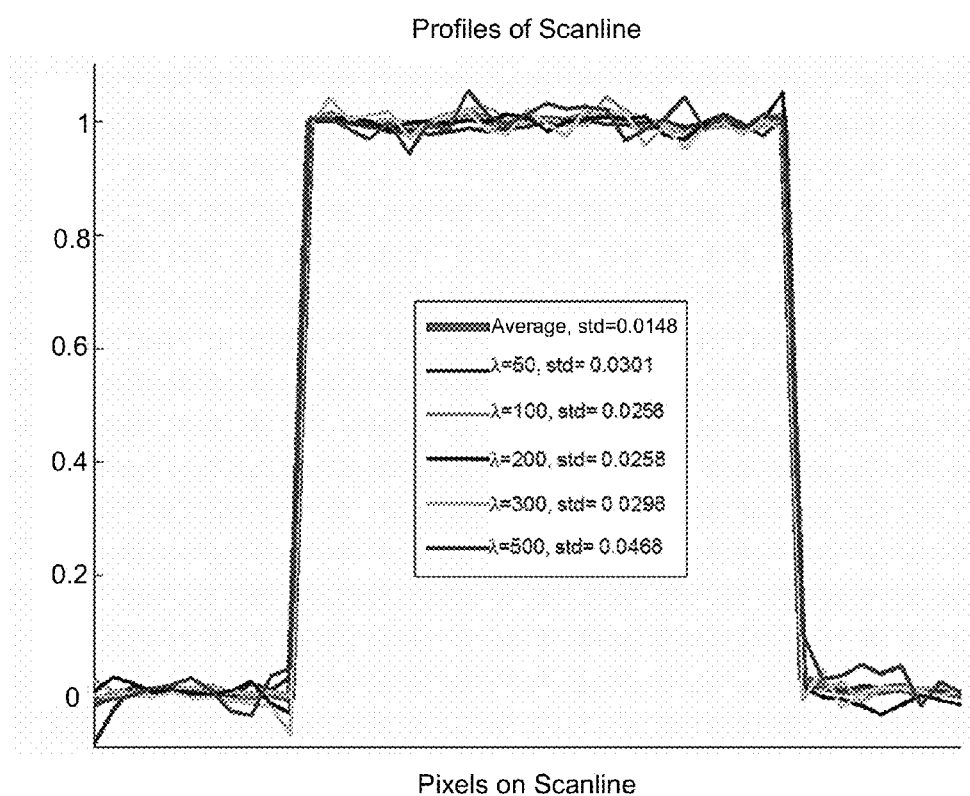
FIG. 23. Profiles of scanlines in FIG. 22. The amount of noises (calculated by standard deviation) are provided in the figure legend.

In FIG. 22, we demonstrate the noise reduction strategy by reconstructing five different χ reconstructions with λ={50, 100, 200, 500, 1000}, and then calculating their average ("multi-recon average"). In each iteration, the χ reconstruction suffers sparse "residual noise" (or comeback noise associated with Bregman iteration), as indicated in dotted circles. The average of multiple reconstructions ((a1) through (a5) with different X values) can effectively reduce the noise, as shown in (b). We mark the sparse comeback noise in dotted circle to show that the TV iterations with different regularization parameter values bring back different residual noises. Therefore, the multi-reconstruction average at the cost of multiple computations can effectively suppress the comeback noise. Quantitative noise reductions and scanline profiles are shown in FIG. 23. The noises (calculated by standard deviation) are provided in the figure's legend.

There are multiple reasons why we invented the "3D TV iteration filtering with a modified filter" to implement the post-recon filtering (reconstruction by using $h_0(r)$) followed by spatial filtering, as follows:

(a) TV iteration can reconstruct the susceptibility map with a powerful de-noising capacity, however, TV iteration may bring back sparse random noises in the uniform region of reconstructed susceptibility map (as demonstrated in simulations).

(b) By using a collection of modified filters h(r) (which are somewhat different, for example, in different DC-term values), we can obtain a collection of susceptibility map reconstructions that have very similar results (due to iteration convergence), but also have different random sparse "comeback" noises. Therefore, we can average the multiple reconstructions to reduce the overall noise.

(c) The multiple TV iteration reconstructions with different h(r) can be executed in parallel processing (using the same MR phase image, but with many h(r) that are somewhat different in their settings).

These advantages are not available by using only "post-recon filtering".

4D Susceptibility Reconstruction

Based on 3D χ reconstruction by CIMRI, we can extend to 4D χ dataset reconstruction, with each snapshot volume of 4D χ dataset reconstructed from the corresponding phase volume in the 4D complex dataset. For a dynamic functional imaging study by BOLD ƒMRI, which is always subject to a stimulus paradigm, denoted by task(t), we can make use of the known stimulus task(t) to ensure a meaningful 4D susceptibility reconstruction. The BOLD model describes a functional activity in terms of susceptibility perturbation as a timeseries of responses to a stimulus task(t) with a time lag. The conventional MR magnitude-based brain activation depiction assumes that the MR magnitude timecourse is synchronous with the stimulus task(t) with a time lag. Therefore, it is rational to assume that the reconstructed susceptibility timecourse is synchronous with the stimulus task(t) with a lag time as well. We term it as "timecourse synchrony" between the timecourse of an observed image response or an reconstructed susceptibility perturbation and the designed stimulus task(t). The MR magnitude timecourse synchrony condition has been accepted for brain mapping and neuroimaging. In this invention, we describe how to make use of susceptibility timecourse synchrony criterion for 4D susceptibility reconstruction.

Figure 24:
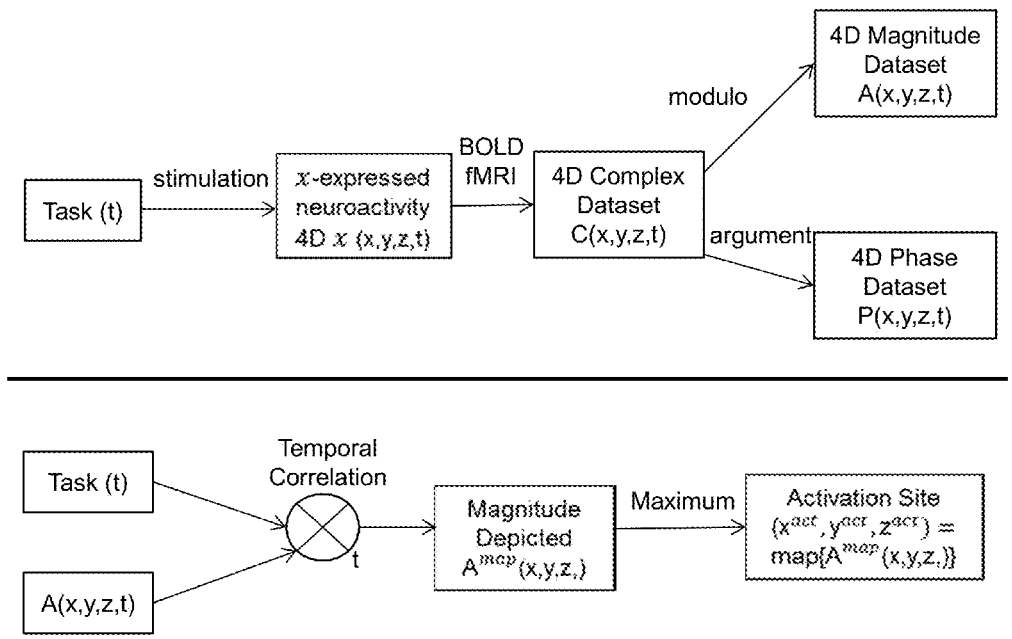
FIG. 24. Upper box: There are only three datasets available for a BOLD ƒMRI study {task(t), A(x,y,z,t), P(x,y,z,t)}. Lower box: the neuroactive site in the FOV can be determined by the temporal correlation between the task(t) and magnitude timecourses.

In order to make use of the known stimulus timecourse task(t) for 4D susceptibility reconstruction, we need to find the neuroactive location in the FOV of brain cortex. In FIG. 24, we show that there are three datasets available for a BOLD ƒMRI study: 1) the external stimulus task(t) (known), 2) the 4D magnitude dataset A(x,y,z,t) (acquired), and 3) the 4D phase dataset P(x,y,z,t) (acquired). What we can do for the BOLD ƒMRI data analysis is to manipulate these three datasets {task(t), A(x,y,z,t), P(x,y,z,t)}, usually by a statistical parameter mapping (SPM). By temporal correlation between the magnitude timecourses and task(t), we can find the neuroactive site ($x^{act}$, $y^{act}$, $z^{act}$) in the FOV, as diagrammed in FIG. 24. FIG. 24 shows: Upper box: There are only three datasets available for a BOLD ƒMRI study {task(t), A(x,y,z,t), P(x,y,z,t)}. Lower box: the neuroactive site in the FOV can be determined by the temporal correlation between the task(t) and magnitude timecourses.

Let $\chi^{true}(x,y,z,t)$ denote the dynamic can be predefined (as the ground truth) and the TV iteration reconstruction $\chi^*(x,y,z,t)$ can be compared with the truth thereby calibrating the parameter setting of {'$\lambda$','$\gamma_1$','$\gamma_2$'}. For real brain functional imaging, the true susceptibility source is unknown (under investigation). It is the neuroimaging principle that the neuroimage can be inferred by observing the brain responses to a task paradigm (external stimulation). Given a task(t), we can find the neuroactive site in the cortical FOV by the local maximal temporal correlation as expressed by $$(x^{act}, y^{act}, z^{act}) = \max_{(x,y,z) \in FOV} \{|A(x, y, z, t) \otimes_t \text{task}(t)|\} \quad (38)$$

where $\otimes_t$ denotes temporal correlation.

Due to spatial convolution associated with T2*MRI technology, the active voxel in the susceptibility source is in the vicinity (neighborhood) of ($x^{act},y^{act},z^{act}$), denoted by neighbor($x^{act},y^{act},z^{act}$), not necessarily at ($x^{act},y^{act},z^{act}$). At the brain active site, we hypothesize that the optimally reconstructed susceptibility timecourse should highly correlate with the task(t), as described by the criterion of timecourse synchrony. That is, under the timecourse synchrony condition, we obtain the reconstructed susceptibility source by:

$$\chi^{recon}(x, y, z, t) = \max_{(x',y',z') \in neighbor(x^{act},y^{act},z^{act})} \{|\chi^*(x', y', z', t) \otimes_t \text{task}(t)|\} \quad (39)$$

where $\chi^*(x,y,z,t)$ is a $\chi$ reconstruction during program running for the snapshot time, t, by the TV-regularized split Bregman iteration algorithm (in Eq. (20)). The output in Eq. (39) is an optimal $\chi$ reconstruction under the criterion of susceptibility synchrony by varying the TV regularization parameter. In algorithm implementation, the $\lambda$-adjustment is continued until the 4D susceptibility source reconstruction produces a highest-as-possible temporal correlation between the timecourse at an activation voxel and the external stimulation. The strategy is diagrammed in FIG. 25, which shows a 4D susceptibility reconstruction under the criterion of susceptibility timecourse synchrony (a way of making use of the external stimulus task(t)), where tcorr(x(t),y(t)) stands for temporal correlation between x(t) and y(t). The neuroactive location ($x^{act}$, $y^{act}$, $z^{act}$) is determined in FIG. 24.

For brain functional susceptibility reconstruction, we suggest a general rule for $\lambda$ selection: A proper $\lambda$ value for the TV reconstruction program should produce a voxel susceptibility timecourse at an active region such that it highly correlates (or anticorrelates) with the external task stimulus paradigm. It is noted that the stimulus paradigm is widely used for postprocessing a BOLD ƒMRI dataset by SPM. In our invention, we make use of the stimulus paradigm in two aspects: 1) for 4D $\chi$ tomographic reconstruction under the criterion of susceptibility timecourse synchrony; and 2) for postprocessing the reconstructed 4D $\chi$ dataset by SPM (in the same ways as performed on the 4D T2* dataset).

Structural $\chi$ Tomography and Functional $\chi$ Tomography

We clarify that the underlying source of T2*MRI is an inhomogeneous magnetic susceptibility distribution, which is mainly attributed to the iron content. Specifically, the $\chi$ distribution of an in vivo brain state consists of static nonheme iron deposit in tissue or organ structure and dynamic heme-iron perturbation in vascular blood associated with a brain functional activity. Interpreting the reconstructed $\chi$ map as the internal iron distribution, we can implement noninvasive iron measurement by CIMRI-based $\chi$ tomography. For tissue iron measurement, we can perform 3D structural $\chi$ tomography, and for dynamic functional heme-iron perturbation measurement, we can perform 4D functional $\chi$ tomography (a timeseries of 3D $\chi$ tomography).

We differentiate structural $\chi$ tomography from functional $\chi$ tomography by the following aspects: 1) The origin of the structural susceptibility source is the nonheme iron deposit in tissues or organs, whereas the origin of the functional susceptibility source is the heme iron perturbation associated with vascular blood magnetism change caused by a functional activity (as described by the BOLD activity); and 2) the structural susceptibility distribution is static (bleeding is also considered as static in the sense that the bleeding motion is very slow in comparison with $T_E$, that usually does not co-occur with the BOLD ƒMRI study) whereas the functional susceptibility perturbation is a dynamic response to a task paradigm. It is noted that a snapshot 3D volume in a 4D BOLD ƒMRI dataset consists of the contributions from both the static structural $\chi$ background (baseline) and the dynamic functional $\chi$ perturbation (activation).

Figure 26:
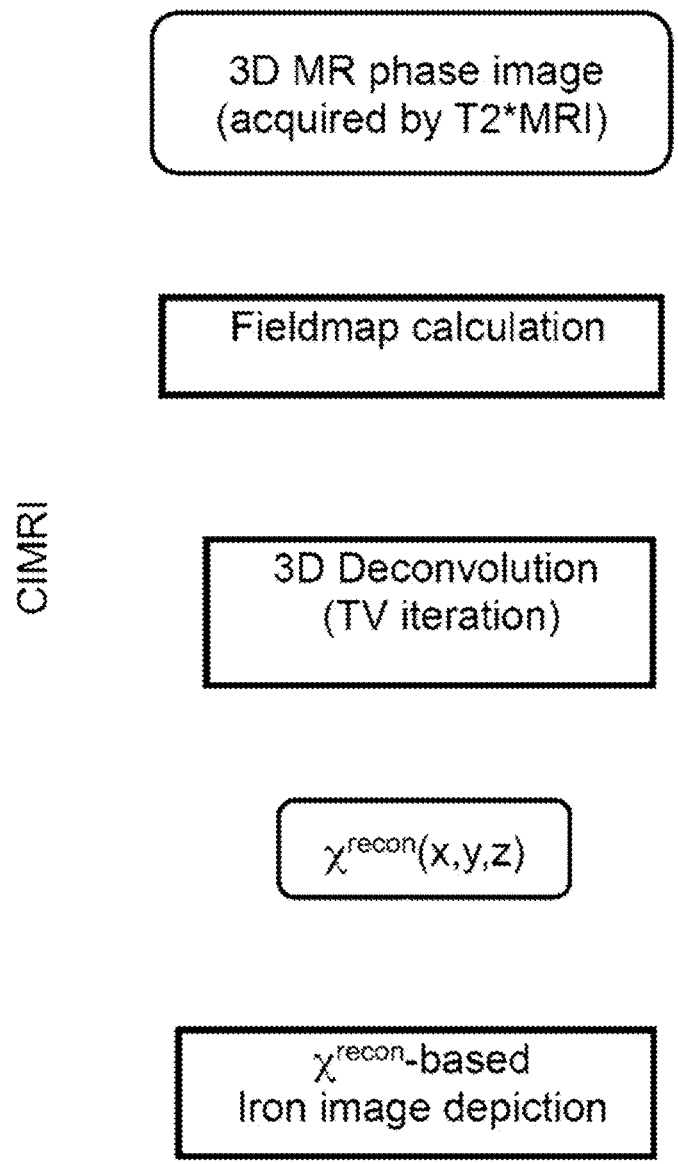
FIG. 26. Structural $\chi$ tomography scheme for susceptibility-based nonheme iron deposit measurement by structural MR imaging and CIMRI (toward applications for tissue and organ iron imaging).

In FIG. 26, we describe a structural $\chi$ tomography scheme for the susceptibility-based nonheme iron measurement in tissues or organs. This scheme is characteristic of the following aspects: 1) It is 3D tomographic reconstruction of the structural $\chi$ distribution (which is different from the voxel-based susceptometry or 2D image-based susceptibility mapping); and 2) The iron deposit image representation is based on the 3D $\chi$ reconstruction by CIMRI from the 3D MR phase image, rather than from the MR magnitude image.

Figures 27A, 27B, 27C:
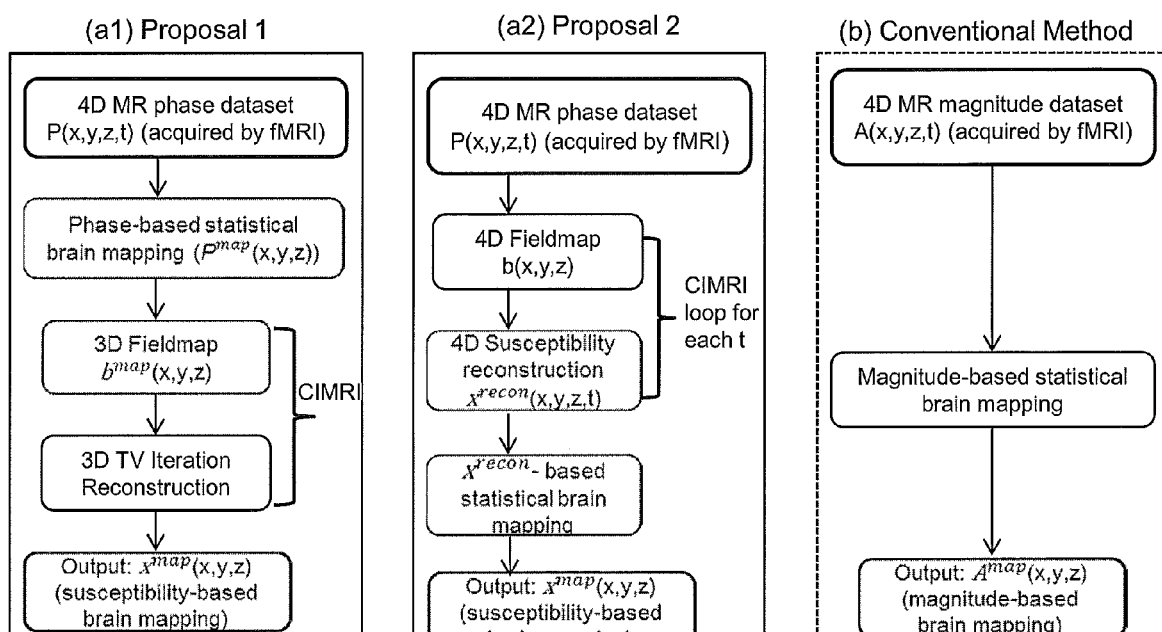
FIG. 27. Two methods for susceptibility-based brain mapping and neuroimaging in (a1) (FIG. 27A) and (a2) (FIG. 27B), which are different from the conventional magnitude-based brain mapping and neuroimage in (b) (FIG. 27C). The method 1 in (a1) (FIG. 27A) is for linear statistical data analysis, and the method 2 in (a2) (FIG. 27B) is for nonlinear linear statistical analysis.
Figure 28:
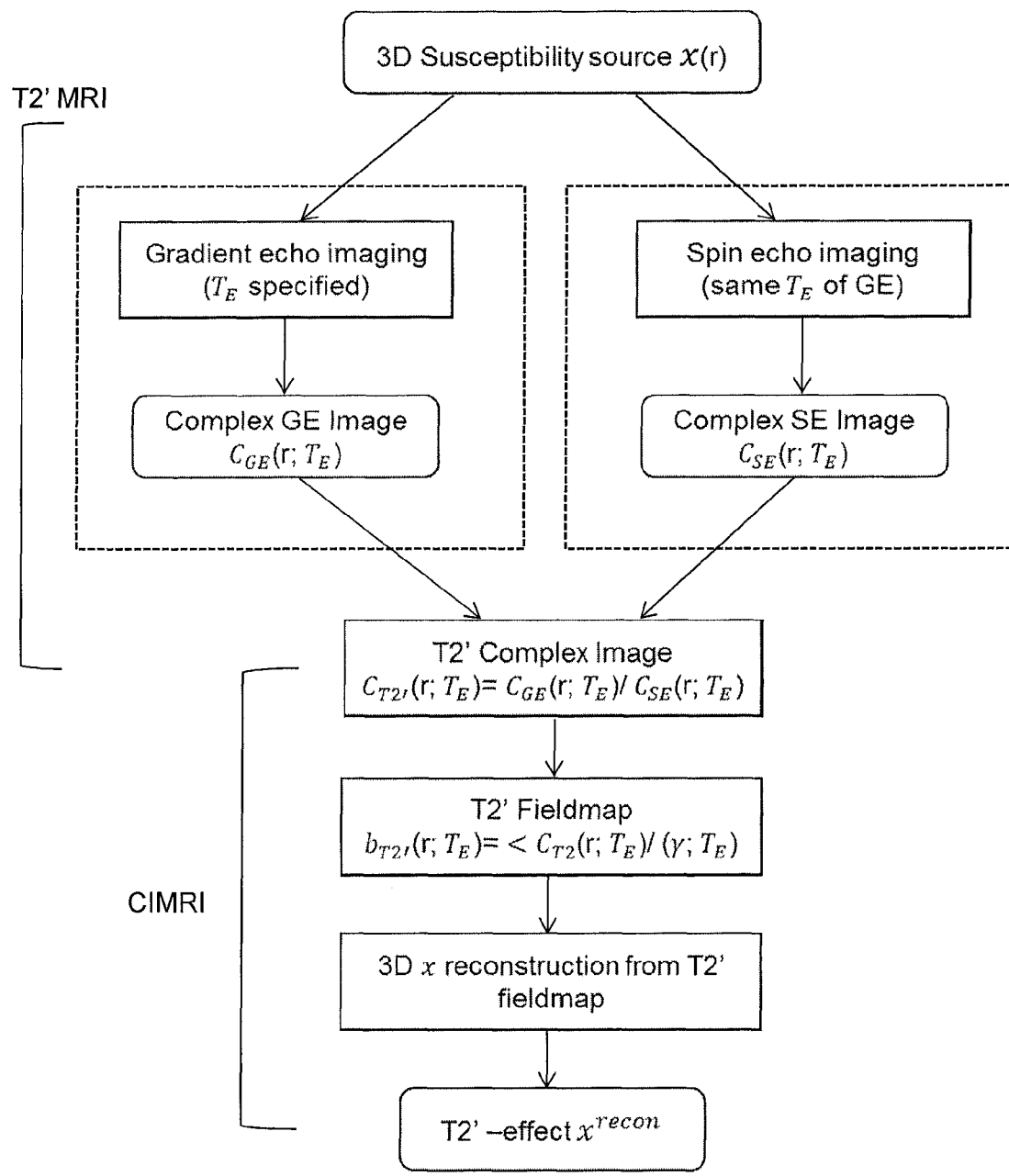
Figure 29:
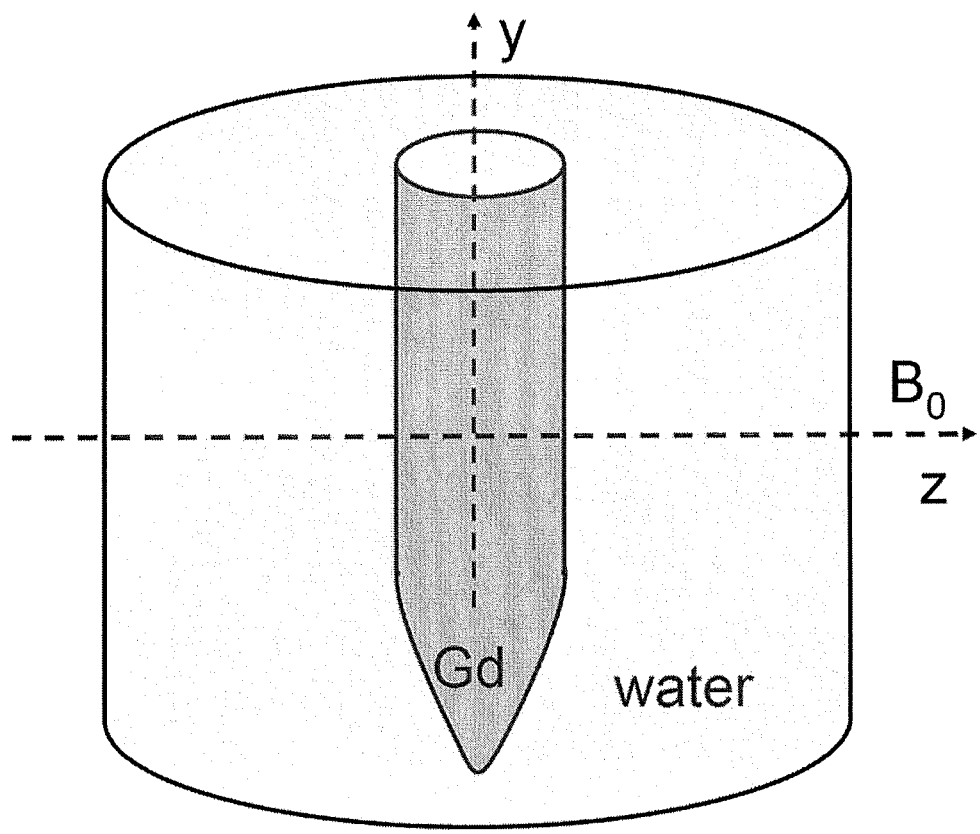
Figure 30:
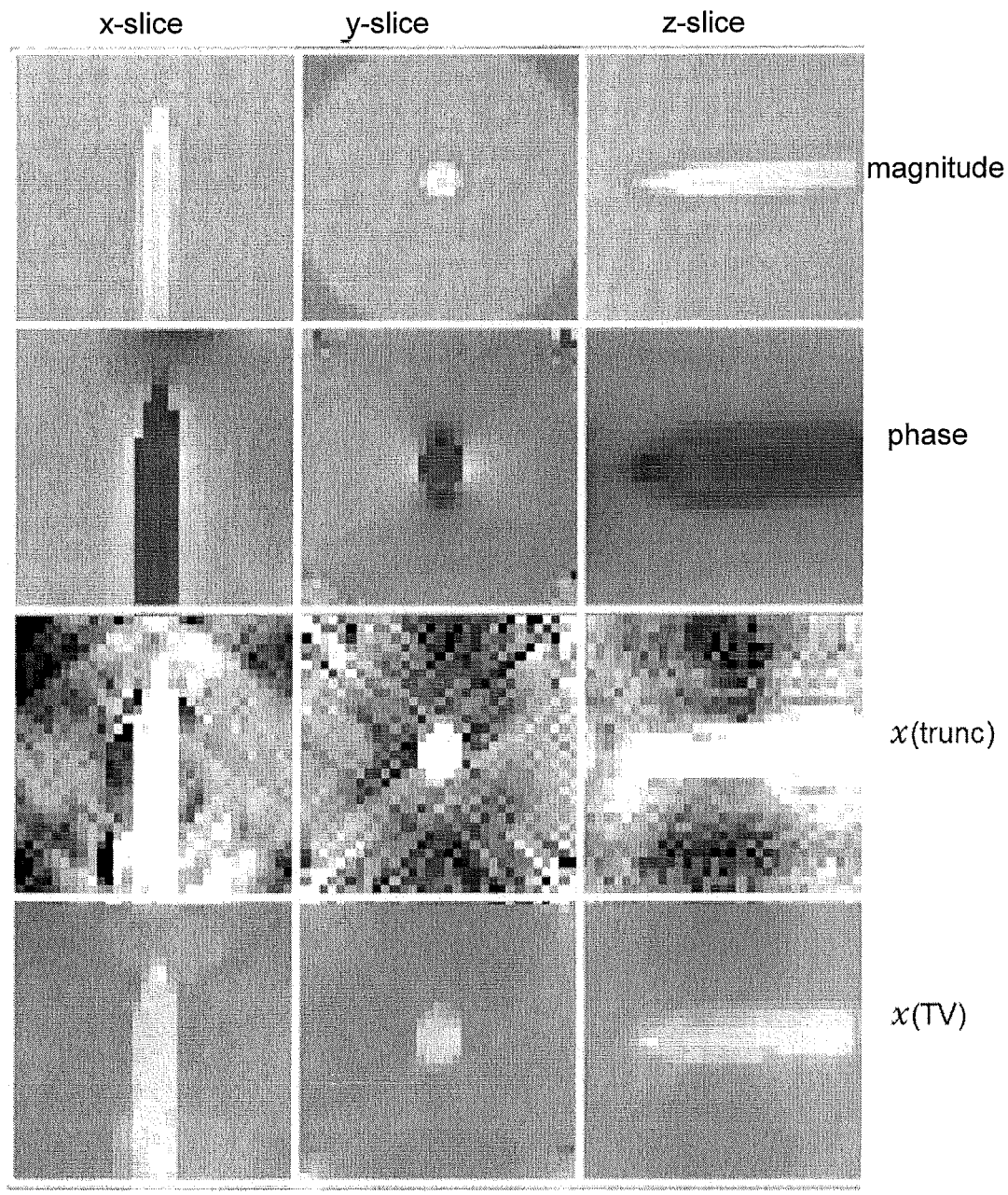
Figure 31:
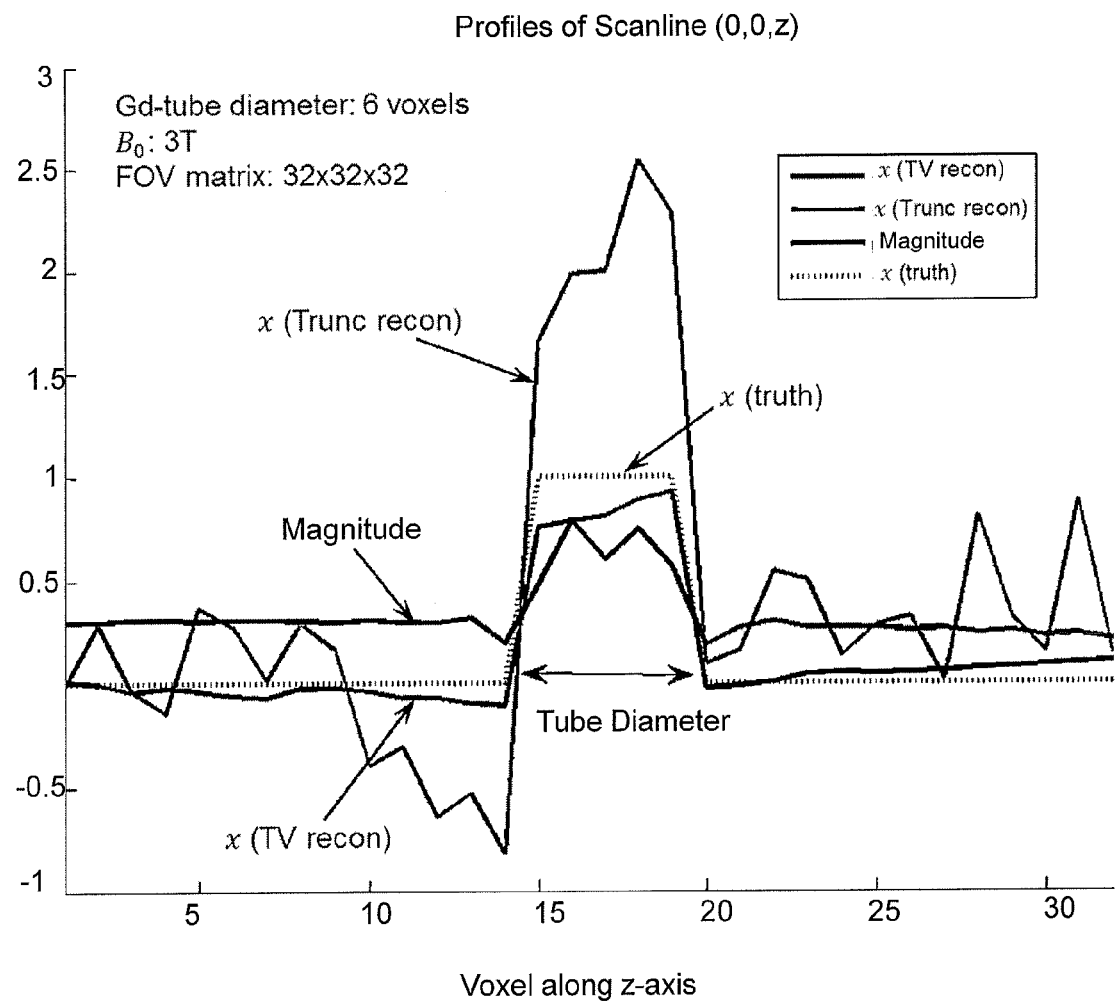
Figure 33:
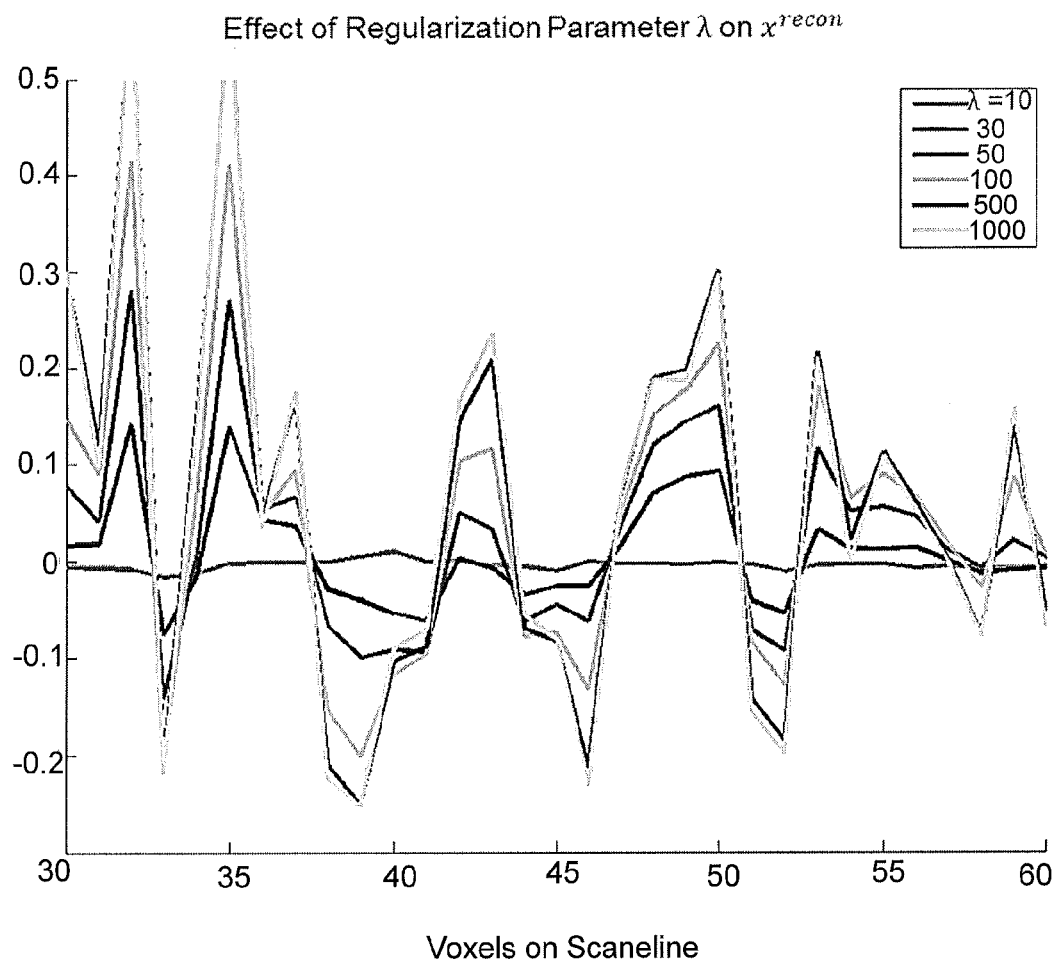
Figure 34:
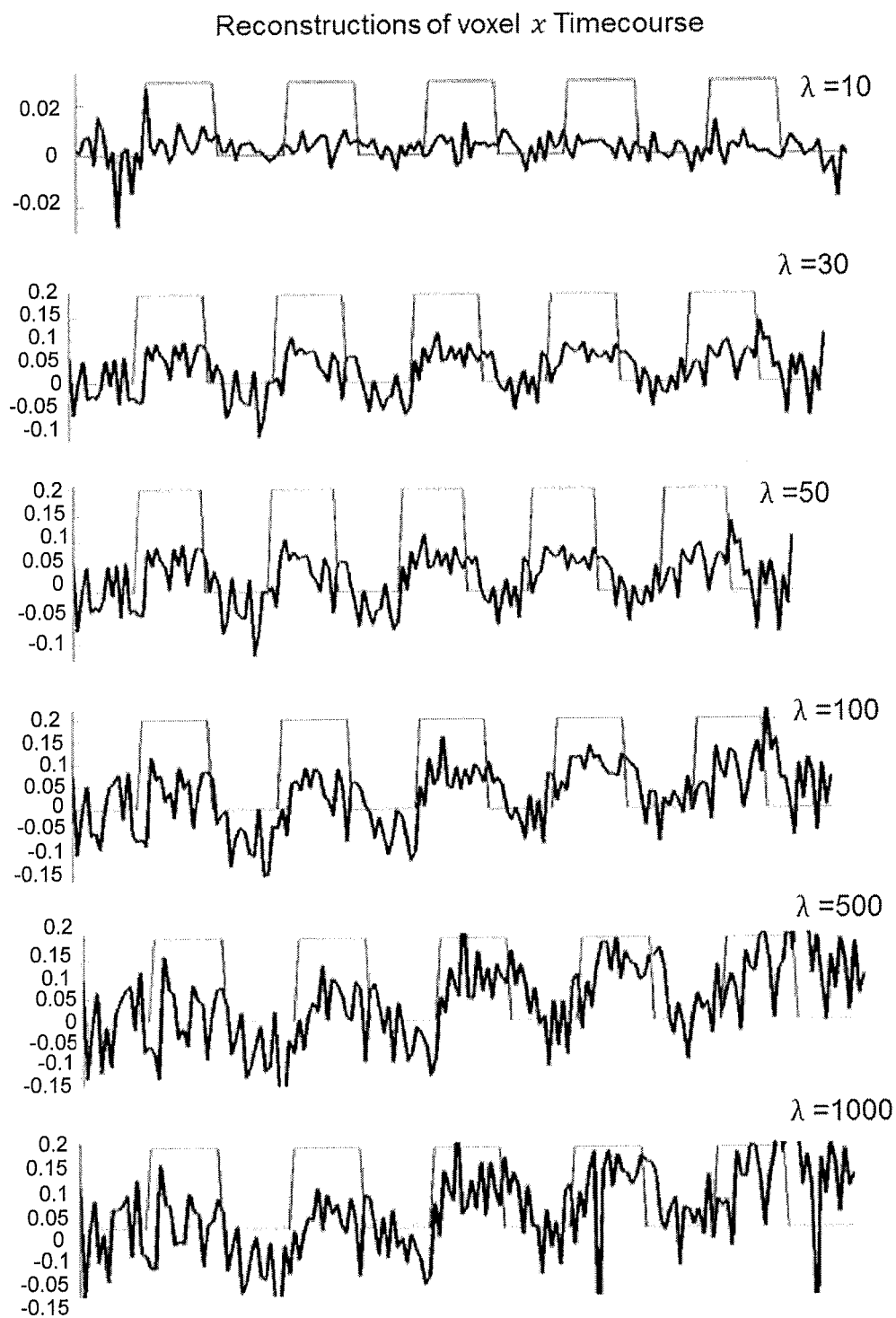
Figure 35:
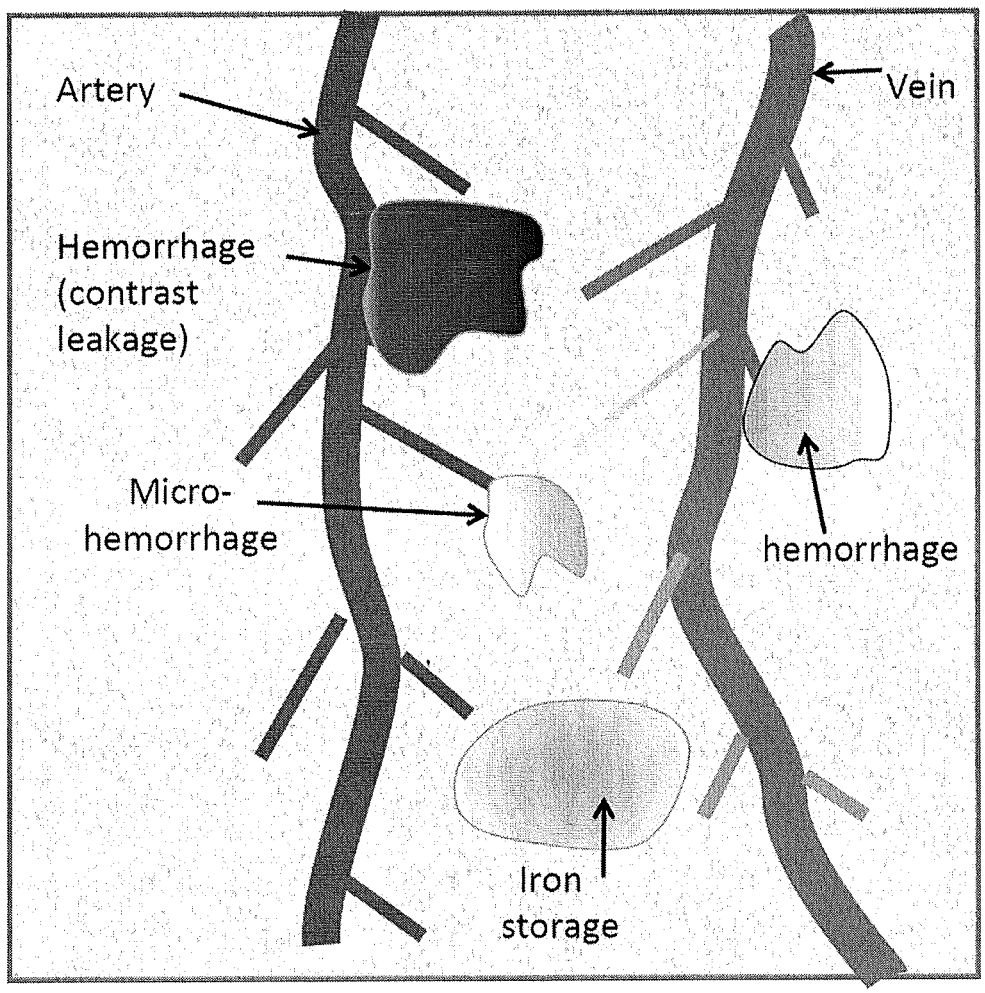
Figure 36A:
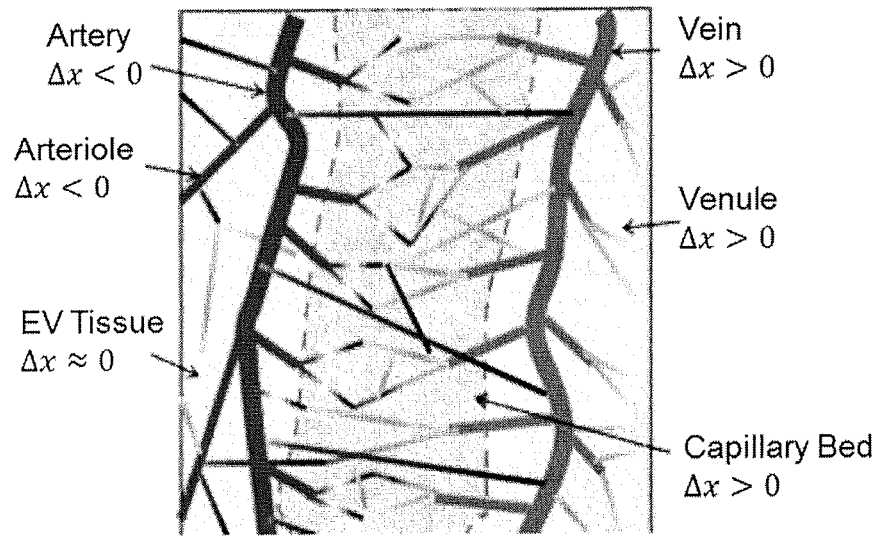
Figure 36B:
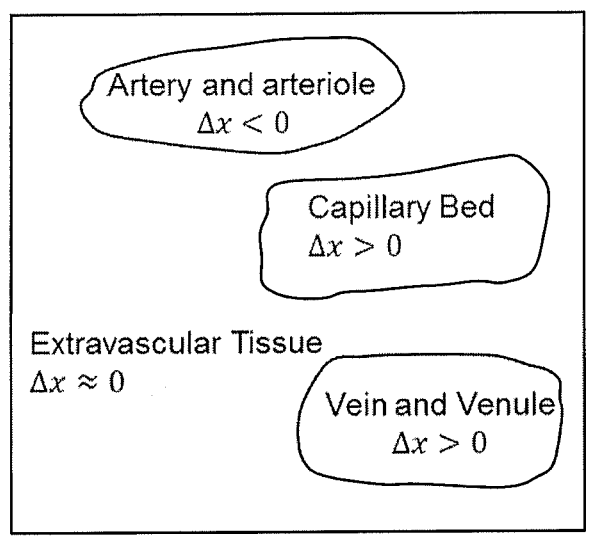
Figure 37:
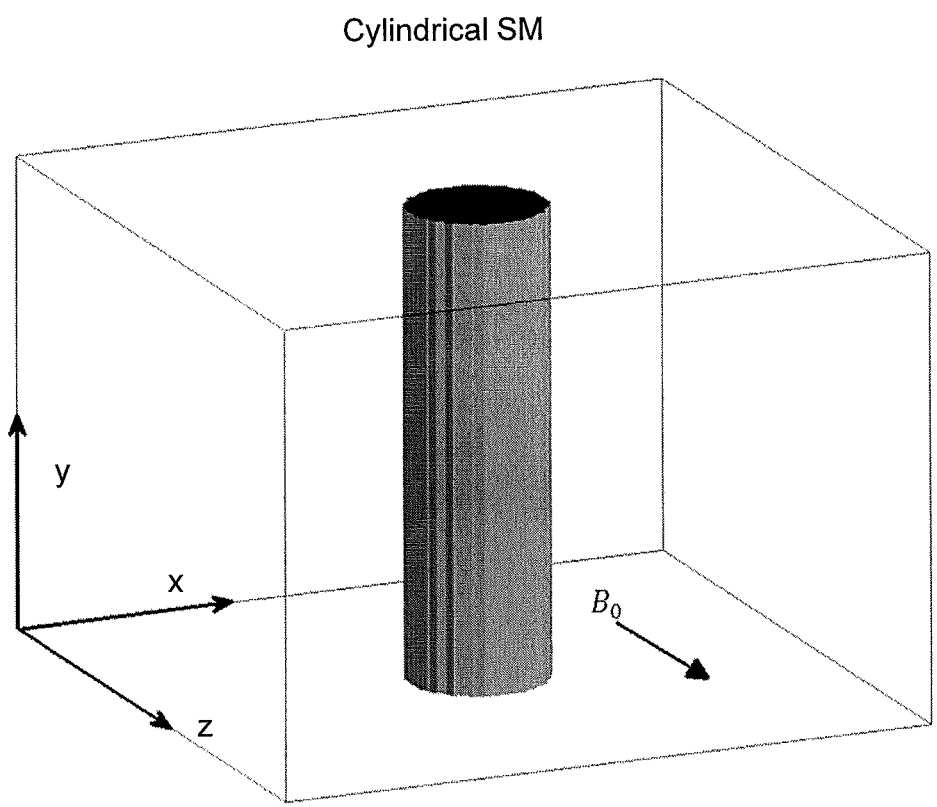
Figure 38A:
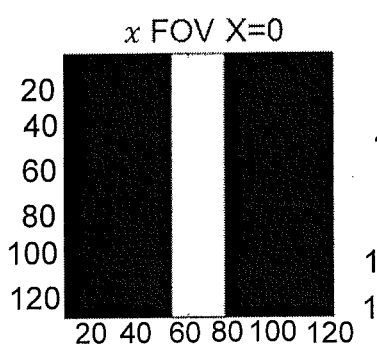
FIG. 38. Top row: three orthogonal cross-sections of the predefined $\chi$ source (FIG. 38A-C). Middle row: fieldmap without noise (FIG. 38D-F). Bottom row: fieldmap with additive Gaussian noise (NoiseLevel=0.1) (FIG. 38 G-I).
Figure 38B:
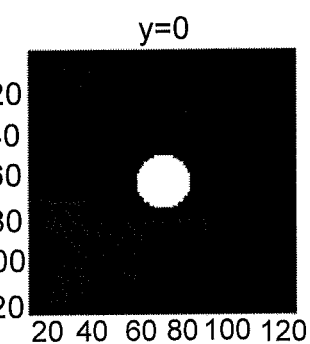
Figure 38C:
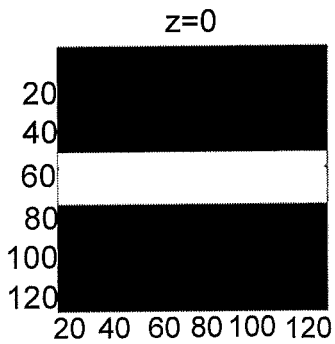
Figure 38D:
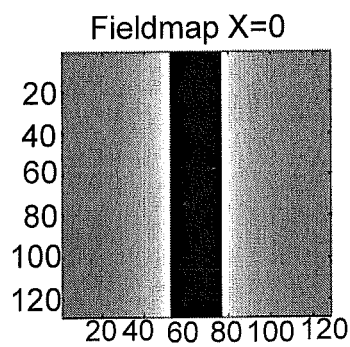
Figure 38E:
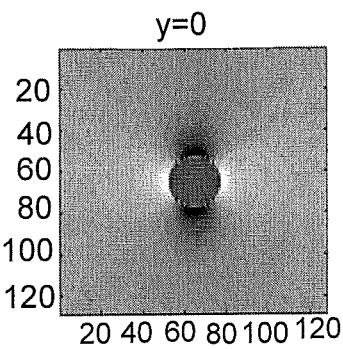
Figure 38F:
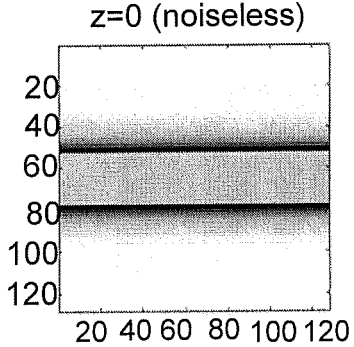
Figure 38G:
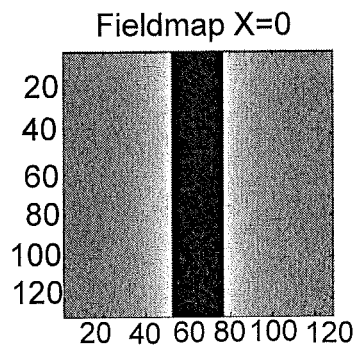
Figure 38H:
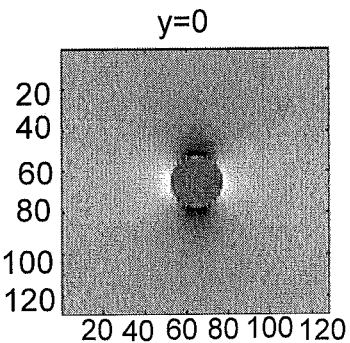
Figure 38I:
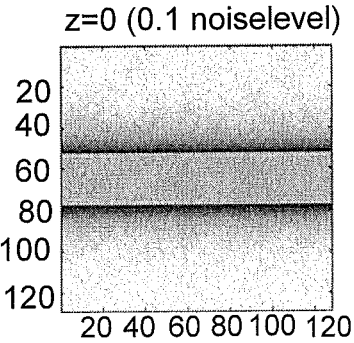
Figure 39:
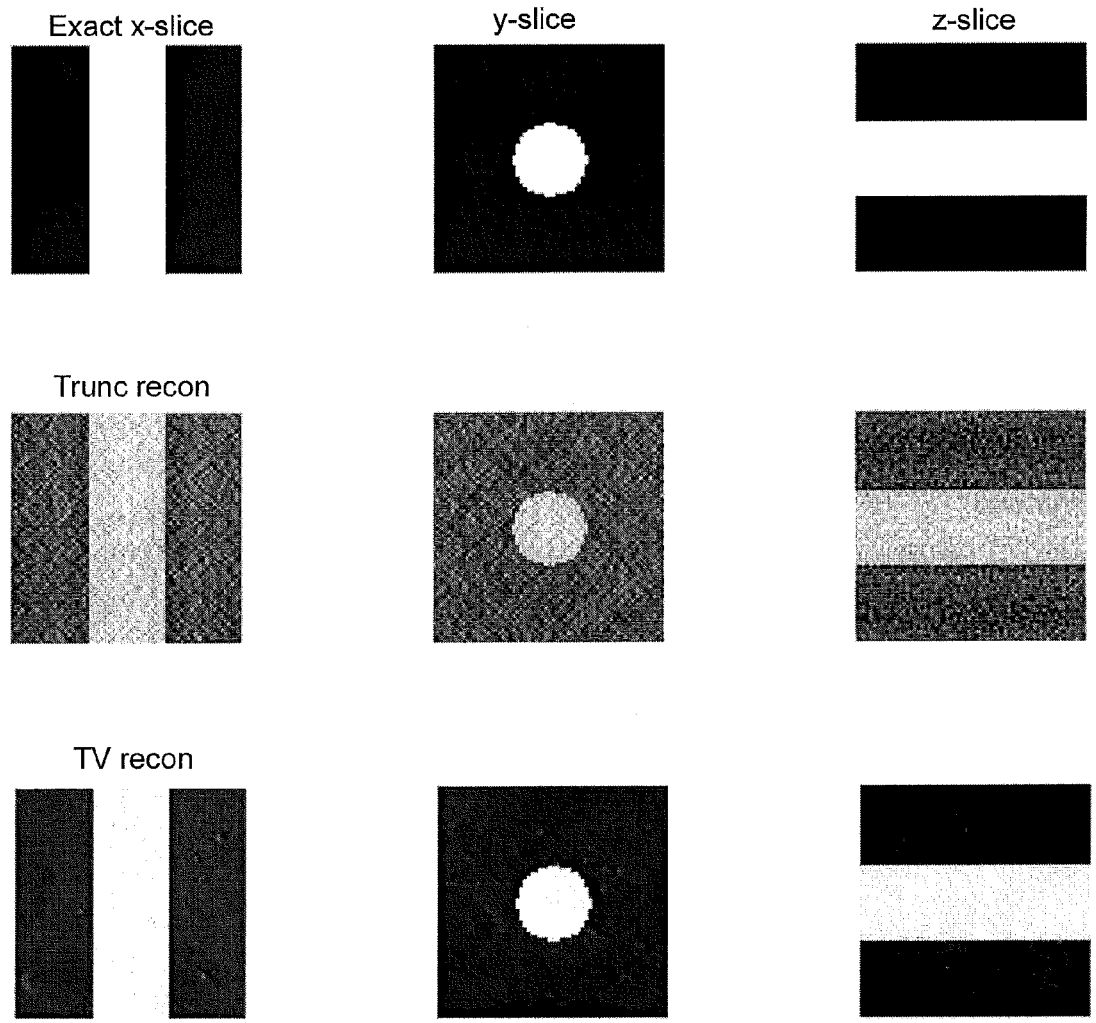
Figure 40:
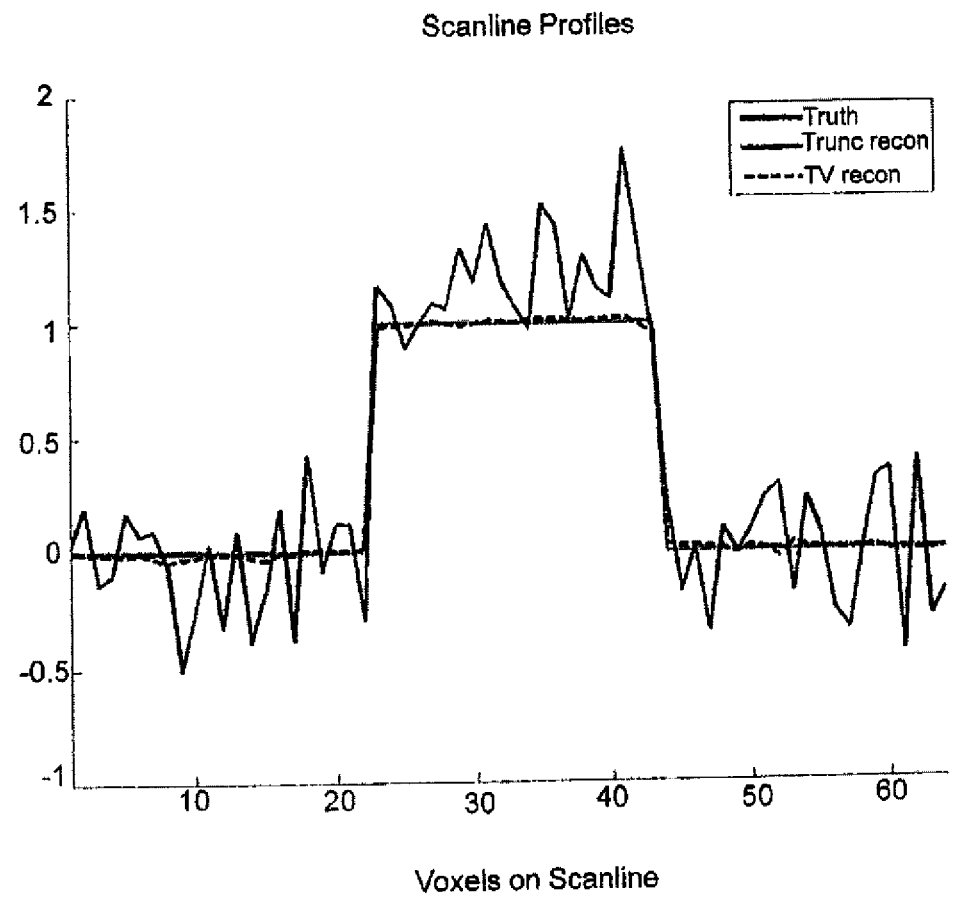
Figure 41:
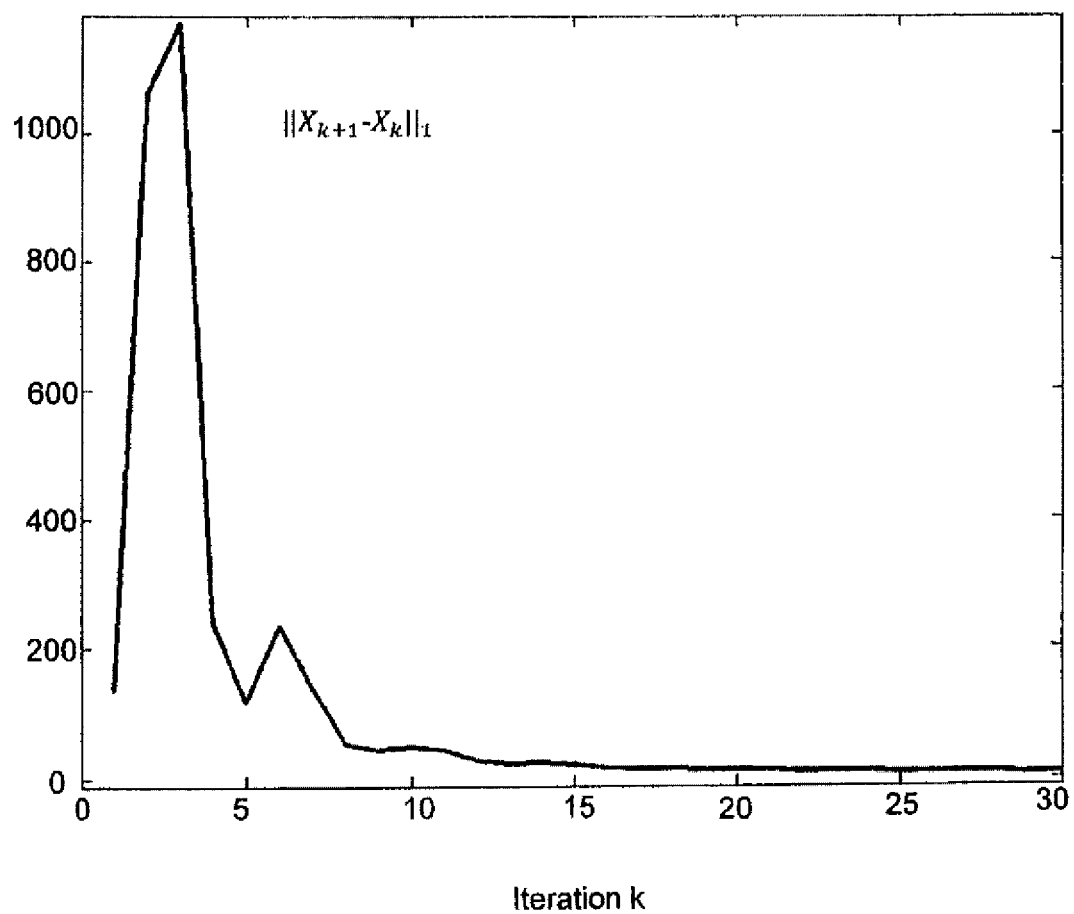
Figure 42:
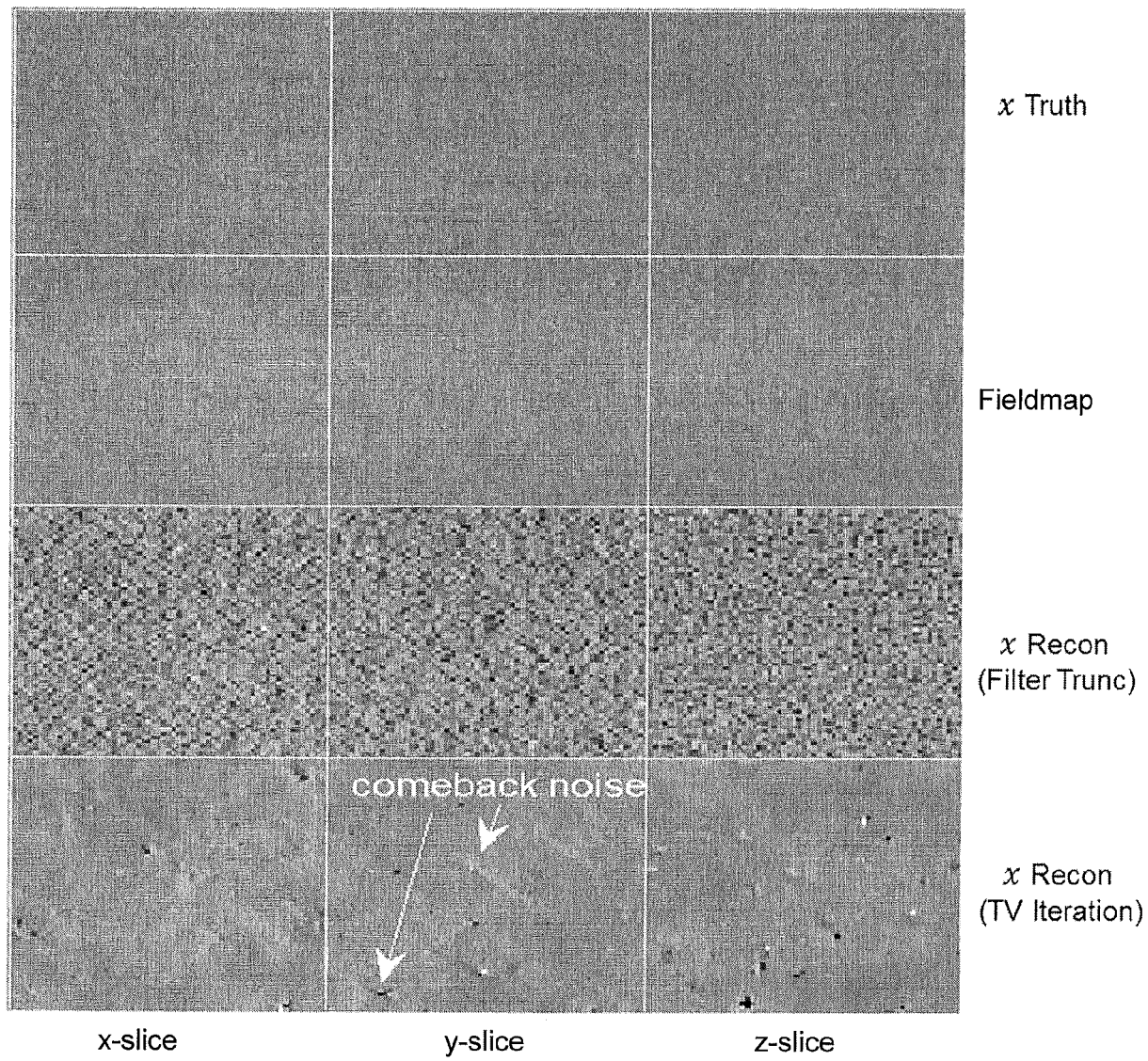

In FIG. 27, we describe two (new) $\chi$-based brain functional mapping schemes, as shown in (a1) and (a2), which are different from the conventional magnitude-based brain functional mapping method, as shown in FIG. 27(b). The two new schemes in FIGS. 27(a1) and (a2) are based on the $\chi$ reconstruction. The first (new) scheme in FIG. 27(a1) is implemented by first calculating the phase-based brain activation map, denoted by $P^{map}(x,y,z)$, and then reconstructing the susceptibility-based activation map, $\chi^{map}(x,y,z)$ by performing CIMRI only once (the fieldmap $b^{map}(x,y,z)$ is calculated from $P^{map}(x,y,z)$ by using Eq. (13) and $\chi^{map}(x,y,z)$ is calculated from $b^{map}(x,y,z)$ by the TV-regularized split Bregman iteration scheme in Eq. (20)).

The second (new) scheme in FIG. 27(a2) is implemented by first reconstructing a 4D susceptibility dataset $\chi^{recon}(x,y,z,t)$ by looping the CIMRI for each time point of t, and then rendering the χ-based statistical brain mapping. Both the first and second new schemes produce an output of χ-based brain activation maps from a 4D BOLD ƒMRI dataset. The second scheme costs more computations than the first scheme; however, the second scheme can accommodate the nonlinearity of T2* phase image acquisition without a linear assumption for SPM and CIMRI.

Let SPM represent the statistical parametric mapping (SPM) exerted on a 4D dataset and its stimulus task(t), and CIMRI the susceptibility reconstruction. Then, we can express the two new schemes (also called "proposals 1 and 2") in FIG. 27 by $$\chi^{map}(x,y,z)=\text{SPM}\{\chi^{recon}(x,y,z,t),\text{task}(t)\} \text{(definition)}$$

$$=\text{SPM}\{\text{CIMRI}\{P(x,y,z,t)\},\text{task}(t)\} \text{(proposal 2)}$$

$$\text{CIMRI}\{\text{SPM}\{P(x,y,z,t),\text{task}(t)\}\} \text{(linear commutation)}$$

$$=\text{CIMRI}\{P^{map}(x,y,z)\} \text{(proposal 1)} \qquad (40)$$

It shows that, if both SPM and CIMRI are linear operations, SPM commutates with CIMRI. In small angle regime, CIMRI is a linear operation because convolution and deconvolution are linear operations. As a result, proposal 2 (which requires multiple CIMRI procedures for each time snapshot in the 4D dataset) can be reduced to proposal 1, which only requires performing CIMRI only once. However, for nonlinear SPM, we can only adopt proposal 2 for susceptibility-based brain mapping, because proposal 1 will incur nonlinear artifacts. FIG. 27 shows our two new proposals of susceptibility-based brain mapping and neuroimaging in (a1) & (a2), which are different from the conventional magnitude-based brain mapping and neuroimage in (b). The proposal 1 in (a1) is for linear statistical data analysis, and the proposal 2 in (a2) is for nonlinear linear statistical analysis.

Since the reconstructed 4D χ dataset can represent the intrinsic neuroactivity more directly and veraciously than the 4D raw MR dataset (magnitude or phase), it is expected that the χ-based brain mapping (proposal 2 in (a2)) and neuroimaging is more truthful than that based on the MR magnitude data. Under linear approximations, the proposal 2 in (a2) can be implemented by the proposal 1 in (a1) with reduced computations (performing CIMRI only once). The conventional BOLD ƒMRI data analysis tools, such as SPM, independent component analysis (ICA), and connectivity graphs, can be applied to the 4D χ dataset without change. We stress that our improvements in BOLD ƒMRI study are based on a 4D χ dataset (susceptibility dataset reconstructed from a 4D MR phase dataset), not on the 4D MR magnitude dataset. The result is that our χ-based BOLD ƒMRI study will provide more truthful neuroimage depiction.

In summary, our methodology of CIMRI-based magnetic susceptibility tomography can be used equally well for both structural χ tomography and functional χ tomography. The structural χ tomography scheme provides a 3D χ source for static iron deposit in tissues or organs (as illustrated schematically in FIG. 26). The functional χ tomography scheme is to reconstruct a 4D χ dataset (a dynamic χ series), which is then used for brain mapping and neuroimaging, as illustrated schematically in FIG. 27.

The rationale behind our x-based image analysis technique is threefold: 1) the underlying source of a structural and functional state (detectable by T2*MRI) is the χ distribution, which is mainly attributed to the iron origin; 2) the MR magnitude image suffers from a local average, and a nonlinear transformation of the χ source; meaning that the MR magnitude image is not a tomographic reproduction of the χ source; 3) the MR phase image is a linear transformation of the susceptibility source in the small angle regime (the 3D convolution is linear)) and the χ source can be reconstructed from the MR phase image by CIMRI (by solving an ill-posed deconvolution); 4) if the statistical postprocessing is linear, it commutates with the CIMRI, thereby reducing the multiple CIMRI repetitions to a one-time CIMRI calculation.

Next, we will discuss how both the $\chi^{recon}$-based iron measurement scheme in FIG. 26 and the $\chi^{recon}$-based BOLD ƒMRI scheme in FIG. 27(a) can be further improved by using the T2' phase images generated by an T2' imaging scheme.

Improvement on Susceptibility Imaging by T2'-Effect Imaging and CIMRI

The principle of T2'-effect signal acquisition is illustrated in FIG. 9, which aims to remove the random motion effect from the T2* signal.

Figure 28:
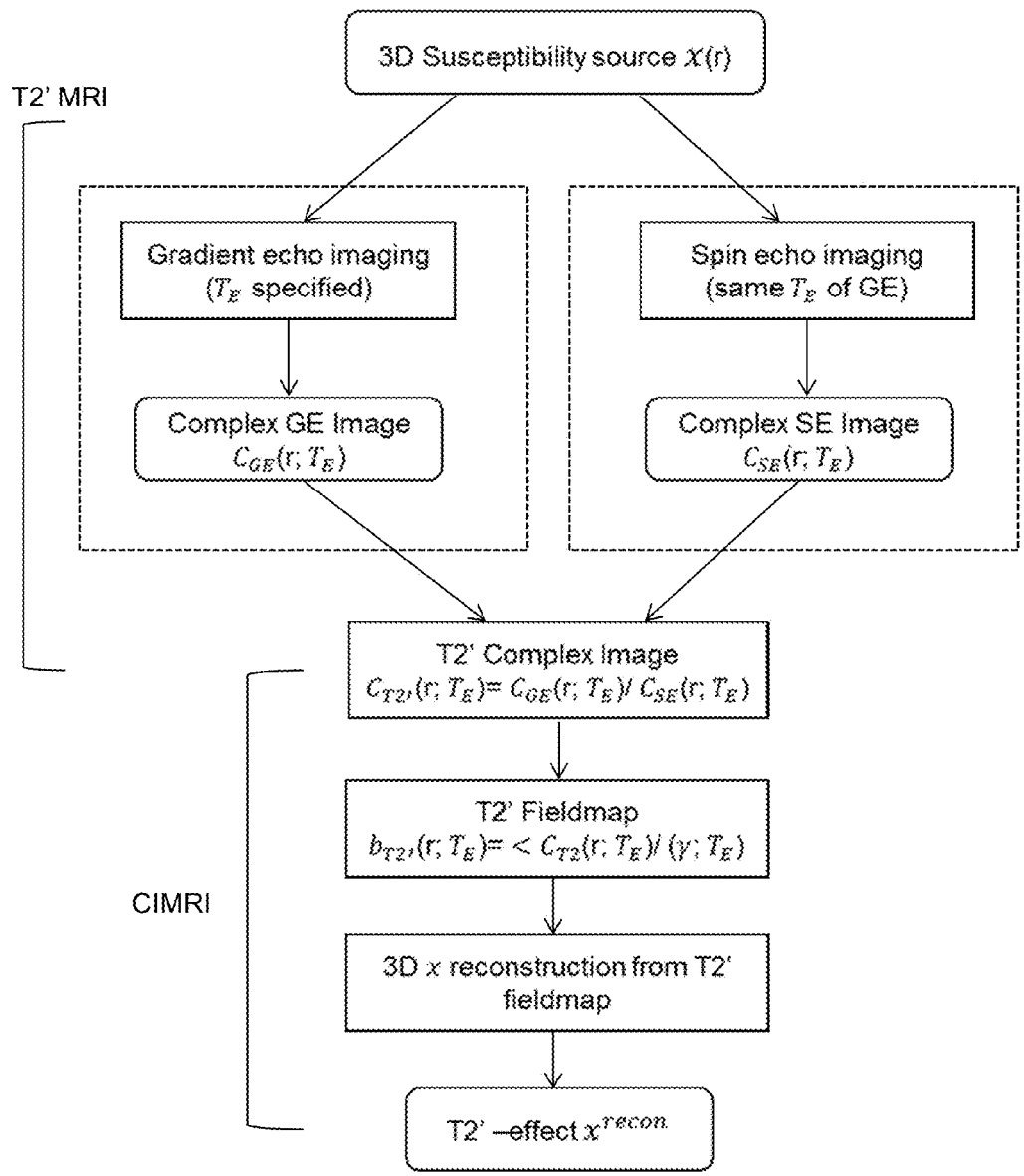
FIG. 28. A method to improve the $\chi$ tomography by T2'MRI and CIMRI. The Gradient-echo image and spin-echo image are acquired for the same $\chi$ source with the same echo time $T_E$. A complex division is used to obtain a complex T2' complex image. A CIMRI analysis is used to reconstruct the susceptibility source from T2' phase image.

We generalize this concept to the principle of T2'-effect imaging, as diagramed by T2'-effect MRI (T2'MRI) in FIG. 28. In comparison with conventional T2*MRI processing, the T2'MRI procedure/analysis can be used to obtain a complex MR image (called T2' complex image) that consists essentially of the static inhomogeneous field effect (e.g., the T2' source). Following doing a T2'MRI procedure, we perform CIMRI-based χ reconstruction. FIG. 28 illustrates schematically the methodology to improve the χ reconstruction, comprising (1) performing T2'MRI and then (2) CIMRI. The Gradient-Echo image and the Spin-Echo image are acquired from the same χ source (i.e., the same object) with the same echo time, $T_E$. A complex division is then used to obtain a complex T2' image. Finally, a CIMRI procedure is used to reconstruct the susceptibility distribution from a T2' phase image extracted from the T2' complex image.

The T2'MRI section in FIG. 28 consists of the following steps: 1) complex SE image acquisition by a spin-echo imaging with a $T_E$; 2) complex GE image acquisition by gradient-recall echo imaging, for the same χ source with the same $T_E$; 3) T2' complex image calculation by a complex division between the complex GE image and the complex SE image. From the T2' complex image, we can calculate (extract) the T2' phase image (by finding the complex argument), with which we can reconstruct the static susceptibility distribution by CIMRI by two steps: a) T2' fieldmap calculation from the T2' phase image and $T_E$, and b) 3D static susceptibility reconstruction from the T2' fieldmap. It is noted that the T2' phase image is calculated by subtracting the T2 phase image from the T2* phase image (as presented earlier). Therefore, the inhomogeneous fieldmap associated with the T2 effect is greatly removed. Note that the method to improve the 3D χ tomography by T2'MRI and CIMRI in FIG. 28 can be extended to 4D dynamic χ tomography.

Currently, the T2* GE image is acquired by an echo planar image (EPI) sequence; and the T2* SE image is acquired by a spin-echo EPI sequence. The main difference between the pair of GE and SE pulse sequences is that the SE sequence includes an additional 180° pulse. The 3D complex image can be constructed by stacking the EPI slices. In future versions, a 3D isotropic complex image may be directly acquired by an echo volumar imaging (EVI) sequence. An EVI sequence is used to acquire a 3D T2* GE complex image, while a SE EVI sequence is used to acquire a 3D T2* SE complex image. The main difference between the EVI sequence and the SE EVI sequence is that the SE EVI includes an additional 180° pulse.

In principle, the T2'MRI corrective procedure prefers a long $T_E$ due to the fact that a long $T_E$ causes a large T2 effect, and a large difference in T2* GE signal and T2* SE signal, and a large signal difference generally increases the digital subtraction stability and accuracy. A double-echo T2'-effect signal can be acquired by the illustration shown in FIG. 9. In general, we can implement multi-echo T2'MRI corrections by repeating the EPI sequence with multiple $T_E$ repetitions.

Phantom MR Experiment

According to medical imaging system development principle, the $\chi$ tomography by our CIMRI model must be tested with phantom experiment before it can be used for practice. In particular, the trustworthiness of CIMRI-based $\chi$ tomography is verified by having a successful comparison with a phantom experimental study.

Figure 29:
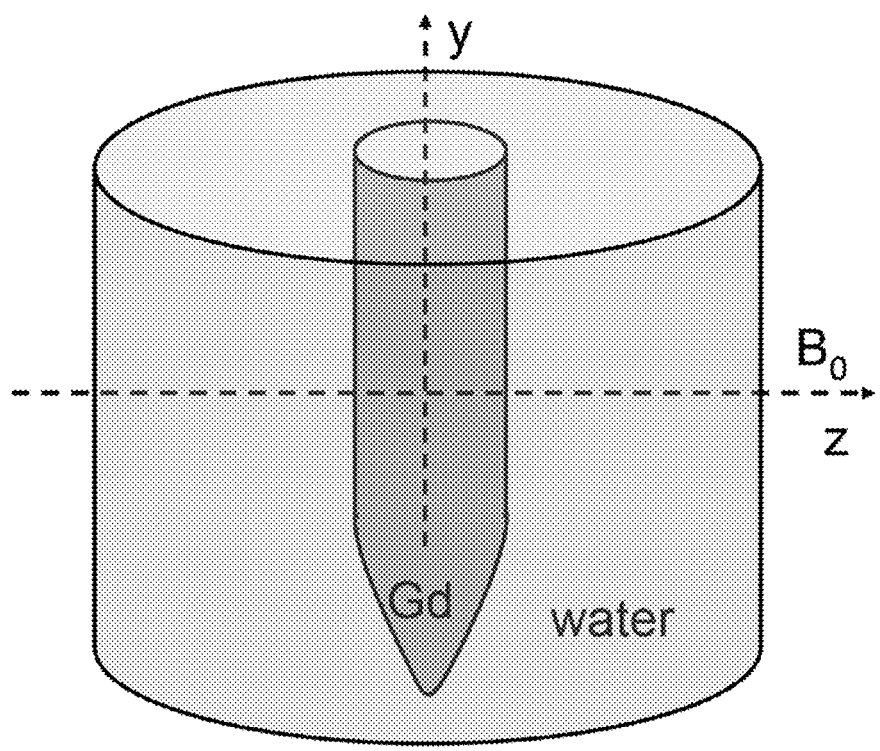
FIG. 29. Gd-filled tube phantom experiment setup. The tube phantom provides a static cylindrical susceptibility distribution, which is used to simulate a snapshot of dynamic susceptibility-expressed physiological process.

We performed a phantom experiment with Gd-filled tube [19], as configured in FIG. 29. An end-tapered plastic tube was filled with a Gd contrast liquid (dilution of clinic Gd solution) and was inserted in a large water tank. The static tube phantom provides a uniform distribution inside the tube of magnetic $\chi$ (ground truth); and it was used in simulations of a snapshot of dynamic $\chi$-expressed physiological process. FIG. 29 shows a Gd-filled tube phantom experiment setup. The tube phantom provides a static cylindrical susceptibility distribution, which is used in simulations of a snapshot of dynamic susceptibility-expressed physiological process.

Figure 30:
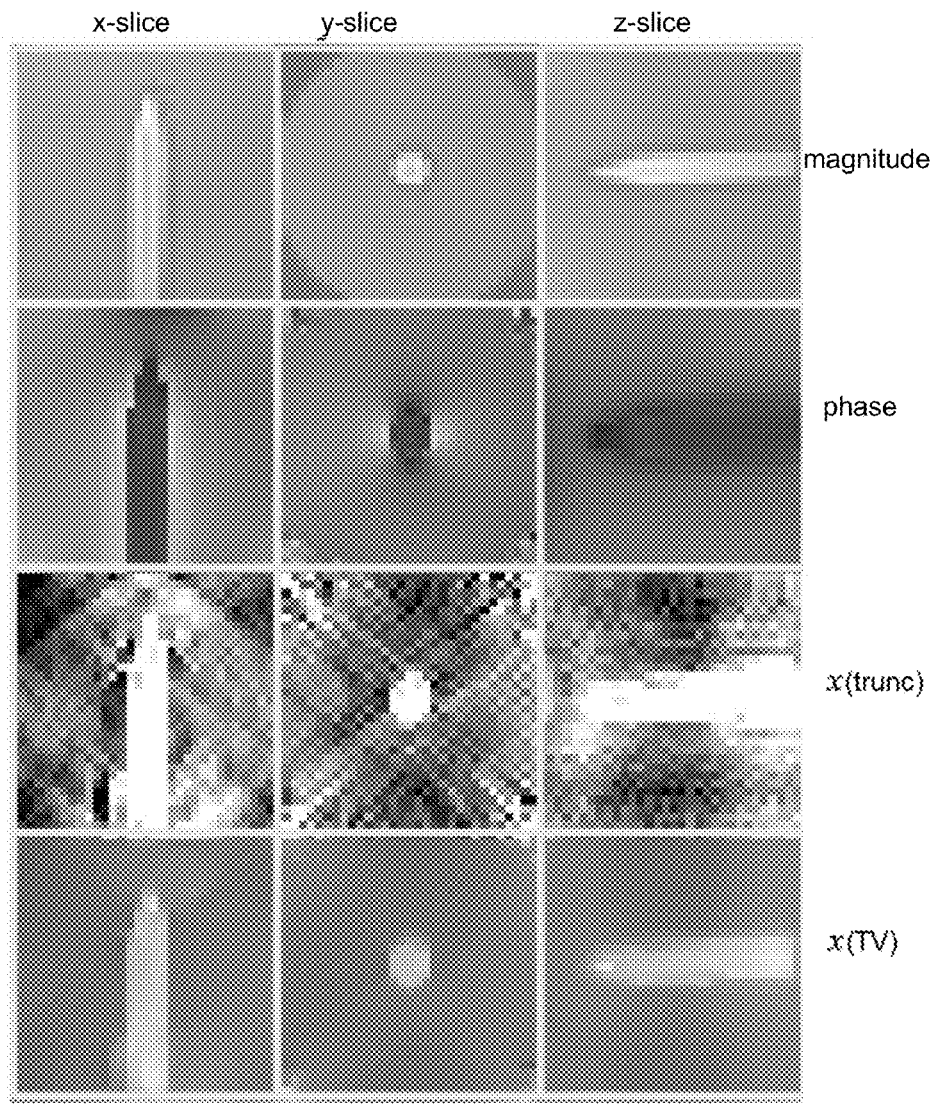
FIG. 30. Phantom experiment results. Row 1 (at top): magnitude image; Row 2: phase image; Row 3: $\chi$ reconstructed from filter truncation method; and Row 4 (at bottom): $\chi$ reconstructed from TV iteration method.
Figure 31:
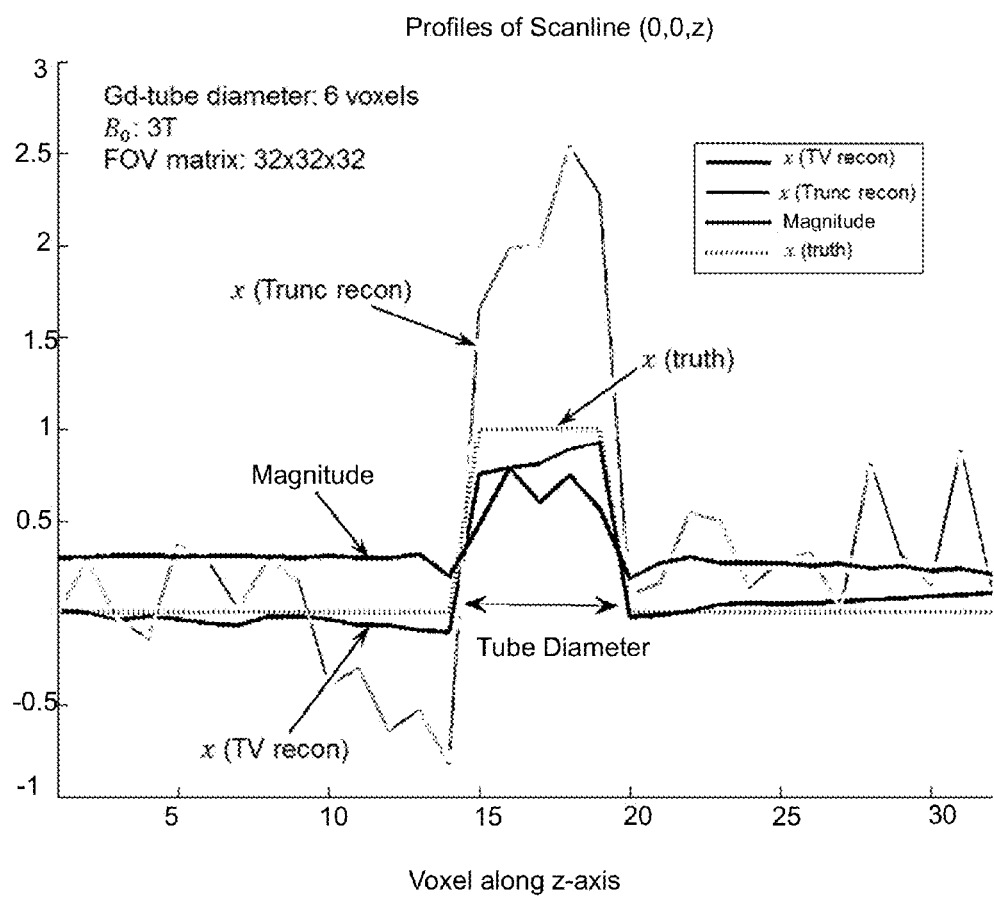
FIG. 31. Quantitative profiles along a cylinder diameter in FIG. 30.
Figure 32A:
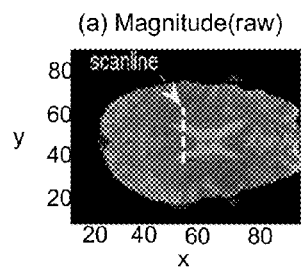
FIG. 32. TV-regularized brain $\chi$ reconstruction from an in vivo experiment dataset. (a) (FIG. 32A) an axial slice of the MR magnitude of brain imaging (where a vertical segment marks a scanline); (b1) (FIG. 32B) the phase image slice; (b2) (FIG. 32C) the smoothed phase; (c1-c6) (FIG. 32D-I) the λ reconstruction from the phase (in (b1.
FIG. 32B)) by using a large range of λ values. Note that the magnitude image is nonnegative as displayed in a greyscale bar range of [0,1], and all other images (phase images and λ reconstructions) are bipolar-valued.
Figure 32B:
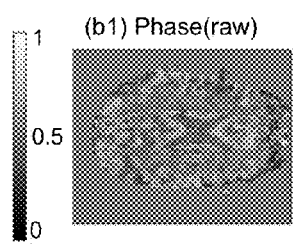
Figure 32C:
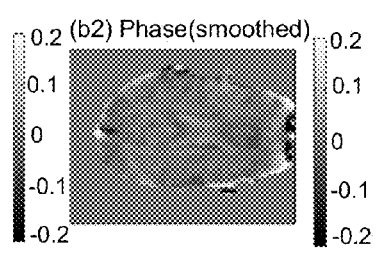
Figure 32D:
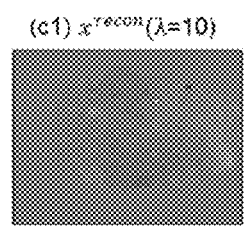
Figure 32E:
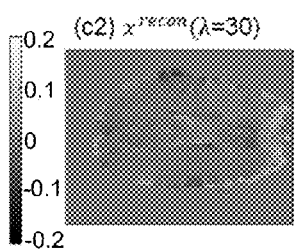
Figure 32F:
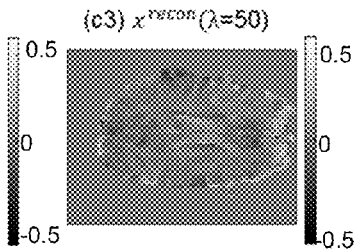
Figure 32G:
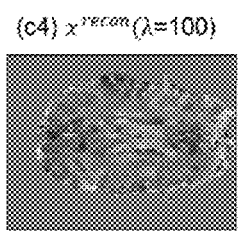
Figure 32H:
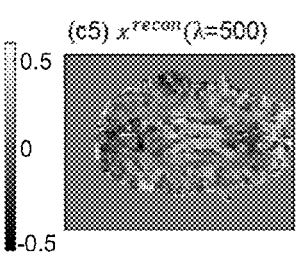
Figure 32I:
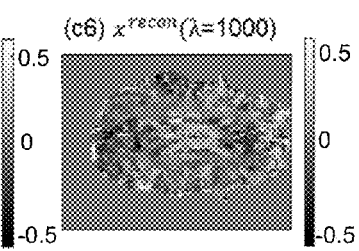

The experimental results of the MR magnitude, the MR phase, and the $\chi$ tomographic reconstructions by both the "filter truncation" and "TV iteration" solvers are shown in FIG. 30. FIG. 30 shows the phantom experiment results. Row 1 (at top): magnitude image; row 2: phase image; row 3: $\chi$ reconstructed from filter truncation method; and row 4 (at bottom): $\chi$ reconstructed from TV iteration method. The quantitative profiles of scanline across a cylinder diameter are shown in FIG. 31.

The Gd-tube phantom experiment for CIMRI-based $\chi$ tomography offers the following information: 1) The MR magnitude image suffers a central dip artifact; 2) The phase image is morphometrically different from the $\chi$ source due to the 3D convolution transformation in Eq. (2); 3) The $\chi$ reconstruction by "filter truncation" method suffers strip artifacts and heavy noises; 4) the TV-iteration method can implement $\chi$ tomography very well because the susceptibility source assumed an uniform distribution inside the cylinder, which agrees with the 'ground truth'.

In Vivo Brain $\chi$ Reconstruction Experiment

After the proof-of-concept study by numerical simulation and phantom test, the next stage was to apply the models and algorithms to real brain imaging for feasibility study.

A real brain imaging experiment was conducted with a healthy subject doing a finger-tapping visuomotor experiment in a Siemens Trio 3T scanner. An EPI complex sequence was used for scanning, with $T_R/T_E$=2000 ms/29 ms, and isotropic voxels (2×2×2 mm³). A brain FOV was localized to cover the motor cortex part (the parietal lobe and frontal lobe in brain) with a 3D matrix in size of 90×90×30. The brain functional imaging experiment produced a 4D complex dataset (90×90×30×165 after image cropping) for a session of 330s scanning. We assume that we can reconstruct the brain $\chi$ source at each snapshot from a MR phase volume in the 4D dataset by our CIMRI model. The results of the in vivo experiment data and $\chi$ reconstructions are reproduced in FIG. 32 (with a slice image from a snapshot volume), which consists of a raw MR magnitude image slice (a), the raw phase counterpart (b1), a smoothed phase (b2), and six $\chi$ reconstructions (c1-c6) with $\lambda$={10,30,50,100,500,1000}. By comparing the phase image (corresponding to the fieldmap) with the six $\chi$ reconstructions, we can see that the $\chi$ reconstruction may take on a smoothing effect at a very small $\lambda$ (<30), and a contrast enhancement at a very large X (>500).

FIG. 32 shows a TV-regularized brain $\chi$ reconstruction from an in vivo experiment dataset, comprising: (a) an axial slice of the MR magnitude of brain imaging (where a vertical segment marks a scanline); (b1) the phase image slice; (b2) the smoothed phase; (c1-c6) the $\chi$ reconstruction from the phase (in (b1)) by using a large range of X values. Note that the magnitude image is nonnegative as displayed in a greyscale bar range of [0,1], and all the images are bipolar-valued.

Figure 33:
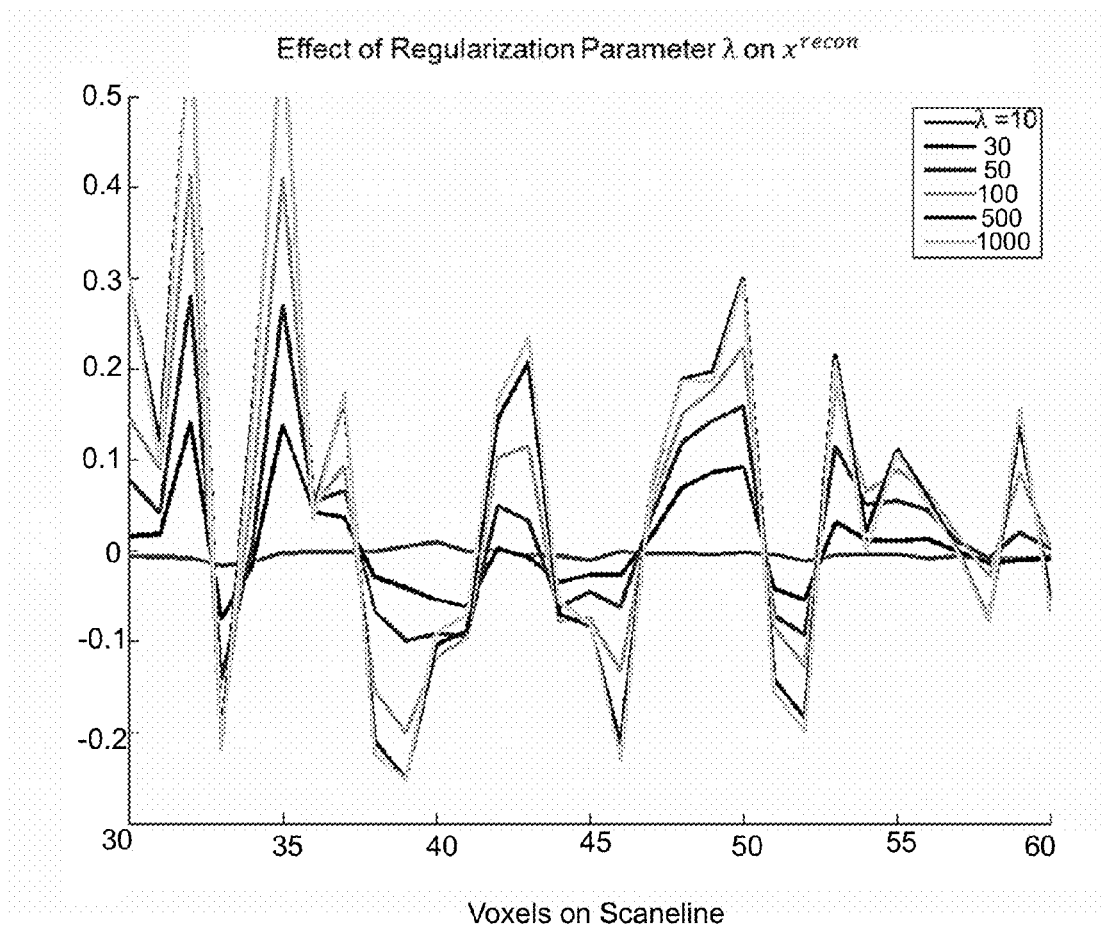
FIG. 33. The scanline profiles extracted from FIG. 32 (c1-c6). It shows that the $\chi$ reconstruction may suffer over-smoothing effect with a small λ value (=10), and a textural enhancement with a very large λ value (>500). In the range of 10<λ<500, the $\chi$ reconstructions are relatively similar and stable in reference to the MR magnitude image for this particular case.

From FIG. 32, we can see that the quality of intracranial $\chi$ tomographic reconstruction by CIMRI is largely dependent upon the selection of the regularization parameter $\lambda$ values. In FIG. 33, we plot the scanline profiles from FIG. 32(c1-c6) for more quantitative inspection (the scanline was marked in FIG. 32(a)). It shows that the $\chi$ reconstruction may suffer from oversmoothing effect for a very small $\lambda$ (e.g., 10), and from contrast enhancement for a very large $\lambda$ (e.g., $\lambda$>1000). It also shows that the $\chi$ reconstruction may assume similar reconstructions for an intermediate range of $\lambda$ values (e.g. in a range of 30-200)

For static brain imaging, the 3D $\chi$ reconstruction should adopt a regularization parameter $\lambda$ value such that the reconstructed $\chi$ map is similar to (but not equal to) the MR magnitude image. From FIG. 32, the reconstructed $\chi$ map with $\lambda$=50 (in FIG. 32(c3)) is the most similar to the MR magnitude image (in FIG. 32(a)).

For dynamic 4D brain functional imaging (BOLD $f$MRI), we can make use of the external stimulus paradigm for 4D $\chi$ reconstruction, as described as susceptibility timecourse synchrony in this invention.

Figure 34:
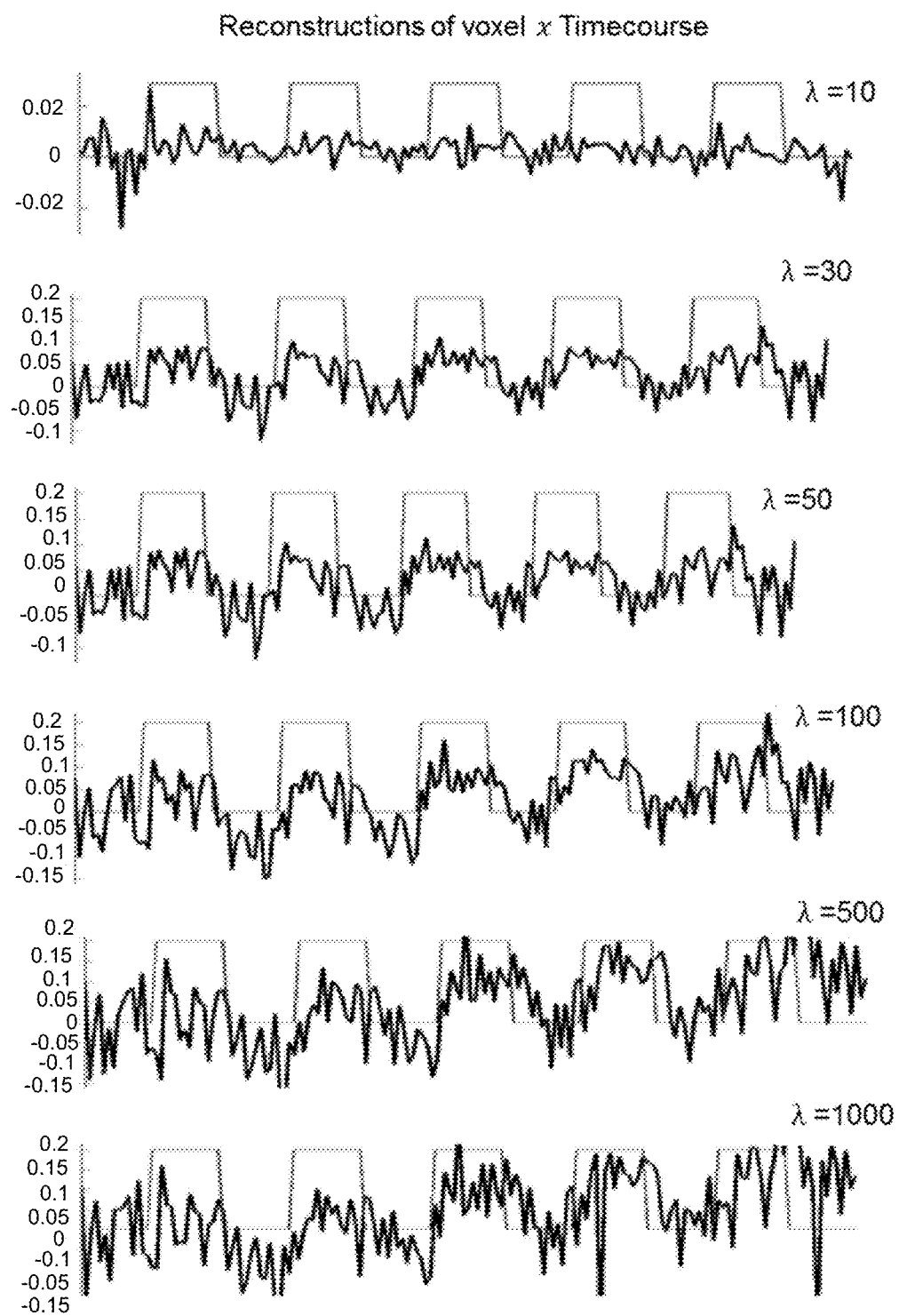
FIG. 34. The reconstructions of $\chi$ timecourse at a voxel in the BOLD active site with regularization parameter λ={10, 30,50,100,500,1000}. The rectangle waveform represent the external stimulus task(t). The timecourse synchrony reconstruction criterion indicates that λ=[20-500] are suitable for 4D $\chi$ reconstruction.

The $\chi$ timecourse reconstructions at a voxel in the BOLD activity site in the BOLD $f$MRI experiment are demonstrated in FIG. 34, for $\lambda$={10,30, 50,100,500,1000}; in which the rectangular waveform represents the external stimulus task(t) (known paradigm) as recorded of the visual clue for the finger-tapping experiment.

From FIG. 34, we can see the following aspects:
1) The $\chi$ reconstruction with a very small $\lambda$ (=10) could not restore the rectangular stimulus paradigm,
2) The $\chi$ reconstruction with a very large $\lambda$ (=1000) could not restore the rectangular stimulus paradigm either,
3) The $\chi$ reconstruction with a range of $\lambda$ values ([20-500]) could restore the rectangular stimulus paradigm very well, and
4) There is time lag between the $\chi$ timecourse and the external rectangular stimulus task(t), that is about 6 ms.

Applications

In the present invention, we developed a number of CIMRI models for reconstructing a 3D $\chi$ source distribution from a 3D MR phase image acquired by T2*MRI, and for reconstructing a 4D $\chi$ dataset from a 4D MR phase dataset. The former is mainly used for structural 3D $\chi$ tomography and the later for functional 4D $\chi$ tomography.

Our structural 3D $\chi$ tomography can be used for iron store measurement in organs (such as liver, spleen, pancreas, heart, brain) and in tissues (contrast agent and blood inside the vasculature, contrast and blood leakage, and in glands). In particular, our method offers an accurate depiction of brain injury (hemorrhage, micro-hemorrhage, stroke) and brain dysfunctions (diseases).

Figure 35:
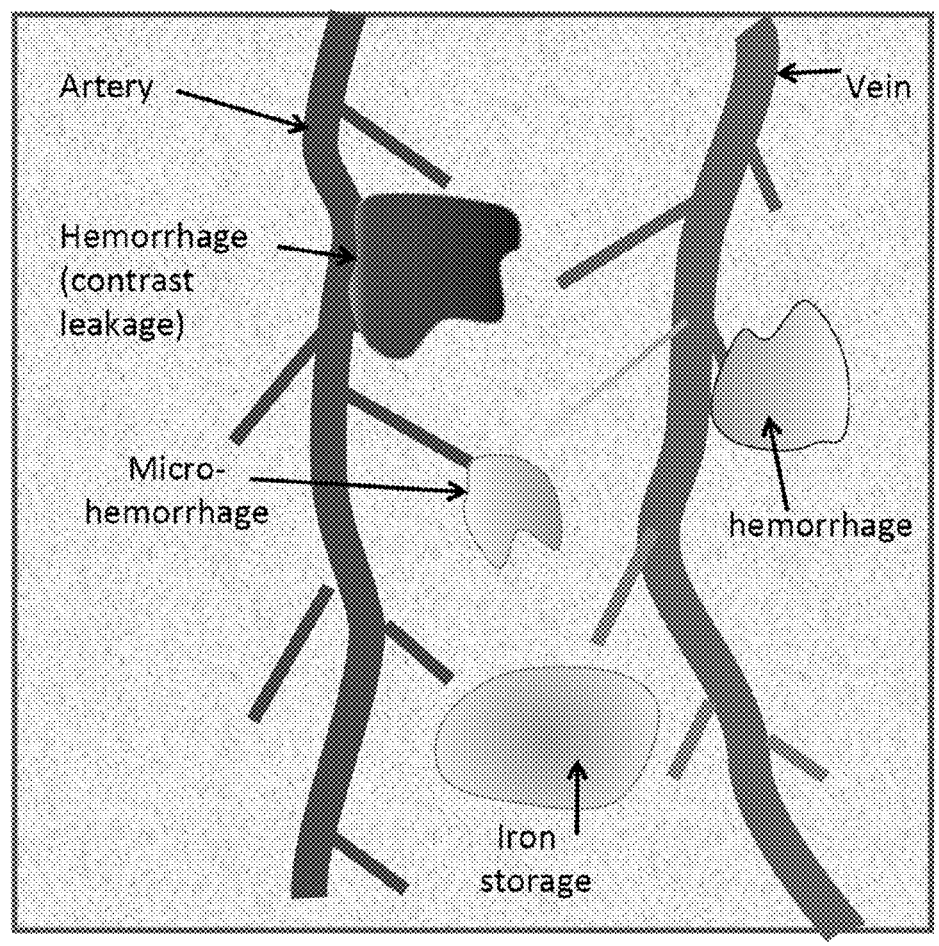
FIG. 35. Illustration of brain structural susceptibility distribution. The hemorrhage and micro-hemorrhage of blood circulation causes spread susceptibility distribution, the static iron deposit also contributes the susceptibility distribution for static structural representation. The iron deposit may occur in tissues and organs, not necessary in proximity to blood streams. The static iron deposit in tissue and organ can be measured by 3D magnetic susceptibility tomography.

In FIG. 35, we illustrate the $\chi$ reconstruction for the image depiction of blood bleeding and microbleeding that occurs in the proximity of vasculatures. As the T2*MRI is widely used for imaging brain trauma, injury, and dysfunction, our method provides a more truthful and accurate 3D tomographic image presentation of brain anatomical states in terms of reconstructed magnetic susceptibility. For biological tissue and organ imaging, the reconstructed magnetic susceptibility can be interpreted as the iron deposit. Therefore our structural $\chi$ tomography can find immediate use in iron deposit measurement of organs (liver, spleen, pancreas, heart, brain) and in tissues, not restricted the regions in the proximity of vasculatures.

FIG. 35 shows an illustration of brain structural susceptibility distribution. The hemorrhage and micro-hemorrhage of blood circulation causes spread susceptibility distribution, the static iron deposit also contributes the susceptibility distribution for static structural representation. The iron deposit may occur in tissues and organs, not necessary in proximity to bloodstreams.

Our 4D functional $\chi$ tomography provides a susceptibility perturbation depiction for a neurovascular BOLD process (including a resting state, and a task-specific paradigm). Since a BOLD $f$MRI study produces a 4D complex dataset, our CIMRI produces a 4D dynamic susceptibility dataset accordingly. In particular, the functional $\chi$ tomography, together with statistical postprocessing, is useful for diagnostic and prognostic imaging of brain function diseases, such as schizophrenia, epilepsy, Alzheimer, aging, and other dysfunctions.

In FIG. 36, we illustrate the BOLD $f$MRI model for capturing the neurovascular-coupled BOLD states at the capillary bed. At the left side is illustrated the blood susceptibility perturbation associated with a BOLD $f$MRI activity. The intravascular blood susceptibility is perturbed by a functional activity, which may cause a negative susceptibility change in the arterial upstream (in artery and arterioles), a positive susceptibility change in capillary bed, and a positive susceptibility change in venous downstream (in venule and vein). In practice, the dominant heme iron susceptibility perturbation occurs in the capillary regions in response to the oxygen delivery and consumption, and the susceptibility perturbation in the arterial upstream is much smaller than that in the venous downstream. In ignorance of arterial blood susceptibility perturbation, the BOLD $f$MRI is mainly attributed to the venous blood susceptibility. In such a case, the BOLD imaging is called a venography [2].

At the right-hand side in FIG. 36 is the conceptual illustration (a snapshot image) of susceptibility perturbation of intravascular blood and in extravascular tissue, which could be negative or positive. The positive and negative bipolar distributions are retained in the phase image, but not in the magnitude image because the magnitude image is a nonnegative representation [19] of a distribution that may consist of positive and negative values. Consequently, the negative susceptibility change will be inverted (called negative inversion) in the MR magnitude image because a magnitude value is nonnegative. It is noted the neuroactivity-caused susceptibility perturbation in terms of heme iron change is too weak to be perceived in a snapshot of MR image (with the background of structural $\chi$ distribution). Usually, the BOLD activity can be extracted from a dynamic 4D dataset (acquired by $f$MRI under a task-specific paradigm) by a statistical postprocessing, such as a temporal correlation technique.

FIG. 36 shows an illustration of blood susceptibility perturbation associated with a BOLD $f$MRI model. The extravascular tissue is the static background structure. The BOLD-induced susceptibility perturbation is attributed to the intravascular blood-borne heme iron disturbance. It is noted that the dynamic heme-iron perturbation is superimposed on the static structural iron background during MR image formation. In a single T2*MRI image, the contributions from the heme iron perturbation and non-heme iron deposit are inseparable.

A preferred embodiment of a method of reconstructing an internal distribution (3D map) of magnetic susceptibility values, $\chi$ $(x,y,z)$, of an object, by using a Computed Inverse Magnetic Resonance Imaging (CIMRI) tomographic procedure, according to the present invention, comprises the following steps:

a) acquiring a 3D complex-valued MR image of the object from a T2*-weighted MRI scan performed by a MRI scanning machine;

b) extracting a 3D T2*MRI phase image, $P(x,y,z;T_E)$, from the 3D complex-valued MR image;

c) calculating a 3D magnetic field map, $b(x,y,z)$, of the z-component ($B_z$) of a susceptibility-induced inhomogeneous magnetic field (created by magnetizing the object in a main field, $B_0$), from the MR phase image, $P(x,y,z;T_E)$, according to Eq. (1A), under phase-unwrapped conditions:

$$b(x, y, z) = \frac{P(x, y, z; T_E)}{\gamma T_E} \quad \text{Eq. (1A)}$$

where: $\gamma$=proton gyromagnetic ratio, and $T_E$=echo time; and d) reconstructing a 3D magnetic susceptibility map, $\chi^{recon}(r)$, of the object by performing a 3D deconvolution on the magnetic field map, $b(r)$, according to Eq. (2A) and Eq. (3A), as follows:

$$b(r)=B_0\chi(r)*h_0(r) \quad \text{Eq. (2A)}$$

and $$\chi^{recon}(r)=b(r)*^{-1}h_0(r)/B_0 \quad \text{Eq. (3A)}$$

where: $r=(x,y,z)$ denotes 3D coordinates in space domain; the symbol * denotes a 3D convolution operator; the symbol $*^{-1}$ denotes a 3D deconvolution operator; and $h_0(r)$ is a standard convolution kernel that is a point magnetic dipole kernel, according to Eq. (4A):

$$h_0(r) = \frac{1}{4\pi} \frac{3z^2 - |r|^2}{|r|^5}. \quad \text{Eq. (4A)}$$

In one embodiment, $T_E<30$ ms when performing functional MR imaging, and $T_E<10$ ms when performing structural MR imaging.

In another embodiment, the modified TV iteration filter, H(k), comprises one or more spatial processing capabilities selected from the group consisting of: lowpass, highpass, bandpass, and bandstop filtering.

In another embodiment, the 3D multiplier filter comprises radial symmetry or asymmetry, for a desirable susceptibility manipulation.

In another embodiment, the steps of estimating one or more appropriate values of the TV regularization parameter, $\lambda$, does not involve using an auxiliary phantom; so the selection of $\lambda$ is self-calibrated by using the accompanying MR magnitude information.

In another embodiment, the method comprises replacing the 3D T2*MRI phase image, $P(x,y,z;T_E)$ in step b) of the preferred method above, with a 3D T2'-effect phase image, $P_{T_2'}(x,y,z;T_E)$; thereby improving the fidelity and accuracy of the reconstructed magnetic susceptibility map, $\chi^{recon}(r)$ by greatly reducing the T2 effect via MR phase angle subtraction (complex division).

In another embodiment, the T2'-effect MRI scheme is extended to multi-echo imaging comprising at least two different echo times, $T_{E1}$ and $T_{E2}$.

In another embodiment, the T2'-effect MRI scheme is extended to multi-echo imaging by repeating echo planar image (EPI) sequences with multiple $T_E$ repetitions.

In another embodiment, the T2'-effect MRI scheme is extended to multi-echo imaging; wherein a 3D isotropic complex image is directly acquired by using an echo volumar imaging (EVI) sequence when imaging; and further wherein an EVI sequence acquires a 3D T2* GE complex image, while a SE EVI sequence acquires a 3D T2* SE complex image; wherein the main difference between the EVI sequence and the SE EVI sequence is that the SE EVI includes an additional 180° pulse for rephasing the non-random static dephasing.

In another embodiment, the object comprises tissues or organs of a body; and wherein the method further comprises measuring a distribution of iron deposits in the tissues or organs of the body by interpreting the 3D reconstructed magnetic susceptibility map, $\chi^{recon}(r)$, as a quantitative distribution of iron deposits in said tissues or organs.

In another embodiment, the method does not comprise using any MR magnitude images; and further wherein the method does not comprise using any exponential decay parameters T1, T2, or T2*; or maps of said exponential decay parameters.

Another embodiment of the present invention comprises a method of performing dynamic, magnetic susceptibility-based ƒMRI brain mapping and neuroimage depiction, using a MRI scanning machine, comprising: replacing a conventional 4D MR magnitude dataset (which is the conventional neuroimaging dataset) with a 4D reconstructed magnetic susceptibility dataset, $\chi^{recon}(r\ t)$; wherein r denotes 3D coordinates (x, y, z) in space domain, and t denotes a snapshot time.

In another embodiment, the 3D T2*MRI phase image, $P(x,y,z;T_E)$, extracted in step b) comprises a wrapped phase image; in which case the preferred method described above further comprises generating a phase-unwrapped phase image, after step b), by performing a phase-unwrapping procedure on the wrapped phase image; followed by calculating the magnetic field map in step c), using the newly-generated phase-unwrapped phase image.

A variety of means and methods can be used for displaying the results of the various method steps used in embodiments of the present invention, including, but not limited to: a) assigning either a gradation of grey values (greylevel bar), or a spectrum of color values (colorbar), to a selected 2D slice of data taken through the 3D map of reconstructed magnetic susceptibility values, $\chi^{recon}(r)$, thereby creating a 2D slice visual image representing a 2D distribution of reconstructed magnetic susceptibility values inside of the object; and, then b) displaying on a computer screen or monitor the resulting 2D slice visual image that represents a 2D distribution of reconstructed magnetic susceptibility values inside of the object. The 3D volume can also be displayed in 3D volume rendering or isosurface rendering. A 3D volume can also be display by a montage of 2D slices. The 4D dataset can be dynamically displayed with a video of 3D rendering.

The methods and method steps, according to the present invention, can be programmed in software in any efficient computer language (such as C, Matlab, Fortran, etc.) and be executed on desktop computers or higher workstations. Currently, we implement our methods in Matlab language on a desktop computer: Intel® Core™ 2 CPU 6600@ 2.40 GHz. 2.39 GHz, 2.00 GB of RAM).

The algorithms can be implemented in multiple programs, which are arranged according to the data flow (T2*MRI and CIMRI programs for numerical simulations, CIMRI programs for phantom and in vivo experiment). Each program is reserved some variables for the adjustable parameters (such as matrix size, newly designed kernel, regularization parameters) that are determined by problem-specific calibration. Based on data saving and reading operations, all the multiple programs can be organized into a single master program for a specific task, thus enabling program automation. The multiple programs can be executed independently on multiprocessors for parallel computations, also in automation (except for parameter adjustment and calibration).

REFERENCES

The following references are incorporated herein by reference:

1. Chavhan, G. B., et al., *Principles, techniques, and applications of T2\*-based MR imaging and its special applications*. Radiographics: a review publication of the Radiological Society of North America, Inc, 2009. 29(5): p. 1433-49.
2. Haacke, E. M., et al., *Magnetic resonance imaging physical principles and sequence design*, 1999, John Wiley & Sons, Inc: New York.
3. Fischer, R. and P. R. Harmatz, *Non-invasive assessment of tissue iron overload*. Hematology/the Education Program of the American Society of Hematology. American Society of Hematology. Education Program, 2009: p. 215-21.
4. Jensen, J. H., et al., *Separate MRI quantification of dispersed (ferritin-like) and aggregated (hemosiderin-like) storage iron*. Magnetic resonance in medicine: official journal of the Society of Magnetic Resonance in Medicine/Society of Magnetic Resonance in Medicine, 2010. 63(5): p. 1201-9.
5. Jensen, P. D., et al., *Non-invasive assessment of tissue iron overload in the liver by magnetic resonance imaging*. British journal of haematology, 1994. 87(1): p. 171-84.
6. Olthof, A. W., et al., *Non-invasive liver iron concentration measurement by MRI: comparison of two validated protocols*. European journal of radiology, 2009. 71(1): p. 116-21.
7. Taher, A. T., K. M. Musallam, and A. Inati, Iron overload: consequences, assessment, and monitoring. Hemoglobin, 2009. 33 Suppl 1: p. S46-57.
8. Walsh, A. J. and A. H. Wilman, *Susceptibility phase imaging with comparison to R2 mapping of iron-rich deep grey matter*. Neuroimage, 2011. 57(2): p. 452-61.
9. Wu, E. X., et al., *Magnetic resonance assessment of iron overload by separate measurement of tissue ferritin and hemosiderin iron*. Annals of the New York Academy of Sciences, 2010. 1202: p. 115-22.
10. Howseman, A. M. and R. W. Bowtell, *Functional magnetic resonance imaging: imaging techniques and contrast mechanisms*. Philos Trans R Soc Lond B Biol Sci, 1999. 354(1387): p. 1179-94.
11. Norris, D. G., *Principles of magnetic resonance assessment of brain function*. Journal of magnetic resonance imaging: JMRI, 2006. 23(6): p. 794-807.
12. Ogawa, S., et al., *Functional brain mapping by blood oxygenation level-dependent contrast magnetic resonance imaging. A comparison of signal characteristics with a biophysical model*. Biophys J, 1993. 64(3): p. 803-12.
13. Stephan, K. E., et al., *Biophysical models of ƒMRI responses*. Curr Opin Neurobiol, 2004. 14(5): p. 629-35.
14. Menon, R. S., et al., *Functional brain mapping using magnetic resonance imaging. Signal changes accompanying visual stimulation*. Invest Radiol, 1992. 27 Suppl 2: p. S47-53.

15. Boxerman, J. L., et al., *MR contrast due to intravascular magnetic susceptibility perturbations*. Magn Reson Med, 1995. 34(4): p. 555-66.
16. Reitz J. R., M. F. J., Christy R. W., *Foundations of electromagntic theo* 1993: Addison-Wesley.
17. Chen, Z. and V. Calhoun, *Computed inverse resonance imaging for magnetic susceptibility map reconstruction.* Journal of computer assisted tomography, 2012. 36(2): p. 265-74.
18. Chen, Z. and V. Calhoun, *Volumetric BOLD fMRI simulation: from neurovascular coupling to multivoxel imaging.* BMC medical imaging, 2012. 12(1): p. 1-8.
19. Chen, Z. and V. D. Calhoun, *Two pitfalls of BOLD fMRI magnitude-based neuroimage analysis: non-negativity and edge effect.* Journal of neuroscience methods, 2011. 199(2): p. 363-9.
20. Chen, Z., Z. Chen, and V. D. Calhoun. *Voxel magnetic field disturbance from remote vasculature in BOLD fMRI*. in *SPIE Medical Imaging*. 79613x. Orlando, Fla.: SPIE.
21. Chen, Z., A. Caprihan, and V. D. Calhoun. *BOLD susceptibility map reconstruction from fMRI by 3D total variation regularization*. in *International society for magnetic resonance in medicine* 2011. Montreal, Canada: ISMRM.
22. Haacke, E. M., et al., *Susceptibility mapping as a means to visualize veins and quantify oxygen saturation.* Journal of magnetic resonance imaging: JMRI, 2010. 32(3): p. 663-76.
23. Li, W., B. Wu, and C. Liu, *Quantitative susceptibility mapping of human brain reflects spatial variation in tissue composition.* Neuroimage, 2011. 55(4): p. 1645-56.
24. Schweser, F., et al., *Quantitative imaging of intrinsic magnetic tissue properties using MRI signal phase: an approach to in vivo brain iron metabolism?* Neuroimage, 2011. 54(4): p. 2789-807.
25. Shmueli, K., et al., *Magnetic susceptibility mapping of brain tissue in vivo using MRI phase data.* Magnetic resonance in medicine: official journal of the Society of Magnetic Resonance in Medicine/Society of Magnetic Resonance in Medicine, 2009. 62(6): p. 1510-22.
26. Wharton, S., A. Schafer, and R. Bowtell, *Susceptibility mapping in the human brain using threshold-based k-space division.* Magn Reson Med, 2010. 63(5): p. 1292-304.
27. de Rochefort, L., et al., *Quantitative susceptibility map reconstruction from MR phase data using bayesian regularization: validation and application to brain imaging.* Magn Reson Med, 2010. 63(1): p. 194-206.
28. Kressler, B., et al., *Nonlinear regularization for per voxel estimation of magnetic susceptibility distributions from MRI field maps.* IEEE Trans Med Imaging, 2010. 29(2): p. 273-81.
29. Li, L., *Magnetic susceptibility quantification for arbitrarily shaped objects in inhomogeneous fields.* Magn Reson Med, 2001. 46(5): p. 907-16.
30. Li, L. and J. S. Leigh, *Quantifying arbitrary magnetic susceptibility distributions with MR.* Magn Reson Med, 2004. 51(5): p. 1077-82.
31. Sepulveda, N. G., I. M. Thomas, and J. P. Wikswo, *Magnetic Susceptibility Tomography for Three-dimensional Imaging of Diamagnetic and Paramagnetic Objects.* IEEE Trans. Magnetics, 1994. 30(6): p. 5062-7.
32. Liu, T., et al., *Calculation of susceptibility through multiple orientation sampling (COSMOS): a method for conditioning the inverse problem from measured magnetic field map to susceptibility source image in MRI.* Magn Reson Med, 2009. 61(1): p. 196-204.
33. Yao, B., et al., *Susceptibility contrast in high field MRI of human brain as a function of tissue iron content.* Neuroimage, 2009. 44(4): p. 1259-66.
34. Leung, A. W., et al., *Magnetic resonance imaging assessment of cardiac and liver iron load in transfusion dependent patients.* Pediatric blood & cancer, 2009. 53(6): p. 1054-9.
35. Marinelli, M., et al., *Total iron-overload measurement in the human liver region by the magnetic iron detector.* IEEE transactions on bio-medical engineering, 2010. 57(9): p. 2295-303.
36. Mitsumori, F., H. Watanabe, and N. Takaya, *Estimation of brain iron concentration in vivo using a linear relationship between regional iron and apparent transverse relaxation rate of the tissue water at 4.7T* Magnetic resonance in medicine: official journal of the Society of Magnetic Resonance in Medicine/Society of Magnetic Resonance in Medicine, 2009. 62(5): p. 1326-30.
37. Papakonstantinou, O., et al., *Quantification of liver iron overload by T2 quantitative magnetic resonance imaging in thalassemia: impact of chronic hepatitis C on measurements.* Journal of pediatric hematology/oncology: official journal of the American Society of Pediatric Hematology/Oncology, 1999. 21(2): p. 142-8.
38. Papakonstantinou, O. G., et al., *Assessment of liver iron overload by T2-quantitative magnetic resonance imaging: correlation of T2-QMRI measurements with serum ferritin concentration and histologic grading of siderosis.* Magnetic resonance imaging, 1995. 13(7): p. 967-77.
39. Chen, Z. and V. Calhoun, *A computational multiresolution BOLD fMRI model.* IEEE Trans. BioMed. Eng, 2011. 58(10): p. 2995-9.
40. Spees, W. M., et al., *Water proton MR properties of human blood at 1.5 Tesla: magnetic susceptibility, $T(1)$, $T(2)$, $T^*(2)$, and non-Lorentzian signal behavior.* Magn Reson Med, 2001. 45(4): p. 533-42.
41. Chen, Z. and V. Calhoun. *Volumetric computational model for neurovascular coupling and BOLD fMRI*. in *Human Brain Mapping*. 2011. Quebec, CA: OHBM.
42. Fang, C. H., et al., *Anatomical variations of hepatic veins: three-dimensional computed tomography scans of 200 subjects.* World journal of surgery, 2012. 36(1): p. 120-4.
43. Gonzalez, R. C. and R. E. Wood, *Ditial image processing*. Third ed2008: Prentice Hall.
44. Cai, J. F., S. Osher, and Z. Shen, *split Bregman Methods and Frame Based Image Restoration*, in *UCLA CAM Report*2009.
45. Chambolle, A. and P. L. Lions, *Image recovery via total variational minimization and related problems.* Numer. Math., 1997. 76: p. 167-88.
46. Chan, T., et al., *Recent developments in total variation image restoration*, in *Handbook of mathematical models in computer vision*, N.C.Y.F. Paragios, Olivier, Editor 2005, Springer.
47. Combettes, P. L. and J. C. Pesquet, *Image restoration subject to a total variation constraint.* IEEE transactions on image processing: a publication of the IEEE Signal Processing Society, 2004. 13(9): p. 1213-22.
48. Goldstein, T. and S. Osher, *The Slit Bregman Method for L1 Regularized Problems,"*. UCLA CAM Report, 2008.
49. Joshi, S. H., et al., *Edge-Enhanced Image Reconstruction Using (TV) Total Variation and Bregman Refinement.* Lect Notes Comput Sci, 2009. 5567 (2009): p. 389-400.
50. Frigyik, B. A., S. Srivastava, and M. R. Gupta, *functional Bregman divergences and Bayesian Estimation of distribtution.* IEEE Trans Information Theory, 2008. 54: p. 5130-9.

51. Osher, S., et al., *An iterative regularization method for total variation-based image restoration*. Multiscale Model. Simul., 2005. 4(2): p. 460-89.
52. Yeo, D. T., J. A. Fessler, and B. Kim, *Motion robust magnetic susceptibility and field inhomogeneity estimation using regularized image restoration techniques for fMRI*. Med Image Comput Comput Assist Interv, 2008. 11(Pt 1): p. 991-8.
53. Holst, B., et al., *T2' imaging indicates decreased tissue metabolism in frontal white matter of MS patients*. Multiple sclerosis, 2009. 15(6): p. 701-7.
54. Chen, Z., et al., *Volumetric BOLD fMRI simulation: from neurovascular coupling to multivoxel imaging*. to be published in BMC Medical Imaging Journal, 2012.

APPENDIX A

Numerical Simulations

A. $\chi$ Tomography Simulation with a Digital Cylinder Phantom

In support of the invention specification describing innovative methods for reconstructing 3D $\chi$ distributions from a magnetic fieldmap, we performed numerical simulations with a digital cylinder phantom. We predefined a cylindrical susceptibility distribution and embedded it in a cubic field of view (FOV), with the main field $B_0$ perpendicular to the cylinder axis, as diagramed in FIG. 37. The digital cylinder phantom assumes a binary volume of FOV in a matrix in size of 128×128×128.

$$\chi(x, y, z) = \begin{cases} 1 & \text{inside cylinder} \\ 0 & \text{otherwise} \end{cases}, (x, y, z) \in FOV \quad (A1)$$

The parameter settings are provided in Table A1.

Figure 37:
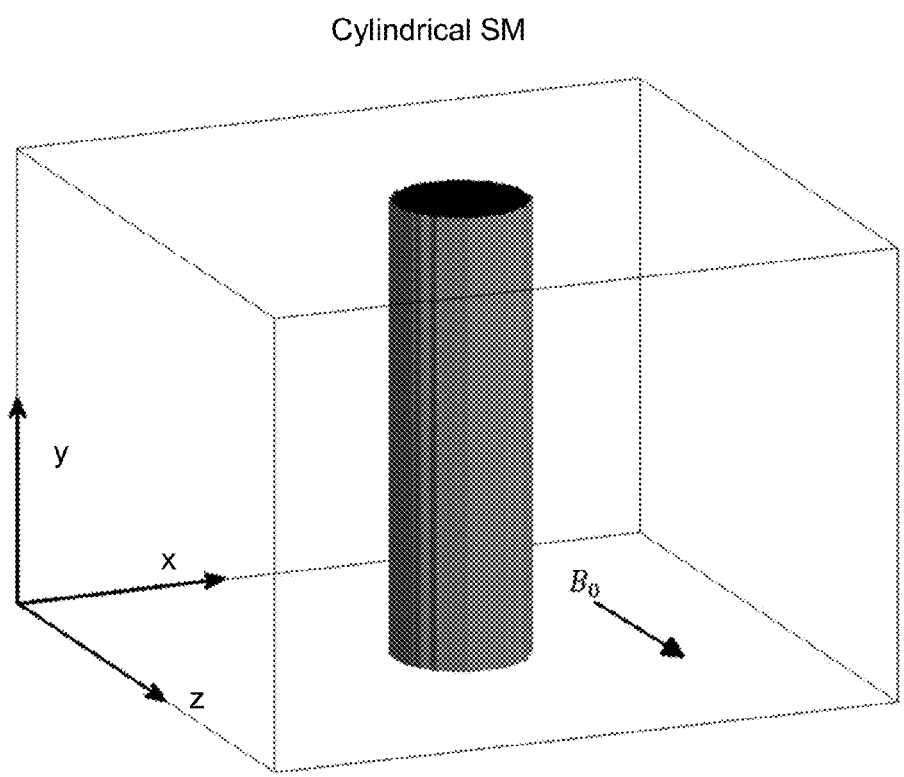
FIG. 37. Geometry for cylindrical $\chi$ reconstruction numerical simulation. The main field is perpendicular to the cylinder.

FIG. 37 Geometry for cylindrical $\chi$ reconstruction simulation. The main MR field is perpendicular to the cylinder's axis.

TABLE A1

Parameter settings for digital cylinder phantom simulation

| Parameters | Settings | Remarks |
|---|---|---|
| $B_0$ | 3 Tesla | Main field |
| FOV matrix | 128 × 128 × 128 | Unit: mm |
| Cylinder diameter | 25 | Unit: mm |
| Susceptibility $\chi$ | 1 ppm (cylinder interior) | SI unit |
| $\chi$ distribution (predefined) | Cylinder in FOV | Ground truth |
| Noise ($\epsilon(x, y, z)$) | randn(128, 128, 128) | Gaussian noise generator |
| NoiseLevel | 0.1 | Standard deviation |

Since the geometry of a cylinder is simple and regular, its fieldmap can be calculated by using a magnetostatic analytic formula [2, 16], or using Eq. (3) (which is valid for an arbitrary geometry). Specifically, we can calculate the fieldmap and add Gaussian additive noise by $$b(x, y, z) = IFT\left\{FT[\chi(x, y, z)] \cdot \left(\frac{1}{3} - \frac{k_z^2}{k^2}\right)\right\} + \varepsilon(x, y, z) \quad (A2)$$

$$\varepsilon(x, y, z) = NoiseLevel \cdot randn(128, 128, 128)$$

where FT and IFT represent Fourier transform and inverse Fourier transform, randn the Gaussian random number generator (a Matlab function), and NoiseLevel controls the standard deviation. The three orthogonal slices for the predefined $\chi$ source and the calculated fieldmap (without and with noise) are displayed in FIG. 38.

FIG. 38 shows: Top row: three orthogonal cross-sections of the predefined $\chi$ source. Middle row: fieldmap without noise. Bottom row: fieldmap with additive Gaussian noise (NoiseLevel=0.1).

As discussed previously, the $\chi$ source distribution can be reconstructed from the fieldmap by solving a 3D inverse problem (deconvolution) using three different types of solvers. Since it is very difficult to find the inverse of a matrix with size 2097152×2097152 (where 2097152=128×128×128), we cannot provide a solution using the "matrix inverse" solver.

We simulate the $\chi$ reconstruction by the "filter truncation" solver by [17]

$$\chi(x, y, z) = IFT\left\{\frac{FT\{b(x, y, z)\}}{h_{trunc}(k) \cdot B_0}\right\} \text{ with} \quad (A3)$$

$$h_{trunc}(k) = \begin{cases} \varepsilon_0 \cdot \text{sgn}(h_0(k)), & |h_0(k)| < \varepsilon_0 \\ h_0(k), & \text{otherwise} \end{cases}$$

Where $\epsilon_0$ is a threshold for filter truncation, which is noise-dependent. In our simulation, we select $\epsilon_0$=1.2×NoiseLevel to suppress the noise. The results are displayed at the middle row in FIG. 39.

Figure 40:
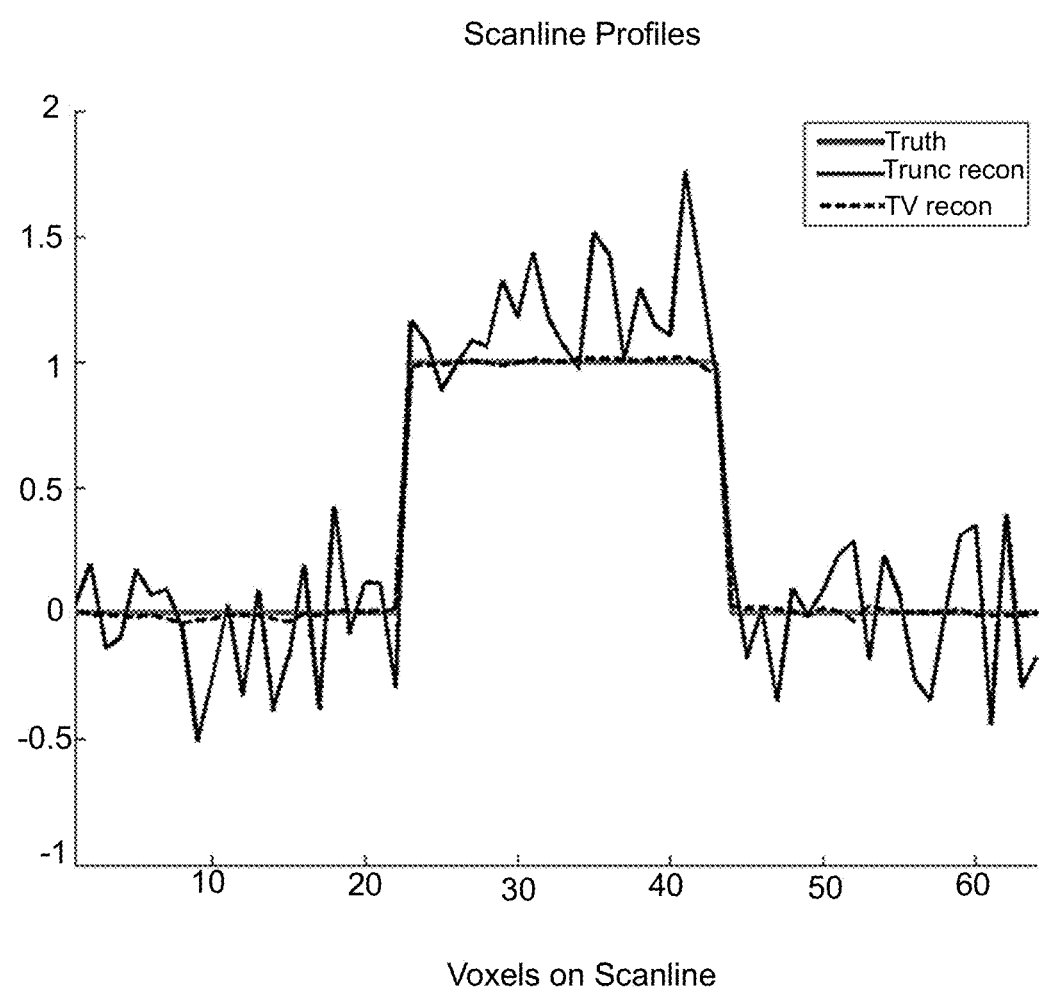
FIG. 40. Quantitative profiles along a diameter of the cylinder phantom in FIG. 37 (the ground truth is a rectangle profile in legend "truth").
Figure 41:
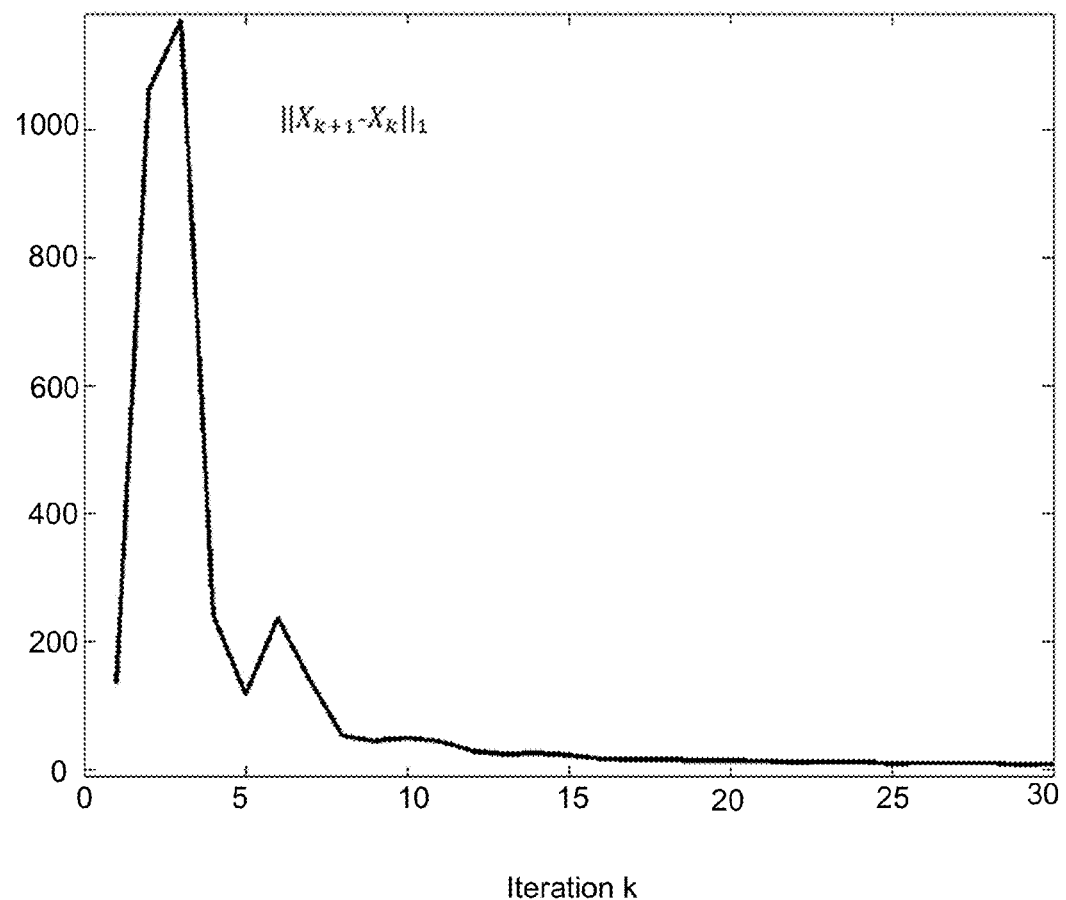
FIG. 41. Convergence of a typical TV iteration.

Finally, we simulated the $\chi$ reconstruction by using the "TV iteration" solver (in Eq. (20)), with the settings of $\{\lambda=100, \gamma_1=\frac{1}{5}, \gamma_2=\frac{1}{8}\}$. The results are displayed at the bottom row in FIG. 39, which compares the results of two different numerical simulations of computed inverse BOLD fMRI for susceptibility source reconstruction with a simple cylinder $\chi$ source (predefined ground truth in the first row), by filter truncation method (in second row) and by the TV-regularized method (in the third row). FIG. 40 shows quantitative profiles along a diameter (scanline) of the cylinder phantom in FIG. 37 (note: the ground truth is a rectangle profile in legend "truth"). FIG. 41 shows the typical convergence behavior of the TV-iteration method. It is seen that the solution converges after about 15 iterations.

A.2 Noise Patterns in $\chi$ Tomography

It has been shown that the $\chi$ tomography by "filter truncation" solver suffers from the heavy noise that manifests as the stripes and textural patterns [17,21-25], which is also demonstrated in FIG. 40 for the digital cylinder phantom simulation. The noise structure associated with the "filter truncation" solver can be explained by the illustration in FIG. 16, wherein any two points in the Fourier domain creates a collection of parallel lines in the space domain, and the superimposition of a multitude of random parallel lines resulting from many random points in the Fourier domain manifests as a clutter noise or textural noise. In contrast, the $\chi$ tomography by "TV iteration" solver suffers only from sparse "comeback" noise [45-50].

Figure 42:
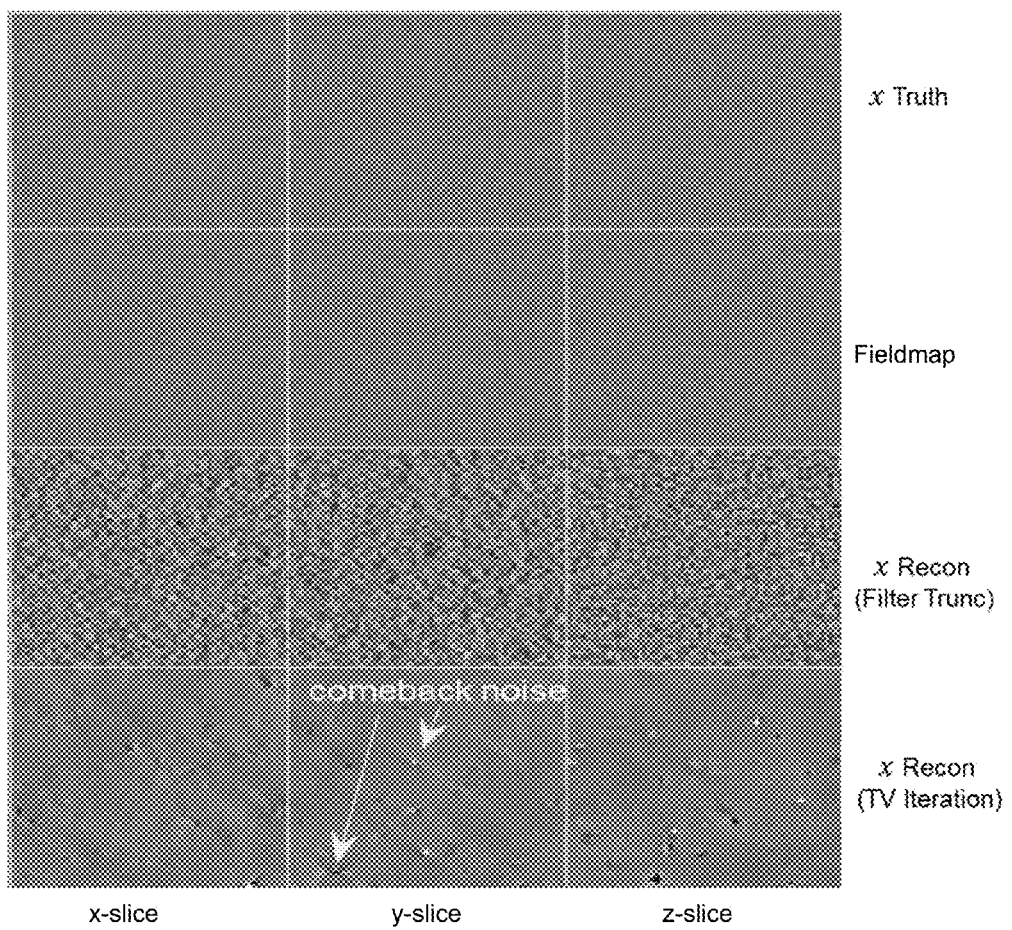
FIG. 42. Comparison of two inverse solvers in a numerical simulation of random noise behavior during $\chi$ reconstruction.
Figure 1:
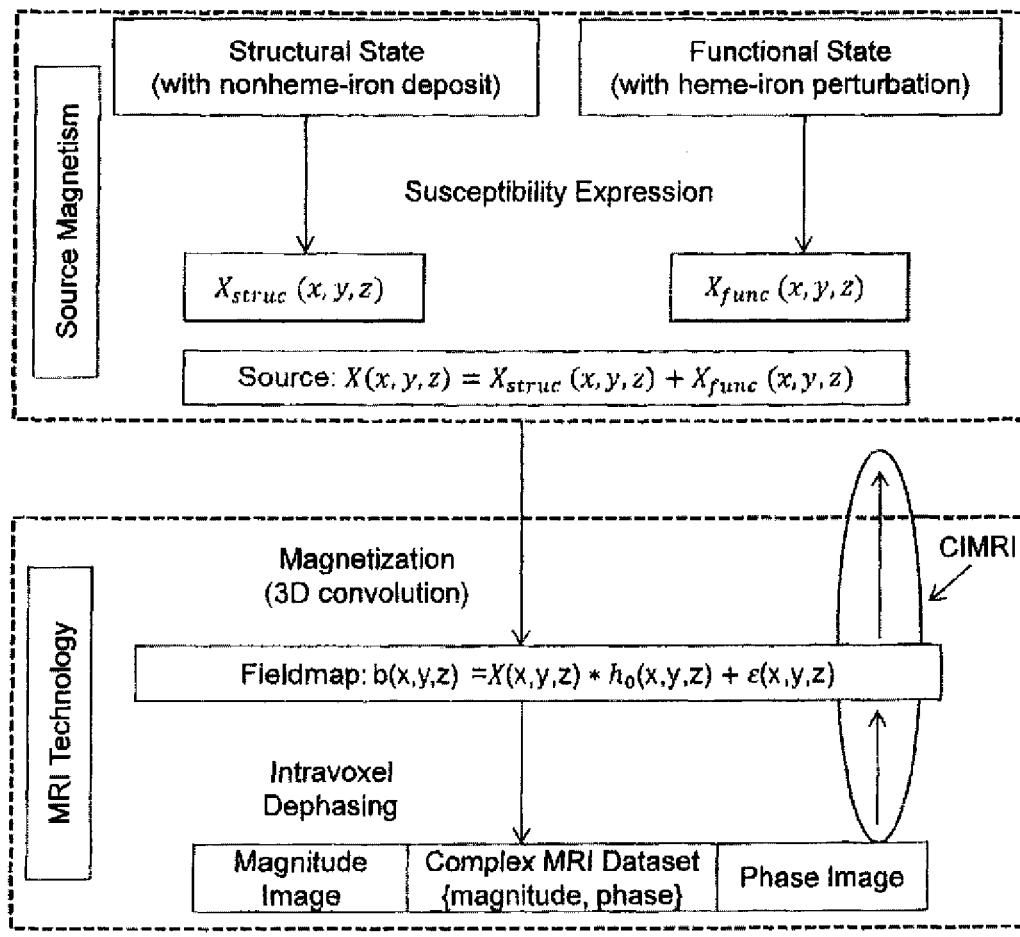
Figure 2A:
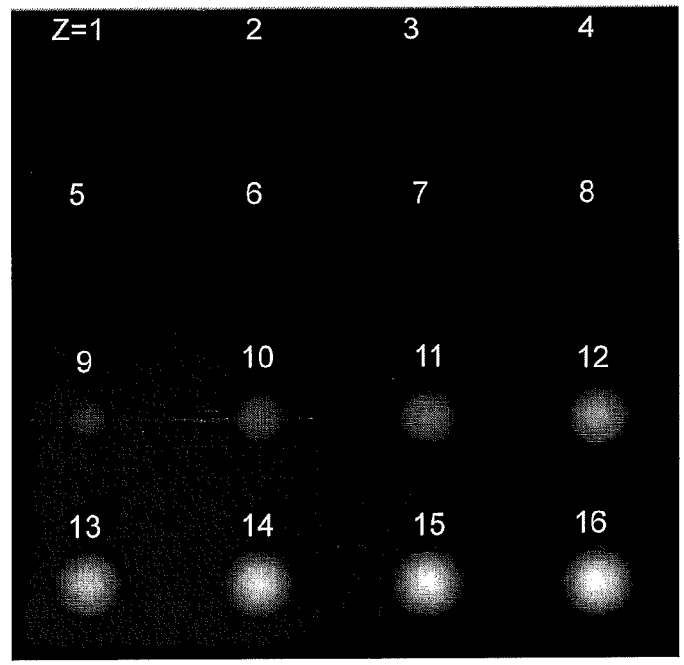
Figure 2B:
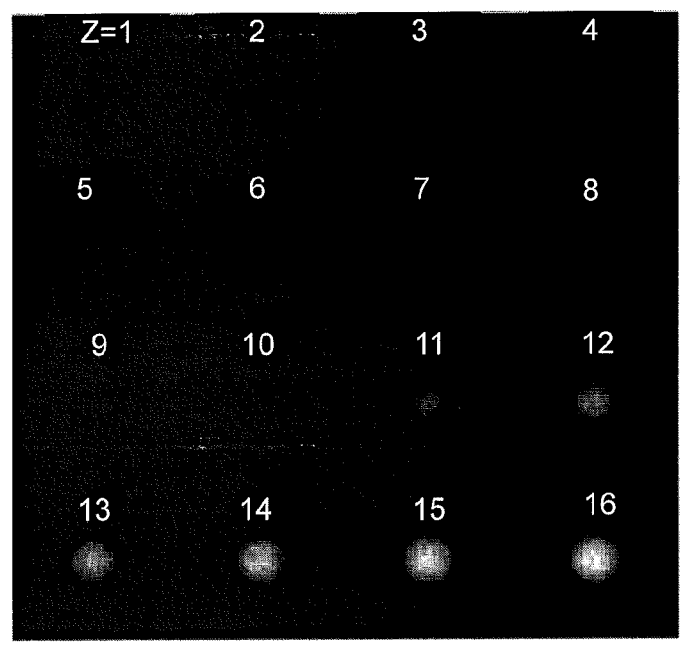
Figure 3A:
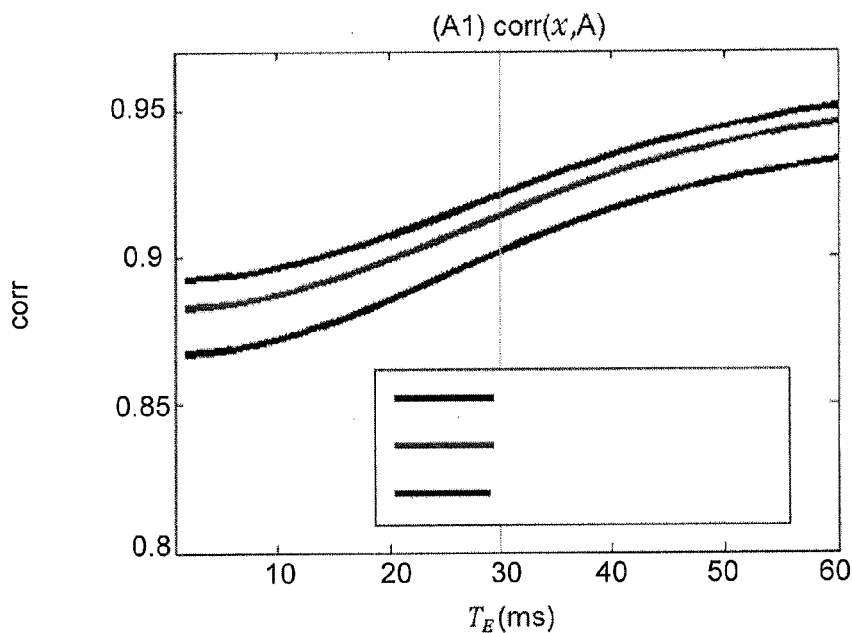
Figure 3B:
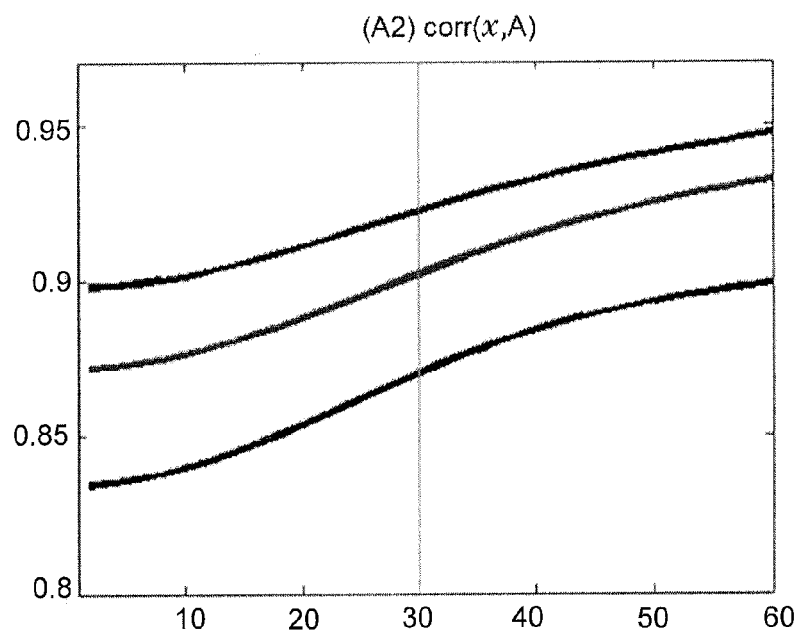
Figure 4A:
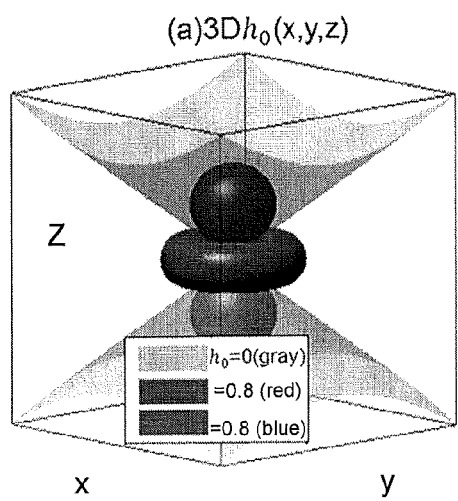
Figure 4B:
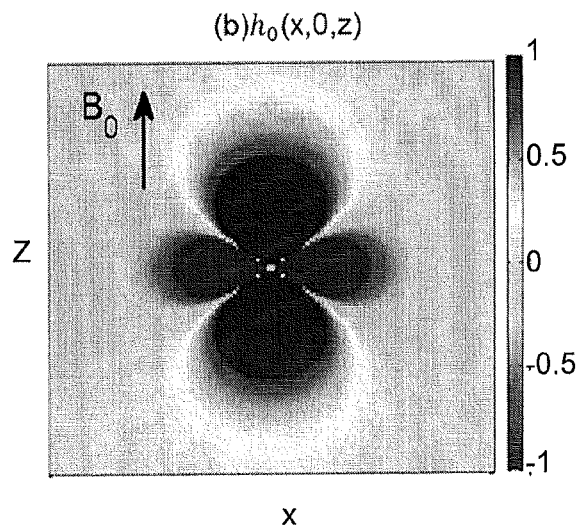
Figure 4C:
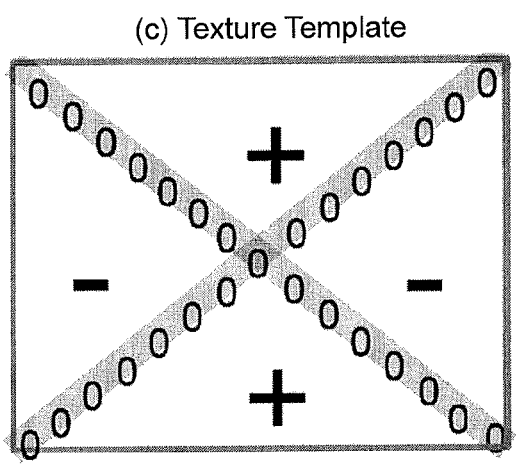
Figure 4D:
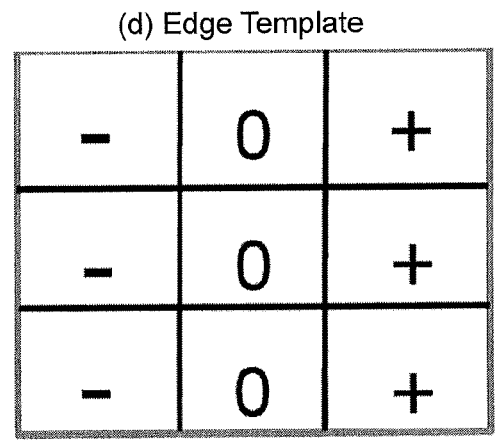
Figure 5A:
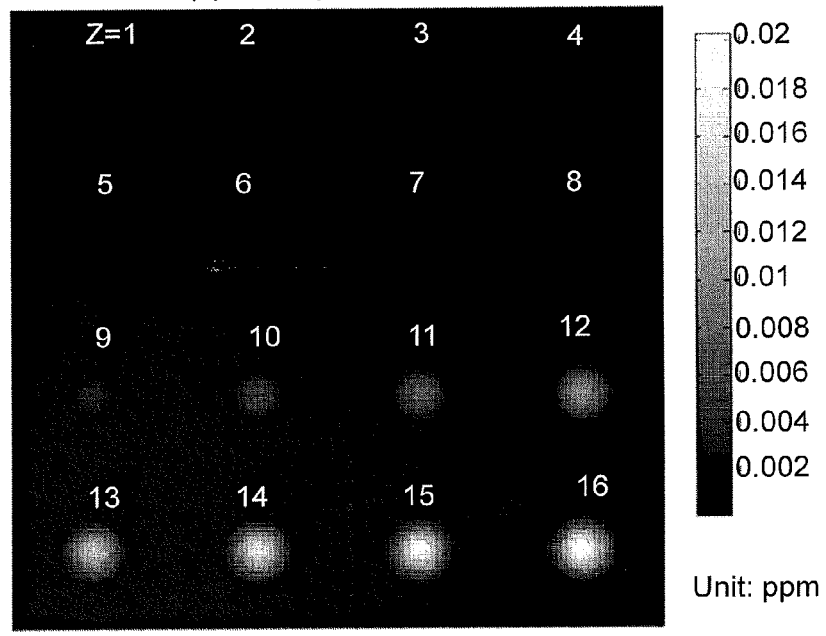
Figure 5B:
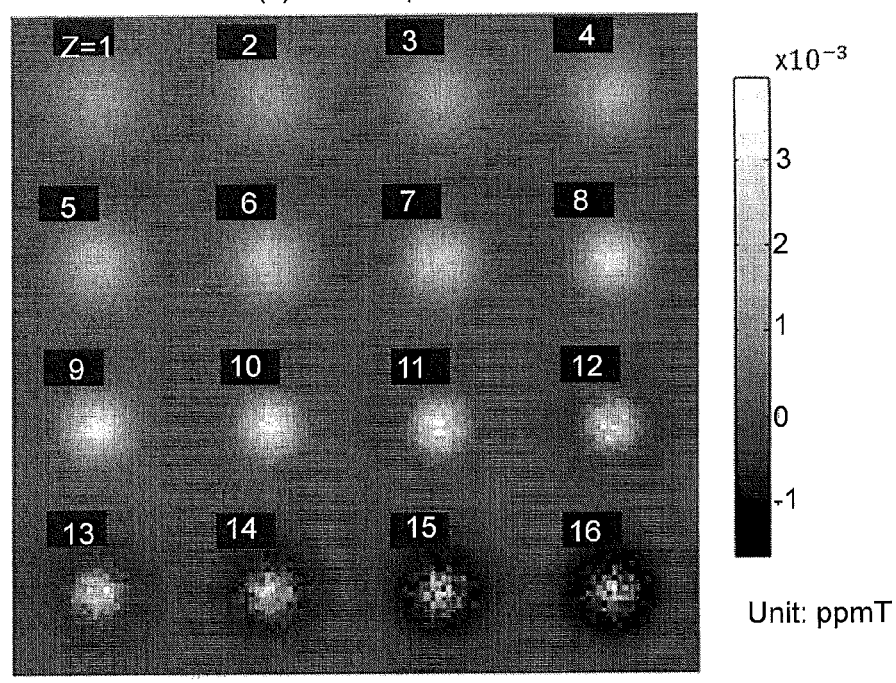
Figure 6:
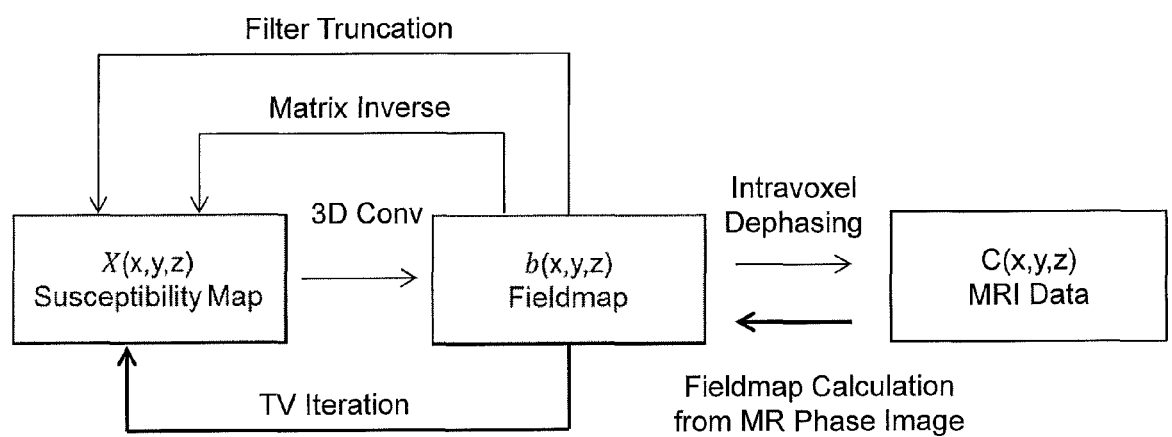
Figure 7A:
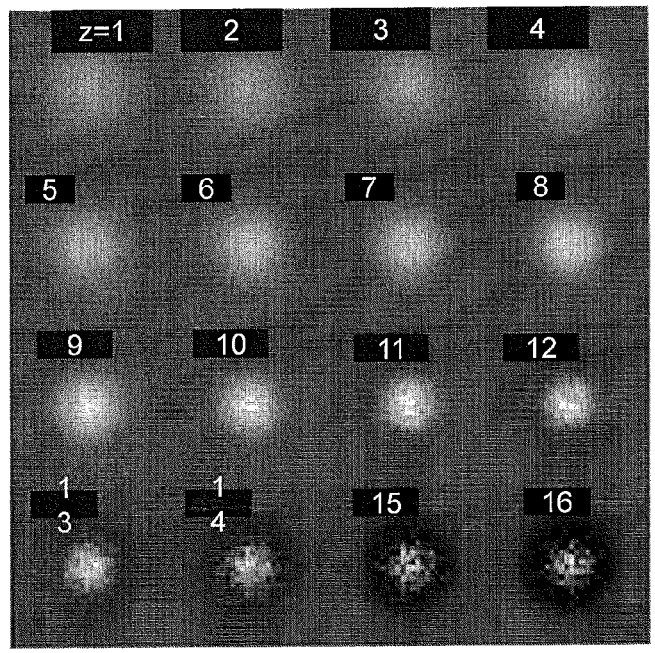
Figure 7B:
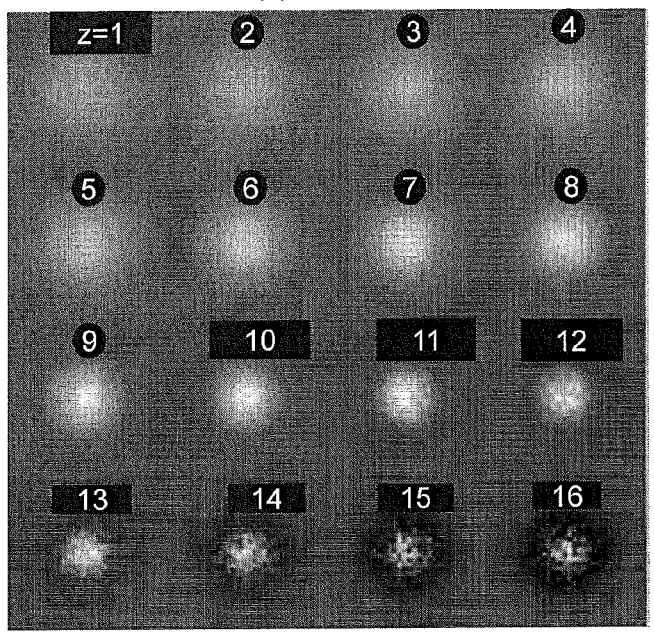
Figure 8A:
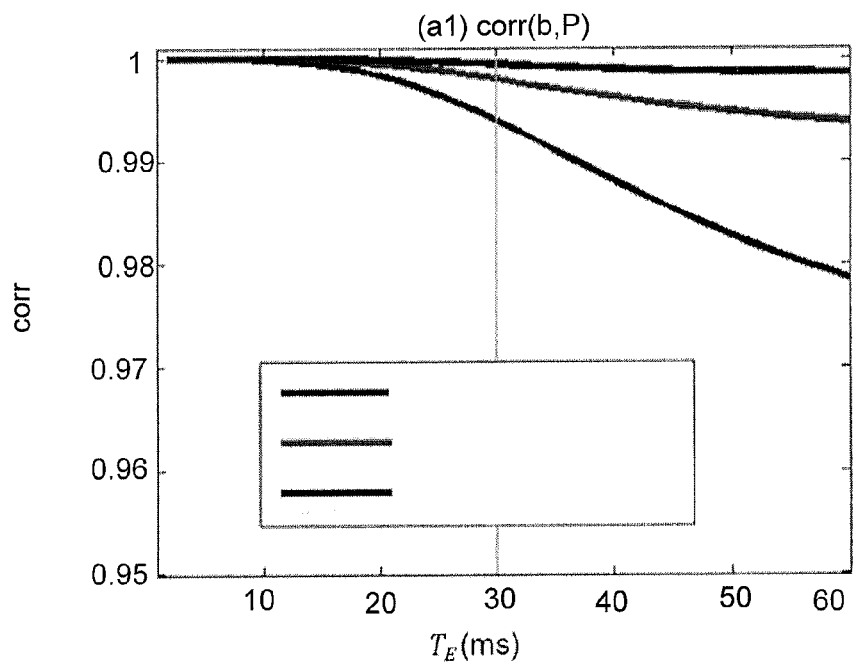
Figure 8B:
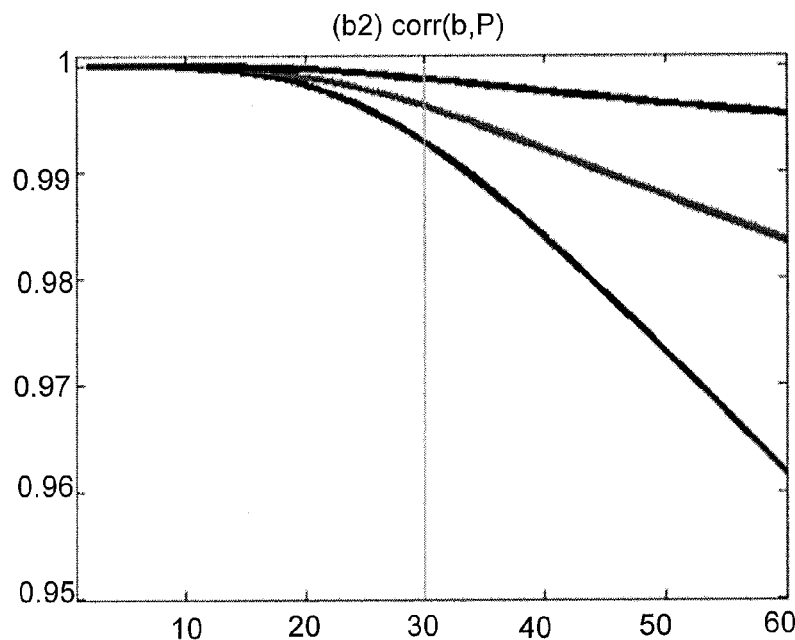
Figure 9A:
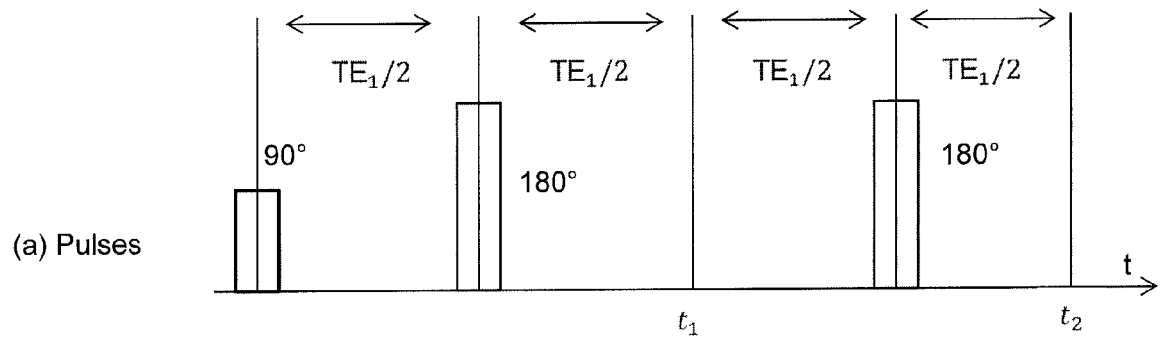
Figure 9B:
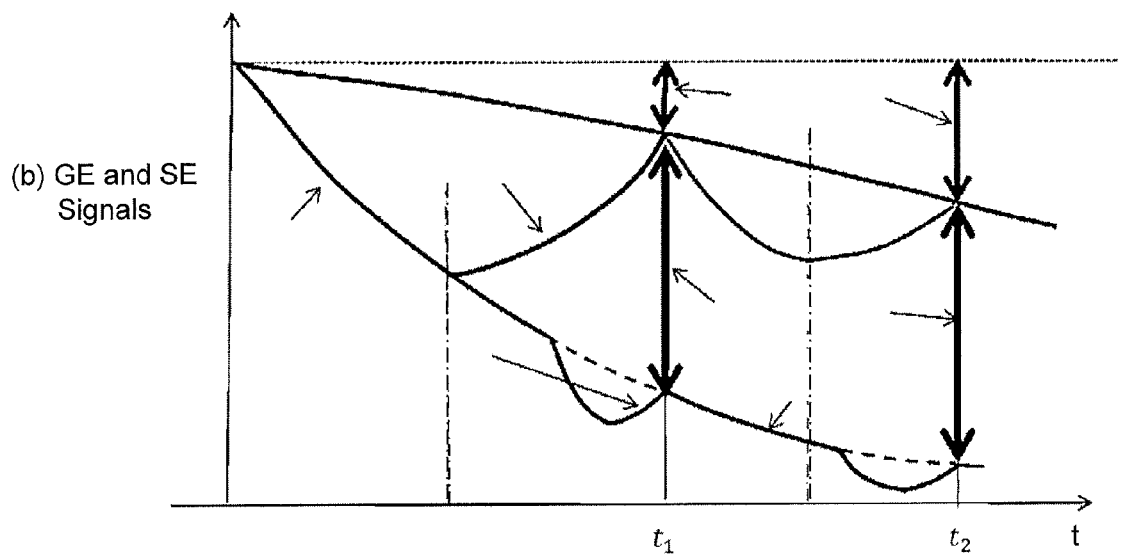
Figure 10:
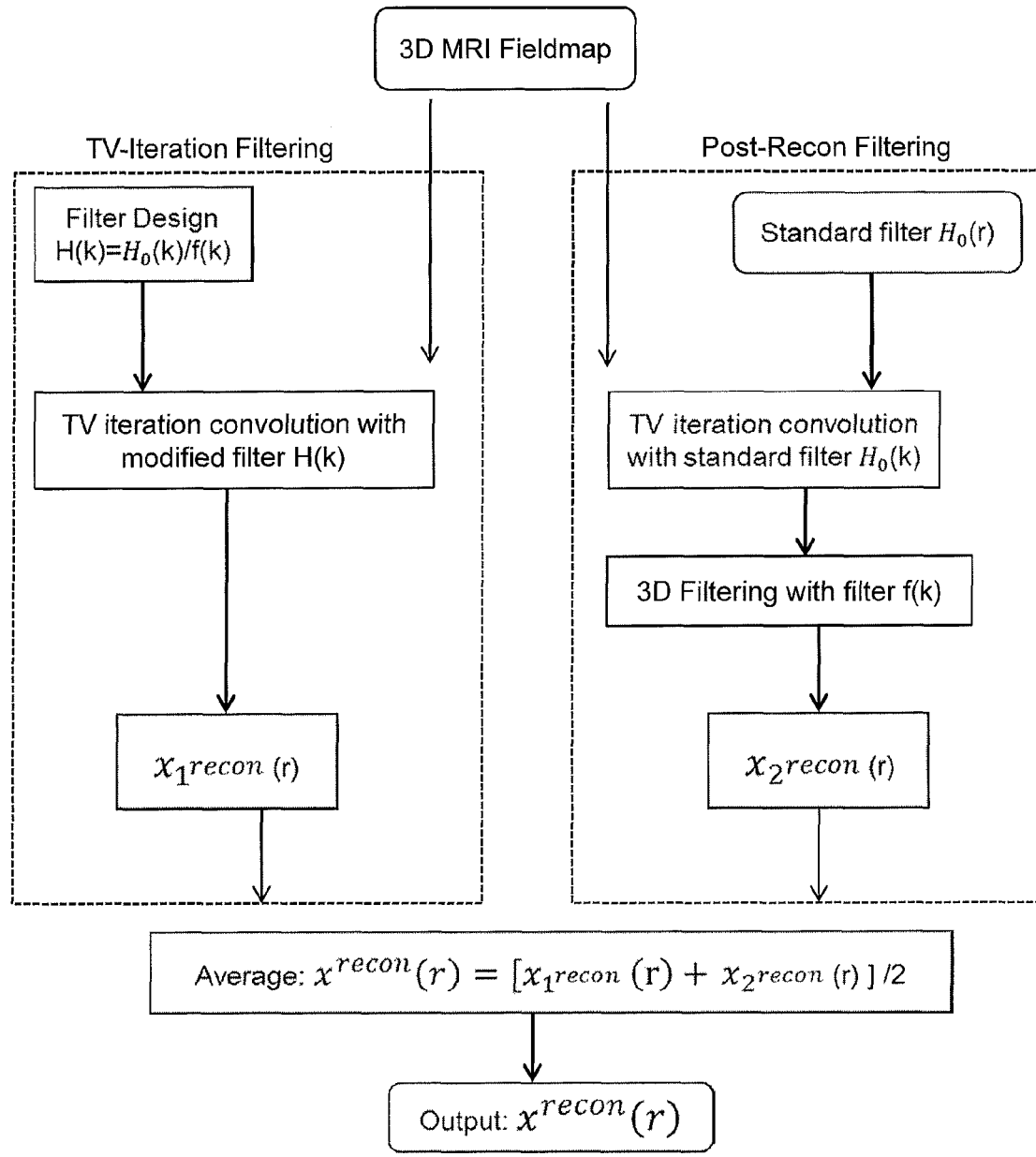
Figure 11:
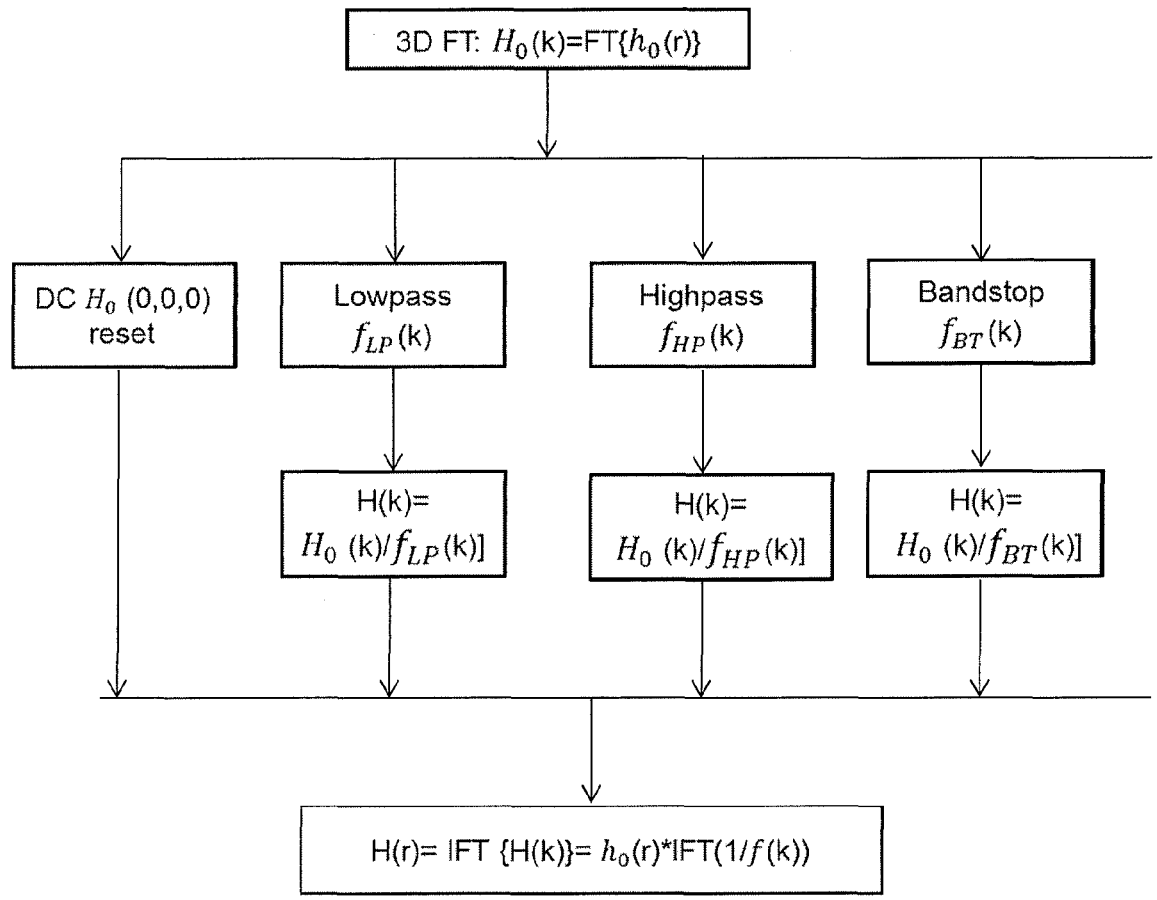
Figure 12A:
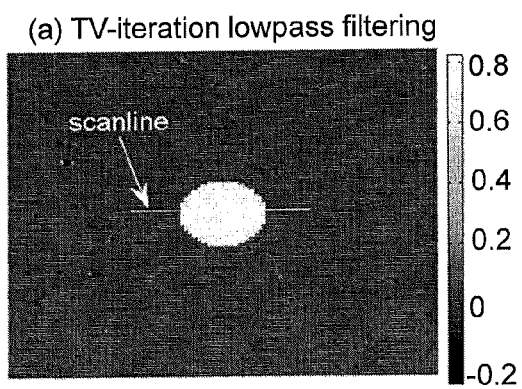
Figure 12B:
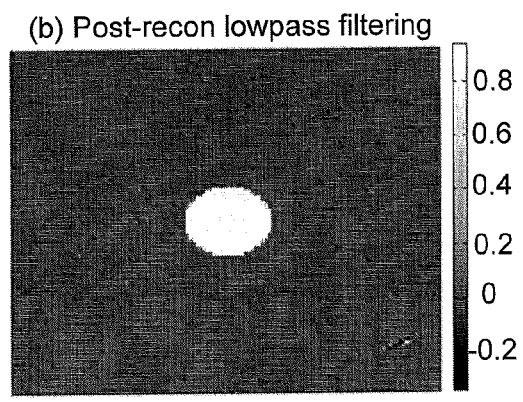
Figure 12C:
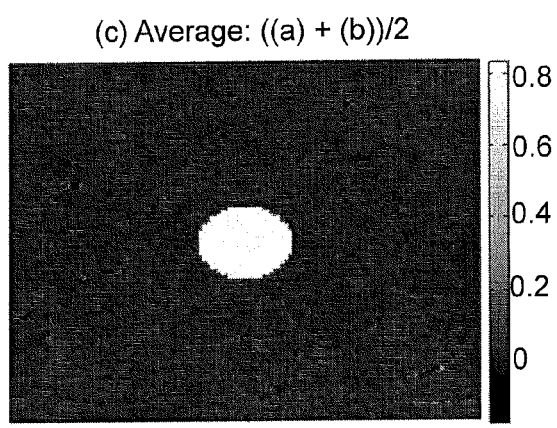
Figure 12D:
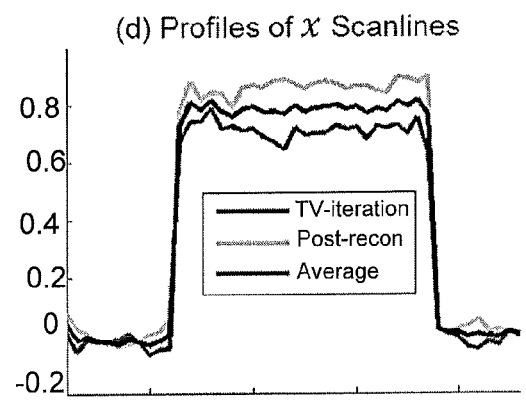
Figure 13:
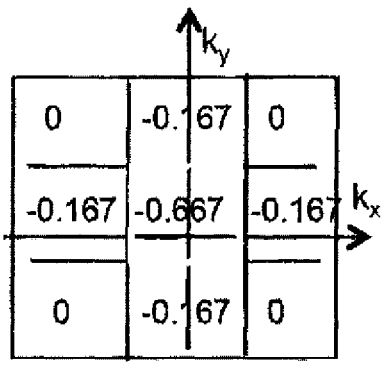
Figure 13:
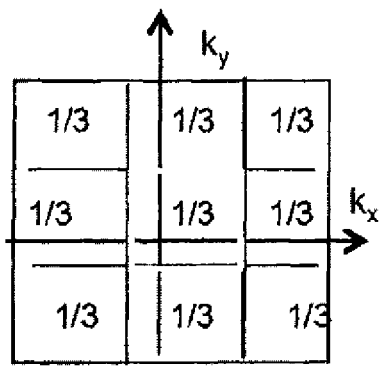
Figure 13:
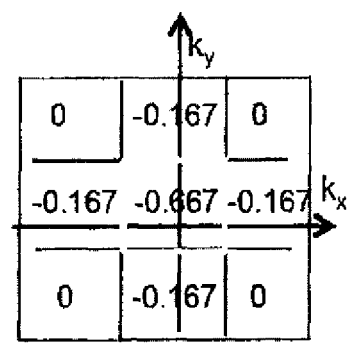
Figure 14A:
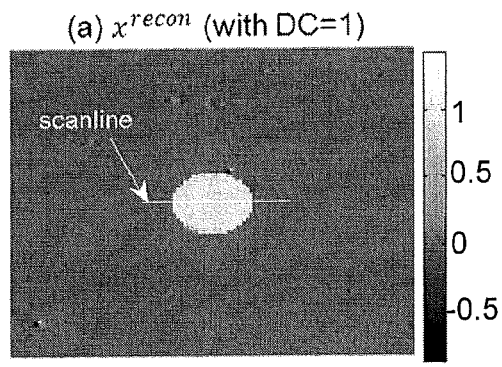
Figure 14B:
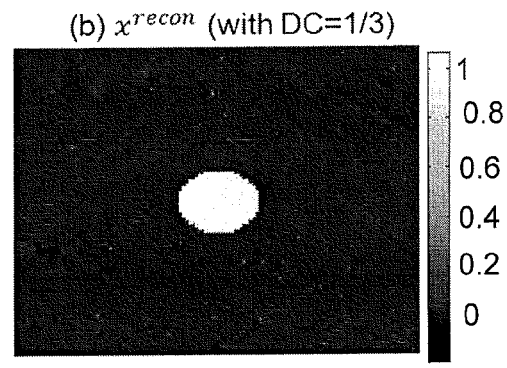
Figure 14C:
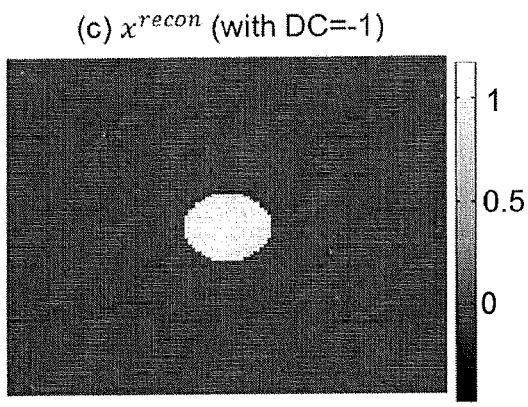
Figure 14D:
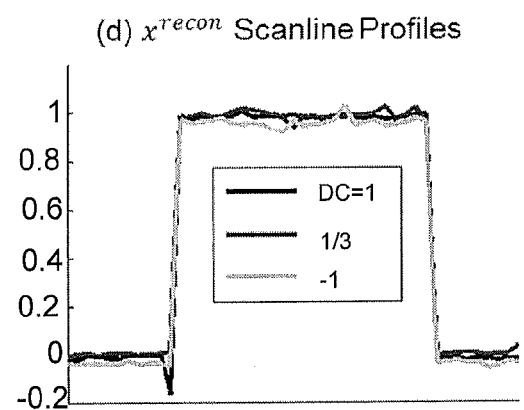
Figure 15:
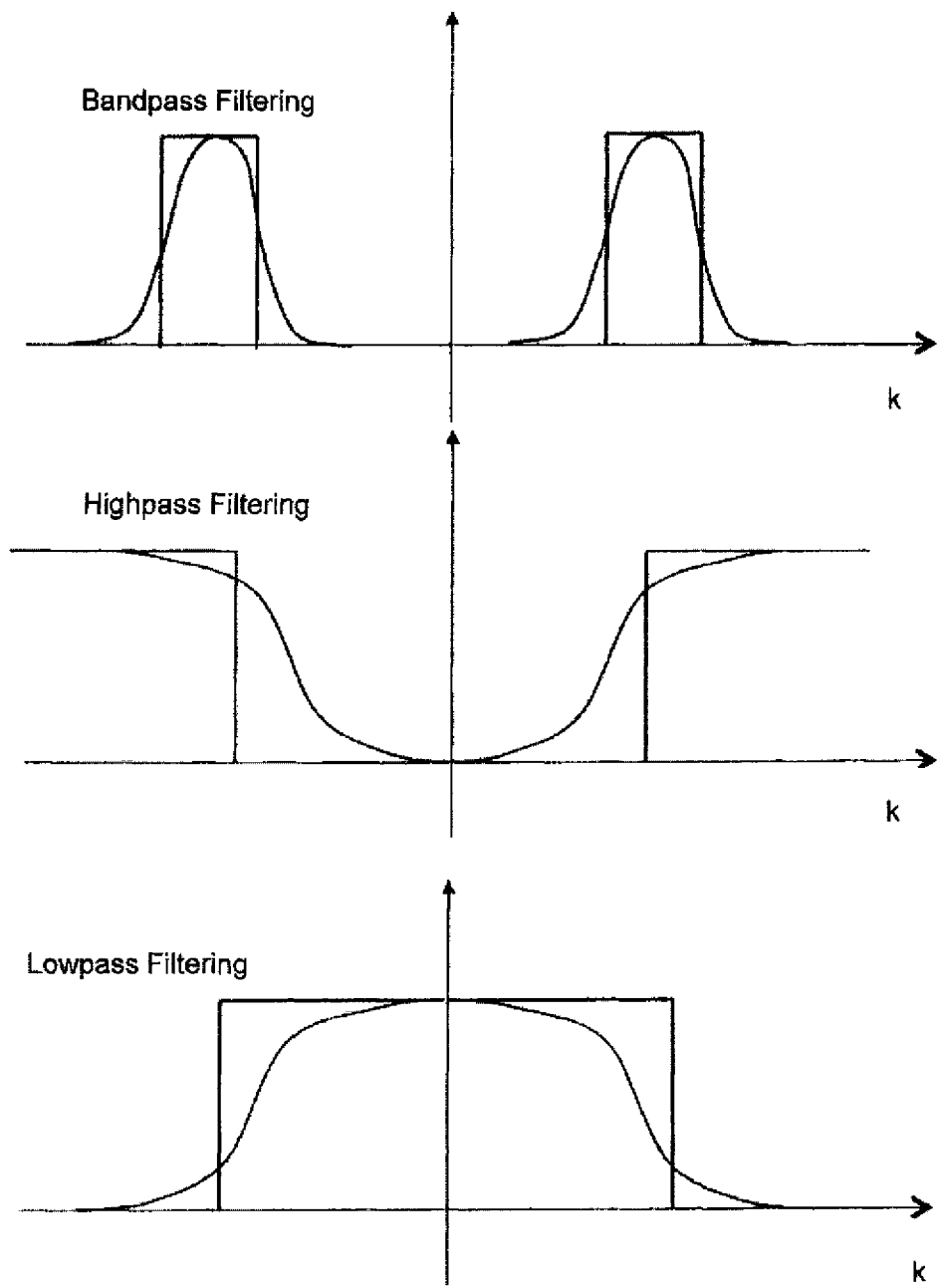
Figure 16A:
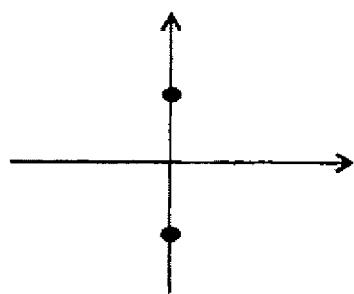
Figure 16A:
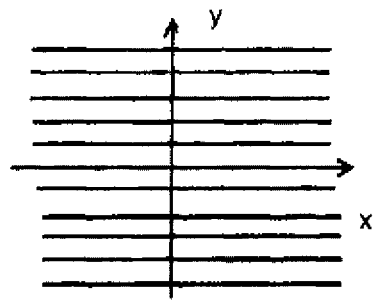
Figure 16B:
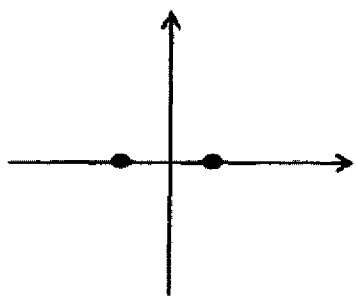
Figure 16B:
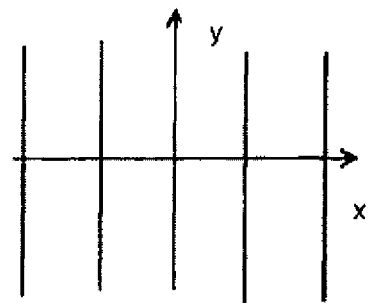
Figure 16C:
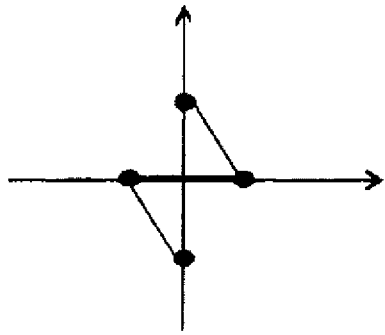
Figure 16C:
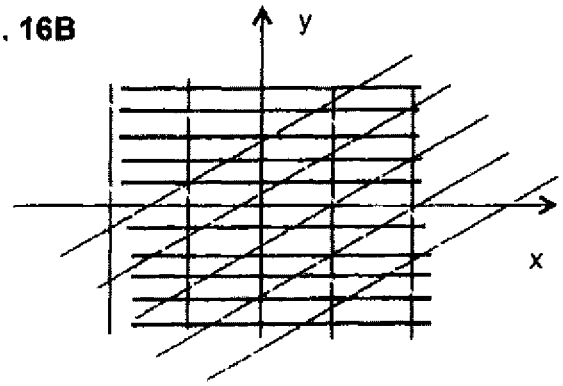
Figure 17A:
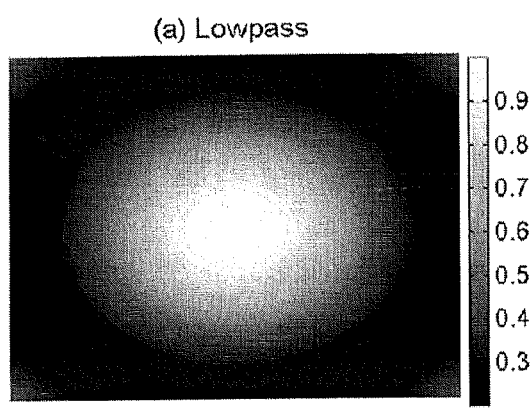
Figure 17B:
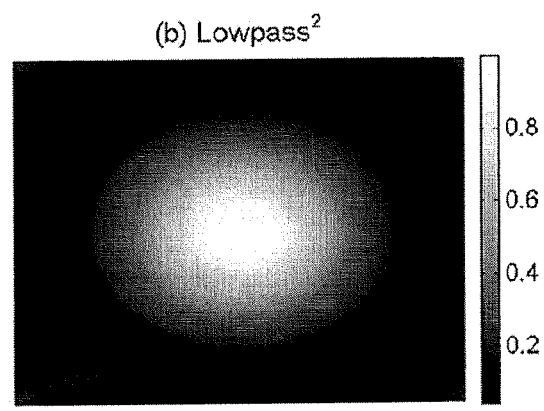
Figure 17C:
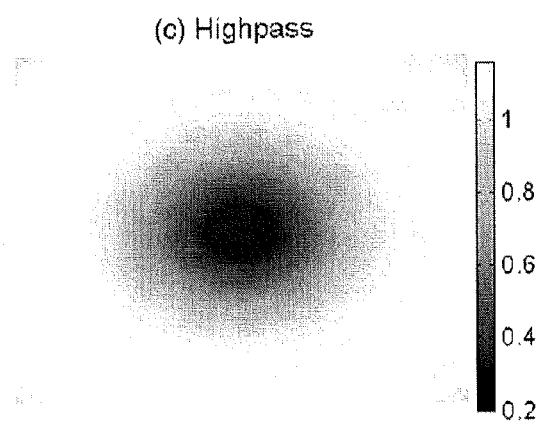
Figure 17D:
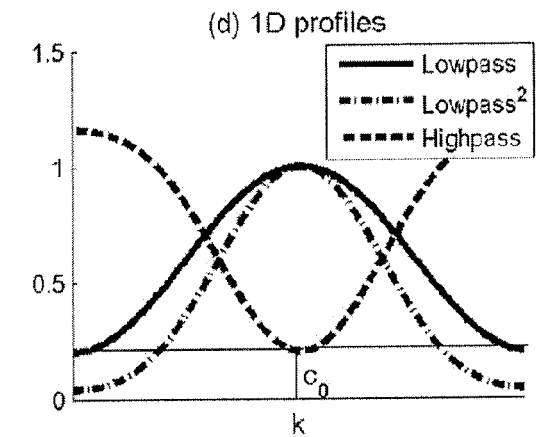
Figure 18A:
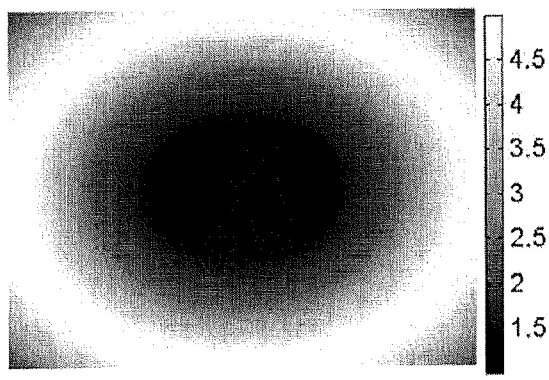
Figure 18B:
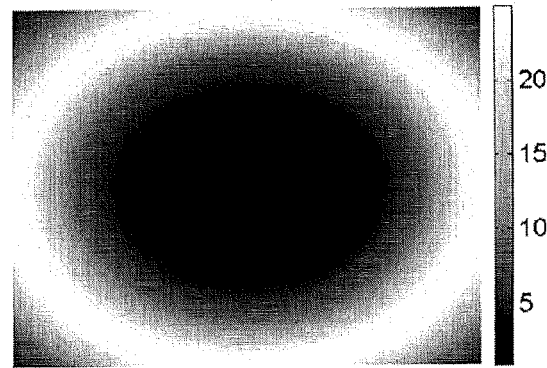
Figure 18C:
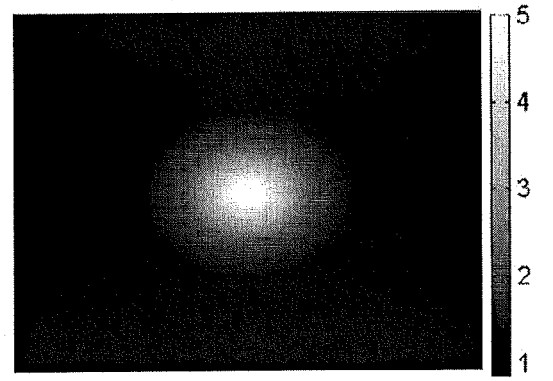
Figure 18D:
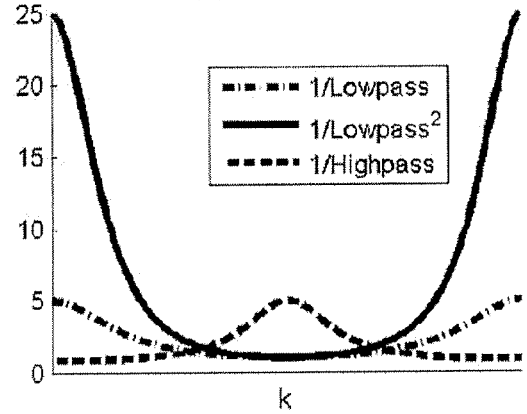
Figure 19A:
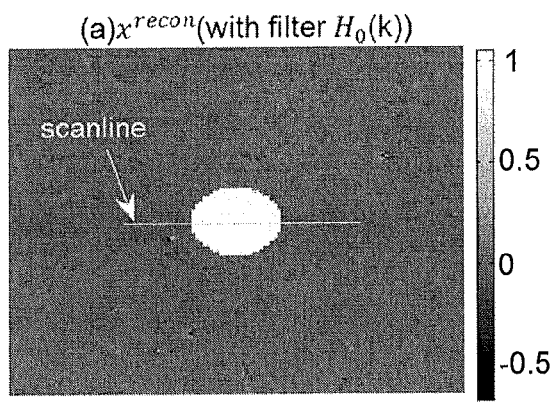
Figure 19B:
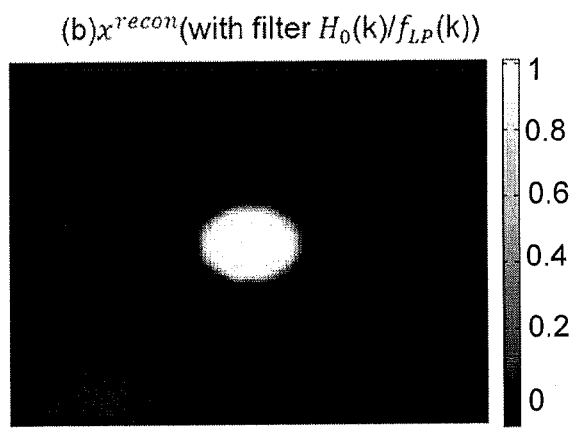
Figure 19C:
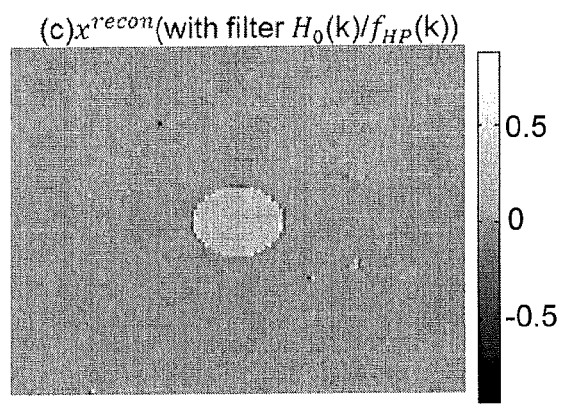
Figure 19D:
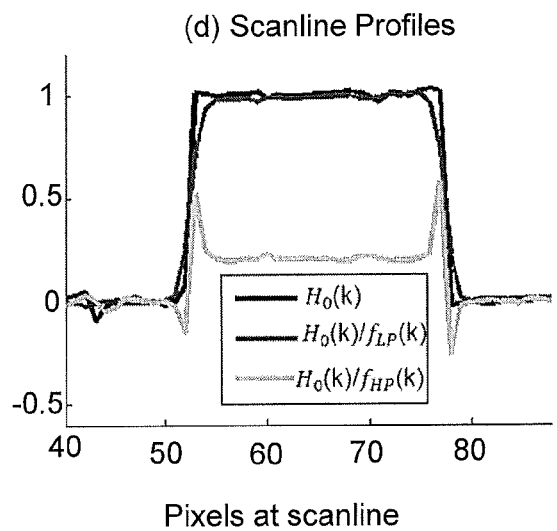
Figure 20:
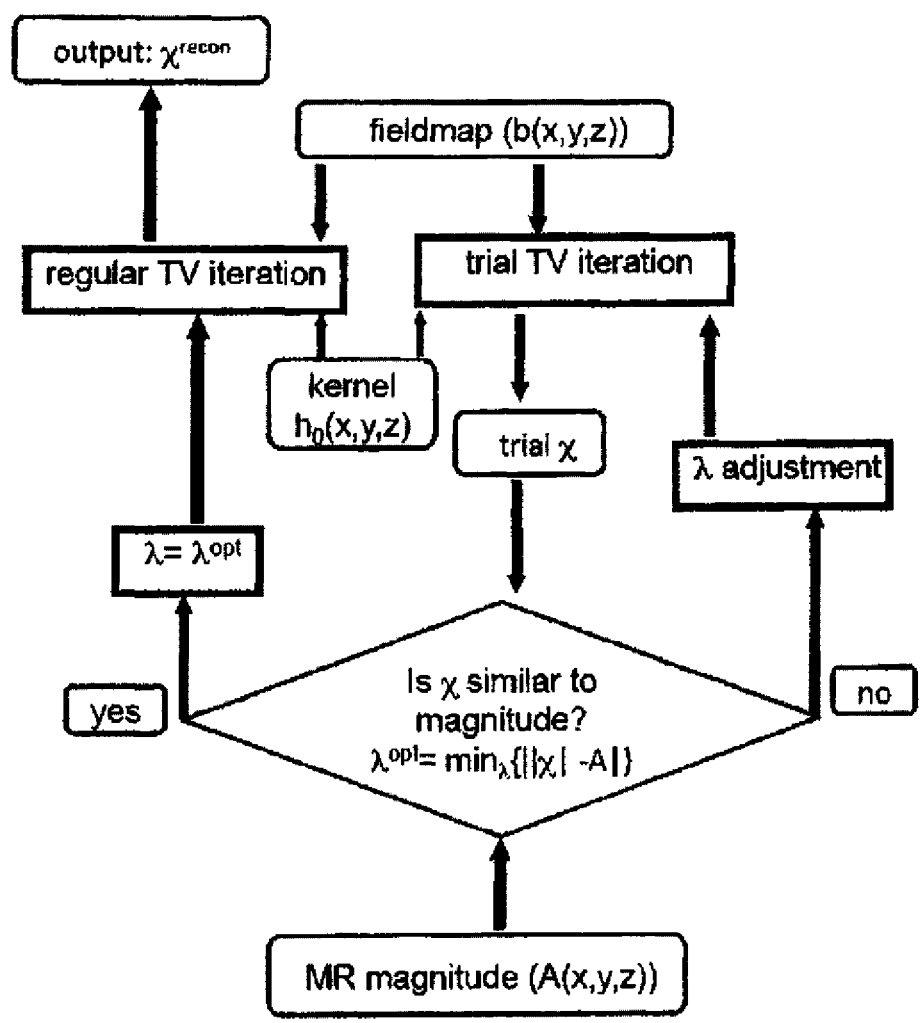
Figure 21:
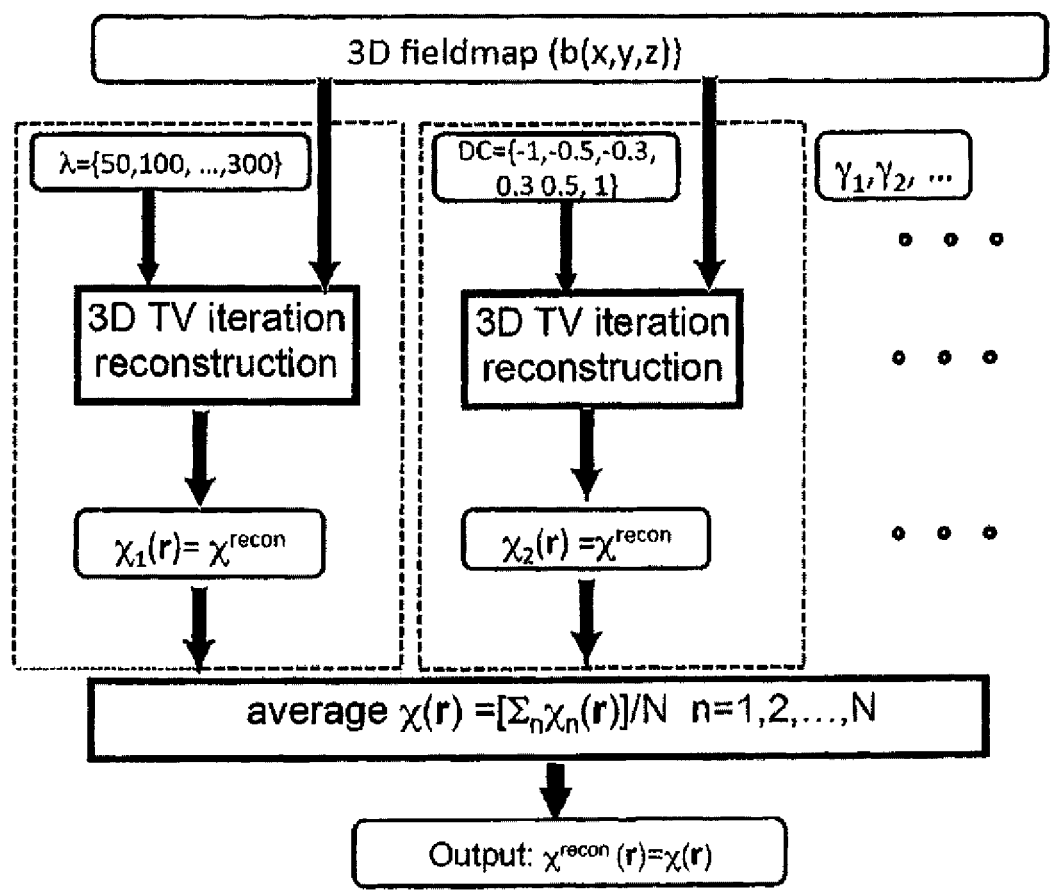
Figure 22A:
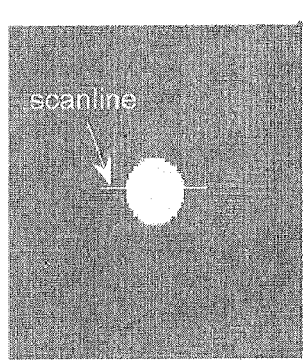
Figure 22B:
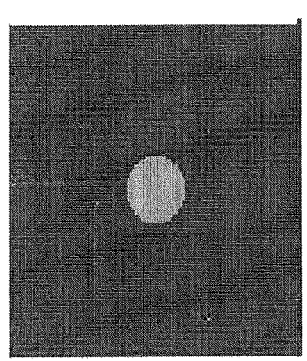
Figure 22C:
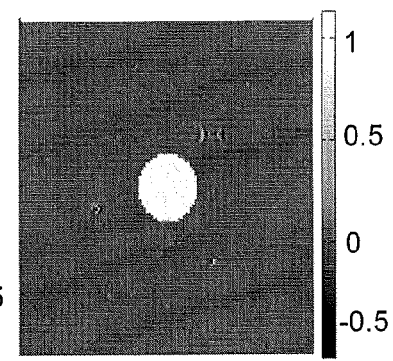
Figure 22D:
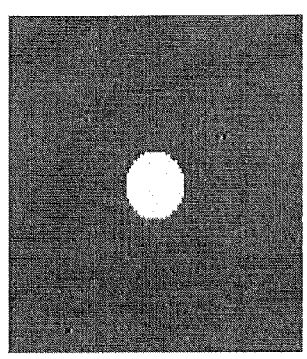
Figure 22E:
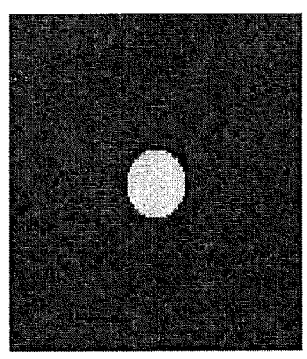
Figure 22F:
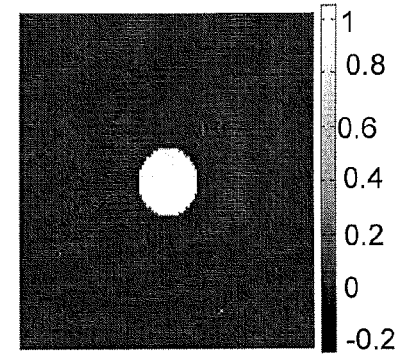
Figure 23:
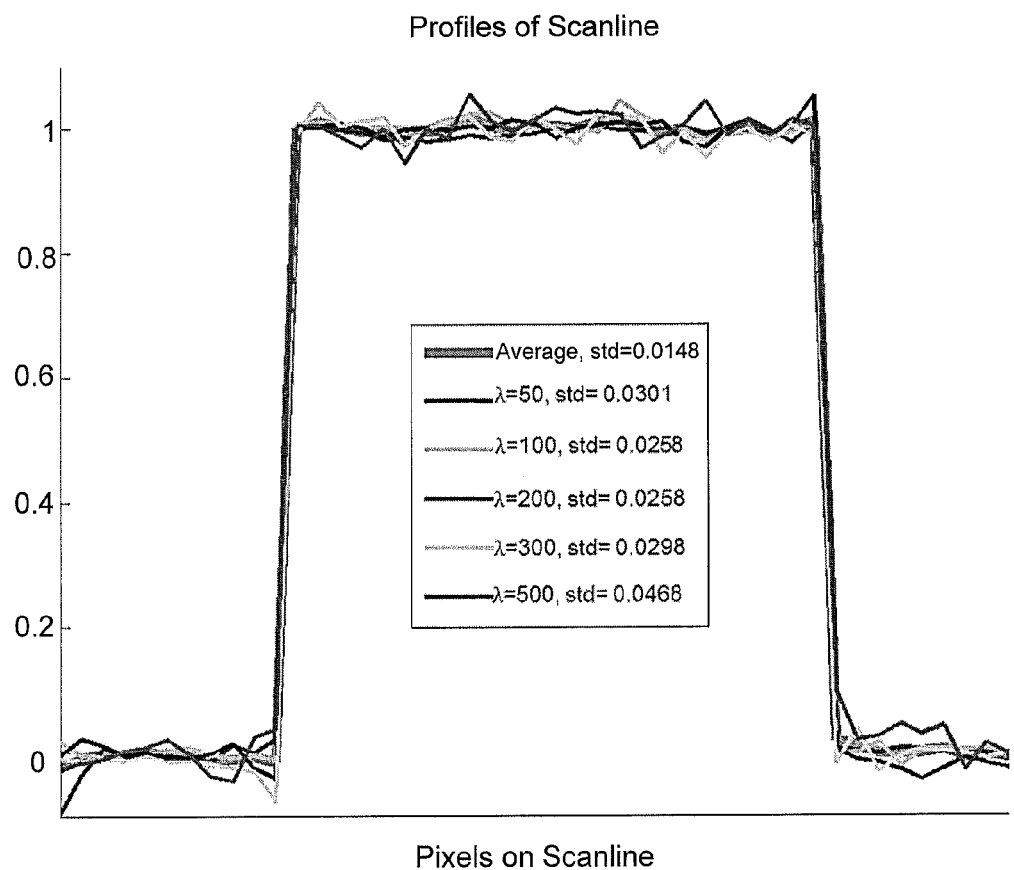
Figure 24:
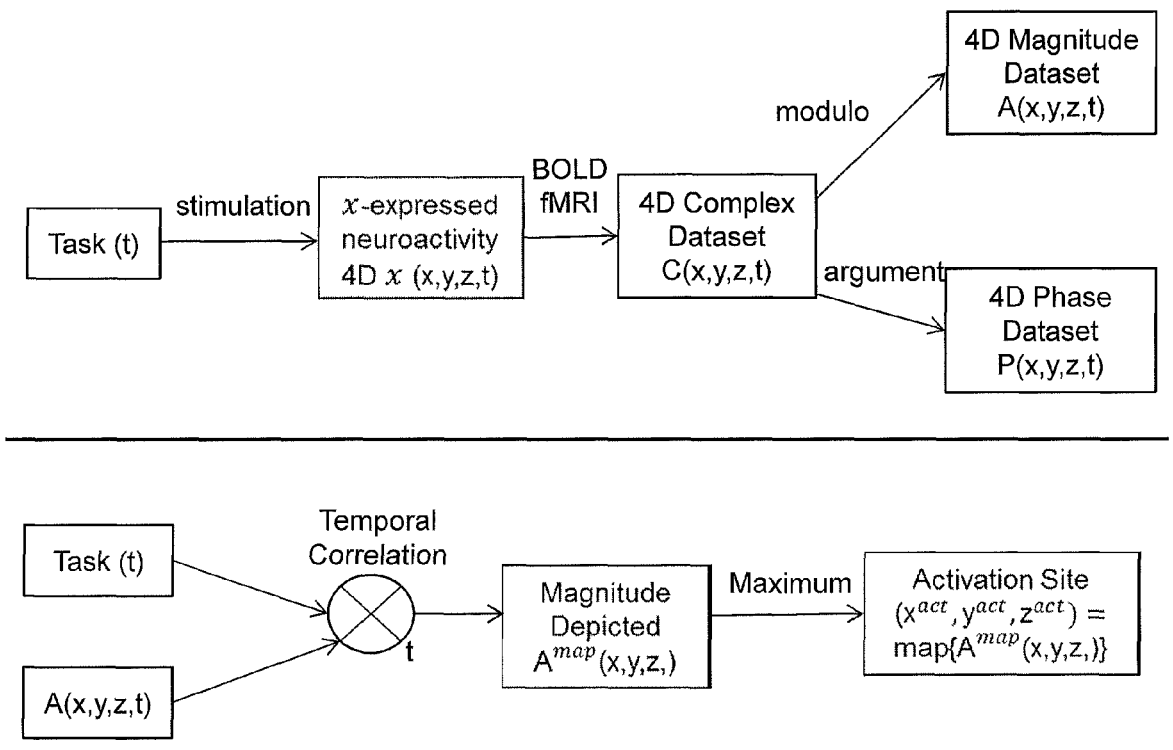
Figure 25:
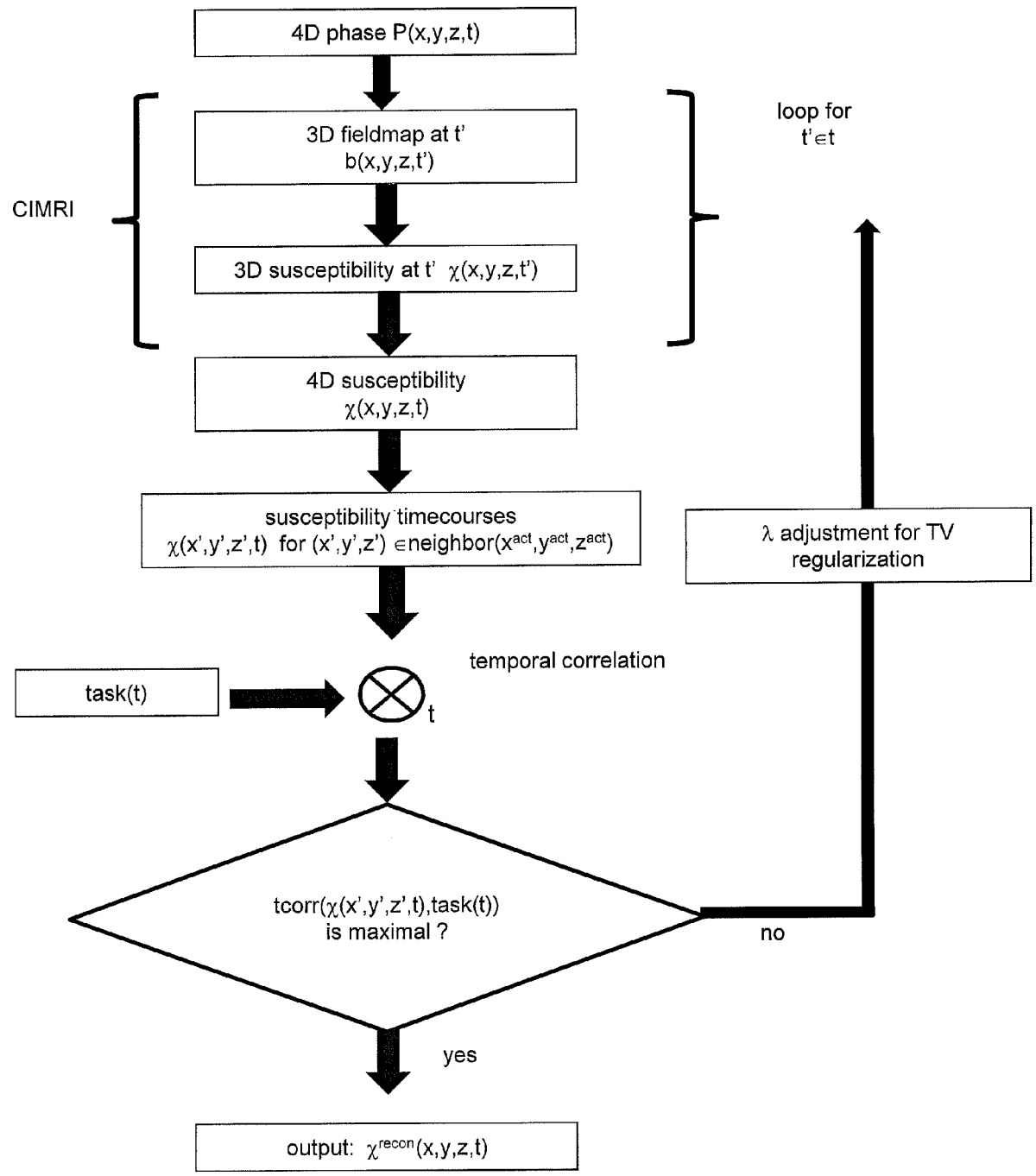
Figure 26:
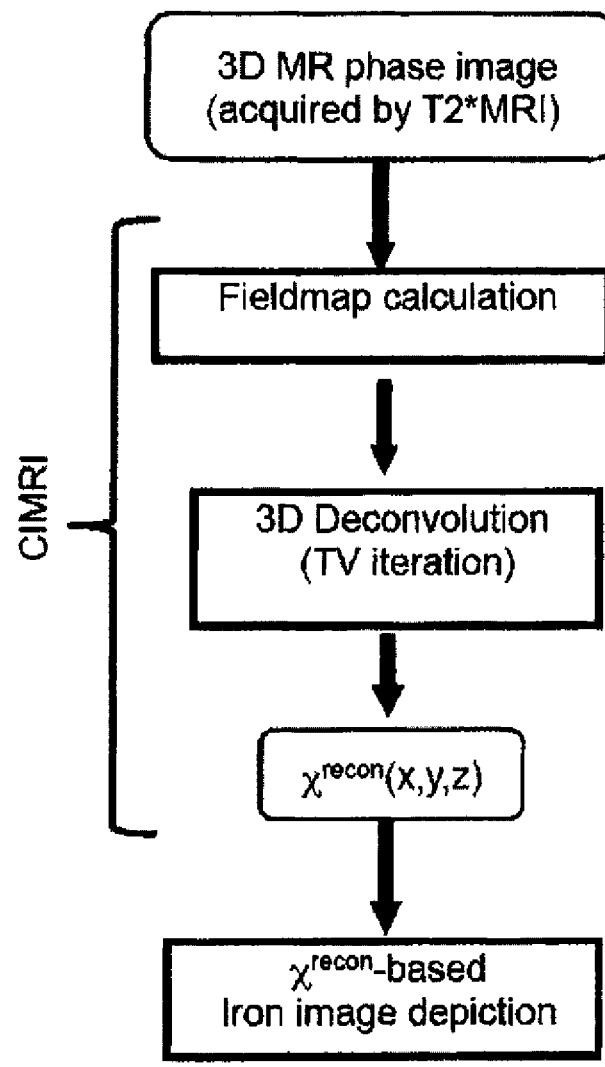

In a second numerical simulation, we observed the behavior of noise throughout the $\chi$ tomography process by: (1) pre-defining a magnetic susceptibility distribution consisting solely of random noise, (2) then calculating the fieldmap and the complex T2* image, and finally, (3) reconstructing the (known) magnetic susceptibility source by two different solver methods: (a) filter truncation inverse filtering, and (b) TV regularized iteration. The numerical simulation results are shown in FIG. 42. It is observed that the filter truncation reconstruction method suffers heavy textural noises (resulting from clutters of numerous random stripes), while the TV iteration method suffers only sparse "comeback noise". One part of our invention is to suppress the sparse "comeback noise" by calculating a multiple reconstruction average, as presented previously.

What is claimed is:

1. A method of reconstructing an internal distribution of magnetic susceptibility values of an object, denoted by χ (x,y,z) and called a 3D map, by using a Computed Inverse Magnetic Resonance Imaging (CIMRI) tomographic procedure, comprising:

a) acquiring a 3D complex-valued MR image of the object from a T2*-weighted MRI (T2*MRI) scan performed by a MRI scanning machine;

b) extracting a 3D T2*MRI phase image, $P(x,y,z;T_E)$, from the 3D complex-valued MR image;

c) calculating a 3D magnetic field map, $b(x,y,z)$, of the z-component ($B_z$) of a susceptibility-induced inhomogeneous magnetic field created by magnetizing the object in a main field, $B_0$, from the MR phase image, $P(x,y,z;T_E)$, under phase-unwrapped conditions or for phase-unwrapped images, according to:

$$b(x, y, z) = \frac{P(x, y, z; T_E)}{\gamma T_E}$$

where: γ=proton gyromagnetic ratio, and $T_E$=echo time; and d) reconstructing a 3D magnetic susceptibility map, $\chi^{recon}(r)$, of the object by performing a 3D deconvolution on the magnetic field map, $b(r)$, according to:

$$b(r)=B_0\chi(r)*h_0(r)$$

and $$\chi^{recon}(r)=b(r)*^{-1}h_0(r)/B_0$$

where: r=(x,y,z) denotes 3D coordinates in space domain; the symbol * denotes a 3D convolution operator; the symbol *$^{-1}$ denotes a 3D deconvolution operator; and $h_0(r)$ is a standard convolution kernel that is a point magnetic dipole kernel, according to:

$$h_0(r) = \frac{1}{4\pi} \frac{3z^2 - |r|^2}{|r|^5}$$

wherein performing the 3D deconvolution comprises executing a 3D Total Variation (TV) regularized iterative convolution scheme, which comprises solving a TV-regularized unconstrained minimization problem, according to:

$$\chi^{recon}(r) = \min_{\chi \in BV} \|\chi(r)\|_{TV} + \frac{\lambda}{2}\|B_0\chi(r) * h_0(r) - b(r)\|_2^2$$

where: BV is a bounded variation function space, λ is a TV regularization parameter $\|\cdot\|_{TV}$ denotes a TV norm, and $\|\cdot\|_2^2$ denotes a $L^2$ norm; and wherein performing the 3D TV-regularized iterative convolution scheme comprises searching over all possible distributions χ∈BV to find an optimal χ-distribution, $\chi^{recon}$, which simultaneously minimizes both: a TV norm, and a data fidelity error measure; and further wherein a method for determining $\chi^{recon}(r)$ comprises solving the 3D minimization problem by using a split Bregman iteration algorithm, according to:

$$\min_{d,v,\chi} \|d(r)\|_{TV} + \frac{\lambda}{2}\|B_0 v - b\|_2^2 + \frac{\gamma_1}{2}\|d - \nabla \chi - a_1\|_2^2 + + \frac{\gamma_2}{2}\|v - h_0 * \chi - a_2\|_2^2$$

with $d = \nabla \chi$ and $v = h_0 * \chi$ and, furthermore, wherein using the split Bregman iteration algorithm comprises transforming the 3D minimization problem into a series of three iteration sub-problems, and then solving each sub-problem by performing a Bregman-distance-based iteration with respect to three interim variables {'d', 'v', 'χ'}; where: 'd' and 'v' are auxiliary variables, 'χ' is the magnetic susceptibility to be reconstructed, λ is the regularization parameter, and the parameters {'$\gamma_1$', '$\gamma_1$', '$a_1$', '$a_2$'} are introduced for efficient algorithm implementation and fast convergence.

2. The method of claim 1, further comprising solving the three sub-problems one-at-a-time with respect to one of the three interim variables {'d', 'v', or 'χ'}, while keeping the other two fixed, using the following algorithm:

Initialize χ=v=$a_2$=0,d=$a_1$=0, tol

Do

Minimization of χ-subproblem with (d,v) fixed;

Minimization of d-subproblem with (χ,v) fixed;

Minimization of v-subproblem with (χ,d) fixed;

Update $a_1$:=$a_1$+∇χ−d

Update $a_2$:=$a_2$+$h_0$*χ−v

While $\|\chi^{current}-\chi^{previous}\|_\infty$<tol

Output: $\chi^{recon}=\chi^{current}$.

3. The method of claim 2, wherein the χ-subproblem, with d and V fixed, is stated as:

$$\min_\chi \frac{\gamma_1}{2}\|d - \nabla \chi - a_1\|_2^2 + \frac{\gamma_2}{2}\|v - h_0 * \chi - a_2\|_2^2,$$

and, further, wherein the solution of χ is obtained in the Fourier domain by solving as follows:

$$\chi = IFT\left\{\frac{\frac{\gamma_2}{\gamma_1} H_0^* \cdot FT\{v - a_2\} - FT\{\nabla \cdot (d - a_1)\}}{\frac{\gamma_2}{\gamma_1} H_0^* \cdot H_0 + (2\pi|k|)^2}\right\}$$

wherein: FT represents a Fourier transform; IFT represents an inverse Fourier transform; $H_0$=FT{$h_0$}; $H_0$* represents the complex conjugate of $H_0$; and k=($k_x,k_y,k_z$) represents 3D coordinates in the Fourier domain.

4. The method of claim 2, wherein the d-subproblem, with v and χ fixed, is stated as:

$$\min_d \|d(r)\|_{TV} + \frac{\gamma_1}{2}\|d - \nabla \chi - a_1\|_2^2$$

and its solution is known in a closed form, according to:

$$d = \frac{\nabla \chi + a_1}{|\nabla \chi + a_1|} \max\{|\nabla \chi + a_1| - 1/\gamma_1, 0\}.$$

5. The method of claim 2, wherein the v-subproblem, with d and $\chi$ fixed, is stated as:

$$\min_v \frac{\lambda}{2} \|B_0 v - b\|_2^2 + \frac{\gamma_2}{2} \|v - h_0 * \chi - a_2\|_2^2$$

and its solution is known in a closed form, according to:

$$v = \frac{h_0 * \chi + a_2 + \frac{\lambda}{\gamma_2}\frac{b}{B_0}}{1 + \frac{\lambda}{\gamma_2}}.$$

6. The method of claim 1, comprising performing the method on a 3D isotropic MR phase image; wherein the 3D complex-valued T2*-weighted MR image is directly acquired by using an EVI (echo volume imaging) pulse sequence, or by stacking image slices acquired by using an EPI (echo planar imaging) pulse sequence; and further wherein the 3D complex-valued T2*-weighted MR image is directly acquired with MRI parameter settings comprising: isotropic voxels, zero oblique that produces axial slices perpendicular to $B_0$, zero inter-voxel gap that makes the slice spacing equal to the slice thickness, small voxel size that implements high spatial resolution, and small $T_E$ that implements fast snapshot capture.

7. The method of claim 1, further comprising designing and using a modified TV iteration filter, H(k), corresponding to 3D iteration kernel h(r) by a 3D Fourier transform, with which the TV regularization scheme produces a reconstructed susceptibility volume that is substantially equivalent to a new susceptibility volume resulting from spatially filtering a standard $h_0$-reconstructed susceptibility volume; wherein designing the modified TV iteration filter, H(k), comprises using the following algorithm:

a) letting $f(k)$ denote a 3D filter designed for post-reconstruction filtering, and then
b) designing the modified TV iteration filter, H(k), according to:

$H(k)=H_0(k)/f(k)$ where: $H_0(k)$ represents a standard magnetic dipole filter $H_0(k)=FT\{h_0(r)\}$, according to:

$$H_0(k_x, k_y, k_z) = \frac{1}{3} - \frac{k_z^2}{(k_x^2 + k_y^2 + k_z^2)}.$$

8. The method of claim 7, wherein the step of designing and using a modified TV-iteration filter comprises: modifying $H_0(k)$ by resetting the DC term $H_0(0,0,0)$ to a value in a typical range of [−1,−0.1] or [0.1, 1]; wherein the setting $H_0(0,0,0)=0$ is not allowed, and $H_0(0,0,0)=\frac{1}{3}$ for a standard $\chi$ reconstruction using a standard dipole filter $H_0(k)$.

9. The method of claim 8, further comprising:
a) using a plurality of TV iteration filters resulting from using different DC-term values;
b) performing parallel TV-iteration susceptibility reconstructions; and then
c) averaging the multiple susceptibility reconstructions together, thereby achieving noise reduction.

10. The method of claim 7, wherein the step of designing and using a modified TV-iteration filter comprises: performing 3D directional filtering by multiplying the 3D standard filter $H_0(k_x,k_y,k_z)$ along $k_x$-, $k_y$-, $k_z$- axis, or along the diagonal lines of the 3D k-space, by a 1D filter comprising high-pass, low-pass, and band-pass filtering capability.

11. The method of claim 7, wherein the step of designing and using a modified TV-iteration filter comprises: performing 3D volumetric filtering by multiplying the 3D standard filter $H_0(k_x,k_y,k_z)$ by another 3D filter capable of low-pass, highpass, and bandpass filtering.

12. The method of claim 7, wherein the step of designing and using a modified TV-iteration filter comprises: using specific formulas for designing post-reconstruction processing filters with 3D lowpass filtering capacity, according to:

$f_{LP}(k)=c_1+c_2\times\cos(\pi k/k_{max})$ s.t. $\min\{f_{LP}(k)\}>0$ $f_{LP}(k)=0.6+0.4\times\cos(\pi k/k_{max})$ (case: $c_1=0.6$ and $c_2$ 0.4 with $k_{max}=\max\{|k|\}$
wherein the limiting condition for a lowpass filter is $\min\{f_{LP}(k)\}>0$, as required by the non-singularity of $1/f_{LP}(k)$; and furthermore where $c_1=0.6$ and $c_2=0.4$, provides the special case that produces $\min\{f_{LP}(k)\}=0.2$; and finally wherein the set of.

13. The method of claim 12, wherein the step of designing and using a modified TV-iteration filter comprises: using specific formulas for designing a post-reconstruction filter with 3D highpass filtering capacity, according to:

$f_{HP}(k)=\max(f_{LP})-f_{LP}(k)+c_0$ s.t. $\min\{f_{HP}(k)\}>0$ $f_{HP}(k)=\max(f_{LP})-f_{LP}(k)+0.2$ (case: $c_0=0.2$)

wherein, as required by $1/f_{HP}(k)$, the limiting condition of $\min\{f_{HP}(k)\}>0$; is imposed and $c_0=0.2$ provides the special case that $\min\{f_{HP}(k)\}=0.2$.

14. The method of claim 13, further comprising reshaping the designed filters, $f_{LP}(k)$ and $f_{HP}(k)$, by an $\alpha$-power law formula, according to:

$f_{LP}(k;\alpha)=[f_{LP}(k)]^\alpha$, $\alpha=\{\frac{1}{2},1,2,3\ldots\}$ $f_{HP}(k;\alpha)=[f_{HP}(k)]^\alpha$, $\alpha=\{\frac{1}{2},1,2,3\ldots\}$ wherein the filter shape in Fourier domain is dilated with $0\leq\alpha\leq1$, and shrunk with $\alpha>1$; and finally wherein the set of parameters of $\{c_0,c_1,c_2,\alpha\}$ are configured under a condition of $\min\{f_{LP}(k)\}>0$ and $\min\{f_{HP}(k)\}>0$, thereby avoiding the singularity of the reciprocal filter $1/f_{LP}(k)$ and $1/f_{HP}(k)$.

15. The method of claim 7, wherein the step of designing and using a modified TV-iteration filter comprises using specific formulas for designing post-reconstruction filters with 3D bandstop (BT) and bandpass (BP) filtering capacity, which are useful for high spatial resolution $\chi$ reconstruction, according to:

$$f_{BP}(k) = 1 - \exp\left(-\frac{|k|^2}{2\pi\sigma_1 k_{max}^2}\right) + \exp\left(-\frac{|k|^2}{2\pi\sigma_2 k_{max}^2}\right), \quad \sigma_1 > \sigma_2 \text{ (bandpass)}$$

$$f_{BT}(k) = \exp\left(-\frac{|k|^2}{2\pi\sigma_1 k_{max}^2}\right) - \exp\left(-\frac{|k|^2}{2\pi\sigma_2 k_{max}^2}\right), \quad \sigma_1 > \sigma_2 \text{ (bandstop)}$$

where $\sigma$ denotes a standard deviation of a Gaussian distribution.

16. The method of claim 7, wherein the step of designing and using a modified TV-iteration filter comprises: using a formula for calculating a modified TV-iteration filter by the reciprocal of the post-reconstruction filter, according to:

$$H(k) = \frac{H_0(k)}{f(k)} \quad \text{(modified filter)}$$

$$h(r) = IFT[H(k)] = h_0(r) * IFT(1/f(k)) \quad \text{(modified kernel)}$$

where IFT denotes inverse Fourier transform; and further wherein the function $f(k)$ comprises a post-reconstruction filter selected from the group consisting of: a DC term reset, a 3D directional filter, a 3D volumetric filter, a 3D lowpass filter, a 3D high pass filter, a lowpass or highpass filter reshaped by $\alpha$-power law formula, a 3D bandstop filter, and a 3D bandpass filter.

17. The method of claim 7, further comprising reducing the susceptibility reconstruction noise by averaging two different sets of reconstructed $\chi$ distributions (Set 1 and Set 2), wherein: Set 1 comprises post-processed reconstructed $\chi$ distributions generated by performing post construction filtering, and Set 2 comprises reconstructed $\chi$ distributions generated by performing TV-iteration filtering with a modified filter according to claim 8.

18. The method of claim 7, further comprising generating a low-noise reconstructed susceptibility map with suppressed sparse residual comeback noise, by:
   a) performing multiple TV iteration susceptibility reconstructions in parallel, which use the same T2*MRI phase image, but have variations in parameter settings of the modified TV iteration filter, $H(k)$; and then
   b) performing a multi-reconstruction average of the multiple parallel reconstructions from step a);
   thereby generating a low-noise reconstructed susceptibility map.

19. The method of claim 1, further comprising performing a MR magnitude-based self-calibration scheme for estimating one or more appropriate values of the TV regularization parameter, $\lambda$; wherein the scheme comprises the following steps, performed in the following order:
   a) extracting a 3D T2*MRI magnitude image, $A(x,y,z;T_E)$, from the 3D complex-valued MR image;
   b) choosing an initial value of the TV regularization parameter, $\lambda$;
   c) generating the reconstructed magnetic susceptibility map, $\lambda^{recon}$;
   d) generating positive-valued version, $|\chi^{recon}|$; of the reconstructed susceptibility map, by taking the absolute value of the reconstructed susceptibility map, $\chi^{recon}$;
   e) comparing the positive-valued version, $|\chi^{recon}|$, of the reconstructed susceptibility map to the 3D T2*MRI magnitude image, $A(x,y,z;T_E)$;
   f) setting $\lambda=\lambda^{optimum}$ if the comparison shows that the two different maps are optimally similar; followed by performing regular TV iterations until convergence is reached; or
   g) adjusting the TV regularization parameter, $\lambda$, to a different value, if the comparison shows that the two different maps are not sufficiently similar; and then
   h) iteratively repeating steps c) through g), using the adjusted value of $\lambda$ from step g), until an optimal similarity is reached.

20. The method of claim 1, wherein the TV regularization parameter, $\lambda$, has a value in the range of 30 to 500, for millimeter resolution images.

21. The method of claim 1, further comprising reconstructing a 3D magnetic susceptibility map, $\chi^{recon}(r,t_0)$, of the object at a snapshot in time, $t_0$, by performing the CIMRI tomographic procedure on a 3D MR phase image extracted at $t=t_0$ from a 4D MR phase dataset, $P(x,y,z,t)$, which was created during a functional MRI (fMRI) session;
   wherein the object comprises a brain cortex; and
   wherein the method further comprises using a susceptibility timecourse synchrony criterion for generating a meaningful 4D susceptibility reconstruction, which is implemented by reproducing a susceptibility timecourse at an active site within the brain such that the susceptibility timecourse at an active site correlates highly with a known external stimulus timecourse, where the maximal correlation can be reached by a lag time as determined by the latent time of hemodynamic response; and
   wherein the method additionally comprises determining the active site's location from a 4D MR magnitude dataset;
   wherein the active site's location corresponds to a region of maximal temporal correlation between a MR magnitude timecourse and the known external stimulus timecourse.

22. The method of claim 21, further comprising replacing the 3D T2*MRI phase image, $P(x,y,z;T_E)$ with a T2'-effect phase image, $P_{T'_2}(x, y, z; T_E)$ by a) acquiring a complex-valued T2*-weighted GE MR image (T2* GE image) of an object, where the T2* GE image is made by a MRI scanner using gradient-echo (GE) pulse sequence and a specified echo time, $T_E$; wherein the T2* GE image includes contributions from both a non-random static inhomogeneous component (T2'-effect) and a random spin-spin interaction component (T2 effect);
   b) acquiring a complex-valued T2*-weighted SE MR image (T2* SE image) of the same object, where the T2* SE image is made by a MRI scanner using spin-echo (SE) pulse sequence and the same echo time ($T_E$) as is specified in step a) for making the T2* GE image; wherein the T2* SE image consists only of the random T2 effect component, with the static inhomogeneous component removed by a refocusing operation of the T2* SE pulse sequence;
   c) generating a complex-valued T2'-effect MR image ($C_{T'_2}$) by performing a complex division between the complex-valued T2*-weighted GE MR image, $C_{GE}(x,y,z;T_E)$, and the complex-valued T2*-weighted SE MR image, $C_{SE}(x,y,z;T_E)$, according to:

$$C_{T'_2}(x,y,z,T_E) = C_{GE}(x,y,z;T_E)/C_{SE}(x,y,z;T_E)$$

d) calculating a T2'-effect phase image, $P_{T'_2}(x, y, z;T_E)$, from the complex-valued T2'-effect MR image, $C_{T'_2}(x, y,z;T_E)$, according to:

$$P_{T'_2}(x,y,z;T_E) = \angle C_{T'_2}(x,y,z;T_E) = \angle C_{GE}(x,y,z;T_E) - \angle C_{SE}(x,y,z;T_E)$$

23. The method of claim 21, further comprising, for linear statistical postprocessing, first calculating a phase-based statistical brain activation map, denoted by $P^{map}(x,y,z)$; and then reconstructing a susceptibility-based brain activation map, $\chi^{map}(x,y,z)$, by performing the CIMRI procedure only once.

24. The method of claim 21, further comprising, for non-linear statistical postprocessing, first reconstructing a 4D magnetic susceptibility dataset, $\chi^{recon}(x,y,z,t)$, by looping the CIMRI procedure on the 4D MR phase dataset, $P(x,y,z,t)$, for each time point, t, within a session; and then rendering statistical postprocessing on the reconstructed 4D susceptibility dataset, $\chi^{recon}(x,y,z,t)$, to produce a $\chi$-based brain activation map, $\chi^{map}(x,y,z)$.

25. The method of claim 1, wherein using the CIMRI tomographic procedure does not involve using matrix algebra or Tikhonov regularization matrix inverse methods; and furthermore wherein the CIMRI tomographic procedure manipulates 3D matrix data in an elementwise manner in the Fourier domain, without involving any matrix-matrix or vector-matrix multiplication rules; and without changing the 3D array format.

26. A method of reconstructing a 4D magnetic susceptibility dataset, $\chi^{recon}(x,y,z,t)$, of an internal dynamic magnetic susceptibility distribution of an object, by repeatedly using a Computed Inverse Magnetic Resonance Imaging (CIMRI) tomographic procedure for a 3D magnetic susceptibility reconstruction at each snapshot time, comprising:

a) acquiring a time-dependent, sequential series of 3D complex-valued MR images, where the images were created using a MRI scanning machine performing multiple T2*-weighted MRI scans on a object during a ƒMRI session;

b) extracting and assembling a 4D T2*MRI phase image dataset, $P(x,y,z,t)$, from the sequential series of 3D complex-valued MR images;

c) calculating a 3D magnetic field map, $b(x,y,z,t')$, at a specific time=t', of the z-component ($B_z$) of a susceptibility-induced inhomogeneous magnetic field created by magnetizing the object in a main field, $B_0$, from the 4D T2*MRI phase image dataset, $P(x,y,z,t)$, according to, under phase-unwrapped conditions:

$$b(x, y, z, t') = \frac{P(x, y, z, t')}{\gamma T_E}$$

where: $\gamma$=proton gyromagnetic ratio, and $T_E$=echo time; then d) reconstructing a 3D magnetic susceptibility map, $\chi^{recon}(r, t')$, at the same specific time=t'; by performing a 3D deconvolution on the 3D magnetic field map, $b(r,t')$, according to:

$$b(r,t') = B_0 \chi(r,t') * h_0(r)$$

and $$\chi^{recon}(r,t') = b(r,t') *^{-1} h_0(r)/B_0$$

where: r=(x,y,z) denotes 3D coordinates in space domain; the symbol * denotes a 3D convolution operator; the symbol $*^{-1}$ denotes a 3D deconvolution operator; and $h_0(r)$ is a standard convolution kernel that is a point magnetic dipole kernel, according to:

$$h_0(r) = \frac{1}{4\pi} \frac{3z^2 - |r|^2}{|r|^5}$$

e) wherein performing the 3D deconvolution in step d) comprises executing a 3D Total Variation (TV) regularized iterative convolution scheme, which comprises solving a TV regularized, unconstrained minimization problem, according to:

$$\chi^{recon}(r) = \min_{\chi \in BV} \|\chi(r)\|_{TV} + \frac{\lambda}{2} \|B_0 \chi(r) * h_0(r) - b(r)\|_2^2$$

where: BV is a bounded variation function space, $\lambda$ is a TV regularization parameter, $\|\cdot\|_{TV}$ denotes a TV norm, and $\|\cdot\|_2^2$ denotes a $L^2$ norm; and further wherein performing the 3D TV regularization scheme comprises searching over all possible distributions $\chi \in BV$ to find an optimal $\chi$ distribution, $\chi^{recon}$, which simultaneously minimizes both: a TV norm, and a data fidelity error measure; and then f) repeating steps c) through e), for a new time: $t'_{new} = t'_{old} + \Delta t$, and then repeating this cycle until the entire ƒMRI session has been reconstructed, where $\Delta t$ is a time interval between two successive snapshots; then g) assembling all of the reconstructed 3D magnetic susceptibility maps from step f) for all time points t'∈t, which cover part or all of an entire ƒMRI session, into a single 4D magnetic susceptibility dataset, $\chi^{recon}(r, t)$; then h) generating one or more magnetic susceptibility timecourses, $\chi(x', y', z', t')$, at one or more specific locations, $(x', y', z')$, of active voxels in the brain that belong to a neighborhood of a neuroactive site, $(x^{act}, y^{act}, z^{act})$; wherein the neuroactive site is found by computing a local maximal temporal correlation, as expressed by:

$$(x^{act}, y^{act}, z^{act}) = \max_{(x,y,z) \in FOV} \{|A(x, y, z, t) \otimes_t \text{task}(t)|\}$$

where: $A(x,y,z,t)$ is a 4D MR magnitude dataset; "task(t)" represents a time-dependent external stimulus; and the symbol $\otimes_t$ denotes performing a temporal correlation;

i) performing a temporal correlation between task(t) and the one or more magnetic susceptibility timecourses, $\chi(x', y', z', t)$; then j) applying a criterion for timecourse synchrony to results of step i), wherein the criterion means that an optimally reconstructed susceptibility timecourse correlates highly with the task(t); and thereby k) obtaining an optimal 4D magnetic susceptibility dataset, $\chi^{recon}(x,y,z,t)$, by performing the temporal correlation and maxima determination, according to:

$$\chi^{recon}(x, y, z, t) = \max_{(x',y',z') \in N(x^{act}, y^{act}, z^{act})} \{|\chi^*(x', y', z', t) \otimes_t \text{task}(t)|\}$$

where $\chi^*(x,y,z,t)$ is a candidate of reconstructed 4D susceptibility datasets during 4D reconstruction optimization, created when a TV regularization parameter, $\lambda$, is varied according to a susceptibility timecourse synchrony criterion; and wherein $\chi^{recon}(x,y,z,t)$ is the optimal 4D magnetic susceptibility dataset obtained when the temporal correlation between the candidate dataset $\chi^*(x,y,z,t)$ and task(t) reaches a maximum.

27. The method of claim 26, further comprising adjusting the TV regularization parameter, $\lambda$, and then repeating steps d) through j), using the adjusted parameter $\lambda$; and furthermore continuing these $\lambda$-adjustment steps until the 4D susceptibility source reconstruction procedure produces a maximum, highest-as possible temporal correlation between a susceptibility timecourse at an activation voxel and the external stimuli, task(t).

* * * * *

UNITED STATES PATENT AND TRADEMARK OFFICE
CERTIFICATE OF CORRECTION

PATENT NO. : 8,886,283 B1  
APPLICATION NO. : 13/526210  
DATED : November 11, 2014  
INVENTOR(S) : Zikuan Chen and Vince D. Calhoun Page 1 of 1

It is certified that error appears in the above-identified patent and that said Letters Patent is hereby corrected as shown below:

In the Claims

Column 50, line 29, Claim 12 "; and finally wherein the" should be deleted

Column 50, line 30, Claim 12 "set of" should be deleted

Column 51, line 23, Claim 17 "construction" should be --reconstruction--

Column 53, line 27, Claim 26 "according" should be deleted

Column 53, line 28, Claim 26 "to ," should be deleted

Column 54, line 63, Claim 27 "as possible" should be --as-possible--

Signed and Sealed this  
Twenty-ninth Day of September, 2015

Michelle K. Lee  
*Director of the United States Patent and Trademark Office*

UNITED STATES PATENT AND TRADEMARK OFFICE
CERTIFICATE OF CORRECTION

PATENT NO. : 8,886,283 B1
APPLICATION NO. : 13/526210
DATED : November 11, 2014
INVENTOR(S) : Chen et al.

It is certified that error appears in the above-identified patent and that said Letters Patent is hereby corrected as shown below:

Please delete Patent 8886283 in its entirety and insert Patent 8886283 in its entirety as shown on the attached pages Signed and Sealed this
Tenth Day of November, 2015

Michelle K. Lee
*Director of the United States Patent and Trademark Office*

(12) United States Patent
Chen et al.

(10) Patent No.: US 8,886,283 B1
(45) Date of Patent: Nov. 11, 2014

(54) 3D AND 4D MAGNETIC SUSCEPTIBILITY TOMOGRAPHY BASED ON COMPLEX MR IMAGES

(75) Inventors: Zikuan Chen, Albuquerque, NM (US); Vince D. Calhoun, Albuquerque, NM (US)

(73) Assignee: STC.UNM, Albuquerque, NM (US)

(*) Notice: Subject to any disclaimer, the term of this patent is extended or adjusted under 35 U.S.C. 154(b) by 0 days.

(21) Appl. No.: 13/526,210

(22) Filed: Jun. 18, 2012

Related U.S. Application Data

(60) Provisional application No. 61/499,459, filed on Jun. 21, 2011.

(51) Int. Cl.
*A61B 5/055* (2006.01)
*G06F 12/08* (2006.01)

(52) U.S. Cl.
CPC ............................. *G06F 12/08* (2013.01)
USPC .......................................... 600/410; 382/128

(58) Field of Classification Search
None
See application file for complete search history.

(56) References Cited

U.S. PATENT DOCUMENTS

| | | | |
|---|---|---|---|
| 4,896,113 A * | 1/1990 | Pelc | 324/309 |
| 5,073,858 A | 12/1991 | Mills | |
| 5,233,992 A | 8/1993 | Holt | |
| 5,560,360 A | 10/1996 | Filler | |
| 6,076,004 A | 6/2000 | Kanayama | |
| 6,208,884 B1 | 3/2001 | Kumar | |
| 6,477,398 B1 | 11/2002 | Mills | |
| 6,603,989 B1 | 8/2003 | Yablonskiy | |
| 6,658,280 B1 | 12/2003 | Haacke | |
| 7,154,269 B1 | 12/2006 | Haacke | |
| 7,298,143 B2 | 11/2007 | Jaermann | |
| 7,382,129 B2 | 6/2008 | Mills | |
| 7,545,966 B2 * | 6/2009 | Lewin et al. | 382/128 |
| 7,642,512 B2 | 1/2010 | Watarai | |
| 7,782,051 B2 | 8/2010 | Haacke | |
| 7,800,367 B2 | 9/2010 | Bhardwaj | |
| 8,054,075 B2 | 11/2011 | Stuber | |

(Continued)

OTHER PUBLICATIONS

Chen, Z. and V. Calhoun, Computed inverse resonance imaging for magnetic susceptibility map reconstruction. Journal of computer assisted tomography, 2012. 36(2): p. 265-74.

(Continued)

*Primary Examiner* — Long V. Le
*Assistant Examiner* — Kevin Pontius
(74) *Attorney, Agent, or Firm* — Valauskas Corder LLC

(57) ABSTRACT

Magnetic susceptibility is the physical property for T2*-weighted magnetic resonance imaging (T2*MRI). The invention relates to methods for reconstructing an internal distribution (3D map) of magnetic susceptibility values, $\chi$ (x,y,z), of an object, from 3D T2*MRI phase images, by using Computed Inverse Magnetic Resonance Imaging (CIMRI) tomography. The CIMRI technique solves the inverse problem of the 3D convolution by executing a 3D Total Variation (TV) regularized iterative convolution scheme, using a split Bregman iteration algorithm. The reconstruction of $\chi$ (x,y,z) can be designed for low-pass, band-pass, and high-pass features by using a convolution kernel that is modified from the standard dipole kernel. Multiple reconstructions can be implemented in parallel, and averaging the reconstructions can suppress noise. 4D dynamic magnetic susceptibility tomography can be implemented by reconstructing a 3D susceptibility volume from a 3D phase volume by performing 3D CIMRI magnetic susceptibility tomography at each snapshot time.

27 Claims, 42 Drawing Sheets

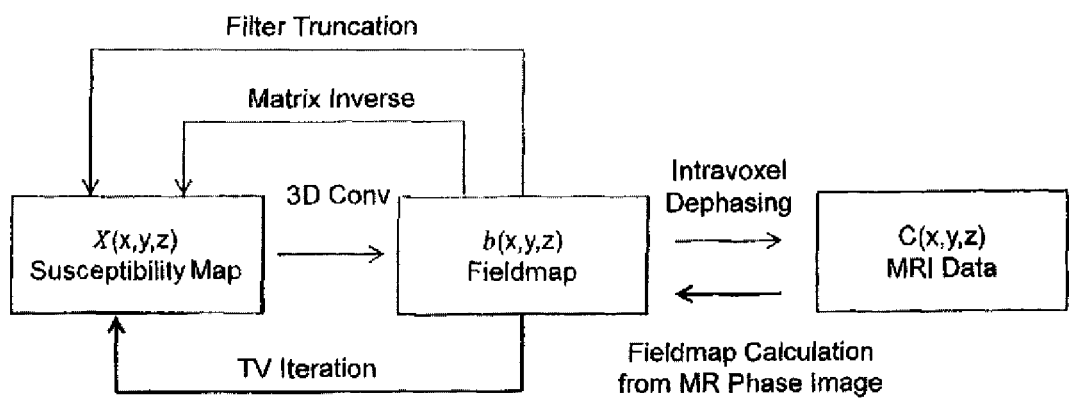

(56) References Cited

U.S. PATENT DOCUMENTS

| | | | |
|---|---|---|---|
| 8,422,756 B2 * | 4/2013 | Haacke et al. | 382/131 |
| 2003/0212322 A1 | 11/2003 | Haacke | |
| 2006/0106300 A1 | 5/2006 | Seppenwoolde | |
| 2010/0002926 A1 | 1/2010 | Dahnke | |
| 2010/0142785 A1 | 6/2010 | Dahnke | |

OTHER PUBLICATIONS

Chen, Z. and V. Calhoun. Volumetric BOLD fMRI simulation: from neurovascular coupling to multivoxel imaging. BMC medical imaging, 2012. 12(1): p. 1-8.

Chen, Z. and V.D. Calhoun, Two pitfalls of BOLD fMRI magnitude-based neuroimage analysis: non-negativity and edge effect. Journal of neuroscience methods, 2011. 199(2): p. 363-9.

Chen, Z., A. Caprihan, and V.D. Calhoun. BOLD susceptibility map reconstruction from fMRI by 3D total variation regularization. In International society for magnetic resonance in medicine 2011. Montreal, Canada: ISMRM.

Chen, Z. and V. Calhoun, A computational multiresolution BOLD fMRI model. IEEE Trans. BioMed. Eng, 2011. 58(10): p. 2995-9.

Chen, Z. and V. Calhoun. Volumetric computational model for neurovascular coupling and BOLD fMRI. In Human Brain Mapping. 2011. Quebec, CA: OHBM.

Chavhan, G.B., et al., Principles, techniques, and applications of T2*-based MR imaging and its special applications. Radiographics : a review publication of the Radiological Society of North America, Inc, 2009. 29(5): p. 1433-49.

Walsh, A.J. and A.H. Wilman, Susceptibility phase imaging with comparison to R2 mapping of iron-rich deep grey matter. Neuroimage, 2011. 57(2): p. 452-61.

Howseman, A.M. and R.W. Bowtell, Functional magnetic resonance imaging: imaging techniques and contrast mechanisms. Philos Trans R Soc Lond B Biol Sci. 1999. 354(1387): p. 1179-94.

Norris, D.G., Principles of magnetic resonance assessment of brain function. Journal of magnetic resonance imaging : JMRI, 2006. 23(6): p. 794-807.

Ogawa, S., et al., Functional brain mapping by blood oxygenation level-dependent contrast magnetic resonance imaging. A comparison of signal characteristics with a biophysical model. Biophys J, 1993. 64(3): p. 803-12.

Boxerman, J.L., et al., MR contrast due to intravascular magnetic susceptibility perturbations. Magn Reson Med. 1995 34(4): p. 555-66.

Haacke, E.M., et al., Susceptibility mapping as a means to visualize veins and quantify oxygen saturation. Journal of magnetic resonance imaging : JMRI, 2010. 32(3): p. 663-76.

Li, W., B. Wu, and C. Liu, Quantitative susceptibility mapping of human brain reflects spatial variation in tissue composition. Neuroimage, 2011. 55(4): p. 1645-56.

Schweser, F., et al., Quantitative imaging of intrinsic magnetic tissue properties using MRI signal phase: an approach to in vivo brain iron metabolism? Neuroimage. 2011. 54(4): p. 2789-807.

Shmueli, K., et al., Magnetic susceptibility mapping of brain tissue in vivo using MRI phase data. Magnetic resonance in medicine : official journal of the Society of Magnetic Resonance in Medicine / Society of Magnetic Resonance in Medicine. 2009. 62(6): p. 1510-22.

Wharton, S., A. Schafer, and R. Bowtell, Susceptibility mapping in the human brain using threshold-based k-space division. Magn Reson Med, 2010. 63(5): p. 1292-304.

de Rochefort, L., et al., Quantitative susceptibility map reconstruction from MR phase data using bayesian regularization: validation and application to brain imaging. Magn Reson Med, 2010. 63(1): p. 194-206.

Kressler, B., et al., Nonlinear regularization for per voxel estimation of magnetic susceptibility distributions from MRI field maps. IEEE Trans Med Imaging, 2010. 29(2): p. 273-81.

Li, L., Magnetic susceptibility quantification for arbitrarily shaped objects in inhomogeneous fields. Magn Reson Med, 2001. 46(5): p. 907-16.

Li, L. and J.S. Leigh, Quantifying arbitrary magnetic susceptibility distributions with MR. Magn Reson Med, 2004. 51(5): p. 1077-82.

Sepulveda, N.G., I.M. Thomas, and J.P. Wikswo, Magnetic Susceptibility Tomography For Three-dimensional Imaging of Diamagnetic and Paramagnetic Objects. IEEE Trans. Magnetics, 1994. 30(6): p. 5062-7.

Liu, T., et al., Calculation of susceptibility through multiple orientation sampling (COSMOS): a method for conditioning the inverse problem from measured magnetic field map to susceptibility source image in MRI. Magn Reson Med, 2009. 61(1): p. 196-204.

Yao, B., et al., Susceptibility contrast in high field MRI of human brain as a function of tissue iron content. Neuroimage, 2009. 44(4): p. 1259-66.

Spees, W.M., et al., Water proton MR properties of human blood at 1.5 Tesla: magnetic susceptibility, T(1), T(2), T*(2), and non-Lorentzian signal behavior. Magn Reson Med, 2001. 45(4): p. 533-42.

Cai, J.F., S. Osher, and Z. Shen, split Bregman Methods and Frame Based Image Restoration, in UCLA CAM Report2009.

Combettes, P.L. and J.C. Pesquet, Image restoration subject to a total variation constraint. IEEE transactions on image processing : a publication of the IEEE Signal Processing Society, 2004. 13(9): p. 1213-22.

Goldstein, T. and S. Osher, The Slit Bregman Method for L1 Regularized Problems,. UCLA CAM Report, 2008.

Osher, S., et al., An iterative regularization method for total variation-based image restoration. Multiscale Model. Simul., 2005. 4(2): p. 460-89.

Holst, B., et al., T2' imaging indicates decreased tissue metabolism in frontal white matter of MS patients. Multiple sclerosis, 2009. 15(6): p. 701-7.

Menon, "Postacquisition Suppression of Large-Vessel BOLD Signals in High-Resolution fMRI", Magnetic Resonance in Medicine 47:1-9 (2002), Canada.

Abe, "Magnetic Resonance Imaging of Iron in Parkinson's Disease", Current Medical Imaging Reviews, 2005, 1, 43-48, Bentham Science Publishers Ltd.

Peyre, "Chambolle's algorithm for the resolution of compressed sensing with TV regularization", http://www.ceremade.dauphine.fr/-peyre/cs-tv/, 2008.

de Rochefort, "Quantitative MR Susceptibility Mapping Using Piece-Wise constant regularized inversion of the magnetic field", Magnetic Resonance in Medicine 60:1003-1009 (2008), Canada.

de Rochefort, "Quantitative MR Susceptibility Map Reconstruction from MR Phase Data Using Bayesian Regularization: Validation and Application to Brain Imaging", Magnetic Resonance in Medicine 63:194-206 (2010), Canada.

Guerquin-Kern, "A Fast Wavelet-Based Reconstruction Method for Magnetic Resonance Imaging", IEEE Transactions on Medical Imaging, vol. 30, No. 9, Sep. 2011.

Haller, "Pitfalls in fMRI", Eur Radiol (2009) 19: 2689-27-6, Published online Jun. 6, 2009, European Society of Radiology.

Holst, "T2' imaging indicates decreased tissue metabolism in frontal white matter of MS patients", Multiple Sclerosis 2009 15:701-707; DOI: 10.1177/1352458509103713., http://msj.sagepub.com.

Liu, "Morphology Enabled Dipole Inversion (MEDI) from a Single-Angle Acquisition: Comparison with COSMOS in Human Brain Imaging", Magnetic Resonance in Medicine 66:777-783 (2011), Canada. Published online Apr. 4, 2011 in Wiley Online Library (wileyonlinelibrary.com).

Liu, "A novel background field removal method for MRI using projection onto dipole fields (PDF)", NMR in Biomedicine, (wileyonlinelibrary.com) DOI:10.1002/nbm.1670, Published online in Wiley Online Library: Mar. 8, 2011.

Ropele, "MRI Assessment of Iron Deposition in Multiple Sclerosis", Journal of Magnetic Resonance Imaging 34:13-21 (2011), DOI 10.1002/jmri.22590. Received Nov. 15, 2010; Accepted Mar. 7, 2011.

Schweser, "Differentiation between diamagnetic and paramagnetic cerebral lesions based on magnetic susceptibility mapping", Med. Phys. 37,, 10 ..., Oct. 2010; 2010 Am. Assoc. Phys. Med. 5165-5178; Medical Physics, vol. 37, No. 10, Oct. 2010, published Sep. 7, 2010; DOI: 10.1118/1.3481505.

(56) References Cited

OTHER PUBLICATIONS

Yan, "Gradient Distortion Correction for Low Frequency Current Density Imaging", Proceedings of the 28th IEEE EMBS Annual International Conference New York City, USA, Aug. 30-Sep. 3, 2006; pp. 260-263; 1-4244-0033-3/06/IEEE. WeD02.1.

Vogel, "Fast, Robust Total Variation-Based Reconstruction of Noisy, Blurred Images", IEEE Transactions on Image Processing, vol. 7, No. 6, Jun. 1998, pp. 813-824 Publisher Item Identifier S 1057-7149(98)04002-0.

Wu, "Whole Brain Susceptibility Mapping Using Compressed Sensing", Magnetic Resonance in Medicine 000:000-000 (2011), pp. 1-11. Canada; Received Oct. 5, 2010; revised Apr. 14, 2011; accepted Apr. 19, 2011. DOI 10.1002/mrm.23000; Published online in Wiley Online Library (wileyonlinelibrary.com).

Chen, Z., Z. Chen, and V.D. Calhoun. Voxel magnetic field disturbance from remote vasculature in BOLD fMRI. In SPIE Medical Imaging. 79613x. Orlando, FL: SPIE, 2011.

\* cited by examiner (a) Susceptibility Map (b) MR Magnitude (a) Pulses (b) GE and SE Signals (b) Average

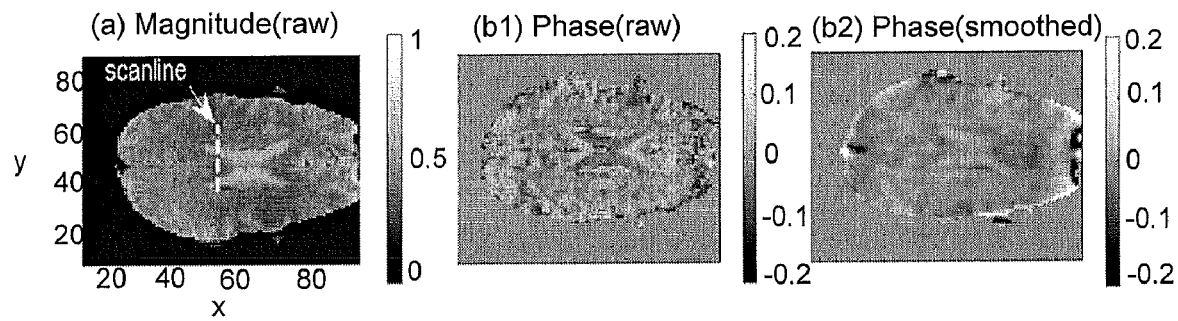
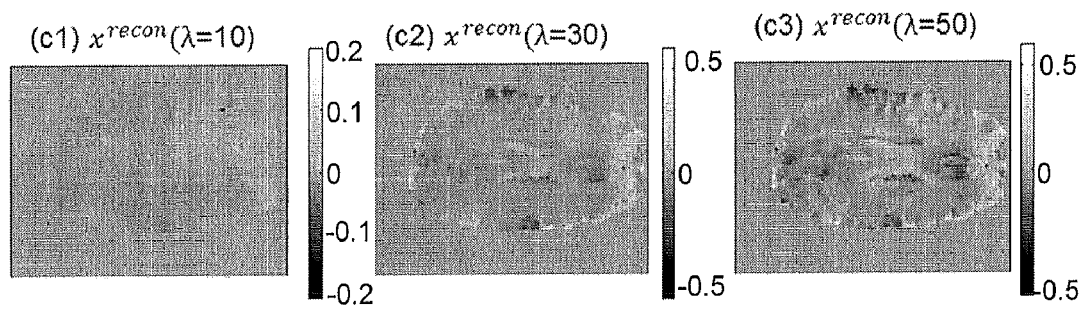
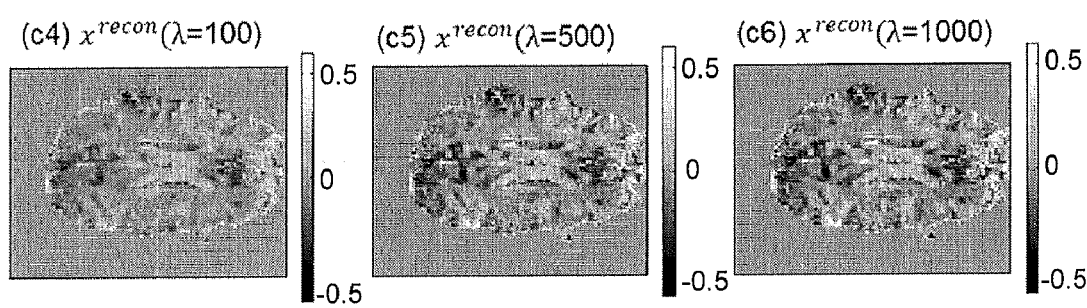
FIG. 32A  FIG. 32B  FIG. 32C
FIG. 32D  FIG. 32E  FIG. 32F
FIG. 32G  FIG. 32H  FIG. 32I

3D AND 4D MAGNETIC SUSCEPTIBILITY TOMOGRAPHY BASED ON COMPLEX MR IMAGES

FEDERALLY SPONSORED RESEARCH

The United States Government has rights in this invention pursuant to Department of Energy Contract No. DE-FG02-08ER64581 with the Mind Research Network; and pursuant to the National Institutes of Health Contract Nos. R01 EB005846 and R01 EB006841 with the University of New Mexico, Electrical and Computer Engineering Department.

CROSS-REFERENCE TO RELATED APPLICATIONS

This application claims the benefit of U.S. Provisional Patent Application Ser. No. 61/499,459, filed Jun. 21, 2011, which is incorporated herein by reference.

BACKGROUND OF THE INVENTION

1. Technical Field

The technical field of the invention is magnetic resonance imaging (MRI) in general, and more specifically: methods and algorithms for generating internal magnetic susceptibility distributions from complex-valued MR images (i.e., MR images containing complex numbers with magnitude and phase parts).

2. Introduction

In magnetic susceptibility tomography, the internal distribution of magnetic susceptibility of an object is determined by applying various configurations of magnetic fields and measuring how the object perturbs them. Measurement of the perturbed magnetic fields can be done using superconducting quantum interference devices (SQUID) called susceptometers or biosusceptometers. However, the present invention is directed to innovative computational techniques and software algorithms that analyze the data generated by magnetic resonance imaging (MRI) scanning machines (MRI scanners). In particular, the present invention primarily uses T2*-weighted images that are generated by MRI scanners using gradient-echo (GE) imaging sequences (also referred to as "T2*MRI").

T2*MRI refers to the detection of transverse magnetization dephasing signal that is caused by a combination of spin-spin relaxation (T2 effect) and magnetic field inhomogeneity (T2' effect) [1, 2]. As a noninvasive 3D imaging modality, the T2*MRI technology has been accepted for both structural iron deposit measurement in tissues and organs [3-9] and for brain functional neuroimaging [1, 10-13]. For general tissue structural imaging, the susceptibility source (denoted by $\chi$) is mainly attributed to the nonheme iron deposit therein; and for brain functional imaging, the total $\chi$ source consists of a neuron-induced heme iron perturbation (superimposed on the static structural susceptibility background), as described by the blood oxygenation level dependent (BOLD) physiological model [12, 14, 15].

In electromagnetism, it is understood that, when an entity of inhomogeneous susceptibility distribution is introduced into a main magnetic field, it will be magnetized through the material and magnetic field interaction mechanism [16]) and disturbs the field distribution by superimposing an inhomogeneous fieldmap on the main field. With the T2*MRI technology, that is a frequency spatial encoding and decoding scheme for multivoxel image acquisition through the applications of field gradients, we obtain a complex-valued MR image (consisting of a pair of magnitude and phase images), of which the MR magnitude is conventionally considered as an MR image of the $\chi$ source.

Magnetic susceptibility is the physical property controlling (driving) the T2*-weighted magnetic resonance imaging modality (T2*MRI). For medical imaging, T2*MRI is used to detect the magnetic susceptibility expression of a tissue or an organ state for quantitative iron measurement. It has been found that the output image of T2*MRI is not an exact representation of the susceptibility source (due to local average and nonlinearity associated with T2*MRI), thus not directly useful for iron measurement.

Based on MRI physics, we clarify that neither the MR magnitude image, nor the MR phase image, is an exact tomographic reproduction of the susceptibility source or the fieldmap [17-19]. In particular, the MR magnitude image is a nonlinear transformation of the $\chi$ source, which may suffer from non-negativity and edge-effect pitfalls [19]; whereas the MR phase image is linearly related to the fieldmap in small angle regime(a linear phase approximation condition)[17, 19]. Due to the 3D convolution transformation during susceptibility magnetization [19, 20], it is not surprising to notice that the fieldmap (or phase image) appears morphologically different from the $\chi$ source: textural, noisy, and blurry. Therefore, in this invention, we strive to reconstruct the intact $\chi$ source from MR phase image.

The T2*MRI technology imposes a series of spatial transformations to the susceptibility source. Toward representing the entity in its intact $\chi$ distribution (by removing the transformations exerted by T2*MRI detection), the $\chi$ tomography is of paramount significance [19, 21-26].

The mainstay of existent publications on magnetic susceptibility mapping can be classified into three main kinds of solvers [17]. The first kind of solver is based on matrix inverse (for the exploitation of the well-established Tikhonov regularization techniques), which however is confronted with large matrix problem (dimensionality curse) because the 3D convolution imaging formula should be converted to 2D matrix-vector-multiplication format as required by matrix algebra [17, 27-31]. Limited to very small volume reconstruction, the report in [31] only deals with 4×4×4 multivoxel image, which is too small to be meaningful. In comparison, our susceptibility tomography technique in this report can easily accommodate a very large volume such as 512×512×512.

The second kind of solver is based on the 3D inverse filtering in 3D Fourier space [22, 25, 26, 32, 33]. This strategy suffers from stripe artifact and image energy shift problem. To deal with the pole singularity (infinites) on the 3D inverse filter, a truncation regularization is always used; hence called "filter truncation". In presence of noise, the filter truncation solver will produce stripe or clutter artifacts. Furthermore, the energy of the filtered image will not be conserved due to the truncation on the inverse filter.

The third kind of solver is a 3D TV-regularized deconvolution method, which is used by preferred embodiments of the present invention to reconstruct a 3D $\chi$ source distribution from a 3D MR phase image[17, 19], as will be described later.

ACRONYMS AND NOTATIONS

3D: three dimension: (x,y,z)
4D: four dimension: (x,y,z,t)
MR: Magnetic Resonance
MRI: Magnetic Resonance Imaging
T2*MRI: T2*-weighted MRI
CIMRI: Computed Inverse MRI ƒMRI: functional MRI
FID: Free Induction Decay
$B_0$: main magnetic field
TE, $T_E$: Echo Time for both spin echo and gradient echo signals
FOV: Field Of View
NAB: NeuroActive Blob
T1 relaxation: Longitudinal magnetization recovery process due to spin-lattice interaction.
T2 relaxation (T2 effect): Transverse magnetization dephasing process due to random spin-spin interaction. (non-refocusable).
T2' relaxation (T2' relaxation): Transverse magnetization dephasing process due to static field inhomogeneity. (refocusable).
T2* relaxation: Total transverse magnetization dephasing process, consisting of T2 effect, T2' effect, and diffusion effect. (partially refocusable).
T2' image: A complex image that is calculated by a complex division of a pair of T2* gradient-echo and spin-echo complex images.
T2' phase image: the phase part of T2'-effect complex image
T2' fieldmap: the fieldmap calculated from a T2'-effect phase image
SE: Spin Echo
GE: Gradient Echo.
EPI: Echo Planar Imaging
EVI: Echo Volume Imaging
BOLD: Blood Oxygenation Level Dependent
TV: Total Variation
DC: Direct Current (electrical engineering term)
FT: Fourier Transformation
IFT: Inverse Fourier Transformation
HP: HighPass
LP: Lowpass
BP: BandPass
BT: BandStop
trunc: truncation
struc: structural
conv: convolution
recon: reconstruction
$r=(x,y,z)$: 3D coordinates in space domain
$k=(k_x,k_y,k_z)$: 3D coordinates in Fourier domain (k-space)
$k_{max}=\max\{|k|\}$: the maximum modulus of k.
$\chi$ tomography: a technique to reproduce an internal magnetic $\chi$ distribution from external measurement data.
$\chi$ reconstruction: reconstructing a magnetic $\chi$ distribution from a MR phase image.
$\chi_0(r)$: $\chi$ reconstruction with magnetic dipole model ($\chi_0(k)$ in Fourier domain).
$\chi(r)$: $\chi$ source, or processed $\chi$, or $\chi$ reconstruction with modified kernel ($\chi(k)$ in Fourier domain).
$\Delta\chi(r)$: susceptibility perturbation in reference to the baseline.
$b(r)$: 3D fieldmap ($b(k)=FT[b(r)]$ in Fourier domain)
$h_0(r)$: point magnetic dipole field (standard 3D convolution kernel).
$H_0(k)\equiv FT[h_0(r)]$: standard $\chi$ reconstruction filter.
$f(k)$: filter for post-recon $\chi$ filtering (as used by $\chi(k)=\chi_0(k)\cdot f(k)$) in Fourier domain).
$H(k)$: modified deconvolution filter ($H(k)=H_0(k)/f(k)=FT[h(r)]$ in Fourier domain
$h(r)$: modified deconvolution kernel (as formed by $h(r)=h_0(r)*FT[1/f(k)]$)
$\epsilon(r)$ Gaussian additive noise ($\epsilon(k)$ in Fourier domain).
$\|\chi\|_{TV}$: TV norm of $\chi$.
$|C|$: taking absolute value of C (complex modulo operation)
$\angle C$: taking phase angle of a complex number C (complex argument operation)
$\lambda$: TV regularization parameter.
$\gamma_1, \gamma_2$: auxiliary parameters of TV iteration
$\Omega(x, y, z)$: voxel at $(x, y, z)$.
$|\Omega(x, y, z)|$: voxel size ($=d_0\times d_0\times d_0$) (MR image resolution)
$c, c_0, c_1, c_2$: constants.
$\epsilon_0$: a threshold for filter truncation ($0<\epsilon_0<<1$).

BRIEF SUMMARY OF THE INVENTION

The $\chi$ reconstruction methods of the present invention are based on our CIMRI model [17]. In this invention, we reconstruct the intact magnetic susceptibility source distribution by a computed inverse magnetic resonance imaging scheme (CIMRI) and use it for static tissue iron measurement and dynamic heme-iron perturbation depiction. In the sense of 3D tomographic susceptibility source reproduction from external T2*MRI observations, the CIMRI is used to implement magnetic susceptibility tomography.

The CIMRI-based 3D susceptibility tomography is implemented by two steps: Step 1: calculating the fieldmap from the MR phase image; Step 2: calculating the susceptibility distribution from the fieldmap (obtained at step 1) by a total-variation-regularized deconvolution method with an implementation of split Bregman iteration. For static brain structural imaging, CIMRI implements 3D magnetic susceptibility tomography; and for dynamic brain functional imaging, CIMRI implements 4D magnetic susceptibility tomography by reconstructing a susceptibility volume from a MR phase volume at each snapshot time.

Our CIMRI method for 3D susceptibility tomography is optimally performed on a volumetric MR image acquired with isotropic voxels and zero oblique angle (with axial slices perpendicular to $B_0$). The reconstructed $\chi$ source can be post-processed by lowpass, highpass, bandpass, and bandstop filtering to extract specific susceptibility features. We show that the post-reconstruction filtering ("post-recon filtering" can be equivalently achieved during TV iteration with a modified filter, termed as "TV-iteration filtering". With a MR phase volume, the "post-recon filtering" and the "TV-iteration filtering" can be implemented in parallel. The two results are averaged to reduce the noise. Since the TV iteration is insensitive to the regularization parameter values, we developed a noise reduction strategy by rendering parallel TV iteration reconstructions (using different parameter values) and then averaging the multiple reconstructions. The reconstructed 3D magnetic susceptibility map is interpreted as a snapshot capture of internal iron distribution.

For a BOLD ƒMRI study on a dynamic physiological process, which produces a 4D MR image dataset; from which we can implement 4D magnetic susceptibility tomography: reconstructing a 4D $\chi$ dataset by applying CIMRI to each snapshot volume. To make use of external stimulus paradigm (always available for BOLD ƒMRI study), we developed a criterion of susceptibility timecourse synchrony for the 4D susceptibility tomography: the reconstructed susceptibility timecourse at an active region should be synchronous with the stimulus timecourse. Upon the reconstruction of a dynamic 4D $\chi$ dataset, we developed a $\chi$-based BOLD activation depiction or neuroimaging, which is implemented with a conventional brain mapping and neuroimaging technique only by replacing the 4D MR magnitude dataset with our reconstructed 4D magnetic susceptibility dataset.

Concerning the fact that the static field inhomogeneity effect (T2' effect) can be refocused or canceled by spin-echo imaging, we invented a unique T2'-effect imaging scheme (shortly T2' imaging) to obtain a T2' complex image. With a T2' complex image, we calculate the T2' phase image and the T2' fieldmap. Supposing the random T2 and diffusion effects are largely repeatable at successive scans under the same circumstance, the $\chi$ reconstruction from a T2' fieldmap improves the $\chi$ tomography fidelity due to the removal of repeatable random T2 and diffusion effects.

In summary, we have developed a CIMRI model for 3D susceptibility tomography, with an implementation of 3D deconvolution by a 3D split Bregman TV-regularized iteration method. We further enhanced the 3D $\chi$ reconstruction by: 1) filtering the reconstructed susceptibility pattern by modifying the TV iteration convolution kernel; 2) performing parallel reconstruction and multi-reconstruction average for noise reduction; and 3) using T2' phase image to improve $\chi$ reconstruction fidelity. We clarify that the MR magnitude image is not a tomographic representation of the $\chi$ source; and that the magnetic susceptibility tomography can be implemented by CIMRI. Accordingly, the 3D magnetic susceptibility tomography can be used for tissue iron measurement. By repeating CIMRI for 3D $\chi$ tomography for each snapshot volume, we can implement 4D $\chi$ tomography for 4D BOLD fMRI study, in which using the 4D $\chi$-dataset provides a more direct and truthful brain functional mapping (or neuroimaging) than using the conventional 4D MR magnitude dataset.

BRIEF DESCRIPTION OF THE DRAWINGS

The accompanying drawings, which are incorporated in and form part of the specification, illustrate various examples of the present invention and, together with the detailed description, serve to explain the principles of the invention.

FIG. 1. The T2*MRI and CIMRI model. The T2*MRI model is decomposed into two modules: "Source Magnetism" (in the upper dotted box) and "MRI technology" (in the lower dotted box). The downward arrows indicate the forward procedure and the upward arrows indicate the backward procedure. The CIMRI model consists of two steps as diagramed in the circle.

FIG. 2. (a) A predefined 3D $\chi$ distribution (16 z-slices of Gaussian blob), and (b) the magnitude image of the T2*MRI simulation.

FIG. 3. The spatial correlations between the T2*MRI magnitude (denoted by A) and the predefined $\chi$ distribution for two intravoxel vasculatures (2-um-radius in (a1) (FIG. 3A) and 4-um-radius in (a2)) (FIG. 3B) and for three voxel sizes (see legend).

FIG. 4 (a) Visualization of the 3D convolution kernel $h_0(x,y,z)$ with three isosurfaces at isovalues of {0, 0.8, −0.8}; (b) a 2D quadruple pattern at a longitudinal plane at $h_0(x,0,z)$; (c) a digital texture detector associated with (b); and (d) a standard 2D digital edge detector. The 3D $h_0(x,y,z)$ is interpreted as a 3D texture template, which can enhance edges and boundaries.

FIG. 5. Demonstration of the morphometric difference between a Gaussian-shaped $\chi$ distribution in (a) and its fieldmap in (b). The 3D volume is represented by 32×32×32 matrix, only z=1:16 slices are displayed (z=16 at the central z-slice). It is noted the conspicuous morphometric discrepancy between the fieldmap and the susceptibility map is due to a 3D convolution transformation.

FIG. 6. The CIMRI model (diagrammed with solid arrows). It consists of two inverse mappings: fieldmap calculation from MR phase image and $\chi$ reconstruction from the fieldmap. There are three solvers for $\chi$ reconstruction from fieldmap: filter truncation, matrix inverse, and TV iteration (our proposal). The forward MRI is diagrammed with rightward arrows.

FIG. 7. (a) Precomputed fieldmap (resulting from a predefined neuroactive blob), and (b) the phase image of T2*MRI simulation. It is noted that the MR phase image can faithfully represent the fieldmap.

FIG. 8. The spatial correlations between the MR phase image and the precomputed fieldmap (see FIG. 7) for two intravoxel vasculatures (2-um-radius in (a1) (FIG. 8A) and 4-um-radius in (a2)) (FIG. 8B) and for three voxel sizes (see legend).

FIG. 9. Illustration of T2'-effect signals with two echo times. (a) A pulse sequence of a 90° tipping pulse and two 180° refocusing pulses (one with $T_{E1}$ and other with $T_{E2}$); (b) T2* SE signal (echoes in black) and T2* GE signal (echoes in red). The T2* SE signals are generated by a pair of 90° and 180° pulses. The T2* GE signals are generated by only a 90° pulse and a reversal readout gradient (not drawn).

FIG. 10. Feature-specified $\chi$ reconstruction by "post-recon filtering" and "TV-iteration filtering" approaches. The "post-recon filtering" approach is carried out by first reconstructing a $\chi$ source with standard TV iteration and then exerting a spatial filtering with a feature-specified filter $f(k)$, as diagramed in the right-hand dotted box. The "TV-iteration filtering" approach is carried out by reconstructing a $\chi$ source with a modified filter $H(k)=H_0(k)/f(k)$, as diagramed in the left-hand dotted box. Two approaches are carried out in parallel, and the two resultant $\chi$ sources are averaged to produce a noise-reduced $\chi$ source.

FIG. 11. 3D convolution filter design. A modified kernel can be obtained by DC term reset, lowpass, highpass, and bandstop filtering. (The bandpass filtering is not shown).

FIG. 12. Demonstration of the equivalence of "TV-iteration filtering" and "post-recon filtering" and the noise reduction by average. (a) $\chi$ reconstruction by "TV-iteration filtering" with a TV iteration filter $H(k)=H_0(k)/f_{LP}(k)$ with $f_{LP}(k)=[0.6+0.4\cos(\pi k/k_{max})]$; (b) The "post-recon filtering" with a lowpass filter $f_{LP}(k)=[0.6+0.4\cos(\pi k/k_{max})]$; (c) the average of (a) and (b); and (d) the profiles of scanline.

FIG. 13. The neighborhood of DC term of the standard filter $H_0(k)$. The DC term assumes ½ (by convention of 0/0=0), which is continuous at the $(k_x,k_y)$ plane, but not continuous along the $k_z$-axis due to {−0.667, ½, −0.667} for voxels at $(k_x,k_y,k_z)=\{(0,0,-1),(0,0,0),(0,0,1)\}$.

FIG. 14 Effect of DC term reset (H(0,0,0)={1,½,−1}) on $\chi$ reconstruction. Cross-sections for reconstructed cylinders with (a) DC=1, (b) DC=½, and (c) DC=−1. The profiles of the scanline (only provided in (a)) is shown in (d). It is seen that the DC value of $H_0(k)$ has little influence on TV-regularized $\chi$ reconstruction (as described "scale invariance").

FIG. 15. Diagram for bandpass, highpass, and lowpass filtering which is applied to a direction along $k_x$-, $k_y$-, $k_z$-axis, and radial direction $k_r$ separately and jointly. The red plots have sharp cutoffs and the black plots are smooth which can suppress Gibbs effect.

FIG. 16. Illustrations of strip feature extraction by designing the filters for horizontal stripe extraction (at top row; FIG. 16A), vertical stripe extraction (at middle row; FIG. 16B), and the extraction for vertical, horizontal, diagonal, and antidiagonal stripes (at bottom row; FIG. 16C). The spatial superimposition of numerous random stripes makes a clutter noise in the reconstruction.

FIG. 17. Demonstration of lowpass (FIG. 17A) and highpass filters (FIG. 17C). It is noted the lowpass filter can be reshaped by a square operation (for example, constricted by Eq. with α=2) (FIG. 17B). FIG. 17D shows the 1D profiles of lowpass, highpass, and lowpass squared filters.

FIG. 18. The reciprocals of the filters in FIG. 17A-D are shown in FIG. 18A-D, respectively.

FIG. 19 Demonstration of $\chi$ reconstructions with (a) standard filter $H(k)=H_0(k)$, (b) lowpass filter $H(k)=H_0(k)/f_{LP}(k)$ with $f_{LP}(k)=[0.6+0.4 \cos(\pi k/k_{max})]^2$, (c) highpass filter $H(k)=H_0(k)/f_{HP}(k)$ with $f_{HP}(k)=1-[0.6+0.4 \cos(\pi k/k_{max})]^2+0.2$. The profiles of the scanline (indicated in (a)) are shown in (d).

FIG. 20. A MR magnitude-based self-calibration scheme for estimating the TV regularization parameter value. The MR magnitude image is used as a reference to compare with the trial TV iteration outcome, thereby determining the initial guess of proper TV iteration parameter values for $\chi$ reconstruction. It is noted that the magnitude is compared with the absolute value of susceptibility.

FIG. 21. Noise reduction strategy by parallel TV iteration (using different parameter values) and multiple reconstruction average.

FIG. 22. Demonstration of noise reduction by multi-recon average. In each iteration, the $\chi$ reconstruction suffers sparse "residual noise" (or comeback noise associated with Bregman iteration), as indicated in dotted circles. The average of multiple reconstructions ((a1) through (a5) with different $\chi$ values) FIG. 22A-E, respectively can effectively reduce the sparse noise as shown in (b) (FIG. 22F).

FIG. 23. Profiles of scanlines in FIG. 22. The amount of noises (calculated by standard deviation) are provided in the figure legend.

FIG. 24. Upper box: There are only three datasets available for a BOLD fMRI study {task(t), A(x,y,z,t), P(x,y,z,t)}. Lower box: the neuroactive site in the FOV can be determined by the temporal correlation between the task(t) and magnitude timecourses.

Figure 25:
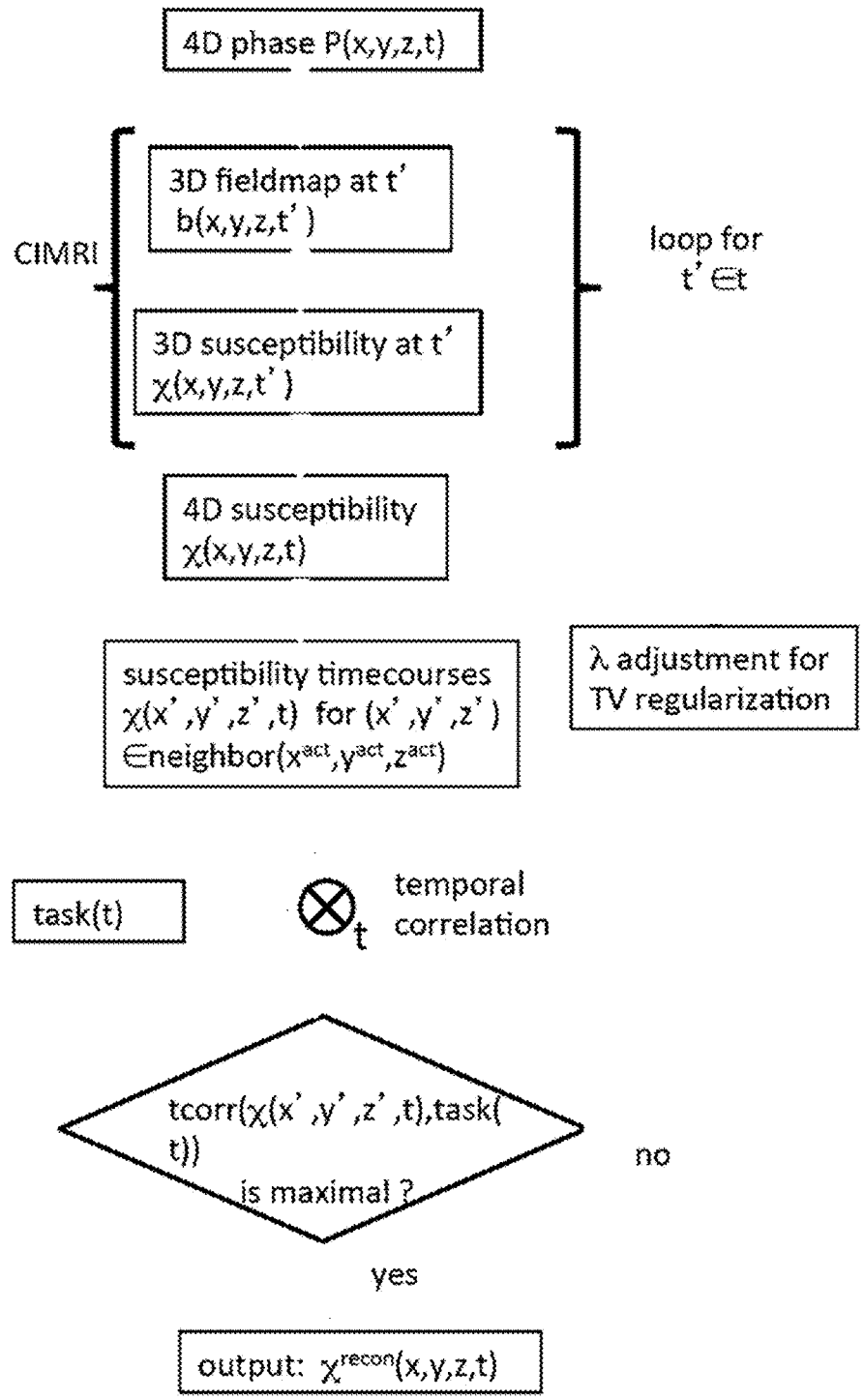
FIG. 25. 4D susceptibility reconstruction under the criterion of susceptibility timecourse synchrony (a way of making use of the external stimulus paradigm task(t)), where tcorr(x(t),y(t)) stands for temporal correlation between x(t) and y(t). The neuroactive location ($x^{act}$, $y^{act}$, $z^{act}$) is determined in FIG. 24.

FIG. 25. 4D susceptibility reconstruction under the criterion of susceptibility timecourse synchrony (a way of making use of the external stimulus paradigm task(t)), where tcorr(x (t),y(t)) stands for temporal correlation between x(t) and y(t). The neuroactive location $(x^{act}, y^{act}, z^{act})$ is determined in FIG. 24.

FIG. 26. Structural $\chi$ tomography scheme for susceptibility-based nonheme iron deposit measurement by structural MR imaging and CIMRI (toward applications for tissue and organ iron imaging).

FIG. 27. Two methods for susceptibility-based brain mapping and neuroimaging in (a1) (FIG. 27A) and (a2) (FIG. 27B), which are different from the conventional magnitude-based brain mapping and neuroimage in (b) (FIG. 27C). The method 1 in (a1) (FIG. 27A) is for linear statistical data analysis, and the method 2 in (a2) (FIG. 27B) is for nonlinear linear statistical analysis.

FIG. 28. A method to improve the $\chi$ tomography by T2'MRI and CIMRI. The Gradient-echo image and spin-echo image are acquired for the same $\chi$ source with the same echo time $T_E$. A complex division is used to obtain a complex T2' complex image. A CIMRI analysis is used to reconstruct the susceptibility source from T2' phase image.

FIG. 29. Gd-filled tube phantom experiment setup. The tube phantom provides a static cylindrical susceptibility distribution, which is used to simulate a snapshot of dynamic susceptibility-expressed physiological process.

FIG. 30. Phantom experiment results. Row 1 (at top): magnitude image; Row 2: phase image; Row 3: $\chi$ reconstructed from filter truncation method; and Row 4 (at bottom): $\chi$ reconstructed from TV iteration method.

FIG. 31. Quantitative profiles along a cylinder diameter in FIG. 30.

FIG. 32. TV-regularized brain $\chi$ reconstruction from an in vivo experiment dataset. (a) (FIG. 32A) an axial slice of the MR magnitude of brain imaging (where a vertical segment marks a scanline); (b1) (FIG. 32B) the phase image slice; (b2) (FIG. 32C) the smoothed phase; (c1-c6) (FIG. 32D-I) the $\lambda$ reconstruction from the phase (in (b1; FIG. 32B)) by using a large range of $\lambda$ values. Note that the magnitude image is nonnegative as displayed in a greyscale bar range of [0,1], and all other images (phase images and $\lambda$ reconstructions) are bipolar-valued.

FIG. 33. The scanline profiles extracted from FIG. 32 (c1-c6). It shows that the $\chi$ reconstruction may suffer oversmoothing effect with a small $\lambda$ value (=10), and a textural enhancement with a very large $\lambda$ value (>500). In the range of $10<\lambda<500$, the $\chi$ reconstructions are relatively similar and stable in reference to the MR magnitude image for this particular case.

FIG. 34. The reconstructions of $\chi$ timecourse at a voxel in the BOLD active site with regularization parameter $\lambda=\{10, 30,50,100,500,1000\}$. The rectangle waveform represent the external stimulus task(t). The timecourse synchrony reconstruction criterion indicates that $\lambda=[20-500]$ are suitable for 4D $\chi$ reconstruction.

FIG. 35. Illustration of brain structural susceptibility distribution. The hemorrhage and micro-hemorrhage of blood circulation causes spread susceptibility distribution, the static iron deposit also contributes the susceptibility distribution for static structural representation. The iron deposit may occur in tissues and organs, not necessary in proximity to blood streams. The static iron deposit in tissue and organ can be measured by 3D magnetic susceptibility tomography.

Figure 36A:
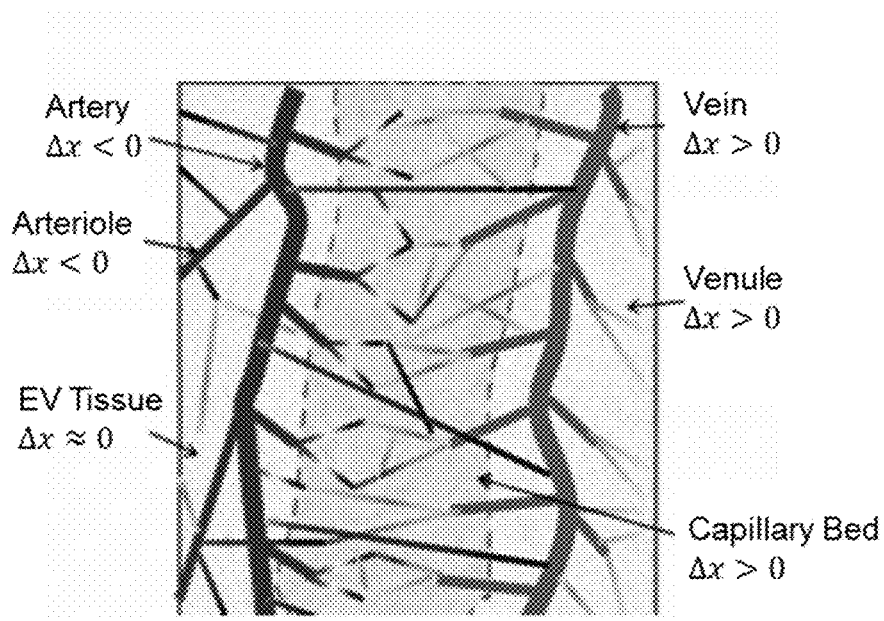
FIGS. 36A and 36B. Illustration of blood susceptibility perturbation associated with a BOLD ƒMRI model. The extravascular tissue is the static background structure. The BOLD-induced susceptibility perturbation is attributed to the intravascular blood-borne heme iron disturbance. The dynamic heme-iron perturbation, superimposed on a static structural iron background, can be measured by 4D magnetic susceptibility tomography.
Figure 36B:
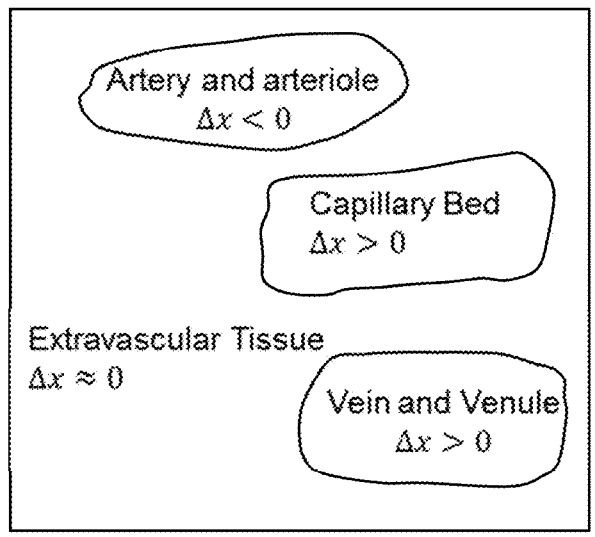

FIGS. 36A and 36B. Illustration of blood susceptibility perturbation associated with a BOLD fMRI model. The extravascular tissue is the static background structure. The BOLD-induced susceptibility perturbation is attributed to the intravascular blood-borne heme iron disturbance. The dynamic heme-iron perturbation, superimposed on a static structural iron background, can be measured by 4D magnetic susceptibility tomography.

FIG. 37. Geometry for cylindrical $\chi$ reconstruction numerical simulation. The main field is perpendicular to the cylinder.

FIG. 38. Top row: three orthogonal cross-sections of the predefined $\chi$ source (FIG. 38A-C). Middle row: fieldmap without noise (FIG. 38D-F). Bottom row: fieldmap with additive Gaussian noise (NoiseLevel-0.1) (FIG. 38 G-I).

Figure 39:
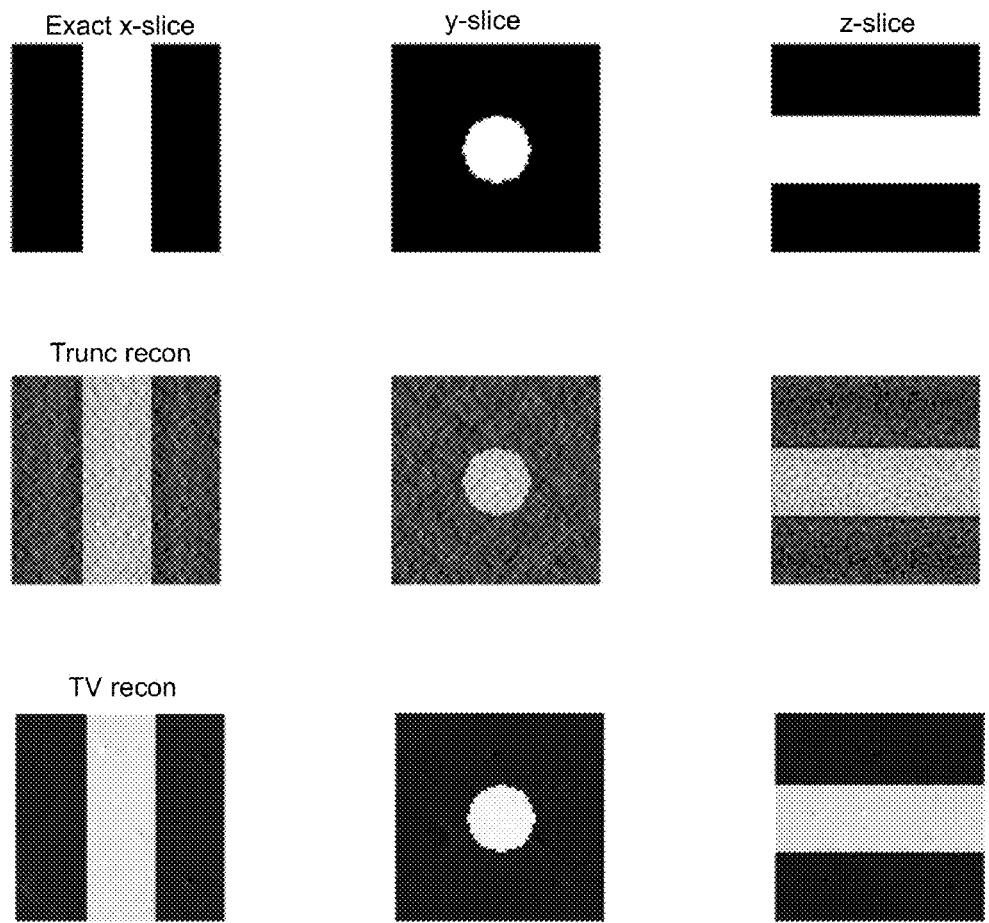
FIG. 39. Numerical simulation results of computed inverse BOLD ƒMRI for susceptibility source reconstruction with a simple cylinder $\chi$ source (predefined ground truth in the first row), by filter truncation method (in second row) and by the TV-regularized method (in the third row).

FIG. 39. Numerical simulation results of computed inverse BOLD fMRI for susceptibility source reconstruction with a simple cylinder $\chi$ source (predefined ground truth in the first row), by filter truncation method (in second row) and by the TV-regularized method (in the third row).

FIG. 40. Quantitative profiles along a diameter of the cylinder phantom in FIG. 37 (the ground truth is a rectangle profile in legend "truth").

FIG. 41. Convergence of a typical TV iteration.

FIG. 42. Comparison of two inverse solvers in a numerical simulation of random noise behavior during $\chi$ reconstruction.

DEFINITIONS

CIMRI: Computed Inverse Magnetic Resonance Imaging. It is a computational model for reconstructing the magnetic susceptibility source of T2*MRI by reversing the forward MRI procedure by computations. It comprises two computation steps: fieldmap calculation from MR phase image and susceptibility calculation from the calculated fieldmap. The CIMRI provides a means for magnetic susceptibility tomography.

Magnetic susceptibility tomography. Reconstruction of internal magnetic susceptibility distribution of an entity through the use of external MR measurement. The magnetic susceptibility tomography can be implemented by a computed inverse magnetic resonance imaging (CI-MRI) model.

3D convolution magnetization. When a foreign nonferrous material is introduced into a magnetic field, it is subject to a magnetization process (due to the material and field interaction), which can be described by a magnetic dipole model in the linear magnetization regime. We describe the nonferrous material magnetization in a field by a 3D convolution model (with the convolution kernel of point magnetic dipole field) and reconstruct the material magnetic susceptibility through the framework of 3D deconvolution image restoration.

Small angle regime. This term refers to a spin precession angle that is very small, such that $\exp(-i\phi) \approx 1 - i\phi$, with $\phi = \gamma \cdot b \cdot T_E$ (Larmor law), where: $\gamma$ denotes gyromagnetic ratio, b the magnetic field disturbance (the main field $B_0$ is excluded in the rotating frame representation), and $T_E$ the precession time (or relaxation time, or echo time in a gradient echo sequence). In small angle regime, the fieldmap and MR phase image are different only by a $T_E$-dependent scale factor. The condition of small angle regime can be reached by MR scanning with a small $T_E$ in a low field.

TV iteration: Total Variation iteration (or TV regularization). It is an iteration procedure for finding the optimal solution that simultaneously minimizes the TV norm and data fidelity. In this invention, we generalized the TV iteration for conventional 2D image restoration to accommodate our 3D deconvolution χ reconstruction (the core technology of CIMRI). We invented a 3D split Bregman iteration algorithm as an effective and efficient implementation of TV-regularized deconvolution problem.

Post-recon processing or Post-recon filtering. This is a postprocessing step exerted on a reconstructed susceptibility distribution. After the χ reconstruction by CIMRI, we process the reconstructed χ by imposing a spatial filtering, so as to produce specific desirable features. Typical post-recon processing strategies include: low-pass, highpass, bandpass, bandstop filtering.

Standard TV iteration and standard χ reconstruction. If the TV iteration uses the kernel of point magnetic dipole field (denoted by $h_0(r)$) (corresponding a standard filter $H_0(k)=FT[h_0(r)]$ in Fourier domain), we refer to the TV iteration as a "standard TV iteration", and the iteration output as the "standard χ reconstruction".

TV-iteration convolution. This term refers to a TV iteration process that uses a modified convolution kernel (based on $h_0(r)$). During a TV iteration process, each iteration is carried out by a 3D convolution with the same convolution kernel h(r) (a modification of $h_0(r)$) and TV regularized minimization. Based on linear filtering theory, we show that a spatial filtering exerted on a 3D reconstructed χ (as described by post-recon filtering) can be equivalently achieved during TV iteration using a modified kernel.

TV-iteration filtering. In practice, the 3D TV-iteration convolution can be efficiently implemented by performing the 3D iteration convolution part using 3D iteration filtering in the Fourier domain. Let h(r) represents the TV-iteration convolution kernel, the TV-iteration filter H(k) is calculated by $H(k)=FT[h(r)]$, where FT stands for Fourier transform.

Reciprocal filter. The filter $1/f(k)$ is called the reciprocal of the filter $f(k)$. Reciprocal filter is also called an inverse filter.

TV-iteration kernel design. This term refers to the design of TV iteration convolution kernel h(r). We design a TV iteration convolution kernel from a filter that is used for post-recon filtering. The convolution kernel design is formed by $h(r) = h_0(r) * IFT[1/f(k)]$, where $h_0(r)$ represents the magnetic dipole kernel, $f(k)$ the filter designed for post-recon filtering, and IFT the inverse Fourier transform.

TV-iteration filter design. In the Fourier domain, the TV-iteration kernel design by $h(r) = h_0(r) * IFT[1/f(k)]$ can be expressed by $H(k) = H_0(k)/f(k)$, which is called "TV-iteration filter design"; where $H_0(k) = FT[h_0(r)]$ represents the magnetic dipole filter, and $f(k)$ the filter designed for post-recon filtering.

Comeback noise or residual noise. This term refers to the random and sparse noise that is brought back during TV iteration. The pattern and distribution of the comeback noise varies during TV iteration process and with the TV iteration setting. Two TV iterations with different parameter settings do not bring back the same noise pattern. The comeback noise is also called residual noise. Usually, the comeback noise randomly and sparsely emerges in uniform regions.

Parallel TV iteration. This term refers to performing multiple TV iterations on the same fieldmap dataset with different iteration parameter settings, which are carried out in a manner of parallel computations. In this invention, we use parallel TV iteration for the purpose of average noise reduction via parallel computations.

Multi-recon average: multi-reconstruction average. The output of parallel TV iteration comprises a multitude of χ reconstructions, which have different residual noise (or comeback noise). We average the multiple χ reconstructions to make a so-called "multi-recon average". The multi-recon average can reduce random sparse comeback noise (at the cost of performing multiple TV reconstructions).

χ tomography. Based on the conclusion that the magnetic susceptibility property (denoted by χ) represents the underlying source of T2*MRI, and that the MR magnitude image is a distortedly transformed image of χ (due to local average and nonlinearity of MRI detection). We developed methods for performing magnetic susceptibility tomography (χ tomography), and we implement it by doing T2*MRI and CIMRI, that is (conceptually), χ tomography=T2*MRI+CIMRI. In this specification, the term "χ tomography" refers to χ tomographic reconstruction from T2*MRI data by CIMRI, and it is used interchangeably with the term "χ reconstruction".

Structural χ tomography (3D χ tomography). The structural χ tomography provides a χ distribution that is interpreted as iron deposit measurement for biological tissue and organs. A χ distribution can be obtained by CIMRI from a complex MR image. In contrast to functional χ tomography, the content of structural reconstructed χ is mainly the static nonheme iron deposit in tissue or organ (the microbleeding is considered as static in relative to small $T_E$).

Functional χ tomography (4D χ tomography). This term refers to as reconstructing the dynamic χ perturbations (imposed on a background) from a 4D complex MR dataset (acquired by BOLD fMRI) by implementing snapshot χ reconstruction by CIMRI. In contrast to structural χ tomography, the content of reconstructed χ at a snapshot time consists of both static nonheme iron deposit (background or baseline) and dynamic heme iron perturbation (due to brain functional activity). In contrast to the conventional magnitude-based brain mapping and neuroimaging, we invented the concept of $\chi$-based functional imaging, which replaces the MR image dataset with the reconstructed $\chi$ dataset. The $\chi$-based functional imaging improves the neuroimage depiction, because the reconstructed $\chi$ distribution is a more direct and truthful representative of the neuroactivity than the MR magnitude image.

Timecourse synchrony. This term refers to a synchronous response to an external stimulus paradigm. At the brain activation region, the MR signal is formed due to the neuroactive response to the external stimulation. Therefore, the signal timecourses are highly correlated with the stimulus timecourse (usually with a time lag of 2 to 4 seconds). With the magnitude timecourse synchrony, we can find the brain active site on the temporal correlation map (the conventional neuroimage depiction technique). Since the underlying source of BOLD $f$MRI signals is the susceptibility perturbation, it is understandable that the internal susceptibility perturbation should be synchronous to the external stimulation (with a time lag due to homodynamic response latency). Therefore, we developed a susceptibility synchrony criterion for reconstructing a meaningful 4D susceptibility dataset. That is, the susceptibility timecourse from the reconstructed 4D susceptibility dataset at the neuroactive regions assumes a high correlation with the external stimulation (with a time lag), where the neuroactive site can be determined by finding the maxima at the 3D magnitude temporal correlation map.

T2* gradient-echo imaging (also T2* imaging). This term refers to acquiring a gradient-echo image, which consists of all the transverse dephasing contributions, including the inhomogeneous fieldmap T2' effect, spin-spin interaction T2 effect, and the proton diffusion effect. The conventional EPI pulse sequence is an implementation of T2* imaging.

- T2* spin-echo imaging (e.g. T2 imaging). This term refers to acquiring a spin-echo image that only captures the T2 and diffusion random effects, with the static inhomogeneity dephasing canceled by 180° pulse refocusing. T2* spin-echo imaging is always called "T2 imaging". We describe T2 image by a different name of "T2* spin-echo imaging" and use it to make a pair of T2* gradient-echo and spin-echo images.

- T2'-effect imaging (T2'MRI). We invented this scheme to obtain a complex image that consists of only static (non-random) inhomogeneous field effect (the T2' effect). The T2'-effect imaging algorithm produces a complex image by a complex division of a T2* GE complex image divided by a T2* SE complex image. The output of T2'-effect imaging, denoted by T2'MRI, is not a map of T2' parameter, so our T2'-effect image scheme is different from the T2' imaging scheme. That is, T2'MRI is different from the conventional T2' imaging in that: T2'MRI deals with the MR images per se, not involving the calculation of T2' decay parameters for T2' imaging.

- T2'-effect phase image (or T2' phase image). The T2'-effect phase image is calculated from T2'-effect complex image, which is in turn calculated from a pair comprising: a T2* GE complex image and a T2* SE complex image, by a complex division.

- T2'-effect fieldmap (or T2' phase image). The T2'-effect fieldmap is proportional to the T2'-effect phase image by a constant factor. The T2'-effect fieldmap consists only of the static inhomogeneous fieldmap with the random T2 effect removed by the T2'-effect image scheme. Therefore, the T2'-effect fieldmap can be used for improving the $\chi$ reconstruction fidelity.

- MR Image. The word "image" (e.g., "a MR phase image") is broadly defined as meaning "a 3D volumetric array (x,y,z) of voxel signal values, whose voxel values are measured at a single $T_E$ value" (i.e., multivoxels). Also, the words: "map", "distribution", "volume", "data", "3D image", "3D map", "3D distribution", "3D volume", "volumetric map", "3D image dataset", and "3D data", are equivalent to, and interchangeable with, the word "image", as it is defined above. The term "4D dataset" refers to a timeseries of MR images with 3D space and 1D time, as denoted by (x,y,z,t). The output of T2*MRI is a 3D MR image, and the output of a BOLD $f$MRI study is a 4D dataset that consists of a timeseries of volumetric (3D MR) images captured by T2*MRI at each snapshot in time.

- MR Signal. Traditionally, a MR signal refers to the free induction decay (FID) behavior of proton spin precessions with respect to relaxation time. In the context of MRI, a MR signal refers to the FID of a specific voxel with respect to the echo time $T_E$. A MR image is a multivoxel array whose voxel values assume the voxel signals at a single value of $T_E$. Both the MR voxel signal and MR multivoxel image are complex-valued in nature. In this invention, we do not need to perform MR signal observation. Instead, we involve MR multivoxel image capture by T2*MRI with a single echo time $T_E$ (or a few of $T_E$'s).

DETAILED DESCRIPTION OF THE INVENTION

It is widely accepted that the MRI technology is an excellent noninvasive imaging modality for biological soft tissue and physiological state imaging. Currently, only the magnitude image of a MR complex image is used to represent a physiological state or a brain interior, whereas the phase image remains largely unused. In this section, we show that the MR magnitude image is not an exact representation of the underlying susceptibility source, and that the MR phase appears textural, noisy, spatially blurred. Our invention makes use of MR phase image for the $\chi$ source reconstruction. Relevant theory, models, algorithms are provided. The algorithm implementations are demonstrated with numerical simulations. Details about the parameter settings, and implementations of two numerical simulation examples are provided in Appendix A. A phantom experiment, and a real human brain imaging experiment, are presented later in separate sections.

In some preferred embodiments of the present invention, the multivoxel values that populate a 3D volumetric array (x,y,z) of multiple voxel signal values (i.e., an "image") are measured at a single TE, using a complex EPI or EVI pulse sequence, after a RF pulse has been applied.

Overall, we describe a new model of computed inverse magnetic resonance imaging (CIMRI) [17] to reconstruct a 3D susceptibility distribution (denoted by x) based on a MR phase volume image acquired by T2*MRI technology (applied to tissue/organ imaging of human subjects or animals). Essentially, the CIMRI model is to reverse the forward T2*MRI procedure by two computational steps: first calculating a fieldmap from a MR phase volume and then calculating a $\chi$ map from the computed fieldmap. In the sense of intact (free from the transformations exerted by T2*MRI) magnetic susceptibility source reconstruction, CIMRI implements magnetic susceptibility tomography (x tomography). The 3D $\chi$ reconstruction algorithm involves a 3D ill-posed deconvolution, for which we developed a 3D total variation (TV) regularized iteration solver with an efficient implementation of split Bregman iteration [17, 21]. For dynamic BOLD $f$MRI study, the output is a 4D complex MR dataset; from which we can reconstruct a 4D χ dataset by reconstructing each 3D snapshot volume with CIMRI (4D χ tomography).

The χ tomography by CIMRI offers a quantitative interpretation of iron deposit in a tissue/organ physiological state, structural or functional, static or dynamic, patient (physiopathology) or healthy, human or animal. Specifically, a reconstructed χ volume for a static tissue/organ state is interpreted as iron deposit therein, and a reconstructed snapshot χ volume in a dynamic BOLD process is interpreted as a composite of static brain structural iron deposit (baseline) and dynamic brain function heme-iron distribution (BOLD activity). It is known that the susceptibility distribution is the underlying source of T2*MRI, and it can represent a physiological state more directly than the MR magnitude image in the sense of its timing closeness and intactness (prior to T2*MRI scanning and being free from imaging transformations) [19]. Therefore, in this invention, we replace the MR image dataset with the reconstructed χ source dataset for more direct and truthful structural and functional brain image depictions.

Some innovative features of our methods of χ tomography using CIMRI include the following aspects:

1. We describe the fieldmap establishment from a 3D χ source via magnetization in a main field by a 3D convolution model, which offers two advantages: explanation of the morphological mismatch between the χ source and the fieldmap (corresponding to phase image), and implementation of 3D χ tomographic reconstruction in the framework of 3D-deconvolution image restoration.
2. We solve the ill-posed 3D deconvolution problem associated with the 3D χ source tomography by a novel and unique 3D split-Bregman TV-regularized iteration method; for which we also developed a self-calibration scheme that selects the regularization parameter values (usually a range of values) by making use of the MR magnitude image to as an initial estimate of χ reconstruction.
3. We developed an improved TV-iteration filtering scheme by using a modified TV iteration filter that can achieve the similar results of spatial post-reconstruction filtering.
4. We discovered that the TV iteration is almost invariant to a wide range of TV regularization parameter values, and it is almost invariant to DC term reset. However, the TV iteration may bring back sparse noise in the uniform regions. We developed a noise reduction strategy by performing parallel TV iteration reconstructions (for the same fieldmap dataset but using different iteration parameter values), followed by a multi-reconstruction average.
5. We generate a 4D χ dataset from a 4D complex MR dataset (acquired by BOLD fMRI) by reconstructing each snapshot susceptibility volume from a MR phase volume in the 4D complex MR dataset by CIMRI. In order to make use of the external stimulus paradigm, we developed a criterion of susceptibility timecourse synchrony: the reconstructed susceptibility timecourse at the brain active site should maximally correlate with the timecourse of external stimulation.
6. We developed a unique T2'-effect imaging scheme to remove the random T2 and diffusion effects by acquiring a pair of T2* gradient-echo and spin-echo complex images and processing them by an element-wise complex division. By calculating the T2' phase image from a T2' complex image and using it for χ reconstruction, we can improve the χ reconstruction fidelity. Our T2'-effect imaging scheme does not involve exponential decay assumption, or the calculation for T2, T2* and T2' parameters.
7. For applications, we developed a brain structural χ tomography scheme for nonheme-iron deposit measurement in tissue and organs, and a brain functional χ tomography scheme for heme-iron perturbation measurement for brain mapping and neuroimaging.

Our CIMRI methods are based on the 3D volumetric MR image that may be acquired by stacking slices (as acquired by EPI for example) or preferably by volume imaging (as acquired by EVI for example). Our reconstruction algorithm is based on 3D volume image, not based on a 2D slice image or on a few number of individual voxels. Our methods do not involve the calculation of susceptibility gradient vector map.

Our CIMRI methods do not use a by-side phantom for MRI data acquisition, and our iterative susceptibility reconstruction algorithm is based on a 3D total-variation-regularized split Bregman iteration on the MR phase volume data per se, not involving by-side phantom data. In our methods, the MR phase image is acquired by the conventional T2*MRI procedure (through the use of a standard 2D EPI sequence or a 3D EVI sequence), which is not involving a particular requirement for anisotropic diffusion imaging.

Basic Concepts of T1, T2, T2', and T2* Signal

According to MRI physics [1, 2], T1 signal represents the longitudinal magnetization recovery after a stimulus of radio frequency (RF) pulse; T2 signal represents the transverse magnetization dephasing due to random spin-spin interaction (even if in a homogeneous field), and T2* signal represents the total transverse magnetization dephasing in an inhomogeneous field, consisting of both the T2 random effect and the inhomogeneous field effect (T2' effect). Assuming an exponential model for signal intensity decay, the T1, T2 and T2* signals are expressed by:

$$M_z(t) = M_z(t=0)(1-\exp(-t/T_1))$$

$$M_1(t) = M_1(t=0)\exp(-t/T_2)\text{(in homogeneous field)}$$

$$M_1(t) = M_1(t=0)\exp(-t/T_2^*)\text{(in inhomogeneous field)} \quad (1)$$

with $1/T_2^* = 1/T_2 + 1/T_2'$

It is noted that among the total T2* signal, the T2-effect contribution is due to random spin-spin interaction which is determined by the media of spin protons, and the T2' effect is due to dephasing in an inhomogeneous field, which represents what we are pursuing in this report. The T2* signal is detected by gradient echo (GE) imaging, which is essentially a free induction decay signal (FID) reflecting the tissue media property. We should point out that, in this report, we do not need to calculate the T2, T2' and T2* parameters by the exponential formulas in Eq. (1); we only deal with complex-valued images per se as resulted from T2 and T2* effects; we obtain a T2' complex image by a complex division of T2* image and T2 image. Concerning the fact that, a T2 signal (due to random spin-spin interaction) is non-refocusable by 180° pulse, and that the T2'signal (dephasing due to inhomogeneous field) is refocusable, and that the T2* signal consists of both T2 and T2' effects, we developed a T2' imaging scheme (by a complex division) that can provide a complex image due to static inhomogeneous field that excludes the unwanted random T2 effect (as well be reported later).

The T2*MRI and CIMRI models

Since we are concerned with an inhomogeneous χ reconstruction from its magnetized inhomogeneous fieldmap, we only address the T2*MRI, which is a non-invasive imaging modality for the measurement of inhomogeneous fieldmap in a main field $B_0$. It is known that the biomagnetism of a biological entity is mainly attributed to iron content. Overall, we describe the forward $\chi$ imaging (T2*MRI) in FIG. 1 by two modules. One is the "Source Magnetism" module (in the upper dotted box), and the other is the "MRI technology" module (in the lower dotted box). As diagramed in FIG. 1 for MRI-based brain imaging, the $\chi$ expression for a snapshot brain state consists of static structural and dynamic functional contribution, as denoted by $\chi(x,y,z)=\chi\text{struc}(x,y,z)+\chi\text{func}(x,y,z)$.

A T2*MRI procedure acquires a complex MR image for the $\chi$ source. We will show that the $\chi$ source distribution can be reconstructed from the MR phase image by reversing the MRI procedure, as designated by CIMRI (computed inverse MRI) in FIG. 1. For dynamic brain imaging, the $\chi$ expression for a brain functional process is a time-dependent 4D $\chi$ dataset, $\chi(x,y,z,t)$, which produces a complex-valued 4D MR image dataset by repeating the T2*MRI for each snapshot capture (as described by BOLD fMRI). We will show that we can reconstruct the 4D $\chi$ expression for a dynamic brain functional process by snapshot $\chi$ reconstruction, thus implementing 4D $\chi$ tomography.

FIG. 1 shows the T2*MRI and CIMRI models. The T2*MRI model is decomposed into two modules: "Source Magnetism" (in the upper dotted box) and "MRI technology" (in the lower dotted box). The downward arrows indicate the forward procedure and the upward arrows indicate the backward procedure. The CIMRI model consists of two steps, as diagramed in the circle.

As diagrammed in FIG. 1, the forward MRI procedure undergoes two steps. The first step is the fieldmap establishment by susceptibility magnetization in a main field $B_0$, which can be expressed by a 3D convolution transformation [20]:

$$b(x,y,z) = B_0\chi(x,y,z) * h_0(x,y,z) + \epsilon(x,y,z) \quad (2)$$

$$\text{with } h_0(x,y,z) = \frac{1}{4\pi}\frac{3z^2-[x^2+y^2+z^2]}{[x^2+y^2+z^2]^{5/2}}$$

(magnetic dipole kernal)

where $B_0$ denotes the main field, $\epsilon(x,y,z)$ the noise, $h_0(x,y,z)$ (or $h_0(r)$) the 3D convolution kernel, which is the magnetic response of a point magnetic dipole at the origin (as described by point magnetic dipole model). In Fourier domain, the 3D convolution is represented by a 3D filtering, that is:

$$FT[b(x,y,z)] = H_0(k_x,k_y,k_z)\cdot FT[\chi(x,y,z)]\cdot B_0 \quad (3)$$

$$\text{with } H_0(k_x,k_y,k_z) = FT[h_0(x,y,z)] = \frac{1}{3} - \frac{k_z^2}{k_x^2+k_y^2+k_z^2}$$

(magnetic dipole filter)

where FT denoted Fourier transform, and $H_0(k_x,k_y,k_z)$ the 3D filter (also denoted by $H_0(k)$, called standard filter) corresponding to the convolution kernel $h_0(x,y,z)$ in Eq. (2). It is noted that the DC term $H_0(0,0,0)$ is undefined due to a term of 0/0 (at $k_x=0$, $k_y=0$, $k_z=0$), which allows to reset it (as will be shown later).

The second forward step in FIG. 1 produces a complex-valued image by an intravoxel dephasing summation. For static intravoxel dephasing (ignoring diffusion effect), the multivoxel image is formed by:

$$C(x,y,z;T_E) = \frac{1}{|\Omega|}\iiint_{\Omega} e^{i\gamma b(x',y',z')T_E} dx'dy'dz' \quad (4)$$

where $\gamma$ denotes the proton gyromagnetic ratio, $T_E$ denotes the echo time (interpreted as an exposure time of T2*MRI), and $\chi(x,y,z)$ denotes the voxel at $(x,y,z)$, and $|\Omega|$ the voxel size.

From the complex-valued output $C(x,y,z)$ acquired by a forward T2*MRI procedure, we can extract its magnitude loss $A(x,y,z)$ and phase accrual $P(x,y,z)$ by $$\begin{cases} A(x,y,z;T_E) = \left|\frac{C(x,y,z;T_E=0)}{C(x,y,z;T_E)}\right| & \text{(magnitude loss)} \\ P(x,y,z;T_E) = \angle\left[\frac{C(x,y,z;T_E)}{C(x,y,z;T_E=0)}\right] & \text{(phase accrual)} \end{cases} \quad (5)$$

The magnitude image $A(x,y,z)$ represents the 3D map of signal loss (decay), and the phase image $P(x,y,z)$ the phase angle accumulation during $T_E$ (decay signals in reference to non-decay signals at $T_E=0$).

Assuming that the voxel signal intensity follows an exponential decay, we can calculate the T2* parameter by:

$C(T_E)=C(T_E=0)\exp(-T_E/T2^*)$ (exponential decay model)

$A(T_E)=1-\exp(-T_E/T2^*)$ (exponential magnitude loss) (6)

with which other researchers have used for T2*-based susceptibility mapping [3, 5, 6, 34-38]. It is noted that, in this report, we do not involve the exponential assumptions in Eq. (6) at all, and we only deal with the 3D T2*-effect images in Eq. (5). Therefore, we claim that our method is dealing with the T2 and T2* images per se, which is different from the T2 and T2*(or R2 and R2*) MR imaging techniques that involve the exponential models and decay rate calculation (requiring multi-time image acquisition through the use of a multi-echo sequence).

It is noted that the fieldmap establishment from susceptibility source by a 3D convolution in Eq. (2) is a linear and spatially spread transformation. Obviously, the complex modulo and complex argument operations in Eq. (5) are non-linear. However, the susceptibility source reconstruction from fieldmap is a linear deconvolution problem. In small angle regime (a linear phase approximation condition), the fieldmap is linearly related to the MR phase image [19, 39], which simplifies the fieldmap calculation in the first inverse step of CIMRI. Nevertheless, the deconvolution of CIMRI is an ill-posed inverse problem that is a non-trivial task.

BOLD fMRI Model

For structural T2*MRI, the source of susceptibility distribution is attributed to the nonheme iron store, denoted by $\chi_{struc}(x,y,z)$. For dynamic BOLD fMRI, the total susceptibility distribution includes additional functional heme-iron contribution, as expressed by $\chi_{total}(x,y,z,t)=\chi_{struc}(x,y,z)+\chi_{func}(x,y,z,t)$ (7)

where the time-dependent susceptibility $\chi_{func}(x,y,z,t)$ is due to the neurovascular-coupled BOLD process. We express the susceptibility dynamics associated with a BOLD activity by [18, 40]

$\chi_{func}(x,y,z,t)=\chi_{blood}\cdot V(x,y,z)\cdot NAB(x,y,z,t)$ $\chi_{blood}=Hct\cdot\chi_{RBC}+(1-Hct)\cdot\chi_{plasma}$ $\chi_{RBC}=\chi_{oxy}+(\chi_{deoxy}-\chi_{oxy})(1-Y)$ (8)

where Y denotes oxygenation level, $H_{ct}$ the blood hematocrit, $V(x,y,z)$ the vasculature-filled region, $NAB(x,y,z,t)$ the neuroactive blob which is modulated by the external stimulation, $\chi_{plasma}$ the magnetic susceptibility of blood plasma, $\chi_{oxy}$ the magnetic susceptibility of oxyhemoglobin, and $\chi_{deoxy}$ the magnetic susceptibility of deoxyhemoglobin with $\chi_{deoxy} - \chi_{oxy} = 0.27 \times 4\pi \times 10^{-6}$ (SI unit). For a BOLD process, we represent a BOLD state in terms of susceptibility perturbation in reference to a baseline state, denoted by $\Delta\chi(x,y,z,t)$, as expressed by $$\Delta\chi(x,y,z,t) = (\chi_{deoxy} - \chi_{oxy})(1-Y) \cdot Hct \cdot V(x,y,z) \cdot NAB(x,y,z,t) \quad (9)$$

The susceptibility perturbation due to a functional activity is the underlying source of BOLD fMRI. Therefore, we can consider the BOLD fMRI as an application of T2*MRI technology to dynamic functional imaging by repeating the T2*MRI procedure for a timeseries of snapshot captures. It is noted that the 4D dataset represents a timeseries of 3D snapshot volumes.

Mismatch Between MR Magnitude Image and χ Source

We have found that there are two pitfalls inherent to the MR-magnitude-based image analysis [19], one is the magnitude's non-negativity nature which confounds the negative susceptibility values and positive susceptibility values; the other is an edge effect associated with the voxel signal formation, which manifests a central dip at a local relative plateau on a fieldmap. As a consequence of non-locality and nonlinearity associated with T2*fMRI, we conclude that the MR magnitude is not an exact representation of the susceptibility source. Fortunately, we have also found [17] that the MR phase image can be used for χ tomographic reconstruction by CIMRI.

In what follows, our description is based on a numerical simulation of T2*MRI. For dynamic functional imaging, the T2*MRI simulation can be considered as a snapshot capture of dynamic BOLD fMRI.

Considering a T2*MRI procedure as a 3D imaging process, we can numerically assess the T2*MRI model by numerical simulation [39, 41, 42]: predefining a susceptibility source, carrying out the forward T2*MRI procedure and producing a complex-valued MR image, and then comparing the output image with the predefined input source. In this way, we can quantitatively show that neither the MR magnitude image nor the MR phase image can exactly reproduce the susceptibility source. In other words, based on numerical simulations we will conclude that the MR image is not a tomographic reproduction of the susceptibility source.

Given a predefined input source (χ) and the calculated output (complex image), we can quantitatively compare the MR magnitude with χ by a spatial correlation as defined by $$corr(A_{:,;}T_E) = \frac{cov\{A(:,;T_E), \chi(:)\}}{std\{A(:,;T_E)\} std\{\chi(:)\}} \quad (10)$$

where $A(:;T_E)$ represents the lexicographically ordered 1D array of the 3D array $A(x,y,z,T_E)$, $\chi(:)$ the 1D lexicographic array of $\chi(x,y,z)$, cov the covariance, std the standard deviation. In Eq. (10), $T_E$ is retained as an explicit parameter to remind the $T_E$-dependence of MR magnitude image. This correlation for matching two patterns is invariant to grayscale normalization (peak=1 is not required), and it produces a value for matching goodness in a range from 0 (completely different) to 1 (perfect matching with a difference of constant factor).

The predefined χ source and the calculated magnitude image are shown in FIG. 2. The quantitative measures of pattern matches for $T_E$ in a range of [0, 60] ms, two vessels sizes (intravoxel structures), and three spatial resolutions are shown in FIG. 3. FIG. 2 shows (a) a predefined 3D χ distribution (16 z-slices of Gaussian blob), and (b) the magnitude image of the T2*MRI simulation. FIG. 3 shows the spatial correlations between the T2*MRI magnitude (denoted by A) and the predefined χ distribution for two intravoxel vasculatures (2-um-radius in (a1) and 4-um-radius in (a2)) and for three voxel sizes (see legend).

The simulation results show that: 1) the pattern match between MR magnitude image and χ source gives rise to a correlation about 0.90, which is affected by voxel size (image resolution), vessel size, and echo time; and 2) a long $T_E$ is preferred to reduce the mismatch.

The simulation was done for a Gaussian-shaped χ distribution (predefined ground truth). In practice, a χ source may assume negative susceptibility value (due to negative diamagnetism of water and blood's diamagnetic oxyhemoglobin). Therefore, we conclude the T2*MRI magnitude image is not an exact representation of the susceptibility source.

As mentioned above, we may explain the mismatch between the magnitude image and the susceptibility source from the following aspects: 1) The MR magnitude image suffers from two pitfalls: non-negativity and edge effect; 2) the process from susceptibility source to MR image acquisition is nonlinear (the summation of complex spin precession phasors is somewhat nonlinear [39], and the complex modulo operation is a severely nonlinear operation).

Morphometric Difference Between Fieldmap (or MR Phase) and χ Source

Considering Eq. (2) as a 3D imaging system, we can describe its 3D imaging transform through the characteristics of its 3D convolution kernel $h_0(r)$. It can be shown that $$\begin{cases} \int\int\int_{(x,y,z)} h_0(x,y,z) dx\,dy\,dz = H_0(0,0,0) & \text{(filter DC} < 1) \\ \int\int\int_{(x,y,z)} |h_0(x,y,z)| dx\,dy\,dz \gg H_0(0,0,0) & \text{(bipolar-valued kernel)} \end{cases} \quad (11)$$

where $H_0(k_x,k_y,k_z)$ is the Fourier transform of $h_0(x,y,z)$ (defined in Eq. (3)). Usually the DC term of the standard 3D filter $H_0(k_x, k_y, k_z)$ assumes $H_0(0,0,0) = 1/3$ (when 0/0=0 is used in Eq. (11)). From the viewpoint of image processing [43], a convolution kernel $h_0(x,y,z)$ that possesses the properties in Eq. (11) serves as a 3D texture enhancer ($H_0(0,0,0)=0$ for texture detector). In FIGS. 4(a) and (b), we visualize the 3D kernel by 3D isosurfaces in (a) and a 2D slice in (b). The textural enhancement interpretation is illustrated in FIG. 4(c), where the template of bipolar-valued quadruple lobes can produce a large value in the fieldmap of a quadruple-patterned susceptibility distribution while greatly suppressing a local plateau. A texture enhancer can serve as an edge enhancer as well, as illustrated with a standard edge detector in FIG. 4(d), but is not optimal for edge detection. That is, the 3D convolution with a bipolar-valued kernel plays a 3D spatial derivative to some extent. FIG. 4 shows: (a) visualization of the 3D convolution kernel $h_0(x,y,z)$ with three isosurfaces at isovalues of {0, 0.8, −0.8}; (b) a 2D quadruple pattern at a longitudinal plane at $h_0(x,0,z)$, (c) a digital texture detector associated with (b); and (d) a standard 2D digital edge detector. The 3D $h_0(x,y,z)$ is interpreted as a 3D texture template which can enhance edges and boundaries.

Some characteristics of the 3D kernel $h_0(x,y,z)$ are summarized as follows [17, 19]:

1) It is of 3D spread distribution (not a point delta function), which explains the non-local property of the fieldmap and MRI phase image.
2) It is a 3D bipolar-valued kernel (not a unimode distribution like a Gaussian shape) and it manifests a 3D texture enhancer as understandable from Eq. (11) and FIGS. 4(b) and (c). Therefore, it is not surprising that the phase image appears noisy. It is noted that the fieldmap of a uniform $\chi$ distribution will be reduced by a factor of $\frac{1}{3}$ ($=H_0(0,0,0)$) during the convolutional magnetization.
3) It bears a 3D zerosurface for $h_0(r)=0$ (see FIGS. 4(a) and (c)), which means the deconvolution is an ill-posed inverse problem.
4) It is anisotropic, which explains the orientation dependence in fieldmap and MRI image.
5) It is of radial symmetry about the origin and revolution symmetry about z-axis (see FIG. 4(a)).

The 3D convolution kernel in FIG. 4 is an unusual integral kernel because of its bipolar-valued multilobes, anisotropic spreading, and 3D zerosurface embedment. Usually, a convolution kernel for image blurring assumes a nonnegative distribution, like a Gaussian-shaped point spread function and a boxcar-shaped motion blurring function. In this report, we describe the fieldmap establishment by a 3D convolution model with a kernel of bipolar-valued multilobes, thereby we can solve the inverse problem (deconvolution) in the framework of image deconvolution restoration. To our knowledge, we are the first time to address the 3D $\chi$ reconstruction problem by extending the 2D image deconvolution restoration technique (TV regularized iteration, as will be presented later) and dealing with the unusual 3D convolution kernels.

Due to the 3D convolution of the $\chi$ source with the 3D unusual kernel in FIG. 4, we explain the morphometric difference between the $\chi$ source and the fieldmap, as demonstrated in FIG. 5. FIG. 5 shows a demonstration of the morphometric difference between a Gaussian-shaped $\chi$ distribution in (a) and its fieldmap in (b). The 3D volume is represented by 32×32×32 matrix, only z=1:16 slices are displayed (z=16 at the central z-slice). It is noted the conspicuous morphometric discrepancy between the fieldmap and the susceptibility map is due to a 3D convolution transformation.

Susceptibility Map Reconstruction from MR Phase Image

In FIG. 1, we decompose a T2*MRI procedure into two modules and diagram the forward procedure by downward arrows and the inverse procedure by upward arrows. In particular, we describe the two-step inverse mappings (from MR phase image to the susceptibility source) by CIMRI (indicated in a circle). For more clarity, we re-diagram the CIRMI model in FIG. 6. FIG. 6 shows the CIMRI model (diagrammed with solid arrows). It consists of two inverse mappings: fieldmap calculation from MR phase image and $\chi$ reconstruction from the fieldmap. There are three solvers for $\chi$ reconstruction from fieldmap: filter truncation, matrix inverse, and TV iteration (our proposal). The forward MRI is diagrammed with rightward arrows. As diagramed in FIG. 6, we decompose the forward MRI procedure into two steps:

Step 1. Fieldmap establishment $b(x,y,z)$ by magnetization of the susceptibility distribution $x(x,y,z)$ in a main field $B_0$, as expressed by Eq. (2).

Step 2. Complex-valued image generation $C(x,y,z)$ by intravoxel dephasing, as expressed by (Eq. (4)).

From the complex image, we obtain the magnitude image and phase image by Eq. (5). We reconstruct the $\chi$ source by a CIMRI model in FIG. 6. Reversing the forward MRI procedure, the CIMRI consists of two inverse mappings: (i) fieldmap calculation from MR phase image, (ii) $\chi$ calculation from fieldmap. The two inverse mapping steps are addressed below with a numerical simulation.

Inverse Step 1: From MR Phase Image to Fieldmap

By numerical simulation, we find that the MR phase image can, in fact, be considered as a faithful reproduction of fieldmap in small angle regime [19, 39] (which is reachable by using a small $T_E$ (<30 ms)). For quantitative match assessment, we can compare the MR phase image with the precomputed fieldmap (an intermediate stage of MRI procedure) by $$\text{corr}(P, b; T_E) = \frac{\text{cov}[P(:;T_E), b(:)]}{\text{std}[P(:;T_E)]\text{std}[b(:)]} \quad (12)$$

The simulation results are shown in FIG. 7 for image visualization and in FIG. 8 for quantitative correlation measures. FIG. 7 shows (a) precomputed fieldmap (resulting from a predefined neuroactive blob), and (b) the phase image of T2*MRI simulation. It is noted that the MR phase image can faithfully represent the fieldmap. FIG. 8 shows the spatial correlations between the MR phase image and the precomputed fieldmap (see FIG. 7) for two intravoxel vasculatures (2-um-radius in (a1) and 4-um-radius in (a2)) and for three voxel sizes (see legend).

Under the condition of small angle regime, we can simplify the fieldmap calculation from MR phase image [19, 39] by $$b(x,y,z;T_E) = c \cdot P(x,y,z;T_E) \text{ with } c = \text{const (in small angle regime)} \quad (13)$$

We point out that a MR scanning with long $T_E$ and in a high main field may violate the small angle regime, where the linear approximation is invalid, and the phase angle in the complex image may get wrapped (with a foldback of $2\pi$). In such scenarios, a phase unwrapping procedure is necessary for phase image calculation.

The simulation results in FIGS. 7 and 8 show that: 1) The phase image is almost an identical reproduction of the fieldmap in small angle regime (a small $T_E$ is required); 2) a long $T_E$ will increase the mismatch, thus not desirable (Note: this requirement is in conflict with the magnitude matching in FIG. 3 where a long $T_E$ is desirable). It is noted that it is irrational to compare the MR phase image with the $\chi$ source, because they are different by a 3D convolution in Eq. (2); so we need to proceed with inverse Step 2.

Inverse Step 2: From Fieldmap to Susceptibility Source

Based on our literature review above, we can classify the types of solvers for the inverse problems of "from fieldmap to susceptibility source" into three categories:

Solver Type 1: 3D filter truncation. This method suffers stripe effect and image energy shift.

Solver Type 2: Matrix inverse. This method is limited by a dimensionality curse, that is, it cannot accommodate a large 3D matrix. (a small 3D matrix, say 16×16×16, cannot offer meaningful image features in a large FOV).

Solver Type 3. 3D TV iteration (our preferred method). This method can produce an excellent image restoration without the sufferings as confronted in previous two methods. The theory, algorithm, and implementation are addressed below.

The three different 3D deconvolution solvers are diagrammed in FIG. 6.

Based on numerical simulation and phantom experiment [17, 18], we conclude that the split Bregman TV iteration algorithm outperforms the others solvers in the following aspects: 1) It preserves edges; 2) It denoises the data such that there is no need to render image smoothing a priori (Note that the TV iteration method was originally developed for 2D image denoising and that smoothing is prone to suppress image features); 3) It can accommodate large 3D phase maps per se without a convolutional matrix conversion; and 4) It is an iteration algorithm that can produce a stable optimal restoration by avoiding the divide-by-zero problem, and in particular, the split Bregman iteration guarantees fast convergence.

The 3D deconvolution associated with the CIMRI involves a point magnetic dipole kernel, which is in nature of 3D distribution. Therefore, CIMRI is optimal for volumetric susceptibility reconstruction from a MR phase volume. In practical implementation, the MR phase volume can be obtained by stacking 2D slices acquired by an EPI sequence. Usually, the slice-stacked volume is anisotropic (in-plane resolution is different from the across-plane resolution). An isotropic volumetric SM reconstruction can be achieved by acquiring an isotropic MR phase volume with isotropic voxels at a zero oblique angle and with no inter-slice gap. For dynamic brain BOLD fMRI study, the inter-slice time lag effect can be eliminated by using an echo volume imaging (EVI) sequence.

TV-Regularized 3D Deconvolution Algorithm

In recent years, the total variation (TV) iteration has been proven to be a very successful image restoration technique. However, the TV iteration methods have only been applied to 2D image restoration (including grayscale image and color vector image) under a regular blurring kernel (a centralized nonnegative distribution). In this subsection, according to the present invention, we generalize the TV-regularized iteration algorithm to accommodate our 3D deconvolution problem, which is characteristic of an unusual 3D convolution kernel of bipolar-valued quadruple lobes.

Mathematically, the TV norm for 3D $x(r)$ is defined as $$\|x\|_{TV} \equiv \sup\left\{\int_\Omega x(r)\nabla \cdot g(r)dr, \|g\|_\infty \leq 1\right\} \quad (14)$$

where g denotes a vector functional variable that is bounded by $|g|\leq 1$. Strictly speaking, $\|x\|_{TV}$ is a semi-norm for that $\|x\|_{TV}=0$ is allowed for $\chi\neq 0$. For a smooth 3D function $\chi(r)$, the TV norm is also given by $$\|x\|_{TV} = \int_\Omega |\nabla x(r)|dr = \int_\Omega \sqrt{|\nabla_x(r)|^2 + |\nabla_y(r)|^2 + |\nabla_z(r)|^2}\, dr \quad (15)$$

Assuming a Gaussian noise model for $\epsilon(r)$, we can solve the inverse problem in Eq. by a TV-regularized unrestraint minimization problem [44-47], as expressed by $$\chi(r) = \min_{r\in BV} \|x(r)\|_{TV} + \frac{\lambda}{2}\|B_0 h_0(r)*\chi(r) - b(r)\|_2^2 \quad (16)$$

where BV is a bounded variation function space, and $\lambda$ is the Lagrange multiplier or the regularization parameter. The TV regularization methodology lies in its searching over all possible distributions ($\chi\in BV$) to find an optimal distribution $\chi^*$ such that it minimizes the TV norm and the data fidelity error simultaneously.

The algorithm implementation of Eq. (16) is nontrivial. Recently researches show that the TV iteration can be effectively implemented by a split Bregman algorithm [21, 44, 48, 49]. The basic idea of the split Bregman algorithm is to transform a constrained optimization problem into a series of unconstrained subproblems; then to solve each subproblem by a Bregman-distance-based iteration. The Bregman distance (or Bregman divergence [50]) is defined for an objective function $J(u)$ as $$D_J(u,v) \equiv J(u) - J(v) - \langle \partial J(v), u-v\rangle \quad (17)$$

where the bracket $\langle,\rangle$ represent inner product, $\partial J(v)$ is an element of the subgradient of function $J$ at $v$. Intuitively, the Bregman distance in Eq. (17) can be thought of as the difference between the value of function $J$ at point $u$ and the value of the first-order Taylor expansion of $J$ around point $v$ evaluated at point $u$. It has been approved that the use of Bregman distance in Eq. (17) can ensure fast convergence.

Let $J(\chi)=\|\chi\|_{TV}$ and set the initial $\chi_0=0$, then the Bregman iteration produces a series $\{\chi_k, k=1,2,\ldots\}$ by $$\chi_{k+1} = \arg\min_{\chi\in BV}\left\{ D_{\|\cdot\|_{TV}}(\chi, \chi_k) + \frac{\lambda}{2}\|B_0 h_0 * \chi - b\|_2^2\right\} \quad (18)$$

$$D_{\|\cdot\|_{TV}}(\chi, \chi_k) = \|\chi\|_{TV} - \|\chi_k\|_{TV} - \langle \partial\|\chi_k\|_{TV}, \chi - \chi_k\rangle$$

It has been shown that the Bregman iteration can also be equivalently achieved by introducing an auxiliary variable $v$ and carrying out the following iteration (with $v_0=0$ for initial setting)

$$\chi_{k+1} = \arg\min_{\chi\in BV}\left\{\|\chi\|_{TV} + \frac{\lambda}{2}\|B_0 h_0 * \chi - b - v_k\|_2^2\right\} \quad (19)$$

$$v_{k+1} = v_k + (b - B_0 h_0 * \chi_{k+1})$$

In the result, the Bregman iteration produces a series of $\{(\chi_k, v_k), k=1,2,\ldots\}$. It is noted that $v_k$ is updated by adding back noise, which is called "comeback noise" or "residual noise". The iteration is stopped when a criterion is satisfied. The "comeback noise" is sparse, which may vary from iteration to iteration.

For solving our 3D deconvolution problem, we need to extend the Bregman iterations in Eq. (18) or (19) to accommodate a 3D minimization problem. We adopt the split Bregman iteration algorithm to handle the inverse problem by splitting it into three subproblems with respect to interim variables {'d', 'v', '$\chi$'}, where 'd' and 'v' are auxiliary variables, and the '$\chi$' is the variable for our solution. For TV-regularized 2D image restoration, we refer readers to previous work [44, 46, 49-52] for mathematical details. For 3D susceptibility volume reconstruction from a 3D fieldmap by solving the 3D deconvolution problem in Eq. (2), we invented a 3D TV-regularized split Bregman TV iteration algorithm [17] according to:

$$\chi^{recon} = \min_{d,v,\chi} \|d(r)\|_{TV} + \frac{\lambda}{2}\|B_0 v - b\|_2^2 + \frac{\gamma_1}{2}\|d - \nabla\chi - a_1\|_2^2 + \frac{\gamma_2}{2}\|v - h * \chi - a_2\|_2^2 \quad (20)$$

with $d = \nabla\chi$ and $v = h * \chi$ where the parameters {'$\gamma_1$', '$\gamma_2$', '$a_1$', '$a_2$'} are introduced for algorithm implementation and fast convergence. It is noted that the 3D convolution in Eq. (20), such as $h*\chi$, can be implemented by 3D filtering in Fourier domain. However, the filter H(k) is not truncated at all, which is different from the inverse filtering solver with a truncated filter ("filter trunc" solver).

In iteration implementation, the 3-subproblems are solved one at a time (with respect to one of $\{d, v, \chi\}$ while keeping the other two fixed). The following input is required: 3D fieldmap b(x,y,z), 3D convolution kernel h(x,y,z) (corresponding to 3D filter by h(x,y,z)=IFT[H($k_x,k_y,k_z$)]), regularization parameter $\lambda$ (adjustable), and convergence control tolerance of error (preset), and maximum iteration number allowed (preset). In summary, the split Bregman TV iteration algorithm for the minimization problem in Eq. (20) can be summarized by the following algorithm [17, 53]:

Initialize $\chi=v=a_2=0$, $d=b_1=0$
Do
    Minimization of $\chi$-subproblem with (d,v) fixed;
    Minimization of d-subproblem with ($\chi$,v) fixed;
    Minimization of v-subproblem with ($\chi$,d) fixed;
    Update $a_1:=a_1+\nabla\chi-d$
    Update $a_2:=a_2+h*\chi-v$
While "not converged"

T2'-Effect Imaging Scheme

It is known that gradient-echo (GE) imaging is used to capture the spin precession dephasing signals by a radio-frequency tipping pulse (a 90° tipping angle or less), and that spin-echo (SE) imaging can refocus static transverse dephasing through the use of an additional 180° pulse. Since the non-refocusable random effect appears in both the GE and SE signals, we are inspired to remove the dynamic random part (albeit incomplete) and extract the refocusable static inhomogeneous effect (also described as T2' effect). The principle of our T2'-effect magnetic resonance imaging (T2'MRI), is illustrated in FIG. 9, with two echoes of different $T_E$'s. FIG. 9 shows an illustration of T2'-effect signals with two echo times. (a) A pulse sequence of a 90° tipping pulse and two 180° refocusing pulses (one with $T_{E1}$ and other with $T_{E2}$); (b) T2* SE signal (echoes in black) and T2* GE signal (echoes in red). The T2* SE signals are generated by a pair of 90° and 180° pulses. The T2* GE signals are generated by only a 90° pulse and a reversal readout gradient (not drawn).

Let $b_{T2*}(x,y,z)$ denote the fieldmap responsible for T2* image formation. Then the complex-valued image acquired by GE imaging with echo time $T_E$ can be expressed by $$C_{GE}(x,y,z;T_E) = \iiint_{(x',y',z') \in \Omega(x,y,z)} \exp\left\{-i\gamma \int_0^{T_E} b_{T2}(x'(t), y'(t), z'(t)) dt\right\} dx'dy'dz' \tag{21}$$

Correspondingly, the complex-valued image acquired by SE imaging is given by $$C_{SE}(x,y,z;T_E) = \iiint_{(x',y',z') \in \Omega(x,y,z)} \exp\left\{-i\gamma \int_0^{T_E/2} b_{T2}(x'(t), y'(t), z'(t)) dt\right\} \exp\left\{i\gamma \int_{T_E/2}^{T_E} b_{T2}(x'(t), y'(t), z'(t)) dt\right\} dx'dy'dz' \tag{22}$$

We can decompose the proton-experienced T2* fieldmap ($b_{T2*}$) into non-random static inhomogeneity part ($b_{T2'}$), random spin-spin interaction part ($b_{T2}$), and random diffusion perturbation part ($b_{diffu}$), that is $$b_{T2*}(x(t),y(t),z(t))=b_{T2'}(x,y,z)+b_{T2}(x(t),y(t),z(t))+b_{diffu}(x(t),y(t),z(t)) \tag{23}$$

It is known that the static dephasing is refocusable by a 180° pulse, and that the dynamic dephasing associated with the random spin-spin interaction and diffusion motion are non-refocusable. We can describe these facts by $$b_{T2'}(x,y,z)=b_{T2'}(x(t),y(t),z(t))=b_{T2'}(x(t+T_E/2),y(t+T_E/2),z(t+T_E/2)) \text{ (refocusable)}$$

$$b_{T2}(x(t),y(t),z(t)) \neq b_{T2}(x(t+T_E/2),y(t+T_E/2),z(t+T_E/2)) \text{ (non-refocusable)}$$

$$b_{diffu}(x(t),y(t),z(t)) \neq b_{diffu}(x(t+T_E/2),y(t+T_E/2),z(t+T_E/2)) \text{ (non-refocusable)} \tag{24}$$

Then, the complex SE image is expressed by $$C_{SE}(x,y,z;T_E) = \tag{25}$$

$$\iiint_{(x',y',z') \in \Omega(x,y,z)} \exp\left\{-i\gamma \int_0^{T_E/2} [b_{T2'}(x',y',z') + b_{T2}(x'(t), y'(t), z'(t)) + b_{diffu}(x'(t), y'(t), z'(t))] dt \right.$$

$$+ i\gamma \int_{T_E/2}^{T_E} [b_{T2'}(x',y',z') + b_{T2}(x'(t), y'(t), z'(t)) + b_{diffu}(x'(t), y'(t), z'(t))] dt \right\} dx'dy'dz' =$$

$$\iiint_{(x',y',z') \in \Omega(x,y,z)} \exp\left\{i\gamma \int_0^{T_E/2} [b_{T2}(x'(t), y'(t), z'(t)) - b_{T2}(x'(t+T_E/2), y'(t+T_E/2), z'(t+T_E/2)) + b_{diffu}(x'(t), y'(t), z'(t)) - b_{diffu}(x'(t+T_E/2), y'(t+T_E/2), z'(t+T_E/2))] dt\right\} dx'dy'dz'$$

Obviously, for a special ideal case in absence of dynamic T2 random effects and diffusion effects, the T2* SE refocusing gives rise to $$C_{SE}(x,y,z;T_E) = \iiint_{(x',y',z') \in \Omega(x,y,z)} \exp\left\{-i\gamma \int_0^{T_E/2} b_{T2}(x',y',z') dt \right. \tag{26}$$

$$\left. + i\gamma \int_{T_E/2}^{T_E} b_{T2}(x', y', z') dt\right\} dx'dy'dz' =$$

$$\iiint_{(x',y',z') \in \Omega(x,y,z)} dx'dy'dz' = |\Omega(x, y, z)| \text{ (perfect refocusing)}$$

Since the T2* GE signal consists of both the T2 effect (random spin-spin interaction and spin diffusion) and T2' effect (static inhomogeneous field) and the T2* SE signal only consists of non-refocusable random T2 effect (that is, the T2* SE signal is the T2-effect signal), it is possible the separate the T2'-effect signal from T2* GE signal by signal decomposition. Concerning the fact that we are dealing with complex-valued MR images, we use complex division to calculate the T2'-effect complex image, as given by $$C_{T2'}(x,y,z;T_E)=C_{GE}(x,y,z;T_E)/C_{SE}(x,y,z;T_E) \tag{27}$$

which is called T2'-effect imaging scheme.

Assuming exponential models for the T2* and T2 magnitude decays, we obtain the T2' magnitude decay that also reveals an exponential decay behavior, that is $$|C_{GE}(x, y, z; T_E)| = |C_{GE}(x, y, z; T_E = 0)|\exp(-T_E/T_2^*) \quad (28)$$

$$|C_{SE}(x, y, z; T_E)| = |C_{SE}(x, y, z; T_E = 0)|\exp(-T_E/T_2)$$

$$|C_{T_2'}(x, y, z; T_E)| =$$

$$\frac{|C_{GE}(x, y, z; T_E)|}{|C_{SE}(x, y, z; T_E)|} = \exp(-T_E/T_2^* + T_E/T_2) = \exp(-T_E/T_2')$$

$$1/T_2' = 1/T_2^* - 1/T_2$$

Therefore the magnitude behavior in Eq. (28) is compatible with the exponential signal intensity decay model [2]. It is seen in Eq. (28) that the maps of T2, T2* and T2' can be calculated by exponentially fitting each voxel intensity decay. The connotations of T2, T2* and T2' values for voxel signal intensity decays are illustrated in FIG. 9(b).

In this specification, we do not need to use the exponential magnitude decay models at all; instead, we are interested in the phase part of T2'-effect complex image. From the T2'-effect phase image, we can calculate the static inhomogeneous fieldmap that excludes the T2 effect, which are given by $$\angle C_{T_2'}(x, y, z; T_E) = \angle C_{GE}(x, y, z; T_E) - \angle C_{SE}(x, y, z; T_E) \quad (T_2'\text{-effect phase image}) \quad (29)$$

$$b_{T_2'}(x, y, z) = \frac{\angle C_{T_2'}(x, y, z; T_E)}{\gamma T_E} \quad (T_2'\text{-effect fieldmap})$$

It is expected that the T2' complex image will greatly remove the T2 effect and diffusion effect (albeit incomplete due to imperfect repeatability of random effect in two different times), thereby improving the χ reconstruction fidelity. In principle, our T2'-effect imaging scheme in Eq. (27) can be extended to two echo times ($T_{E1}$ and $T_{E2}$), as illustrated in FIG. 9. Because our T2'-effect imaging scheme by Eq. (27) is a complex image manipulation and it does not involves the calculations of the T2, T2* and T2' parameters, we claim that our T2'-effect imaging scheme is quite different from the T2' imaging technique as reported in [53]. More generally, the T2'MRI scheme can be extended to multi-echo imaging (with more than two echo times).

We should point out that, on one hand, the T2'MRI method cannot completely remove the random T2 and diffusion effects because of the imperfect repeatability of sheer randomness in two successive scans; on the other hand, the signals resulting from random T2 and diffusion effects are largely repeatable for different tissue types. Therefore, the T2'MRI method can remove the tissue-type-dependent T2 and diffusion effects.

3D χ Reconstructions with Specific Desirable Features

In digital image processing, the spatial structure of an image can be characterized by its spatial frequency in Fourier domain and can be modified by spatial filtering with a spatial frequency filter. After the reconstruction of a 3D χ distribution (through a TV iteration with the standard kernel $h_d(r)$), we can post-process the 3D χ source for enhancing or suppressing specific features by 3D spatial filtering with a designed filter. The typical filtering schemes include lowpass (LP), highpass (HP), bandstop (BT), and bandpass (BP). We call the post-processing of a reconstructed χ map a "post-recon filtering" approach. We will show that it is possible to accomplish the post-reconstruction filtering equivalently during the TV iteration using a designed filter, for which we call a "TV-iteration filtering" approach. In principle, both "TV-iteration filtering" approach and the "post-recon filtering" approach can produce the same results because the TV iteration algorithm is a linear procedure which allows a linear spatial filtering to be inserted in the iteration process or to be exerted after the iteration reconstruction.

Based on numerical simulation, we find that two approaches may produce similar results but are different in noise pattern due to the randomness of sparse comeback noise associated with a TV iteration. Accordingly, we developed new methods to render parallel TV iterations: one is "post-recon filtering" and the other is "TV-iteration filtering" as diagramed in FIG. 10. Since the two schemes produce the same results, we can perform an average to produce a noise-reduced result, as diagrammed in FIG. 10.

FIG. 10 shows feature-specified χ reconstruction by "post-recon filtering" and "TV-iteration filtering" approaches. The "post-recon filtering" approach is carried out by first reconstructing a χ source with standard TV iteration and then exerting a spatial filtering with a feature-specified filter $f(k)$, as diagramed in the right-hand dotted box. The "TV-iteration filtering" approach is carried out by reconstructing a χ source with a modified filter $H(k)=H_0(k)/f(k)$, as diagramed in the left-hand dotted box. Two approaches are carried out in parallel, and the two resultant χ sources are averaged to produce a noise-reduced χ source. The "filter design" part in the "TV-iteration filtering" approach (in the left-hand dotted box in FIG. 10) is drawn in FIG. 11. As one output in FIG. 11, we also convert the designed filter in Fourier domain into a convolution kernel in space domain by inverse Fourier transform (IFT). FIG. 11 shows a scheme for 3D convolution filter design. A modified kernel can be obtained by DC term reset, lowpass, highpass, and bandstop filtering. (The bandpass filtering is not shown).

In FIG. 12, we provide numerical simulations for two susceptibility filtering schemes in FIG. 10. It demonstrates that a lowpass filtering on a reconstructed susceptibility map can be equivalently achieved by "TV iteration filtering" and "post-recon filtering". Let $f_{LP}(k)=[0.6+0.4\cos(\pi k/k_{max})]$ represent the lowpass filter used for "post-recon filtering", then the same result can be achieved by "TV-iteration filtering" with a TV-iteration filter $H(k)=H_0(k)/f_{LP}(k)$, where $H_0(k)$ represents the standard magnetic dipole filter. It is noted that the post-recon filter $f_{LP}(k)$ is used in the TV-iteration filter in a reciprocal way. It is seen in FIG. 12 that the two filtering schemes produce the same results except for a difference in noise. Therefore, we can reduce the noise by average, as shown in FIGS. 12(c) and (d). FIG. 12 shows the demonstration of the equivalence of "TV-iteration filtering" and "post-recon filtering" and the noise reduction by average: (a) χ reconstruction by "TV-iteration filtering" with a TV iteration filter $H(k)=H_0(k)/f_{LP}(k)$ with $f_{LP}(k)=[0.6+0.4\cos(\pi k/k_{max})]$; (b) The "post-recon filtering" with a lowpass filter $f_{LP}(k)=[0.6+0.4\cos(\pi k/k_{max})]$; (c) the average of (a) and (b); and (d) the profiles of scanline.

Effect of DC Term Reset

As shown in Eq. (3), the 3D filter $H_0$ bears an undefined DC term at $(k_x,k_y,k_z)=(0,0,0)$. With the convention of 0/0=0, the neighborhood values around the 3D filter DC term are shown in FIG. 13. It is seen that, the setting of $H_0(0,0,0)=\frac{1}{3}$ is continuous at the $k_x k_y$-plane (in FIG. 13(b)), but not continuous along the $k_z$-axis ($H_0(0,0,k_z)=\{-0.667, \frac{1}{3}, -0.667\}$ for voxels at $(k_x,k_y,k_z)=\{(0,0,-1),(0,0,0),(0,0,1)\}$. We can reset the DC term value to provide a modified kernel for TV iteration as one approach of iteration convolution kernel design in FIG. 11. FIG. 13 shows the neighborhood of DC term of the standard filter $H_0(k)$. The DC term assumes $\frac{1}{3}$ (by convention of 0/0=0), which is continuous at the $(k_x,k_y)$ plane, but not continuous along the $k_z$-axis due to $\{-0.667, \frac{1}{3}, -0.667\}$ for voxels at $(k_x,k_y,k_z)=\{(0,0,-1),(0,0,0),(0,0,1)\}$.

From Eq. (11), it can be shown that $$\int\int\int_{(x,y,z)} c \cdot h_0(x, y, z) dx dy dz = c \cdot H_0(0, 0, 0). \qquad (30)$$

c is a constant

This indicates that if the DC term $H_0(0,0,0)$ is modified by a multiplicative constant, c, it is equivalent to multiplying the kernel by the same constant. In other words, the TV-iteration reconstruction with a modified filter of a scaled DC term will produce similar result that is different mainly by a scale of c, which we call "scale invariance" (a built-in functionality of TV-regularized iteration). Due to the comeback noise effect associated with the TV iteration, two TV iterations with different DC terms will produce similar results that are different by noise patterns (randomness and sparseness). Therefore, we can make use of this "scale invariance" phenomenon for noise reduction purpose (as will be addressed later). Numerical simulations of TV-iterated $\chi$ reconstruction with a modified $H_0$ that are different in $H_0(0,0,0)$ value are demonstrated in FIG. 14.

Although there is an uncertainty (due to 0/0) associated with the DC term of the filter $H_0(k)$, our simulation shows that: 1) $H_0(0,0,0)=0$ is not allowed; 2) The TV iteration reconstruction is insensitive to the DC term values and signs (as can be seen FIG. 14). We suggest to reset the filter DC term value in a range of $0.1<|H_0(0,0,0)|<1$ to provide a modified kernel to TV iteration. The $\chi$ reconstructions from different DC values can be carried out in parallel, and then averaged over the multiple reconstructions, which suppresses the noise. FIG. 14 shows the effect of DC term reset ($H(0,0,0)=\{1, \frac{1}{3}, -1\}$) on $\chi$ reconstruction. Cross-sections for reconstructed cylinders with (a) DC=1, (b) DC=$\frac{1}{3}$, and (c) DC=-1. The profiles of the scanline (only provided in (a)) is shown in (d). It is seen that the DC value of $H_0(k)$ has little influence on TV-regularized $\chi$ reconstruction (as described "scale invariance"). To some extent, the DC reset plays a seed of randomness in parallel TV iteration reconstructions.

Reciprocal Filter

We have shown that the susceptibility source map can be reconstructed by a TV-regularized split Bregman iteration algorithm (see, e.g., Eq. (20)). However, the solution can be changed by using a new convolution kernel, h(r), that is a modification of the standard dipole kernel $h_0(r)$. Suppose the use of the standard point magnetic dipole kernel $h_0(r)$, or its modified version h(r), produces a solution $\chi_0^{recon}$ (or $\chi^{recon}$, respectively), that is $$\begin{cases} \chi_0^{recon} = \min_{d,v} \|d(r)\|_{TV} + \frac{\lambda}{2}\|B_0 - b\|_2^2 + \\ \frac{\gamma_1}{2}\|d - \nabla\chi - a_1\|_2^2 + \frac{\gamma_2}{2}\|v - h_0 * \chi - a_2\|_2^2 \\ \chi^{recon} = \min_{d,v} \|d(r)\|_{TV} + \frac{\lambda}{2}\|B_0 v - b\|_2^2 + \\ \frac{\gamma_1}{2}\|d - \nabla\chi - a_1\|_2^2 + \frac{\gamma_2}{2}\|v - h*\chi - a_2\|_2^2 \end{cases} \qquad (31)$$

If $\chi^{recon}$ is more desirable than $\chi_0^{recon}$, then we can obtain $\chi^{recon}$ from $\chi_0^{recon}$ by performing a 3D spatial filtering with a filter $f(k)$ (or by a 3D convolution with a kernel $f(r)$), that is $$\chi^{recon}(k) = \chi_0^{recon}(k) \cdot f(k) \text{ (3D filtering)}$$

or $\chi^{recon}(r) = \chi_0^{recon}(r) * f(r)$ (3D convolution)   (32)

We call Eq. (32) a "post-recon filtering" because $\chi^{recon}$ is obtained by filtering the susceptibility source $\chi_0^{recon}$ (that was reconstructed by using the standard kernel $h_0(r)$). Alternatively, as seen in Eq. (31), $\chi^{recon}$ can also be directly reconstructed from the fieldmap by using a modified filter H(k) (corresponding to a modified kernel h(r)). It can be shown that, the filter (or kernel) modification is given by $$H(k) = \frac{H_0(k)}{f(k)} \qquad \text{(modified filter)} \qquad (33)$$

or $h(r) = IFT[H(k)] = h_0(r) * IFT[1/f(k)]$ (modified kernel)

where IFT denotes Inverse Fourier Transform. When the modified filter H(k) obtained in Eq. (33) is used in the 3D susceptibility reconstruction by the TV iteration in Eq. (31), we say that the 3D susceptibility is reconstructed by a "TV-iteration filtering". We will show that the TV-regularized iteration convolution scheme using a new kernel h(r) (corresponding to TV-iteration filtering using a new filter H(k)) (in Eq. (33)) to reconstruct a susceptibility source $\chi^{recon}$ by Eq. (31), such that is has the same features as resulting from post-recon filtering using a filter $f(k)$ in Eq. (32).

As a result, we can achieve a feature-specific susceptibility reconstruction by at least two different ways: 1) post-recon filtering using a filter $f(k)$ in Eq. (32), or 2) TV-iteration filtering using a new filter H(k) in Eq. (33). It is noted in Eq. (33) that the filter used in the post-recon $\chi$ filtering is reciprocal to that used in the filter modification for TV-iteration filtering.

Convolution Kernel Design

Some typical 1D filters are shown in FIG. 15. We can use the 1D filters to modify the filter $H_0(k_x,k_y,k_z)$ along $k_x$-, $k_y$-, and $k_z$-axis: or along diagonal lines of 3D Fourier domain. FIG. 15 shows diagram for bandpass, highpass, and lowpass filtering, which is applied to a direction along $k_x$-, $k_y$-, $k_z$-axis, and radial direction k, separately and jointly. The red plots have sharp cutoffs and the black plots are smooth. which can suppress Gibbs effect.

It is known that two points in Fourier domain correspond to a collection of parallel lines in the space domain. In FIG. 16, we show that the stripe features can be exacted (or enhanced) by the designed kernels. In the presence of noise, some points on the zerosurface may escape the truncation regularization. Any two points will produce a collection of parallel lines, with the interline distance determined by the two-point distance in Fourier domain, the strength by the two-point values. In this way, we can explain the streak artifacts associated with the "filter truncation" solver. FIG. 16 shows illustrations of stripe feature extraction by designing the filters for horizontal stripe extraction (at top row), vertical stripe extraction (at middle row), and the extraction for vertical, horizontal, diagonal, and anti-diagonal stripes (at bottom row). The superimposition of numerous random stripes manifests as a clutter noise in the $\chi$ reconstructions.

In implementation of the filter design for "post-recon filtering" (in Eq. (32)), we can make a basic lowpass filter using a cosine function $$f_{LP}(k) = c_1 + c_2 \times \cos(\pi k/k_{max}) \; s.t. \; \min\{f_{LP}(k)\} > 0$$

$$f_{LP}(k) = 0.6 + 0.4 \times \cos(\pi k/k_{max}) (\text{case: } c_1 = 0.6 \text{ and } c_2 0.4) \quad (34)$$

with $k_{max} = \max\{|k|\}$
The condition for a lowpass filter is $\min\{f_{LP}(k)\} > 0$, as required by the non-singularity of $1/f_{LP}(k)$. In Eq. (34), we provide a special case of $c_1 = 0.6$ and $c_2 = 0.4$, which produces $\min\{f_{LP}(k)\} = 0.2$.

Based on a lowpass filter $f_{LP}(k)$, we can make a highpass filter by $$f_{HP}(k) = \max(f_{LP}) - f_{LP}(k) + c_0 \; s.t. \; \min\{f_{HP}(k)\} > 0$$

$$f_{HP}(k) = \max(f_{LP}) - f_{LP}(k) + 0.2 (\text{case: } c_0 = 0.2) \quad (35)$$

As required by $1/f_{HP}(k)$, we impose the highpass filter a condition of $\min\{f_{HP}(k)\} > 0$. In Eq. (35), we also provide a special case of $c_0 = 0.2$ such that $\min\{f_{HP}(k)\} = 0.2$.

Considering $f_{LP}(k)$ and $f_{HP}(k)$ obtained by Eqs. (34) and (35) are basic lowpass and highpass filters, we can also reshape them by applying a power law, that is $$f_{LP}(k;\alpha) = [f_{LP}(k)]^{\alpha}, \alpha = \{\frac{1}{2}, 1, 2, 3 \ldots\}$$

$$f_{HP}(k;\alpha) = [f_{HP}(k)]^{\alpha}, \alpha = \{\frac{1}{2}, 1, 2, 3 \ldots\} \quad (36)$$

It is noted that the filter shape can be dilated with $0 \le \alpha \le 1$ and shrunk with $\alpha > 1$. In this way, we can design different lowpass and highpass filters by selecting proper values for the parameters of $\{c_0, c_1, c_2, \alpha\}$.

In FIG. 17, we demonstrate (with a 2D slice display) a lowpass filter $f_{LP}(k)$ in (a), a squared lowpass filter $f_{LP}(k;2)$ in (b), and a highpass filter $f_{HP}(k)$ in (c), as well as 1D profiles. FIG. 17 shows demonstration of lowpass and highpass filters. It is noted the lowpass filter can be reshaped by a square operation (for example, constricted by Eq. (36) with $\alpha = 2$).

Given a post-recon filter, we can calculate the corresponding TV-iteration filter by using Eq. (33). In implementation of the filter design for "TV-iteration filtering", we can calculate the reciprocal filters $1/f_{LP}(k;\alpha)$ and $1/f_{HP}(k;\alpha)$, where the infinite should be carefully avoided through a small offset $c_{0 \to 0}$ in Eq. (35). The reciprocals of the filters in FIG. 17 are displayed in FIG. 18.

In FIG. 19, we demonstrate the TV-iterated $\chi$ reconstructions with the standard filter ($H_0(k)$), a lowpass filter ($H_0(k)/f_{LP}(k)$), and a highpass filter (($H_0(k)/f_{HP}(k)$). It is seen that the lowpass-filtering reconstruction smoothes the image, and highpass reconstruction enhances the edges. FIG. 19 shows demonstration of $\chi$ reconstructions with (a) standard filter $H(k) = H_0(k)$, (b) lowpass filter $H(k) = H_0(k)/f_{LP}(k)$ with $f_{LP}(k) = [0.6 + 0.4 \cos(\pi k/k_{max})]^2$, (c) highpass filter $H(k) = H_0(k)/f_{HP}(k)$ with $f_{HP}(k) = 1 - [0.6 + 0.4 \cos(\pi k/k_{max})]^2 + 0.2$. The profiles of the scanline (indicated in (a)) are shown in FIG. 19(d).

We also designed the bandstop (BT) and bandpass (BP) filters:

$$f_{BP}(k) = 1 - \exp\left(-\frac{|k|^2}{2\pi\sigma_1 k_{max}^2}\right) + \exp\left(-\frac{|k|^2}{2\pi\sigma_2 k_{max}^2}\right), \; \sigma_1 > \sigma_2 \; (bandpass)$$

$$f_{BT}(k) = \exp\left(-\frac{|k|^2}{2\pi\sigma_1 k_{max}^2}\right) - \exp\left(-\frac{|k|^2}{2\pi\sigma_2 k_{max}^2}\right), \; \sigma_1 > \sigma_2 \; (bandstop) \quad (37)$$

where $\sigma$ denotes the standard deviation of Gaussian distribution, which controls the shape of filter. Based on our numerical simulations, we find that the bandstop and bandpass filtering is useful for high spatial resolution $\chi$ reconstruction.

From our experience, the "post-recon filtering" by a filter $f(k)$ in Eq. (32), and the "TV-iteration filtering" by a filter $H(k)$ in Eq. (33) can achieve similar results, with a difference in residual noise. Therefore, we can safely use an average of the two to obtain a noise-reduced $\chi$ source, while maintaining the desirable $f(k)$ filtering features.

Estimation of TV Iteration Parameter ($\lambda$) by Self-Calibration Scheme

The TV-regularized deconvolution algorithm in Eq. (16) involves a regularization parameter $\lambda$, whose value should be preset for a TV iteration. For numerical simulation and phantom study, we can determine the proper values for $\lambda$ by comparing the iteration output with the predefined input (known). For phantom experiment, we can also compare the TV iteration output with the known phantom pattern, which is called system calibration in medical imaging. In practice, however, a phantom may be unavailable, or the magnetic susceptibility property of the phantom may deviate far differently from that of the imaging target. In such cases, especially for brain imaging where the brain interior susceptibility distribution remains unknown, we need find a way to estimate the TV iteration parameter value to ensure that the output of the TV iteration is a meaningful $\chi$ reconstruction.

Our research [17] has shown that the brain interior $\chi$ reconstruction is closely dependent upon the regularization parameter $\lambda$ selection; a very small $\lambda$ may result in oversmoothing effect, while a very large $\lambda$ may result in textural noise enhancement. It is noted that, although the MR magnitude image is not an exact representation of the unknown susceptibility source, it is a good estimate [17, 19]. Therefore, we can make use of the MR magnitude image as a guide for the TV iteration during the trial-and-error stage. Specifically, we can estimate the regularization parameter value by comparing the iteration output with the MR magnitude image of an unknown bio-physiological entity under MR scanning. In this way, we calibrate the $\chi$ tomographic imaging system based on the MR magnitude image of the $\chi$ source itself, without using a phantom, we can implement a self-calibration scheme for TV-regularized $\chi$ reconstruction. As a result, we developed a self-calibrated TV iteration parameter estimation scheme, which is shown in FIG. 20. FIG. 20 shows a magnitude-based self-calibration scheme for the TV regularization parameter value estimation. The MR magnitude image is used as a reference to compare with the trial TV iteration outcome, thereby determining the proper TV iteration parameter values for $\chi$ reconstruction. It is noted that the magnitude is compared with the absolute value of the susceptibility value (which can be positive or negative valued).

The "$\lambda$ adjustment" box in FIG. 20 is for estimating an appropriate value, or a range, for the regularization parameter $\lambda$, by using the MR magnitude image as a guide or an initial estimate of $\chi$ source. Specifically, by comparing (usually by visual comparison) a reconstructed susceptibility source with the MR magnitude image during the trial iteration, we can estimate proper values for the TV regularization parameter. It is understandable that the MR magnitude image is not identical to the reconstructed susceptibility source (due to the magnitude's nonnegativity and T2*MRI nonlinearity). It is noted that we take into account the magnitude's non-negativity by comparing the magnitude image with the absolute value of reconstructed susceptibility. Although the magnitude image is somewhat different from the susceptibility source, it is good enough to estimate the TV regularization parameter $\lambda$, because $\lambda$ may assume a wide range of values. Given an appropriate estimate of TV regularization parameter, the TV iteration convergence can reduce the iteration error, and produce a more direct and truthful result. In conclusion, for a single T2*MRI complex image, we can reconstruct its magnetic susceptibility distribution from the phase image by implementing a CIMRI tomographic procedure with a TV regularized iteration algorithm, in which we can make use of the MR magnitude image for calibrating (choosing) the TV regularization parameter, $\lambda$, without requiring use of an auxiliary phantom calibration.

Noise Reduction Scheme by Parallel TV Iterations and Average

As reported above, the TV iteration may bring back sparse noise in $\chi$ reconstruction (see Eq. (19)). The comeback noise is different from the structure noise pattern in the fieldmap (phase image), that is, two iteration processes that are different by parameter settings may produce similar results that are different by residual noise pattern. Therefore, we developed a noise reduction strategy for $\chi$ reconstruction by multiple TV iterations, followed by a multi-reconstruction average. Since different TV iterations can be carried out in parallel computation, we call it "parallel TV iterations". By incorporating the DC term resetting approach, we implemented a parallel TV iteration scheme, as illustrated in FIG. 21. FIG. 21 shows a noise reduction strategy by parallel TV iteration (using different parameter values) and multiple reconstruction average. In summary, the purpose of performing multiple $\chi$ reconstructions by parallel TV iterations is for noise reduction by averaging.

In implementation, the TV regularization parameter $\lambda$ may assume a large range of values, typically from 20 to 1000, which is problem-specific. Therefore, a variety of $\lambda$ values can be used for TV iterations to produce a multiple of $\chi$ reconstructions that are similar and different in residual noise. By averaging over the multiple $\lambda$-variation $\chi$ reconstructions, we obtain a noise-reduced $\chi$ source. The $\lambda$-varied $\chi$ reconstructions can be used together with the scale-invariant $\chi$ reconstructions (through resetting of DC term values). The variations of auxiliary parameters $\gamma_1$ and $\gamma_2$ can also be used for multiple $\chi$ reconstructions (Typically, the values of $\gamma_1 = \frac{1}{5}$ and $\gamma_2 = \frac{1}{8}$ are preset). In general, any and all of the variations of parameters {regularization $\lambda$, DC term $H_0(0,0,0)$, auxiliary parameter $\gamma_1$ and $\gamma_2$} can be used for multiple $\chi$ reconstructions. The multiple reconstructions are carried out in parallel (at the cost of doing multiple computations). Then, the multi-reconstruction average is performed to produce a noise-reduced $\chi$ source.

In FIG. 22, we demonstrate the noise reduction strategy by reconstructing five different $\chi$ reconstructions with $\lambda = \{50,$ 100, 200, 500, 1000}, and then calculating their average ("multi-recon average"). In each iteration, the $\chi$ reconstruction suffers sparse "residual noise" (or comeback noise associated with Bregman iteration), as indicated in dotted circles. The average of multiple reconstructions ((a1) through (a5) with different X values) can effectively reduce the noise, as shown in (b). We mark the sparse comeback noise in dotted circle to show that the TV iterations with different regularization parameter values bring back different residual noises. Therefore, the multi-reconstruction average at the cost of multiple computations can effectively suppress the comeback noise. Quantitative noise reductions and scanline profiles are shown in FIG. 23. The noises (calculated by standard deviation) are provided in the figure's legend.

There are multiple reasons why we invented the "3D TV iteration filtering with a modified filter" to implement the post-recon filtering (reconstruction by using $h_0(r)$) followed by spatial filtering, as follows:

(a) TV iteration can reconstruct the susceptibility map with a powerful de-noising capacity, however, TV iteration may bring back sparse random noises in the uniform region of reconstructed susceptibility map (as demonstrated in simulations).

(b) By using a collection of modified filters $h(r)$ (which are somewhat different, for example, in different DC-term values), we can obtain a collection of susceptibility map reconstructions that have very similar results (due to iteration convergence), but also have different random sparse "comeback" noises. Therefore, we can average the multiple reconstructions to reduce the overall noise.

(c) The multiple TV iteration reconstructions with different $h(r)$ can be executed in parallel processing (using the same MR phase image, but with many $h(r)$ that are somewhat different in their settings).

These advantages are not available by using only "post-recon filtering".

4D Susceptibility Reconstruction

Based on 3D $\chi$ reconstruction by CIMRI, we can extend to 4D $\chi$ dataset reconstruction, with each snapshot volume of 4D $\chi$ dataset reconstructed from the corresponding phase volume in the 4D complex dataset. For a dynamic functional imaging study by BOLD fMRI, which is always subject to a stimulus paradigm, denoted by task(t), we can make use of the known stimulus task(t) to ensure a meaningful 4D susceptibility reconstruction. The BOLD model describes a functional activity in terms of susceptibility perturbation as a timeseries of responses to a stimulus task(t) with a time lag. The conventional MR magnitude-based brain activation depiction assumes that the MR magnitude timecourse is synchronous with the stimulus task(t) with a time lag. Therefore, it is rational to assume that the reconstructed susceptibility timecourse is synchronous with the stimulus task(t) with a lag time as well. We term it as "timecourse synchrony" between the timecourse of an observed image response or an reconstructed susceptibility perturbation and the designed stimulus task(t). The MR magnitude timecourse synchrony condition has been accepted for brain mapping and neuroimaging. In this invention, we describe how to make use of susceptibility timecourse synchrony criterion for 4D susceptibility reconstruction.

In order to make use of the known stimulus timecourse task(t) for 4D susceptibility reconstruction, we need to find the neuroactive location in the FOV of brain cortex. In FIG. 24, we show that there are three datasets available for a BOLD fMRI study: 1) the external stimulus task(t) (known), 2) the 4D magnitude dataset $A(x,y,z,t)$ (acquired), and 3) the 4D phase dataset $P(x,y,z,t)$ (acquired). What we can do for the BOLD fMRI data analysis is to manipulate these three datasets {task(t), A(x,y,z,t), P(x,y,z,t)}, usually by a statistical parameter mapping (SPM). By temporal correlation between the magnitude timecourses and task(t), we can find the neuroactive site ($x^{act}$, $y^{act}$, $z^{act}$) in the FOV, as diagrammed in FIG. 24. FIG. 24 shows: Upper box: There are only three datasets available for a BOLD fMRI study {task(t), A(x,y,z,t), P(x,y,z,t)}. Lower box: the neuroactive site in the FOV can be determined by the temporal correlation between the task(t) and magnitude timecourses.

Let $\chi^{true}(x,y,z,t)$ denote the dynamic can be predefined (as the ground truth) and the TV iteration reconstruction $\chi^*(x,y,z,t)$ can be compared with the truth thereby calibrating the parameter setting of {'$\lambda$','$\gamma_1$','$\gamma_2$'}. For real brain functional imaging, the true susceptibility source is unknown (under investigation). It is the neuroimaging principle that the neuroimage can be inferred by observing the brain responses to a task paradigm (external stimulation). Given a task(t), we can find the neuroactive site in the cortical FOV by the local maximal temporal correlation as expressed by $$(x^{act}, y^{act}, z^{act}) = \max_{(x,y,z) \in FOV} \{|A(x, y, z, t) \otimes_t task(t)|\} \quad (38)$$

where $\otimes_t$ denotes temporal correlation.

Due to spatial convolution associated with T2*MRI technology, the active voxel in the susceptibility source is in the vicinity (neighborhood) of ($x^{act},y^{act},z^{act}$), denoted by neighbor($x^{act},y^{act},z^{act}$), not necessarily at ($x^{act},y^{act},z^{act}$). At the brain active site, we hypothesize that the optimally reconstructed susceptibility timecourse should highly correlate with the task(t), as described by the criterion of timecourse synchrony. That is, under the timecourse synchrony condition, we obtain the reconstructed susceptibility source by:

$$\chi^{recon}(x, y, z, t) = \max_{(x',y',z') \in neighbor(x^{act},y^{act},z^{act})} \|\chi^*(x', y', z', t) \otimes_t task(t)\| \quad (39)$$

where $\chi^*(x,y,z,t)$ is a $\chi$ reconstruction during program running for the snapshot time, t, by the TV-regularized split Bregman iteration algorithm (in Eq. (20)). The output in Eq. (39) is an optimal $\chi$ reconstruction under the criterion of susceptibility synchrony by varying the TV regularization parameter. In algorithm implementation, the $\lambda$-adjustment is continued until the 4D susceptibility source reconstruction produces a highest-as-possible temporal correlation between the timecourse at an activation voxel and the external stimulation. The strategy is diagrammed in FIG. 25, which shows a 4D susceptibility reconstruction under the criterion of susceptibility timecourse synchrony (a way of making use of the external stimulus task(t)), where tcorr(x(t),y(t)) stands for temporal correlation between x(t) and y(t). The neuroactive location ($x^{act}$, $y^{act}$, $z^{act}$) is determined in FIG. 24.

For brain functional susceptibility reconstruction, we suggest a general rule for X selection: A proper $\lambda$ value for the TV reconstruction program should produce a voxel susceptibility timecourse at an active region such that it highly correlates (or anticorrelates) with the external task stimulus paradigm. It is noted that the stimulus paradigm is widely used for postprocessing a BOLD fMRI dataset by SPM. In our invention, we make use of the stimulus paradigm in two aspects: 1) for 4D $\chi$ tomographic reconstruction under the criterion of susceptibility timecourse synchrony; and 2) for postprocessing the reconstructed 4D $\chi$ dataset by SPM (in the same ways as performed on the 4D T2* dataset).

Structural $\chi$ Tomography and Functional $\chi$ Tomography

We clarify that the underlying source of T2*MRI is an inhomogeneous magnetic susceptibility distribution, which is mainly attributed to the iron content. Specifically, the $\chi$ distribution of an in vivo brain state consists of static nonheme iron deposit in tissue or organ structure and dynamic heme-iron perturbation in vascular blood associated with a brain functional activity. Interpreting the reconstructed $\chi$ map as the internal iron distribution, we can implement noninvasive iron measurement by CIMRI-based $\chi$ tomography. For tissue iron measurement, we can perform 3D structural $\chi$ tomography, and for dynamic functional heme-iron perturbation measurement, we can perform 4D functional $\chi$ tomography (a timeseries of 3D $\chi$ tomography).

We differentiate structural $\chi$ tomography from functional $\chi$ tomography by the following aspects: 1) The origin of the structural susceptibility source is the nonheme iron deposit in tissues or organs, whereas the origin of the functional susceptibility source is the heme iron perturbation associated with vascular blood magnetism change caused by a functional activity (as described by the BOLD activity); and 2) structural susceptibility distribution is static (bleeding is also considered as static in the sense that the bleeding motion is very slow in comparison with $T_E$, that usually does not co-occur with the BOLD fMRI study) whereas the functional susceptibility perturbation is a dynamic response to a task paradigm. It is noted that a snapshot 3D volume in a 4D BOLD fMRI dataset consists of the contributions from both the static structural $\chi$ background (baseline) and the dynamic functional $\chi$ perturbation (activation).

In FIG. 26, we describe a structural $\chi$ tomography scheme for the susceptibility-based nonheme iron measurement in tissues or organs. This scheme is characteristic of the following aspects: 1) It is 3D tomographic reconstruction of the structural $\chi$ distribution (which is different from the voxel-based susceptometry or 2D image-based susceptibility mapping); and 2) The iron deposit image representation is based on the 3D $\chi$ reconstruction by CIMRI from the 3D MR phase image, rather than from the MR magnitude image.

In FIG. 27, we describe two (new) $\chi$-based brain functional mapping schemes, as shown in (a1) and (a2), which are different from the conventional magnitude-based brain functional mapping method, as shown in FIG. 27(b). The two new schemes in FIGS. 27(a1) and (a2) are based on the $\chi$ reconstruction. The first (new) scheme in FIG. 27(a1) is implemented by first calculating the phase-based brain activation map, denoted by $P^{map}(x,y,z)$, and then reconstructing the susceptibility-based activation map, $\chi^{map}(x,y,z)$ by performing CIMRI only once (the fieldmap $b^{map}(x,y,z)$ is calculated from $P^{map}(x,y,z)$ by using Eq. (13) and $\chi^{map}(x,y,z)$ is calculated from $b^{map}(x,y,z)$ by the TV-regularized split Bregman iteration scheme in Eq. (20)).

The second (new) scheme in FIG. 27(a2) is implemented by first reconstructing a 4D susceptibility dataset $\chi^{recon}(x,y,z,t)$ by looping the CIMRI for each time point of t, and then rendering the $\chi$-based statistical brain mapping. Both the first and second new schemes produce an output of $\chi$-based brain activation maps from a 4D BOLD fMRI dataset. The second scheme costs more computations than the first scheme; however, the second scheme can accommodate the nonlinearity of T2* phase image acquisition without a linear assumption for SPM and CIMRI.

Let SPM represent the statistical parametric mapping (SPM) exerted on a 4D dataset and its stimulus task(t), and CIMRI the susceptibility reconstruction. Then, we can express the two new schemes (also called "proposals 1 and 2") in FIG. 27 by $$\chi^{map}(x,y,z) = SPM\{\chi^{recon}(x,y,z,t), task(t)\} \text{(definition)}$$

$$= SPM\{CIMRI\{P(x,y,z,t)\}, task(t)\} \text{(proposal 2)}$$

$$CIMRI\{SPM\{P(x,y,z,t), task(t)\}\} \text{(linear commutation)}$$

$$= CIMRI\{P^{map}(x,y,z)\} \text{(proposal 1)} \qquad (40)$$

It shows that, if both SPM and CIMRI are linear operations, SPM commutates with CIMRI. In small angle regime, CIMRI is a linear operation because convolution and deconvolution are linear operations. As a result, proposal 2 (which requires multiple CIMRI procedures for each time snapshot in the 4D dataset) can be reduced to proposal 1, which only requires performing CIMRI only once. However, for nonlinear SPM, we can only adopt proposal 2 for susceptibility-based brain mapping, because proposal 1 will incur nonlinear artifacts. FIG. 27 shows our two new proposals of susceptibility-based brain mapping and neuroimaging in (a1) & (a2), which are different from the conventional magnitude-based brain mapping and neuroimage in (b). The proposal 1 in (a1) is for linear statistical data analysis, and the proposal 2 in (a2) is for nonlinear linear statistical analysis.

Since the reconstructed 4D $\chi$ dataset can represent the intrinsic neuroactivity more directly and veraciously than the 4D raw MR dataset (magnitude or phase), it is expected that the x-based brain mapping (proposal 2 in (a2)) and neuroimaging is more truthful than that based on the MR magnitude data. Under linear approximations, the proposal 2 in (a2) can be implemented by the proposal 1 in (a1) with reduced computations (performing CIMRI only once). The conventional BOLD fMRI data analysis tools, such as SPM, independent component analysis (ICA), and connectivity graphs, can be applied to the 4D $\chi$ dataset without change. We stress that our improvements in BOLD fMRI study are based on a 4D $\chi$ dataset (susceptibility dataset reconstructed from a 4D MR phase dataset), not on the 4D MR magnitude dataset. The result is that our $\chi$-based BOLD fMRI study will provide more truthful neuroimage depiction.

In summary, our methodology of CIMRI-based magnetic susceptibility tomography can be used equally well for both structural $\chi$ tomography and functional $\chi$ tomography. The structural $\chi$ tomography scheme provides a 3D $\chi$ source for static iron deposit in tissues or organs (as illustrated schematically in FIG. 26). The functional $\chi$ tomography scheme is to reconstruct a 4D $\chi$ dataset (a dynamic $\chi$ series), which is then used for brain mapping and neuroimaging, as illustrated schematically in FIG. 27.

The rationale behind our x-based image analysis technique is threefold: 1) the underlying source of a structural and functional state (detectable by T2*MRI) is the $\chi$ distribution, which is mainly attributed to the iron origin; 2) the MR magnitude image suffers from a local average, and a nonlinear transformation of the $\chi$ source; meaning that the MR magnitude image is not a tomographic reproduction of the $\chi$ source; 3) the MR phase image is a linear transformation of the susceptibility source in the small angle regime (the 3D convolution is linear)) and the $\chi$ source can be reconstructed from the MR phase image by CIMRI (by solving an ill-posed deconvolution); 4) if the statistical postprocessing is linear, it commutates with the CIMRI, thereby reducing the multiple CIMRI repetitions to a one-time CIMRI calculation.

Next, we will discuss how both the $\chi^{recon}$-based iron measurement scheme in FIG. 26 and the $\chi^{recon}$-based BOLD fMRI scheme in FIG. 27(a) can be further improved by using the T2' phase images generated by an T2' imaging scheme.

Improvement on Susceptibility Imaging by T2'-Effect Imaging and CIMRI

The principle of T2'-effect signal acquisition is illustrated in FIG. 9, which aims to remove the random motion effect from the T2* signal.

We generalize this concept to the principle of T2'-effect imaging, as diagramed by T2'-effect MRI (T2'MRI) in FIG. 28. In comparison with conventional T2*MRI processing, the T2'MRI procedure/analysis can be used to obtain a complex MR image (called T2' complex image) that consists essentially of the static inhomogeneous field effect (e.g., the T2' source). Following doing a T2'MRI procedure, we perform CIMRI-based $\chi$ reconstruction. FIG. 28 illustrates schematically the methodology to improve the $\chi$ reconstruction, comprising (1) performing T2'MRI and then (2) CIMRI. The Gradient-Echo image and the Spin-Echo image are acquired from the same $\chi$ source (i.e., the same object) with the same echo time, $T_E$. A complex division is then used to obtain a complex T2' image. Finally, a CIMRI procedure is used to reconstruct the susceptibility distribution from a T2' phase image extracted from the T2' complex image.

The T2'MRI section in FIG. 28 consists of the following steps: 1) complex SE image acquisition by a spin-echo imaging with a $T_E$; 2) complex GE image acquisition by gradient-recall echo imaging, for the same $\chi$ source with the same $T_E$; 3) T2' complex image calculation by a complex division between the complex GE image and the complex SE image. From the T2' complex image, we can calculate (extract) the T2' phase image (by finding the complex argument), with which we can reconstruct the static susceptibility distribution by CIMRI by two steps: a) T2' fieldmap calculation from the T2' phase image and $T_E$, and b) 3D static susceptibility reconstruction from the T2' fieldmap. It is noted that the T2' phase image is calculated by subtracting the T2 phase image from the T2* phase image (as presented earlier). Therefore, the inhomogeneous fieldmap associated with the T2 effect is greatly removed. Note that the method to improve the 3D $\chi$ tomography by T2'MRI and CIMRI in FIG. 28 can be extended to 4D dynamic $\chi$ tomography.

Currently, the T2* GE image is acquired by an echo planar image (EPI) sequence; and the T2* SE image is acquired by a spin-echo EPI sequence. The main difference between the pair of GE and SE pulse sequences is that the SE sequence includes an additional 180° pulse. The 3D complex image can be constructed by stacking the EPI slices. In future versions, a 3D isotropic complex image may be directly acquired by an echo volumar imaging (EVI) sequence. An EVI sequence is used to acquire a 3D T2* GE complex image, while a SE EVI sequence is used to acquire a 3D T2* SE complex image. The main difference between the EVI sequence and the SE EVI sequence is that the SE EVI includes an additional 180° pulse.

In principle, the T2'MRI corrective procedure prefers a long $T_E$ due to the fact that a long $T_E$ causes a large T2 effect, and a large difference in T2* GE signal and T2* SE signal, and a large signal difference generally increases the digital subtraction stability and accuracy. A double-echo T2'-effect signal can be acquired by the illustration shown in FIG. 9. In general, we can implement multi-echo T2'MRI corrections by repeating the EPI sequence with multiple $T_E$ repetitions.

Phantom MR Experiment

According to medical imaging system development principle, the $\chi$ tomography by our CIMRI model must be tested with phantom experiment before it can be used for practice. In particular, the trustworthiness of CIMRI-based $\chi$ tomography is verified by having a successful comparison with a phantom experimental study.

We performed a phantom experiment with Gd-filled tube [19], as configured in FIG. 29. An end-tapered plastic tube was filled with a Gd contrast liquid (dilution of clinic Gd solution) and was inserted in a large water tank. The static tube phantom provides a uniform distribution inside the tube of magnetic $\chi$ (ground truth); and it was used in simulations of a snapshot of dynamic $\chi$-expressed physiological process. FIG. 29 shows a Gd-filled tube phantom experiment setup. The tube phantom provides a static cylindrical susceptibility distribution, which is used in simulations of a snapshot of dynamic susceptibility-expressed physiological process.

The experimental results of the MR magnitude, the MR phase, and the $\chi$ tomographic reconstructions by both the "filter truncation" and "TV iteration" solvers are shown in FIG. 30. FIG. 30 shows the phantom experiment results. Row 1 (at top): magnitude image; row 2: phase image; row 3: $\chi$ reconstructed from filter truncation method; and row 4 (at bottom): $\chi$ reconstructed from TV iteration method. The quantitative profiles of scanline across a cylinder diameter are shown in FIG. 31.

The Gd-tube phantom experiment for CIMRI-based $\chi$ tomography offers the following information: 1) The MR magnitude image suffers a central dip artifact; 2) The phase image is morphometrically different from the $\chi$ source due to the 3D convolution transformation in Eq. (2); 3) The $\chi$ reconstruction by "filter truncation" method suffers strip artifacts and heavy noises; 4) the TV-iteration method can implement $\chi$ tomography very well because the susceptibility source assumed an uniform distribution inside the cylinder, which agrees with the 'ground truth'.

In Vivo Brain $\chi$ Reconstruction Experiment

After the proof-of-concept study by numerical simulation and phantom test, the next stage was to apply the models and algorithms to real brain imaging for feasibility study.

A real brain imaging experiment was conducted with a healthy subject doing a finger-tapping visuomotor experiment in a Siemens Trio 3T scanner. An EPI complex sequence was used for scanning, with $T_R/T_E=2000$ ms/29 ms, and isotropic voxels ($2\times2\times2$ mm³). A brain FOV was localized to cover the motor cortex part (the parietal lobe and frontal lobe in brain) with a 3D matrix in size of $90\times90\times30$. The brain functional imaging experiment produced a 4D complex dataset ($90\times90\times30\times165$ after image cropping) for a session of 330s scanning. We assume that we can reconstruct the brain $\chi$ source at each snapshot from a MR phase volume in the 4D dataset by our CIMRI model. The results of the in vivo experiment data and $\chi$ reconstructions are reproduced in FIG. 32 (with a slice image from a snapshot volume), which consists of a raw MR magnitude image slice (a), the raw phase counterpart (b1), a smoothed phase (b2), and six $\chi$ reconstructions (c1-c6) with $\lambda=\{10,30,50,100,500,1000\}$. By comparing the phase image (corresponding to the fieldmap) with the six $\chi$ reconstructions, we can see that the $\chi$ reconstruction may take on a smoothing effect at a very small $\lambda$ (<30), and a contrast enhancement at a very large X (>500).

FIG. 32 shows a TV-regularized brain $\chi$ reconstruction from an in vivo experiment dataset, comprising: (a) an axial slice of the MR magnitude of brain imaging (where a vertical segment marks a scanline); (b1) the phase image slice; (b2) the smoothed phase; (c1-c6) the $\chi$ reconstruction from the phase (in (b1)) by using a large range of X values. Note that the magnitude image is nonnegative as displayed in a greyscale bar range of [0,1], and all the images are bipolar-valued.

From FIG. 32, we can see that the quality of intracranial $\chi$ tomographic reconstruction by CIMRI is largely dependent upon the selection of the regularization parameter $\lambda$ values. In FIG. 33, we plot the scanline profiles from FIG. 32(c1-c6) for more quantitative inspection (the scanline was marked in FIG. 32(a)). It shows that the $\chi$ reconstruction may suffer from oversmoothing effect for a very small $\lambda$ (e.g., 10), and from contrast enhancement for a very large $\lambda$ (e.g., $\lambda$>1000). It also shows that the $\chi$ reconstruction may assume similar reconstructions for an intermediate range of $\lambda$ values (e.g. in a range of 30-200).

For static brain imaging, the 3D $\chi$ reconstruction should adopt a regularization parameter $\lambda$ value such that the reconstructed $\chi$ map is similar to (but not equal to) the MR magnitude image. From FIG. 32, the reconstructed $\chi$ map with $\lambda=50$ (in FIG. 32(c3)) is the most similar to the MR magnitude image (in FIG. 32(a)).

For dynamic 4D brain functional imaging (BOLD fMRI), we can make use of the external stimulus paradigm for 4D $\chi$ reconstruction, as described as susceptibility timecourse synchrony in this invention.

The $\chi$ timecourse reconstructions at a voxel in the BOLD activity site in the BOLD fMRI experiment are demonstrated in FIG. 34, for $\lambda=\{10,30,50,100,500,1000\}$; in which the rectangular waveform represents the external stimulus task(t) (known paradigm) as recorded of the visual clue for the finger-tapping experiment.

From FIG. 34, we can see the following aspects:
1) The $\chi$ reconstruction with a very small $\lambda$ (=10) could not restore the rectangular stimulus paradigm,
2) The $\chi$ reconstruction with a very large $\lambda$ (=1000) could not restore the rectangular stimulus paradigm either,
3) The $\chi$ reconstruction with a range of $\lambda$ values ([20-500]) could restore the rectangular stimulus paradigm very well, and
4) There is time lag between the $\chi$ timecourse and the external rectangular stimulus task(t), that is about 6 ms.

Applications

In the present invention, we developed a number of CIMRI models for reconstructing a 3D $\chi$ source distribution from a 3D MR phase image acquired by T2*MRI, and for reconstructing a 4D $\chi$ dataset from a 4D MR phase dataset. The former is mainly used for structural 3D $\chi$ tomography and the later for functional 4D $\chi$ tomography.

Our structural 3D $\chi$ tomography can be used for iron store measurement in organs (such as liver, spleen, pancreas, heart, brain) and in tissues (contrast agent and blood inside the vasculature, contrast and blood leakage, and in glands). In particular, our method offers an accurate depiction of brain injury (hemorrhage, micro-hemorrhage, stroke) and brain dysfunctions (diseases).

In FIG. 35, we illustrate the $\chi$ reconstruction for the image depiction of blood bleeding and microbleeding that occurs in the proximity of vasculatures. As the T2*MRI is widely used for imaging brain trauma, injury, and dysfunction, our method provides a more truthful and accurate 3D tomographic image presentation of brain anatomical states in terms of reconstructed magnetic susceptibility. For biological tissue and organ imaging, the reconstructed magnetic susceptibility can be interpreted as the iron deposit. Therefore our structural $\chi$ tomography can find immediate use in iron deposit measurement of organs (liver, spleen, pancreas, heart, brain) and in tissues, not restricted the regions in the proximity of vasculatures.

FIG. 35 shows an illustration of brain structural susceptibility distribution. The hemorrhage and micro-hemorrhage of blood circulation causes spread susceptibility distribution, the static iron deposit also contributes the susceptibility distribution for static structural representation. The iron deposit may occur in tissues and organs, not necessary in proximity to bloodstreams.

Our 4D functional $\chi$ tomography provides a susceptibility perturbation depiction for a neurovascular BOLD process (including a resting state, and a task-specific paradigm). Since a BOLD fMRI study produces a 4D complex dataset, our CIMRI produces a 4D dynamic susceptibility dataset accordingly. In particular, the functional $\chi$ tomography, together with statistical postprocessing, is useful for diagnostic and prognostic imaging of brain function diseases, such as schizophrenia, epilepsy, Alzheimer, aging, and other dysfunctions.

In FIG. 36, we illustrate the BOLD fMRI model for capturing the neurovascular-coupled BOLD states at the capillary bed. At the left side is illustrated the blood susceptibility perturbation associated with a BOLD fMRI activity. The intravascular blood susceptibility is perturbed by a functional activity, which may cause a negative susceptibility change in the arterial upstream (in artery and arterioles), a positive susceptibility change in capillary bed, and a positive susceptibility change in venous downstream (in venule and vein). In practice, the dominant heme iron susceptibility perturbation occurs in the capillary regions in response to the oxygen delivery and consumption, and the susceptibility perturbation in the arterial upstream is much smaller than that in the venous downstream. In ignorance of arterial blood susceptibility perturbation, the BOLD fMRI is mainly attributed to the venous blood susceptibility. In such a case, the BOLD imaging is called a venography [2].

At the right-hand side in FIG. 36 is the conceptual illustration (a snapshot image) of susceptibility perturbation of intravascular blood and in extravascular tissue, which could be negative or positive. The positive and negative bipolar distributions are retained in the phase image, but not in the magnitude image because the magnitude image is a nonnegative representation [19] of a distribution that may consist of positive and negative values. Consequently, the negative susceptibility change will be inverted (called negative inversion) in the MR magnitude image because a magnitude value is non-negative. It is noted the neuroactivity-caused susceptibility perturbation in terms of heme iron change is too weak to be perceived in a snapshot of MR image (with the background of structural $\chi$ distribution). Usually, the BOLD activity can be extracted from a dynamic 4D dataset (acquired by fMRI under a task-specific paradigm) by a statistical postprocessing, such as a temporal correlation technique.

FIG. 36 shows an illustration of blood susceptibility perturbation associated with a BOLD fMRI model. The extravascular tissue is the static background structure. The BOLD-induced susceptibility perturbation is attributed to the intravascular blood-borne heme iron disturbance. It is noted that the dynamic heme-iron perturbation is superimposed on the static structural iron background during MR image formation. In a single T2*MRI image, the contributions from the heme iron perturbation and non-heme iron deposit are inseparable.

A preferred embodiment of a method of reconstructing an internal distribution (3D map) of magnetic susceptibility values, $\chi$ (x,y,z), of an object, by using a Computed Inverse Magnetic Resonance Imaging (CIMRI) tomographic procedure, according to the present invention, comprises the following steps:

a) acquiring a 3D complex-valued MR image of the object from a T2*-weighted MRI scan performed by a MRI scanning machine;

b) extracting a 3D T2*MRI phase image, $P(x,y,z;T_E)$, from the 3D complex-valued MR image;

c) calculating a 3D magnetic field map, $b(x,y,z)$, of the z-component ($B_z$) of a susceptibility-induced inhomogeneous magnetic field (created by magnetizing the object in a main field, $B_0$), from the MR phase image, $P(x,y,z;T_E)$, according to Eq. (1A), under phase-unwrapped conditions;

$$b(x,y,z) = \frac{P(x,y,z;T_E)}{\gamma T_E} \quad \text{Eq. (1A)}$$

where: $\gamma$=proton gyromagnetic ratio, and $T_E$=echo time: and d) reconstructing a 3D magnetic susceptibility map, $\chi^{recon}(r)$, of the object by performing a 3D deconvolution on the magnetic field map, $b(r)$, according to Eq. (2A) and Eq. (3A), as follows:

$$b(r) = B_0 \chi(r) * h_0(r) \quad \text{Eq. (2A)}$$

and $$\chi^{recon}(r) = b(r) *^{-1} h_0(r)/B_0 \quad \text{Eq. (3A)}$$

where: $r=(x,y,z)$ denotes 3D coordinates in space domain; the symbol * denotes a 3D convolution operator; the symbol $*^{-1}$ denotes a 3D deconvolution operator; and $h_0(r)$ is a standard convolution kernel that is a point magnetic dipole kernel, according to Eq. (4A):

$$h_0(r) = \frac{1}{4\pi} \frac{3z^2 - |r|^2}{|r|^5} \quad \text{Eq. (4A)}$$

In one embodiment, $T_E<30$ ms when performing functional MR imaging, and $T_E<10$ ms when performing structural MR imaging.

In another embodiment, the modified TV iteration filter, $H(k)$, comprises one or more spatial processing capabilities selected from the group consisting of: lowpass, highpass, bandpass, and bandstop filtering.

In another embodiment, the 3D multiplier filter comprises radial symmetry or asymmetry, for a desirable susceptibility manipulation.

In another embodiment, the steps of estimating one or more appropriate values of the TV regularization parameter, $\lambda$, does not involve using an auxiliary phantom; so the selection of $\lambda$ is self-calibrated by using the accompanying MR magnitude information.

In another embodiment, the method comprises replacing the 3D T2*MRI phase image, $P(x,y,z;T_E)$ in step b) of the preferred method above, with a 3D T2'-effect phase image, $P_{T2'}(x,y,z;T_E)$; thereby improving the fidelity and accuracy of the reconstructed magnetic susceptibility map, $\chi^{recon}(r)$ by greatly reducing the T2 effect via MR phase angle subtraction (complex division).

In another embodiment, the T2'-effect MRI scheme is extended to multi-echo imaging comprising at least two different echo times, $T_{E1}$ and $T_{E2}$.

In another embodiment, the T2'-effect MRI scheme is extended to multi-echo imaging by repeating echo planar image (EPI) sequences with multiple $T_E$ repetitions.

In another embodiment, the T2'-effect MRI scheme is extended to multi-echo imaging; wherein a 3D isotropic complex image is directly acquired by using an echo volumar imaging (EVI) sequence when imaging; and further wherein an EVI sequence acquires a 3D T2* GE complex image, while a SE EVI sequence acquires a 3D T2* SE complex image; wherein the main difference between the EVI sequence and the SE EVI sequence is that the SE EVI includes an additional 180° pulse for rephasing the non-random static dephasing.

In another embodiment, the object comprises tissues or organs of a body; and wherein the method further comprises measuring a distribution of iron deposits in the tissues or organs of the body by interpreting the 3D reconstructed magnetic susceptibility map, $\chi^{recon}(r)$, as a quantitative distribution of iron deposits in said tissues or organs.

In another embodiment, the method does not comprise using any MR magnitude images; and further wherein the method does not comprise using any exponential decay parameters T1, T2, or T2*; or maps of said exponential decay parameters.

Another embodiment of the present invention comprises a method of performing dynamic, magnetic susceptibility-based fMRI brain mapping and neuroimage depiction, using a MRI scanning machine, comprising: replacing a conventional 4D MR magnitude dataset (which is the conventional neuroimaging dataset) with a 4D reconstructed magnetic susceptibility dataset, $\chi^{recon}(r,t)$; wherein r denotes 3D coordinates (x, y, z) in space domain, and t denotes a snapshot time.

In another embodiment, the 3D T2*MRI phase image, $P(x,y,z;T_E)$, extracted in step b) comprises a wrapped phase image; in which case the preferred method described above further comprises generating a phase-unwrapped phase image, after step b), by performing a phase-unwrapping procedure on the wrapped phase image; followed by calculating the magnetic field map in step c), using the newly-generated phase-unwrapped phase image.

A variety of means and methods can be used for displaying the results of the various method steps used in embodiments of the present invention, including, but not limited to: a) assigning either a gradation of grey values (greylevel bar), or a spectrum of color values (colorbar), to a selected 2D slice of data taken through the 3D map of reconstructed magnetic susceptibility values, $\chi^{recon}(r)$, thereby creating a 2D slice visual image representing a 2D distribution of reconstructed magnetic susceptibility values inside of the object; and, then b) displaying on a computer screen or monitor the resulting 2D slice visual image that represents a 2D distribution of reconstructed magnetic susceptibility values inside of the object. The 3D volume can also be displayed in 3D volume rendering or isosurface rendering. A 3D volume can also be display by a montage of 2D slices. The 4D dataset can be dynamically displayed with a video of 3D rendering.

The methods and method steps, according to the present invention, can be programmed in software in any efficient computer language (such as C, Matlab, Fortran, etc.) and be executed on desktop computers or higher workstations. Currently, we implement our methods in Matlab language on a desktop computer: Intel® Core™ 2 CPU 6600@ 2.40 GHz. 2.39 GHz, 2.00 GB of RAM).

The algorithms can be implemented in multiple programs, which are arranged according the data flow (T2*MRI and CIMRI programs for numerical simulations, CIMRI programs for phantom and in vivo experiment). Each program is reserved some variables for the adjustable parameters (such as matrix size, newly designed kernel, regularization parameters) that are determined by problem-specific calibration. Based on data saving and reading operations, all the multiple programs can be organized into a single master program for a specific task, thus enabling program automation. The multiple programs can be executed independently on multiprocessors for parallel computations, also in automation (except for parameter adjustment and calibration).

REFERENCES

The following references are incorporated herein by reference:

1. Chavhan, G. B., et al., *Principles, techniques, and applications of T2\*-based MR imaging and its special applications.* Radiographics: a review publication of the Radiological Society of North America, Inc, 2009. 29(5): p. 1433-49.
2. Haacke, E. M., et al., *Magnetic resonance imaging physical principles and sequence design*, 1999, John Wiley & Sons, Inc: New York.
3. Fischer, R. and P. R. Harmatz, *Non-invasive assessment of tissue iron overload.* Hematology/the Education Program of the American Society of Hematology. American Society of Hematology. Education Program, 2009: p. 215-21.
4. Jensen, J. H., et al., *Separate MRI quantification of dispersed (ferritin-like) and aggregated (hemosiderin-like) storage iron.* Magnetic resonance in medicine: official journal of the Society of Magnetic Resonance in Medicine/ Society of Magnetic Resonance in Medicine, 2010. 63(5): p. 1201-9.
5. Jensen, P. D., et al., *Non-invasive assessment of tissue iron overload in the liver by magnetic resonance imaging.* British journal of haematology, 1994. 87(1): p. 171-84.
6. Olthof, A. W., et al., *Non-invasive liver iron concentration measurement by MRI: comparison of two validated protocols.* European journal of radiology, 2009. 71(1): p. 116-21.
7. Taher, A. T., K. M. Musallam, and A. Inati, Iron overload: consequences, assessment, and monitoring. Hemoglobin, 2009. 33 Suppl 1: p. S46-57.
8. Walsh, A. J. and A. H. Wilman, *Susceptibility phase imaging with comparison to R2 mapping of iron-rich deep grey matter.* Neuroimage, 2011. 57(2): p. 452-61.
9. Wu, E. X., et al., *Magnetic resonance assessment of iron overload by separate measurement of tissue ferritin and hemosiderin iron.* Annals of the New York Academy of Sciences, 2010. 1202: p. 115-22.
10. Howseman, A. M. and R. W. Bowtell, *Functional magnetic resonance imaging: imaging techniques and contrast mechanisms.* Philos Trans R Soc Lond B Biol Sci, 1999. 354(1387): p. 1179-94.
11. Norris, D. G., *Principles of magnetic resonance assessment of brain function.* Journal of magnetic resonance imaging: JMRI, 2006. 23(6): p. 794-807.
12. Ogawa, S., et al., *Functional brain mapping by blood oxygenation level-dependent contrast magnetic resonance imaging. A comparison of signal characteristics with a biophysical model.* Biophys J, 1993. 64(3): p. 803-12.
13. Stephan, K. E., et al., *Biophysical models of fMRI responses.* Curr Opin Neurobiol, 2004. 14(5): p. 629-35.
14. Menon, R. S., et al., *Functional brain mapping using magnetic resonance imaging. Signal changes accompanying visual stimulation.* Invest Radiol, 1992. 27 Suppl 2: p. S47-53.
15. Boxerman, J. L., et al., *MR contrast due to intravascular magnetic susceptibility perturbations.* Magn Reson Med, 1995. 34(4): p. 555-66.
16. Reitz J. R., M. F. J., Christy R. W., *Foundations of electromagntic theo* 1993: Addison-Wesley.

17. Chen, Z. and V. Calhoun, *Computed inverse resonance imaging for magnetic susceptibility map reconstruction.* Journal of computer assisted tomography, 2012. 36(2): p. 265-74.
18. Chen, Z. and V. Calhoun, *Volumetric BOLD fMRI simulation: from neurovascular coupling to multivoxel imaging.* BMC medical imaging, 2012. 12(1): p. 1-8.
19. Chen, Z. and V. D. Calhoun, *Two pitfalls of BOLD fMRI magnitude-based neuroimage analysis: non-negativity and edge effect.* Journal of neuroscience methods, 2011. 199(2): p. 363-9.
20. Chen, Z., Z. Chen, and V. D. Calhoun. *Voxel magnetic field disturbance from remote vasculature in BOLD fMRI.* in SPIE Medical Imaging. 79613x. Orlando, Fla.: SPIE.
21. Chen, Z., A. Caprihan, and V. D. Calhoun. *BOLD susceptibility map reconstruction from fMRI by 3D total variation regularization.* in International society for magnetic resonance in medicine 2011. Montreal, Canada: ISMRM.
22. Haacke, E. M., et al., *Susceptibility mapping as a means to visualize veins and quantify oxygen saturation.* Journal of magnetic resonance imaging: JMRI, 2010. 32(3): p. 663-76.
23. Li, W., B. Wu, and C. Liu, *Quantitative susceptibility mapping of human brain reflects spatial variation in tissue composition.* Neuroimage, 2011. 55(4): p. 1645-56.
24. Schweser, F., et al., *Quantitative imaging of intrinsic magnetic tissue properties using MRI signal phase: an approach to in vivo brain iron metabolism? Neuroimage,* 2011. 54(4): p. 2789-807.
25. Shmueli, K., et al., *Magnetic susceptibility mapping of brain tissue in vivo using MRI phase data.* Magnetic resonance in medicine: official journal of the Society of Magnetic Resonance in Medicine/Society of Magnetic Resonance in Medicine, 2009. 62(6): p. 1510-22.
26. Wharton, S., A. Schafer, and R. Bowtell, *Susceptibility mapping in the human brain using threshold-based k-space division.* Magn Reson Med, 2010. 63(5): p. 1292-304.
27. de Rochefort, L., et al., *Quantitative susceptibility map reconstruction from MR phase data using bayesian regularization: validation and application to brain imaging.* Magn Reson Med, 2010. 63(1): p. 194-206.
28. Kressler, B., et al., *Nonlinear regularization for per voxel estimation of magnetic susceptibility distributions from MRI field maps.* IEEE Trans Med Imaging, 2010. 29(2): p. 273-81.
29. Li, L., *Magnetic susceptibility quantification for arbitrarily shaped objects in inhomogeneous fields.* Magn Reson Med, 2001. 46(5): p. 907-16.
30. Li, L. and J. S. Leigh, *Quantifying arbitrary magnetic susceptibility distributions with MR.* Magn Reson Med, 2004. 51(5): p. 1077-82.
31. Sepulveda, N. G., J. M. Thomas, and J. P. Wikswo, *Magnetic Susceptibility Tomography for Three-dimensional Imaging of Diamagnetic and Paramagnetic Objects.* IEEE Trans. Magnetics, 1994. 30(6): p. 5062-7.
32. Liu, T., et al., *Calculation of susceptibility through multiple orientation sampling (COSMOS): a method for conditioning the inverse problem from measured magnetic field map to susceptibility source image in MRI.* Magn Reson Med, 2009. 61(1): p. 196-204.
33. Yao, B., et al., *Susceptibility contrast in high field MRI of human brain as a function of tissue iron content.* Neuroimage, 2009. 44(4): p. 1259-66.
34. Leung, A. W., et al., *Magnetic resonance imaging assessment of cardiac and liver iron load in transfusion dependent patients.* Pediatric blood & cancer, 2009. 53(6): p. 1054-9.
35. Marinelli, M., et al., *Total iron-overload measurement in the human liver region by the magnetic iron detector.* IEEE transactions on bio-medical engineering, 2010. 57(9): p. 2295-303.
36. Mitsumori, F., H. Watanabe, and N. Takaya, *Estimation of brain iron concentration in vivo using a linear relationship between regional iron and apparent transverse relaxation rate of the tissue water at 4.7T* Magnetic resonance in medicine: official journal of the Society of Magnetic Resonance in Medicine/Society of Magnetic Resonance in Medicine, 2009. 62(5): p. 1326-30.
37. Papakonstantinou, O., et al., *Quantification of liver iron overload by T2 quantitative magnetic resonance imaging in thalassemia: impact of chronic hepatitis C on measurements.* Journal of pediatric hematology/oncology: official journal of the American Society of Pediatric Hematology/Oncology, 1999. 21(2): p. 142-8.
38. Papakonstantinou, O. G., et al., *Assessment of liver iron overload by T2-quantitative magnetic resonance imaging: correlation of T2-QMRI measurements with serum ferritin concentration and histologic grading of siderosis.* Magnetic resonance imaging, 1995. 13(7): p. 967-77.
39. Chen, Z. and V. Calhoun, *A computational multiresolution BOLD fMRI model.* IEEE Trans. BioMed. Eng, 2011. 58(10): p. 2995-9.
40. Spees, W. M., et al., *Water proton MR properties of human blood at 1.5 Tesla: magnetic susceptibility, T(1), T(2), T*(2), and non-Lorentzian signal behavior.* Magn Reson Med, 2001. 45(4): p. 533-42.
41. Chen, Z. and V. Calhoun. *Volumetric computational model for neurovascular coupling and BOLD fMRI.* in Human Brain Mapping. 2011. Quebec, CA: OHBM.
42. Fang, C. H., et al., *Anatomical variations of hepatic veins: three-dimensional computed tomography scans of 200 subjects.* World journal of surgery, 2012. 36(1): p. 120-4.
43. Gonzalez, R. C. and R. E. Wood, *Ditial image processing.* Third ed2008: Prentice Hall.
44. Cai, J. F., S. Osher, and Z. Shen, *split Bregman Methods and Frame Based Image Restoration,* in *UCLA CAM Report*2009.
45. Chambolle, A. and P. L. Lions, *Image recovery via total variational minimization and related problems.* Numer. Math., 1997. 76: p. 167-88.
46. Chan, T., et al., *Recent developments in total variation image restoration,* in *Handbook of mathematical models in computer vision,* N.C.Y.F. Paragios, Olivier, Editor 2005, Springer.
47. Combettes, P. L. and J. C. Pesquet, *Image restoration subject to a total variation constraint.* IEEE transactions on image processing: a publication of the IEEE Signal Processing Society, 2004. 13(9): p. 1213-22.
48. Goldstein, T. and S. Osher, *The Slit Bregman Method for L1 Regularized Problems,".* UCLA CAM Report, 2008.
49. Joshi, S. H., et al., *Edge-Enhanced Image Reconstruction Using (TV) Total Variation and Bregman Refinement.* Lect Notes Comput Sci, 2009. 5567 (2009): p. 389-400.
50. Frigyik, B. A., S. Srivastava, and M. R. Gupta, *functional Bregman divergences and Bayesian Estimation of distribution.* IEEE Trans Information Theory, 2008. 54: p. 5130-9.
51. Osher, S., et al., *An iterative regularization method for total variation-based image restoration.* Multiscale Model. Simul., 2005. 4(2): p. 460-89.

52. Yeo, D. T., J. A. Fessler, and B. Kim, *Motion robust magnetic susceptibility and field inhomogeneity estimation using regularized image restoration techniques for fMRI.* Med Image Comput Comput Assist Interv, 2008. 11(Pt 1): p. 991-8.
53. Holst, B., et al., *T2' imaging indicates decreased tissue metabolism in frontal white matter of MS patients.* Multiple sclerosis, 2009. 15(6): p. 701-7.
54. Chen, Z., et al., *Volumetric BOLD fMRI simulation: from neurovascular coupling to multivoxel imaging.* to be published in BMC Medical Imaging Journal, 2012.

APPENDIX A

Numerical Simulations

A. χ Tomography Simulation with a Digital Cylinder Phantom

In support of the invention specification describing innovative methods for reconstructing 3D χ distributions from a magnetic fieldmap, we performed numerical simulations with a digital cylinder phantom. We predefined a cylindrical susceptibility distribution and embedded it in a cubic field of view (FOV), with the main field $B_0$ perpendicular to the cylinder axis, as diagramed in FIG. 37. The digital cylinder phantom assumes a binary volume of FOV in a matrix in size of 128×128×128.

$$x(x, y, z) = \begin{cases} 1 & \text{inside cylinder} \\ 0 & \text{otherwise} \end{cases}, (x, y, z) \in FOV \quad (A1)$$

The parameter settings are provided in Table A1.

FIG. 37 Geometry for cylindrical χ reconstruction simulation. The main MR field is perpendicular to the cylinder's axis.

TABLE A1

Parameter settings for digital cylinder phantom simulation

| Parameters | Settings | Remarks |
|---|---|---|
| $B_0$ | 3 Tesla | Main field |
| FOV matrix | 128 × 128 × 128 | Unit: mm |
| Cylinder diameter | 25 | Unit: mm |
| Susceptibility χ | 1 ppm (cylinder interior) | SI unit |
| χ distribution (predefined) | Cylinder in FOV | Ground truth |
| Noise (ε(x, y, z)) | randn(128, 128, 128) | Gaussian noise generator |
| NoiseLevel | 0.1 | Standard deviation |

Since the geometry of a cylinder is simple and regular, its fieldmap can be calculated by using a magnetostatic analytic formula [2, 16], or using Eq. (3) (which is valid for an arbitrary geometry). Specifically, we can calculate the fieldmap and add Gaussian additive noise by $$b(x, y, z) = IFT\left\{FT[x(x, y, z)]\cdot\left(\frac{1}{3} - \frac{k_z^2}{k^2}\right)\right\} + \varepsilon(x, y, z) \quad (A2)$$

$$\varepsilon(x, y, z) = NoiseLevel \cdot randn(128, 128, 128)$$

where FT and IFT represent Fourier transform and inverse Fourier transform, randn the Gaussian random number generator (a Matlab function), and NoiseLevel controls the standard deviation. The three orthogonal slices for the predefined χ source and the calculated fieldmap (without and with noise) are displayed in FIG. 38.

FIG. 38 shows: Top row: three orthogonal cross-sections of the predefined χ source. Middle row: fieldmap without noise. Bottom row: fieldmap with additive Gaussian noise (NoiseLevel 0.1).

As discussed previously, the χ source distribution can be reconstructed from the fieldmap by solving a 3D inverse problem (deconvolution) using three different types of solvers. Since it is very difficult to find the inverse of a matrix with size 2097152×2097152 (where 2097152 = 128×128×128), we cannot provide a solution using the "matrix inverse" solver.

We simulate the χ reconstruction by the "filter truncation" solver by [17]

$$x(x, y, z) = IFT\left\{\frac{FT[b(x, y, z)]}{h_{trunc}(k) \cdot B_0}\right\} \text{ with} \quad (A3)$$

$$h_{trunc}(k) = \begin{cases} \varepsilon_0 \cdot sgn(h_0(k)), & |h_0(k)| < \varepsilon_0 \\ h_0(k), & \text{otherwise} \end{cases}$$

Where $\varepsilon_0$ is a threshold for filter truncation, which is noise-dependent. In our simulation, we select $\varepsilon_0$ 1.2×NoiseLevel to suppress the noise. The results are displayed at the middle row in FIG. 39.

Finally, we simulated the χ reconstruction by using the "TV iteration" solver (in Eq. (20)), with the settings of $\{\lambda=100, \gamma_1=\frac{1}{3}, \gamma_2=\frac{1}{8}\}$. The results are displayed at the bottom row in FIG. 39, which compares the results of two different numerical simulations of computed inverse BOLD fMRI for susceptibility source reconstruction with a simple cylinder χ source (predefined ground truth in the first row), by filter truncation method (in second row) and by the TV-regularized method (in the third row). FIG. 40 shows quantitative profiles along a diameter (scanline) of the cylinder phantom in FIG. 37 (note: the ground truth is a rectangle profile in legend "truth"). FIG. 41 shows the typical convergence behavior of the TV-iteration method. It is seen that the solution converges after about 15 iterations.

A.2 Noise Patterns in χ Tomography

It has been shown that the χ tomography by "filter truncation" solver suffers from the heavy noise that manifests as the stripes and textural patterns [17,21-25], which is also demonstrated in FIG. 40 for the digital cylinder phantom simulation. The noise structure associated with the "filter truncation" solver can be explained by the illustration in FIG. 16, wherein any two points in the Fourier domain creates a collection of parallel lines in the space domain, and the superimposition of a multitude of random parallel lines resulting from many random points in the Fourier domain manifests as a clutter noise or textural noise. In contrast, the χ tomography by "TV iteration" solver suffers only from sparse "comeback" noise [45-50].

In a second numerical simulation, we observed the behavior of noise throughout the χ tomography process by: (1) pre-defining a magnetic susceptibility distribution consisting solely of random noise, (2) then calculating the fieldmap and the complex T2* image, and finally, (3) reconstructing the (known) magnetic susceptibility source by two different solver methods: (a) filter truncation inverse filtering, and (b) TV regularized iteration. The numerical simulation results are shown in FIG. 42. It is observed that the filter truncation reconstruction method suffers heavy textural noises (resulting from clutters of numerous random stripes), while the TV iteration method suffers only sparse "comeback noise". One part of our invention is to suppress the sparse "comeback noise" by calculating a multiple reconstruction average, as presented previously.

What is claimed is:

1. A method of reconstructing an internal distribution of magnetic susceptibility values of an object, denoted by $\chi(x,y,z)$ and called a 3D map, by using a Computed Inverse Magnetic Resonance Imaging (CIMRI) tomographic procedure, comprising:
   a) acquiring a 3D complex-valued MR image of the object from a T2*-weighted MRI (T2*MRI) scan performed by a MRI scanning machine;
   b) extracting a 3D T2*MRI phase image, $P(x,y,z;T_E)$, from the 3D complex-valued MR image;
   c) calculating a 3D magnetic field map, $b(x,y,z)$, of the z-component ($B_z$) of a susceptibility-induced inhomogeneous magnetic field created by magnetizing the object in a main field, $B_0$, from the MR phase image, $P(x,y,z;T_E)$, under phase-unwrapped conditions or for phase-unwrapped images, according to:

$$b(x,y,z) = \frac{P(x,y,z;T_E)}{\gamma T_E}$$

where: $\gamma$=proton gyromagnetic ratio, and $T_E$=echo time; and
   d) reconstructing a 3D magnetic susceptibility map, $\chi^{recon}(r)$, of the object by performing a 3D deconvolution on the magnetic field map, $b(r)$, according to:

$$b(r) = B_0 \chi(r) * h_0(r)$$

and $$\chi^{recon}(r) = b(r) *^{-1} h_0(r)/B_0$$

where: $r=(x,y,z)$ denotes 3D coordinates in space domain; the symbol * denotes a 3D convolution operator; the symbol $*^{-1}$ denotes a 3D deconvolution operator; and $h_0(r)$ is a standard convolution kernel that is a point magnetic dipole kernel, according to:

$$h_0(r) = \frac{1}{4\pi} \frac{3z^2 - |r|^2}{|r|^5}$$

wherein performing the 3D deconvolution comprises executing a 3D Total Variation (TV) regularized iterative convolution scheme, which comprises solving a TV-regularized unconstrained minimization problem, according to:

$$\chi^{recon}(r) = \min_{\chi \in BV} \|\chi(r)\|_{TV} + \frac{\lambda}{2} \|B_0 \chi(r) * h_0(r) - b(r)\|_2^2$$

where: BV is a bounded variation function space, $\lambda$ is a TV regularization parameter $\|\cdot\|_{TV}$ denotes a TV norm, and $\|\cdot\|_2^2$ denotes a $L^2$ norm; and
   wherein performing the 3D TV-regularized iterative convolution scheme comprises searching over all possible distributions $\chi \in BV$ to find an optimal $\chi$-distribution, $\chi^{recon}$, which simultaneously minimizes both: a TV norm, and a data fidelity error measure; and further wherein a method for determining $\chi^{recon}(r)$ comprises solving the 3D minimization problem by using a split Bregman iteration algorithm, according to:

$$\min_{d,v,\chi} \|d(r)\|_{TV} + \frac{\lambda}{2}\|B_0 v - b\|_2^2 + \frac{\gamma_1}{2}\|d - \nabla\chi - a_1\|_2^2 + \frac{\gamma_2}{2}\|v - h_0 * \chi - a_2\|_2^2$$

with $d = \nabla\chi$ and $v = h_0 * \chi$ and, furthermore, wherein using the split Bregman iteration algorithm comprises transforming the 3D minimization problem into a series of three iteration sub-problems, and then solving each sub-problem by performing a Bregman-distance-based iteration with respect to three interim variables {'d', 'v', '$\chi$'}; where: 'd' and 'v' are auxiliary variables, '$\chi$' is the magnetic susceptibility to be reconstructed, $\lambda$ is the regularization parameter, and the parameters {'$\gamma_1$', '$\gamma_1$', '$a_1$', '$a_2$'} are introduced for efficient algorithm implementation and fast convergence.

2. The method of claim 1, further comprising solving the three sub-problems one-at-a-time with respect to one of the three interim variables {'d', 'v', or '$\chi$'}, while keeping the other two fixed, using the following algorithm:

Initialize $\chi = v = a_2 = 0, d = a_1 = 0$, tol

Do
   Minimization of $\chi$-subproblem with (d,v) fixed;
   Minimization of d-subproblem with ($\chi$,v) fixed;
   Minimization of v-subproblem with ($\chi$,d) fixed;
   Update $a_1 := a_1 + \nabla\chi - d$
   Update $a_2 := a_2 + h_0 * \chi - v$
While $\|\chi^{current} - \chi^{previous}\|_\infty < $ tol
Output: $\chi^{recon} = \chi^{current}$.

3. The method of claim 2, wherein the $\chi$-subproblem, with d and V fixed, is stated as:

$$\min_{\chi} \frac{\gamma_1}{2}\|d - \nabla\chi - a_1\|_2^2 + \frac{\gamma_2}{2}\|v - h_0 * \chi - a_2\|_2^2,$$

and, further, wherein the solution of $\chi$ is obtained in the Fourier domain by solving as follows:

$$\chi = IFT\left\{\frac{\frac{\gamma_2}{\gamma_1} H_0^* \cdot FT(v - a_2) - FT(\nabla \cdot (d - a_1))}{\frac{\gamma_2}{\gamma_1} H_0^* \cdot H_0 + (2\pi k)^2}\right\}$$

wherein: FT represents a Fourier transform; IFT represents an inverse Fourier transform; $H_0 = FT\{h_0\}$; $H_0^*$ represents the complex conjugate of $H_0$; and $k=(k_x,k_y,k_z)$ represents 3D coordinates in the Fourier domain.

4. The method of claim 2, wherein the d-subproblem, with v and $\chi$ fixed, is stated as:

$$\min_{d} \|d(r)\|_{TV} + \frac{\gamma_1}{2}\|d - \nabla\chi - a_1\|_2^2$$

and its solution is known in a closed form, according to:

$$d = \frac{\nabla \chi + a_1}{|\nabla \chi + a_1|} \max(||\nabla \chi + a_1| - 1/\gamma_1, 0).$$

5. The method of claim 2, wherein the v-subproblem, with d and $\chi$ fixed, is stated as:

$$\min_v \frac{\lambda}{2}\|B_0 v - b\|_2^2 + \frac{\gamma_2}{2}\|v - h_0 * \chi - a_2\|_2^2$$

and its solution is known in a closed form, according to:

$$v = \frac{h_0 * \chi + a_2 + \frac{\lambda}{\gamma_2}\frac{b}{B_0}}{1 + \frac{\lambda}{\gamma_2}}.$$

6. The method of claim 1, comprising performing the method on a 3D isotropic MR phase image; wherein the 3D complex-valued T2*-weighted MR image is directly acquired by using an EVI (echo volume imaging) pulse sequence, or by stacking image slices acquired by using an EPI (echo planar imaging) pulse sequence; and further wherein the 3D complex-valued T2*-weighted MR image is directly acquired with MRI parameter settings comprising: isotropic voxels, zero oblique that produces axial slices perpendicular to $B_0$, zero inter-voxel gap that makes the slice spacing equal to the slice thickness, small voxel size that implements high spatial resolution, and small $T_E$ that implements fast snapshot capture.

7. The method of claim 1, further comprising designing and using a modified TV iteration filter, H(k), corresponding to 3D iteration kernel h(r) by a 3D Fourier transform, with which the TV regularization scheme produces a reconstructed susceptibility volume that is substantially equivalent to a new susceptibility volume resulting from spatially filtering a standard $h_0$-reconstructed susceptibility volume; wherein designing the modified TV iteration filter, H(k), comprises using the following algorithm:
a) letting $f(k)$ denote a 3D filter designed for post-reconstruction filtering, and then
b) designing the modified TV iteration filter, H(k), according to:

$$H(k) = H_0(k)/f(k)$$

where: $H_0(k)$ represents a standard magnetic dipole filter $H_0(k) = FT\{h_0(r)\}$, according to:

$$H_0(k_x, k_y, k_z) = \frac{1}{3} - \frac{k_z^2}{(k_x^2 + k_y^2 + k_z^2)}.$$

8. The method of claim 7, wherein the step of designing and using a modified TV-iteration filter comprises: modifying $H_0(k)$ by resetting the DC term $H_0(0,0,0)$ to a value in a typical range of $[-1,-0.1]$ or $[0.1, 1]$; wherein the setting $H_0(0,0,0)=0$ is not allowed, and $H_0(0,0,0)=1/3$ for a standard $\chi$ reconstruction using a standard dipole filter $H_0(k)$.

9. The method of claim 8, further comprising:
a) using a plurality of TV iteration filters resulting from using different DC-term values;
b) performing parallel TV-iteration susceptibility reconstructions; and then
c) averaging the multiple susceptibility reconstructions together, thereby achieving noise reduction.

10. The method of claim 7, wherein the step of designing and using a modified TV-iteration filter comprises: performing 3D directional filtering by multiplying the 3D standard filter $H_0(k_x,k_y,k_z)$ along $k_x$-, $k_y$-, $k_z$- axis, or along the diagonal lines of the 3D k-space, by a 1D filter comprising high-pass, low-pass, and band-pass filtering capability.

11. The method of claim 7, wherein the step of designing and using a modified TV-iteration filter comprises: performing 3D volumetric filtering by multiplying the 3D standard filter $H_0(k_x,k_y,k_z)$ by another 3D filter capable of low-pass, highpass, and bandpass filtering.

12. The method of claim 7, wherein the step of designing and using a modified TV-iteration filter comprises: using specific formulas for designing post-reconstruction processing filters with 3D lowpass filtering capacity, according to:

$$f_{LP}(k) = c_1 + c_2 \times \cos(\pi k/k_{max}) \text{ s.t. } \min\{f_{LP}(k)\} > 0$$

$$f_{LP}(k) = 0.6 + 0.4 \times \cos(\pi k/k_{max})(\text{case: } c_1 = 0.6 \text{ and } c_2 = 0.4$$

with $k_{max} = \max\{|k|\}$
wherein the limiting condition for a lowpass filter is $\min\{f_{LP}(k)\} > 0$, as required by the non-singularity of $1/f_{LP}(k)$; and furthermore where $c_1 = 0.6$ and $c_2 = 0.4$, provides the special case that produces $\min\{f_{LP}(k)\} = 0.2$.

13. The method of claim 12, wherein the step of designing and using a modified TV-iteration filter comprises: using specific formulas for designing a post-reconstruction filter with 3D highpass filtering capacity, according to:

$$f_{HP}(k) = \max(f_{LP}) - f_{LP}(k) + c_0 \text{ s.t. } \min\{f_{HP}(k)\} > 0$$

$$f_{HP}(k) = \max(f_{LP}) - f_{LP}(k) + 0.2 \text{ (case: } c_0 = 0.2)$$

wherein, as required by $1/f_{HP}(k)$, the limiting condition of $\min\{f_{HP}(k)\} > 0$; is imposed and $c_0 = 0.2$ provides the special case that $\min\{f_{HP}(k)\} = 0.2$.

14. The method of claim 13, further comprising reshaping the designed filters, $f_{LP}(k)$ and $f_{HP}(k)$, by an $\alpha$-power law formula, according to:

$$f_{LP}(k;\alpha) = \{f_{LP}(k)\}^\alpha, \alpha = \{1/2, 1, 2, 3, \ldots\}$$

$$f_{HP}(k;\alpha) = \{f_{HP}(k)\}^\alpha, \alpha = \{1/2, 1, 2, 3, \ldots\}$$

wherein the filter shape in Fourier domain is dilated with $0 \leq \alpha \leq 1$, and shrunk with $\alpha > 1$; and finally wherein the set of parameters of $\{c_0, c_1, c_2, \alpha\}$ are configured under a condition of $\min\{f_{LP}(k)\} > 0$ and $\min\{f_{HP}(k)\} > 0$, thereby avoiding the singularity of the reciprocal filter $1/f_{LP}(k)$ and $1/f_{HP}(k)$.

15. The method of claim 7, wherein the step of designing and using a modified TV-iteration filter comprises using specific formulas for designing post-reconstruction filters with 3D bandstop (BT) and bandpass (BP) filtering capacity, which are useful for high spatial resolution $\chi$ reconstruction, according to:

$$f_{BP}(k) = 1 - \exp\left(-\frac{|k|^2}{2\pi\sigma_1^2 k_{max}^2}\right) + \exp\left(-\frac{|k|^2}{2\pi\sigma_2^2 k_{max}^2}\right), \sigma_1 > \sigma_2 \text{ (bandpass)}$$

$$f_{BT}(k) = \exp\left(-\frac{|k|^2}{2\pi\sigma_1^2 k_{max}^2}\right) - \exp\left(-\frac{|k|^2}{2\pi\sigma_2^2 k_{max}^2}\right), \sigma_1 > \sigma_2 \text{ (bandstop)}$$

where $\sigma$ denotes a standard deviation of a Gaussian distribution.

16. The method of claim 7, wherein the step of designing and using a modified TV-iteration filter comprises: using a formula for calculating a modified TV-iteration filter by the reciprocal of the post-reconstruction filter, according to:

$$H(k) = \frac{H_0(k)}{f(k)}$$ (modified filter)

$$h(r) = IFT[H(k)] = h_0(r) * IFT(1/f(k))$$ (modified kernel)

where IFT denotes inverse Fourier transform; and further wherein the function $f(k)$ comprises a post-reconstruction filter selected from the group consisting of: a DC term reset, a 3D directional filter, a 3D volumetric filter, a 3D lowpass filter, a 3D high pass filter, a lowpass or highpass filter reshaped by α-power law formula, a 3D bandstop filter, and a 3D bandpass filter.

17. The method of claim 7, further comprising reducing the susceptibility reconstruction noise by averaging two different sets of reconstructed χ distributions (Set 1 and Set 2), wherein: Set 1 comprises post-processed reconstructed χ distributions generated by performing post reconstruction filtering, and Set 2 comprises reconstructed χ distributions generated by performing TV-iteration filtering with a modified filter according to claim 8.

18. The method of claim 7, further comprising generating a low-noise reconstructed susceptibility map with suppressed sparse residual comeback noise, by:
   a) performing multiple TV iteration susceptibility reconstructions in parallel, which use the same T2*MRI phase image, but have variations in parameter settings of the modified TV iteration filter, H(k); and then
   b) performing a multi-reconstruction average of the multiple parallel reconstructions from step a);
   thereby generating a low-noise reconstructed susceptibility map.

19. The method of claim 1, further comprising performing a MR magnitude-based self-calibration scheme for estimating one or more appropriate values of the TV regularization parameter, λ; wherein the scheme comprises the following steps, performed in the following order:
   a) extracting a 3D T2*MRI magnitude image, $A(x,y,z;T_E)$, from the 3D complex-valued MR image;
   b) choosing an initial value of the TV regularization parameter, λ;
   c) generating the reconstructed magnetic susceptibility map, $\chi^{recon}$;
   d) generating positive-valued version, $|\chi^{recon}|$, of the reconstructed susceptibility map, by taking the absolute value of the reconstructed susceptibility map, $\chi^{recon}$;
   e) comparing the positive-valued version, $|\chi^{recon}|$, of the reconstructed susceptibility map to the 3D T2*MRI magnitude image, $A(x,y,z;T_E)$;
   f) setting $\lambda = \lambda^{optimum}$ if the comparison shows that the two different maps are optimally similar; followed by performing regular TV iterations until convergence is reached; or
   g) adjusting the TV regularization parameter, λ, to a different value, if the comparison shows that the two different maps are not sufficiently similar; and then
   h) iteratively repeating steps c) through g), using the adjusted value of λ from step g), until an optimal similarity is reached.

20. The method of claim 1, wherein the TV regularization parameter, λ, has a value in the range of 30 to 500, for millimeter resolution images.

21. The method of claim 1, further comprising reconstructing a 3D magnetic susceptibility map, $\chi^{recon}(r,t_0)$, of the object at a snapshot in time, $t_0$, by performing the CIMRI tomographic procedure on a 3D MR phase image extracted at $t=t_0$ from a 4D MR phase dataset, $P(x,y,z,t)$, which was created during a functional MRI (fMRI) session;
   wherein the object comprises a brain cortex; and
   wherein the method further comprises using a susceptibility timecourse synchrony criterion for generating a meaningful 4D susceptibility reconstruction, which is implemented by reproducing a susceptibility timecourse at an active site within the brain such that the susceptibility timecourse at an active site correlates highly with a known external stimulus timecourse, where the maximal correlation can be reached by a lag time as determined by the latent time of hemodynamic response; and
   wherein the method additionally comprises determining the active site's location from a 4D MR magnitude dataset;
   wherein the active site's location corresponds to a region of maximal temporal correlation between a MR magnitude timecourse and the known external stimulus timecourse.

22. The method of claim 21, further comprising replacing the 3D T2*MRI phase image, $P(x,y,z;T_E)$ with a T2'-effect phase image, $P_{T2'}(x, y, z; T_E)$ by a) acquiring a complex-valued T2*-weighted GE MR image (T2* GE image) of an object, where the T2* GE image is made by a MRI scanner using gradient-echo (GE) pulse sequence and a specified echo time, $T_E$; wherein the T2* GE image includes contributions from both a non-random static inhomogeneous component (T2'-effect) and a random spin-spin interaction component (T2 effect);
   b) acquiring a complex-valued T2*-weighted SE MR image (T2* SE image) of the same object, where the T2* SE image is made by a MRI scanner using spin-echo (SE) pulse sequence and the same echo time ($T_E$) as is specified in step a) for making the T2* GE image; wherein the T2* SE image consists only of the random T2 effect component, with the static inhomogeneous component removed by a refocusing operation of the T2* SE pulse sequence;
   c) generating a complex-valued T2'-effect MR image ($C_{T2'}$) by performing a complex division between the complex-valued T2*-weighted GE MR image, $C_{GE}(x,y,z;T_E)$, and the complex-valued T2*-weighted SE MR image, $C_{SE}(x,y,z;T_E)$, according to:

$$C_{T2'}(x,y,z;T_E) = C_{GE}(x,y,z;T_E)/C_{SE}(x,y,z;T_E)$$

d) calculating a T2'-effect phase image, $P_{T2'}(x, y, z;T_E)$, from the complex-valued T2'-effect MR image, $C_{T2'}(x, y,z;T_E)$, according to:

$$P_{T2'}(x,y,z;T_E) = \angle C_{T2'}(x,y,z,T_E) = \angle C_{GE}(x,y,z;T_E) - \angle C_{SE}(x,y,z;T_E)$$

23. The method of claim 21, further comprising, for linear statistical postprocessing, first calculating a phase-based statistical brain activation map, denoted by $P^{map}(x,y,z)$; and then reconstructing a susceptibility-based brain activation map, $\chi^{map}(x,y,z)$, by performing the CIMRI procedure only once.

24. The method of claim 21, further comprising, for nonlinear statistical postprocessing, first reconstructing a 4D magnetic susceptibility dataset, $\chi^{recon}(x,y,z,t)$, by looping the CIMRI procedure on the 4D MR phase dataset, $P(x,y,z,t)$, for each time point, t, within a session; and then rendering statistical postprocessing on the reconstructed 4D susceptibility dataset, $\chi^{recon}(x,y,z,t)$, to produce a χ-based brain activation map, $\chi^{map}(x,y,z)$.

25. The method of claim 1, wherein using the CIMRI tomographic procedure does not involve using matrix algebra or Tikhonov regularization matrix inverse methods; and furthermore wherein the CIMRI tomographic procedure manipulates 3D matrix data in an elementwise manner in the Fourier domain, without involving any matrix-matrix or vector-matrix multiplication rules; and without changing the 3D array format.

26. A method of reconstructing a 4D magnetic susceptibility dataset, $\chi^{recon}(x,y,z,t)$, of an internal dynamic magnetic susceptibility distribution of an object, by repeatedly using a Computed Inverse Magnetic Resonance Imaging (CIMRI) tomographic procedure for a 3D magnetic susceptibility reconstruction at each snapshot time, comprising:

a) acquiring a time-dependent, sequential series of 3D complex-valued MR images, where the images were created using a MRI scanning machine performing multiple T2*-weighted MRI scans on a object during a fMRI session;

b) extracting and assembling a 4D T2*MRI phase image dataset, $P(x,y,z,t)$, from the sequential series of 3D complex-valued MR images;

c) calculating a 3D magnetic field map, $b(x,y,z,t')$, at a specific time=t', of the z-component ($B_z$) of a susceptibility-induced inhomogeneous magnetic field created by magnetizing the object in a main field, $B_0$, from the 4D T2*MRI phase image dataset, $P(x,y,z,t)$, under phase-unwrapped conditions:

$$b(x,y,z,t') = \frac{P(x,y,z,t')}{\gamma T_E}$$

where: $\gamma$=proton gyromagnetic ratio, and $T_E$=echo time; then d) reconstructing a 3D magnetic susceptibility map, $\chi^{recon}(r, t')$, at the same specific time=t', by performing a 3D deconvolution on the 3D magnetic field map, $b(r,t')$, according to:

$$b(r,t') = B_0 \chi(r,t') * h_0(r)$$

and $$\chi^{recon}(r,t') = b(r,t') *^{-1} h_0(r)/B_0$$

where: $r=(x,y,z)$ denotes 3D coordinates in space domain; the symbol * denotes a 3D convolution operator; the symbol $*^{-1}$ denotes a 3D deconvolution operator; and $h_0(r)$ is a standard convolution kernel that is a point magnetic dipole kernel, according to:

$$h_0(r) = \frac{1}{4\pi} \frac{3z^2 - |r|^2}{|r|^5}$$

e) wherein performing the 3D deconvolution in step d) comprises executing a 3D Total Variation (TV) regularized iterative convolution scheme, which comprises solving a TV regularized, unconstrained minimization problem, according to:

$$\chi^{recon}(r) = \min_{\chi \in BV} \|\chi(r)\|_{TV} + \frac{\lambda}{2} \|B_0 \chi(r) * h_0(r) - b(r)\|_2^2$$

where: BV is a bounded variation function space, $\lambda$ is a TV regularization parameter, $\|\cdot\|_{TV}$ denotes a TV norm, and $\|\cdot\|_2^2$ denotes a $L^2$ norm; and further wherein performing the 3D TV regularization scheme comprises searching over all possible distributions $\chi \in BV$ to find an optimal $\chi$ distribution, $\chi^{recon}$, which simultaneously minimizes both: a TV norm, and a data fidelity error measure; and then f) repeating steps c) through e), for a new time: $t'_{new} = t'_{old} + \Delta t$, and then repeating this cycle until the entire fMRI session has been reconstructed, where $\Delta t$ is a time interval between two successive snapshots; then g) assembling all of the reconstructed 3D magnetic susceptibility maps from step f) for all time points t'$\in$t, which cover part or all of an entire fMRI session, into a single 4D magnetic susceptibility dataset, $\chi^{recon}(r, t)$; then h) generating one or more magnetic susceptibility timecourses, $\chi(x', y', z', t')$, at one or more specific locations, $(x', y', z')$, of active voxels in the brain that belong to a neighborhood of a neuroactive site, $(x^{act}, y^{act}, z^{act})$; wherein the neuroactive site is found by computing a local maximal temporal correlation, as expressed by:

$$(x^{act}, y^{act}, z^{act}) = \max_{(x,y,z) \in FOV} \|A(x, y, z, t) \otimes task(t)\|$$

where: $A(x,y,z,t)$ is a 4D MR magnitude dataset; "task(t)" represents a time-dependent external stimulus; and the symbol $\otimes$ denotes performing a temporal correlation;

i) performing a temporal correlation between task(t) and the one or more magnetic susceptibility timecourses, $\chi(x', y', z', t)$; then j) applying a criterion for timecourse synchrony to results of step i), wherein the criterion means that an optimally reconstructed susceptibility timecourse correlates highly with the task(t); and thereby k) obtaining an optimal 4D magnetic susceptibility dataset, $\chi^{recon}(x,y,z,t)$, by performing the temporal correlation and maxima determination, according to:

$$\chi^{recon}(x, y, z, t) = \max_{(x',y',z') \in N(x^{act}, y^{act}, z^{act})} \|\chi^*(x', y', z', t) \otimes task(t)\|$$

where $\chi^*(x,y,z,t)$ is a candidate of reconstructed 4D susceptibility datasets during 4D reconstruction optimization, created when a TV regularization parameter, $\lambda$, is varied according to a susceptibility timecourse synchrony criterion; and wherein $\chi^{recon}(x,y,z,t)$ is the optimal 4D magnetic susceptibility dataset obtained when the temporal correlation between the candidate dataset $\chi^*(x,y,z,t)$ and task(t) reaches a maximum.

27. The method of claim 26, further comprising adjusting the TV regularization parameter, $\lambda$, and then repeating steps d) through j), using the adjusted parameter $\lambda$; and furthermore continuing these $\lambda$-adjustment steps until the 4D susceptibility source reconstruction procedure produces a maximum, highest-as-possible temporal correlation between a susceptibility timecourse at an activation voxel and the external stimuli, task(t).

* * * * *